(12) United States Patent
Chen et al.

(10) Patent No.: US 11,444,249 B2
(45) Date of Patent: Sep. 13, 2022

(54) ORGANIC ELECTROLUMINESCENT MATERIALS AND DEVICES

(71) Applicant: Universal Display Corporation, Ewing, NJ (US)

(72) Inventors: Hsiao-Fan Chen, Ewing, NJ (US); Tongxiang (Aaron) Lu, Ewing, NJ (US); Nicholas J. Thompson, Ewing, NJ (US); Eric A. Margulies, Ewing, NJ (US); George Fitzgerald, Ewing, NJ (US); Jerald Feldman, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 534 days.

(21) Appl. No.: 16/124,312

(22) Filed: Sep. 7, 2018

(65) Prior Publication Data

US 2019/0074449 A1    Mar. 7, 2019

Related U.S. Application Data

(60) Provisional application No. 62/555,187, filed on Sep. 7, 2017.

(51) Int. Cl.
*H01L 51/00* (2006.01)
*C07D 209/86* (2006.01)
(Continued)

(52) U.S. Cl.
CPC ........ *H01L 51/0072* (2013.01); *C07D 209/86* (2013.01); *C07D 265/38* (2013.01);
(Continued)

(58) Field of Classification Search
CPC .. C07D 209/86; C07D 265/38; C07D 401/04; C07D 401/10; C07D 401/14;
(Continued)

(56) References Cited

U.S. PATENT DOCUMENTS 4,769,292 A    9/1988    Tang
5,061,569 A    10/1991    Vanslyke
(Continued)

FOREIGN PATENT DOCUMENTS

EP    0650955    5/1995
EP    1238981    9/2002
(Continued)

OTHER PUBLICATIONS

Journal of Materials Chemistry, (2012), 22(26), pp. 13260-13267. (Year: 2012).*

(Continued)

*Primary Examiner* — Dawn L Garrett
(74) *Attorney, Agent, or Firm* — Riverside Law LLP

(57) ABSTRACT

Compounds that are organic radicals that can have a dual function. The compounds can be fluorescent emitters that emit in the near-IR. The compounds can also facilitate reverse intersystem crossing (RISC) to convert triplet excitons in an OLED to singlet excited states to maximize utilization of generated excitons in the OLED and approach 100% internal quantum efficiency.

20 Claims, 2 Drawing Sheets

(51) Int. Cl.
*C07D 403/04* (2006.01)
*C07D 401/04* (2006.01)
*C07D 413/04* (2006.01)
*C07D 401/14* (2006.01)
*C07D 265/38* (2006.01)
*C07D 401/10* (2006.01)
*C09K 11/06* (2006.01)
*C07D 487/04* (2006.01)
*H01L 51/50* (2006.01)

(52) U.S. Cl.
CPC ......... *C07D 401/04* (2013.01); *C07D 401/10* (2013.01); *C07D 401/14* (2013.01); *C07D 403/04* (2013.01); *C07D 413/04* (2013.01); *C07D 487/04* (2013.01); *C09K 11/06* (2013.01); *H01L 51/006* (2013.01); *H01L 51/0052* (2013.01); *H01L 51/0054* (2013.01); *H01L 51/0055* (2013.01); *H01L 51/0056* (2013.01); *H01L 51/0058* (2013.01); *H01L 51/0059* (2013.01); *H01L 51/0061* (2013.01); *H01L 51/0067* (2013.01); *H01L 51/0071* (2013.01); *H01L 51/0074* (2013.01); *C09K 2211/1018* (2013.01); *H01L 51/5012* (2013.01); *H01L 51/5016* (2013.01)

(58) Field of Classification Search
CPC .. C07D 403/04; C07D 413/04; C07D 487/04; C09K 11/06; C09K 2211/1018; H01L 51/0052; H01L 51/0054; H01L 51/0055; H01L 51/0056; H01L 51/0058; H01L 51/0059; H01L 51/006; H01L 51/0061; H01L 51/0067; H01L 51/0071; H01L 51/0072; H01L 51/0074; H01L 51/5012; H01L 51/5016

See application file for complete search history.

(56) References Cited

U.S. PATENT DOCUMENTS

| | | | |
|---|---|---|---|
| 5,247,190 A | 9/1993 | Friend | |
| 5,457,565 A * | 10/1995 | Namiki | H01L 51/5092 257/103 |
| 5,703,436 A | 12/1997 | Forrest | |
| 5,707,745 A | 1/1998 | Forrest | |
| 5,834,893 A | 11/1998 | Bulovic | |
| 5,844,363 A | 12/1998 | Gu | |
| 6,013,982 A | 1/2000 | Thompson | |
| 6,087,196 A | 7/2000 | Sturm | |
| 6,091,195 A | 7/2000 | Forrest | |
| 6,097,147 A | 8/2000 | Baldo | |
| 6,294,398 B1 | 9/2001 | Kim | |
| 6,303,238 B1 | 10/2001 | Thompson | |
| 6,337,102 B1 | 1/2002 | Forrest | |
| 6,468,819 B1 | 10/2002 | Kim | |
| 6,528,187 B1 | 3/2003 | Okada | |
| 6,687,266 B1 | 2/2004 | Ma | |
| 6,835,469 B2 | 12/2004 | Kwong | |
| 6,921,915 B2 | 7/2005 | Takiguchi | |
| 7,087,321 B2 | 8/2006 | Kwong | |
| 7,090,928 B2 | 8/2006 | Thompson | |
| 7,154,114 B2 | 12/2006 | Brooks | |
| 7,250,226 B2 | 7/2007 | Tokito | |
| 7,279,704 B2 | 10/2007 | Walters | |
| 7,332,232 B2 | 2/2008 | Ma | |
| 7,338,722 B2 | 3/2008 | Thompson | |
| 7,393,599 B2 | 7/2008 | Thompson | |
| 7,396,598 B2 | 7/2008 | Takeuchi | |
| 7,431,968 B1 | 10/2008 | Shtein | |
| 7,445,855 B2 | 11/2008 | Mackenzie | |
| 7,534,505 B2 | 5/2009 | Lin | |
| 7,968,146 B2 | 6/2011 | Wagner | |
| 8,409,729 B2 | 4/2013 | Zeng | |
| 2002/0034656 A1 | 3/2002 | Thompson | |
| 2002/0134984 A1 | 9/2002 | Igarashi | |
| 2002/0158242 A1 | 10/2002 | Son | |
| 2003/0138657 A1 | 7/2003 | Li | |
| 2003/0152802 A1 | 8/2003 | Tsuboyama | |
| 2003/0162053 A1 | 8/2003 | Marks | |
| 2003/0175553 A1 | 9/2003 | Thompson | |
| 2003/0230980 A1 | 12/2003 | Forrest | |
| 2004/0036077 A1 | 2/2004 | Ise | |
| 2004/0137267 A1 | 7/2004 | Igarashi | |
| 2004/0137268 A1 | 7/2004 | Igarashi | |
| 2004/0174116 A1 | 9/2004 | Lu | |
| 2005/0025993 A1 | 2/2005 | Thompson | |
| 2005/0112407 A1 | 5/2005 | Ogasawara | |
| 2005/0176953 A1 * | 8/2005 | Tuan | C07C 13/64 540/107 |
| 2005/0238919 A1 | 10/2005 | Ogasawara | |
| 2005/0244673 A1 | 11/2005 | Satoh | |
| 2005/0260441 A1 | 11/2005 | Thompson | |
| 2005/0260449 A1 | 11/2005 | Walters | |
| 2006/0008670 A1 | 1/2006 | Lin | |
| 2006/0202194 A1 | 9/2006 | Jeong | |
| 2006/0240279 A1 | 10/2006 | Adamovich | |
| 2006/0251923 A1 | 11/2006 | Lin | |
| 2006/0263635 A1 | 11/2006 | Ise | |
| 2006/0280965 A1 | 12/2006 | Kwong | |
| 2007/0190359 A1 | 8/2007 | Knowles | |
| 2007/0278938 A1 | 12/2007 | Yabunouchi | |
| 2008/0015355 A1 | 1/2008 | Schafer | |
| 2008/0018221 A1 | 1/2008 | Egen | |
| 2008/0106190 A1 | 5/2008 | Yabunouchi | |
| 2008/0124572 A1 | 5/2008 | Mizuki | |
| 2008/0220265 A1 | 9/2008 | Xia | |
| 2008/0297033 A1 | 12/2008 | Knowles | |
| 2009/0008605 A1 | 1/2009 | Kawamura | |
| 2009/0009065 A1 | 1/2009 | Nishimura | |
| 2009/0017330 A1 | 1/2009 | Iwakuma | |
| 2009/0030202 A1 | 1/2009 | Iwakuma | |
| 2009/0039776 A1 | 2/2009 | Yamada | |
| 2009/0045730 A1 | 2/2009 | Nishimura | |
| 2009/0045731 A1 | 2/2009 | Nishimura | |
| 2009/0101870 A1 | 4/2009 | Prakash | |
| 2009/0108737 A1 | 4/2009 | Kwong | |
| 2009/0115316 A1 | 5/2009 | Zheng | |
| 2009/0165846 A1 | 7/2009 | Johannes | |
| 2009/0167162 A1 | 7/2009 | Lin | |
| 2009/0179554 A1 | 7/2009 | Kuma | |
| 2013/0026452 A1 | 1/2013 | Kottas | |
| 2013/0119354 A1 | 5/2013 | Ma | |
| 2014/0027755 A1 * | 1/2014 | Mujica-Fernaud | C07D 471/14 257/40 |
| 2014/0054564 A1 | 2/2014 | Kim | |
| 2015/0318487 A1 | 11/2015 | Ito | |
| 2016/0099415 A1 * | 4/2016 | Li | H01L 51/0052 257/40 |
| 2016/0285016 A1 | 9/2016 | Kwong | |

FOREIGN PATENT DOCUMENTS

| | | |
|---|---|---|
| EP | 1725079 | 11/2006 |
| EP | 2034538 | 3/2009 |
| EP | 2551932 | 1/2013 |
| EP | 2977378 | 1/2016 |
| JP | 200511610 | 1/2005 |
| JP | 2007123392 | 5/2007 |
| JP | 2007254297 | 10/2007 |
| JP | 2008074939 A | 4/2008 |
| JP | 2010135467 | 6/2010 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2004111066 | 12/2004 |
| WO | 2005014551 | 2/2005 |
| WO | 2005019373 | 3/2005 |

(56) References Cited

FOREIGN PATENT DOCUMENTS

| | | |
|---|---|---|
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |
| WO | 2008057394 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 A2 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010011390 | 1/2010 |
| WO | 2010111175 | 9/2010 |
| WO | 2010126234 | 11/2010 |

OTHER PUBLICATIONS

Intl. J. of Quantum Chem., (2001), 85(4/5), pp. 619-635. (Year: 2001).*
Wong, Wai-Yeung, "Multifunctional Iridium Complexes Based on Carbazole Modules as Highly Efficient Electrophosphors," Angew. Chem. Int. Ed., 45:7800-7803 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode: an Isoindole Derivative," Chem. Mater., 15(16):3148-3151 (2003).
Okumoto, Kenji et al., "Green Fluorescent Organic Light-Emitting Device with External Quantum Efficiency of Nearly 10%," Appl. Phys. Lett., 89:063504-1-063504-3 (2006).
Paulose, Betty Marie Jennifer S, et al., "First Examples of Alkenyl Pyridines as Organic Ligands for Phosphorescent Iridium Complexes," Adv. Mater., 16(22):2003-2007 (2004).
Tang, C.W. and VanSlyke, S.A., "Organic Electroluminescent Diodes," Appl. Phys. Lett., 51(12):913-915 (1987).
T. Ostergard et al., "Langmuir-Blodgett Light-Emitting Diodes Of Poly(3-Hexylthiophene): Electro-Optical Characteristics Related to Structure," Synthetic Metals, 87:171-177 (1997).
Tung, Yung-Liang et al., "Organic Light-Emitting Diodes Based on Charge-Neutral Ru II PHosphorescent Emitters," Adv. Mater., 17(8):1059-1064 (2005).
Van Slyke, S. A. et al., "Organic Electroluminescent Devices with Improved Stability," Appl. Phys. Lett, 69(15 ):2160-2162 (1996).
Wong, Keith Man-Chung et al., "A Novel Class of Phosphorescent Gold(III) Alkynyl-Based Organic Light-Emitting Devices with Tunable Colour," Chem. Commun., 2906-2908 (2005).
Adachi, Chihaya et al., "Organic Electroluminescent Device Having a Hole Conductor as an Emitting Layer," Appl. Phys. Lett., 55(15):1489-1491 (1989).
Baldo et al., "Highly Efficient Phosphorescent Emission from Organic Electroluminescent Devices," Nature, vol. 395,151-154, (1998).
Gao, Zhiqiang et al., "Bright-Blue Electroluminescence From a Silyl-Substituted ter-(phenylene-vinylene) derivative," Appl. Phys. Lett., 74(6):865-867 (1999).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Wang, Y. et al., "Highly Efficient Electroluminescent Materials Based on Fluorinated Organometallic Iridium Compounds," Appl. Phys. Lett., 79(4):449-451 (2001).
Kwong, Raymond C. et al., "High Operational Stability of Electrophosphorescent Devices," Appl. Phys. Lett., 81(1):162-164 (2002).
Holmes, R.J. et al., "Blue Organic Electrophosphorescence Using Exothermic Host-Guest Energy Transfer," Appl. Phys. Lett., 82(15):2422-2424 (2003).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
Adachi, Chihaya et al., "High-Efficiency Red Electrophosphorescence Devices," Appl. Phys. Lett., 78(11):1622-1624 (2001).
Hamada, Yuji et al., "High Luminance in Organic Electroluminescent Devices with Bis(10-hydroxybenzo[h]quinolinato)beryllium as an Emitter," Chem. Lett., 905-906 (1993).
Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).
Baldo et al., "Very high-efficiency green organic light-emitting devices based on electrophosphorescence," Appl. Phys. Lett., vol. 75, No. 3, 4-6 (1999).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Niu, Yu-Hua et al., "Highly Efficient Electrophosphorescent Devices with Saturated Red Emission from a Neutral Osmium Complex," Chem. Mater., 17(13):3532-3536 (2005).
Lo, Shih-Chun et al., "Blue Phosphorescence from Iridium(III) Complexes at Room Temperature," Chem. Mater., 18(21):5119-5129 (2006).
Takizawa, Shin-ya et al., "Phosphorescent Iridium Complexes Based on 2-Phenylimidazo[1,2-a]pyridine Ligands: Tuning of Emission Color toward the Blue Region and Application to Polymer Light-Emitting Devices," Inorg. Chem., 46(10):4308-4319 (2007).
Lamansky, Sergey et al., "Synthesis and Characterization of Phosphorescent Cyclometalated Iridium Complexes," Inorg. Chem., 40(7):1704-1711 (2001).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Noda, Tetsuya and Shirota,Yasuhiko, "5,6-Bis(dinnesitylboryl)-2,2'-bithiophene and 5,5"-Bis(dimesitylbory1)-2,2':5',2"-terthiophene as a Novel Family of Electron-Transporting Amorphous Molecular Materials," J. Am. Chem. Soc., 120 (37):9714-9715 (1998).
Sakamoto, Youichi et al., "Synthesis, Characterization, and Electron-Transport Property of Perfluorinated Phenylene Dendrimers," J. Am. Chem. Soc., 122(8):1832-1833 (2000).
Adachi, Chihaya et al., "Nearly 100% Internal Phosphorescence Efficiency in an Organic Light Emitting Device," J. Appl. Phys., 90(10):5048-5051 (2001).
Shirota, Yasuhiko et al., "Starburst Molecules Based on p-Electron Systems as Materials for Organic Electroluminescent Devices," Journal of Luminescence, 72-74:985-991 (1997).

(56) References Cited

OTHER PUBLICATIONS

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kido, Junji et al.,"1,2,4-Triazole Derivative as an Electron Transport Layer in Organic Electroluminescent Devices," Jpn. J. Appl. Phys., 32:L917-L920 (1993).
Guo, Tzung-Fang et al., "Highly Efficient Electrophosphorescent Polymer Light-Emitting Devices," Organic Electronics, 1:15-20 (2000).
Palilis, Leonidas C., "High Efficiency Molecular Organic Light-Emitting Diodes Based On Silole Derivatives And Their Exciplexes," Organic Electronics, 4:113-121 (2003).
Ikeda, Hisao et al., "P-185: Low-Drive-Voltage OLEDs with a Buffer Layer Having Molybdenum Oxide," SID Symposium Digest, 37:923-926 (2006).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Salbeck, J. et al., "Low Molecular Organic Glasses for Blue Electroluminescence," Synthetic Metals, 91:209-215 (1997).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Hung, L.S. et al., "Anode Modification in Organic Light-Emitting Diodes by Low-Frequency Plasma Polymerization of CHF3,"Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Eley et al., 1967, "Semiconductivity of Organic Substances Part II—Electrical Properties of Substitued Allyl Radicals," Transactions of the Faraday Society 63:902-10.
Hattori et al., 2014, "Luminescence, Stability, and Proton Response of an Open-Shell (3,5-Dichloro-4-pyridyl)bis(2,4,6-trichlorophenyl)methyl Radical," Angew. Chem. Int. Ed. 53:11845-11848.
Matveeva et al., 2011, "Luminescent Properties of New Naphthylnitroxyl Radicals," High Energy Chem. 45:416.
Müllegger et al., 2012, "Interactions and Self-Assembly of Stable Hydrocarbon Radicals on a Metal Support," J. Phys. Chem. C 116:22587-22594.
Obolda et al., 2016, Up to 100% Formation Ratio of Doublet Exciton in Deep-Red Organic Light-Emitting Diodes Based on Neutral π☐ Radical,ACS Appl. Mater. Interfaces, 8:35472-35478.
Peng et al., "Organic light-emitting diodes using open-shell molecule as emitter: the emission from doublet," Physics 1-12.
Peng et al., 2015, "Organic Light-Emitting Diodes Using a Neutral p Radical as Emitter: The Emission from a Doublet," Angew. Chem. Int. Ed. 54:7091-7095.
Ratera and Veciana, 2012, "Playing with organic radicals as building blocks for functional molecular materials," Chem. Soc. Rev., 41:303-349.

\* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 62/555,187, filed Sep. 7, 2017, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

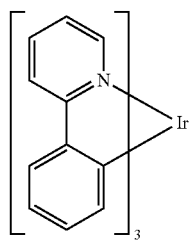

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

SUMMARY

A compound that has the structure selected from the group consisting of Formulae BB, BC, BD, BE, BF, and BF:

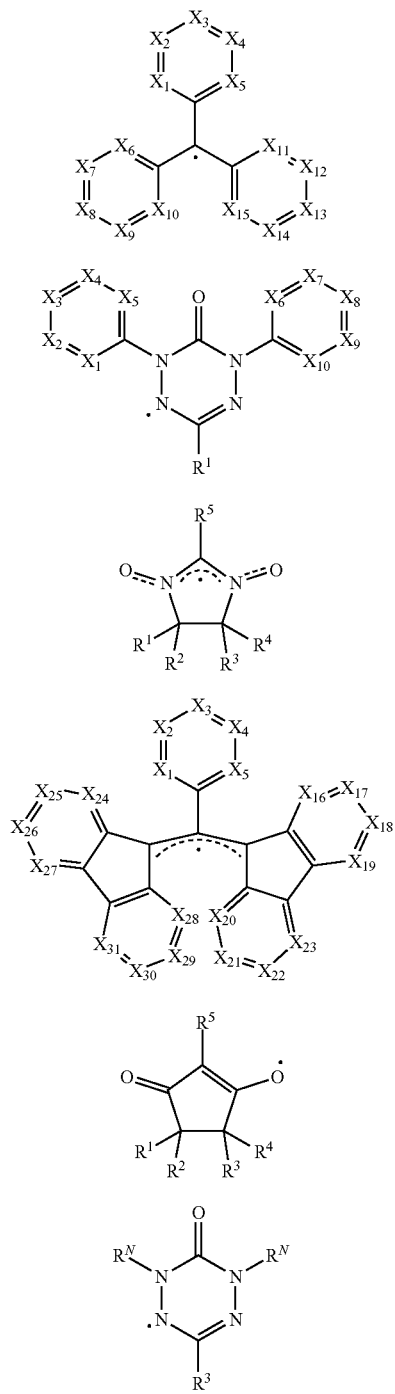

For the respective compounds of the Formulae BB, BC, BD, BE, BF, and BF:

$X_1$ to $X_5$ are independently selected from $CR^A$ or N;
$X_6$ to $X_{10}$ are independently selected from $CR^B$ or N;
$X_{11}$ to $X_{15}$ are independently selected from $CR^C$ or N;
$X_{16}$ to $X_{23}$ are independently selected from $CR^D$ or N;
$X_{24}$ to $X_{31}$ are independently selected from $CR^E$ or N;
$R^A$, $R^B$, $R^C$, $R^D$, and $R^E$ independently represent mono to the maximum allowable substitution, or no substitution;

each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;

$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;

wherein at least one of $R^1$ to $R^5$, $R^A$, $R^B$, $R^C$, $R^D$, or $R^E$ includes a polycyclic group selected from the group consisting of:

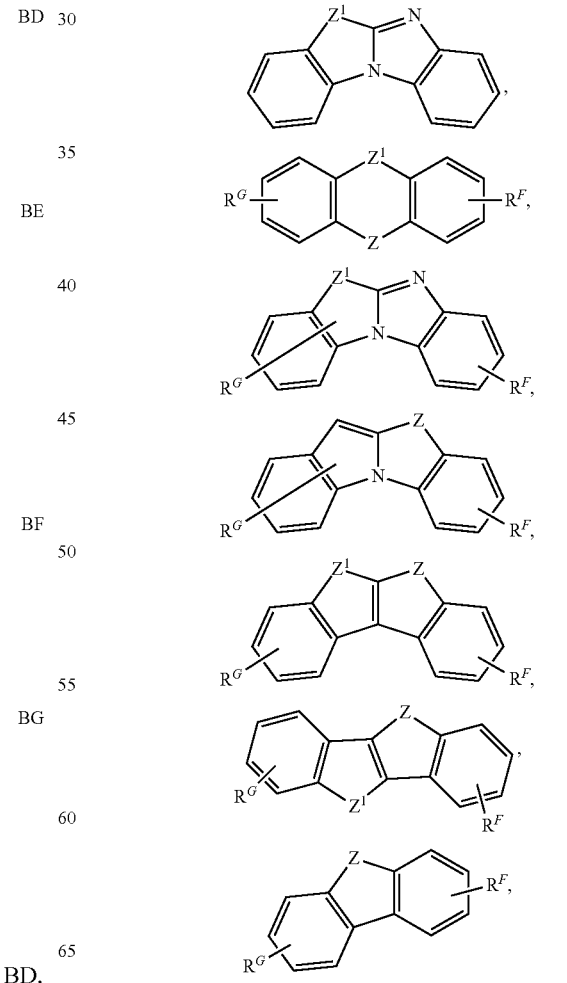

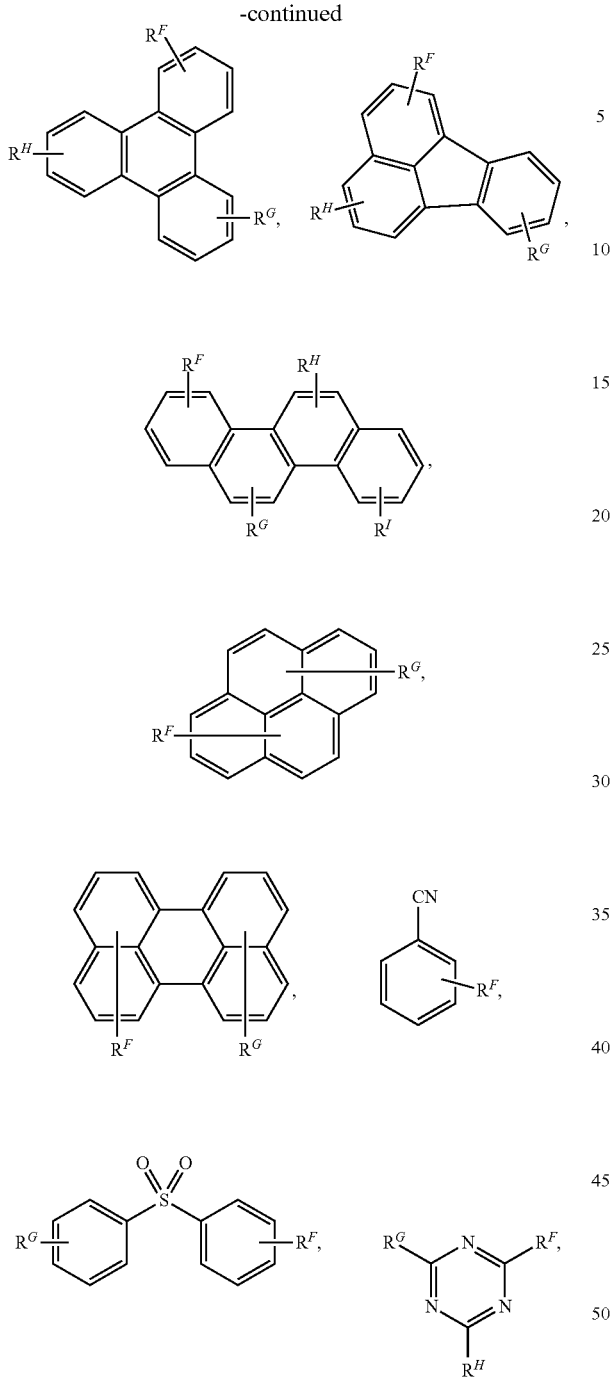

and any aza-analogue of each thereof, each of which is optionally substituted with $R^P$, wherein $R^P$ is selected from the group consisting of deuterium, fluorine, chlorine, alkyl, cycloalkyl, amino, aryl, heteroaryl, silyl, nitrile, and combinations thereof;

wherein $R^F$ to $R^I$ are independently selected from the group consisting of deuterium, fluorine, chlorine, alkyl, cycloalkyl, amino, aryl, heteroaryl, silyl, nitrile, and combinations thereof; and Z and $Z^1$ are independently selected from the group consisting of O, S, Se, $NR^N$, CR'CR", SiR'R", and GeR'R", wherein R' and R" are independently $R^N$;

with the proviso that the following compound is excluded

A compound of formula A-L-B; wherein component A is a fluorescent emitter, which includes fluorescent compounds that are known and referred to as thermally-assisted delayed fluorescence emitters. Component B comprises a structure selected from the group consisting of Formulae BB, BC, BD, BE, BF, and BF, above; and L is a direct bond or an organic linker.

A formulation or mixture of a component A and a component B. Component A is a fluorescent emitter that includes fluorescent compounds known and referred to as thermally-assisted delayed fluorescence emitters. Component B comprises a structure selected from the group consisting of Formulae BB, BC, BD, BE, BF, and BF, above.

An organic light emitting diode/device (OLED) that includes an anode, a cathode, and an organic layer disposed between the anode and the cathode. The organic layer includes a compound selected from the group consisting of Formulae BB, BC, BD, BE, BF, and BF, above. In one embodiment, the organic layer further includes a Component A which is fluorescent emitter, and includes fluorescent compounds that are known and referred to as thermally-assisted delayed fluorescence emitters. In another embodiment, the OLED includes an organic layer with a compound of formula A-L-B above. Again, Component A is a fluorescent emitter that includes fluorescent compounds known and referred to as thermally-assisted delayed fluorescence emitters. Component B comprises a structure selected from the group consisting of Formulae BB, BC, BD, BE, BF, and BF, above. Component L is an organic linker.

A consumer product that includes any one of the OLEDs described directly above.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
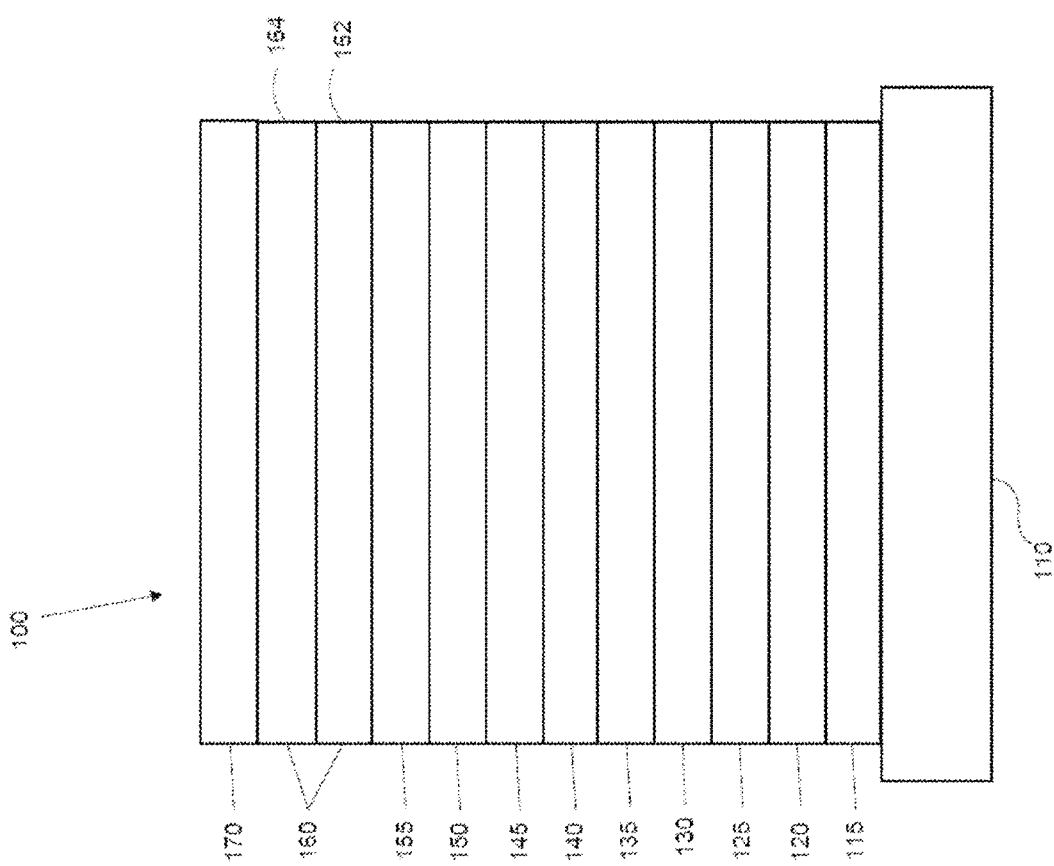
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

The invention is directed to select organic radicals. The organic radicals can have a dual function. First, many of the inventive organic radicals are known to be fluorescent emitters with an emission in a range from 700 nm to 1100 nm. Second, and perhaps more importantly, the doublet state of the organic radical can facilitate reverse intersystem crossing (RISC) to convert triplet excitons in an OLED to singlet excited states to maximize utilization of excitons generated in the OLED to approach 100% internal quantum efficiency. Radical-assisted RISC can be achieved by both chemical and physical blending of a fluorescent emitter and the organic radical into an emissive layer of an OLED device. In addition to radical-assisted RISC, if a pendent organic radical is conjugated to the fluorescent emitter, the emitter becomes a doublet emitter that also utilize all injected carriers to approach 100% internal quantum efficiency. Many of these organic radicals are what those skilled in the art would deem to be air-stable.

The organic radical can facilitate reverse intersystem crossing (RISC) when the radical and the emitter have no electronic communication (for example, compound 77, 2015, 2984, etc.), or make the fluorescent emitter become a doublet emitter when the radical can interact with the fluorescent chromophore through resonance (for example, compound 69, 715, 1038, etc.). In both cases, the radical in combination with a fluorescent emitter makes it possible to achieve 100% internal quantum efficiency (IQE) in an OLED. So far there are only two types of emitters that are widely used and can approach 100% IQE: i) phosphorescent emitters and ii) TADF (thermal-assisted delay fluorescence) emitters. Radical-assisted RISC emitters and doublet emitters will be the next generation highly efficient OLED emitters.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
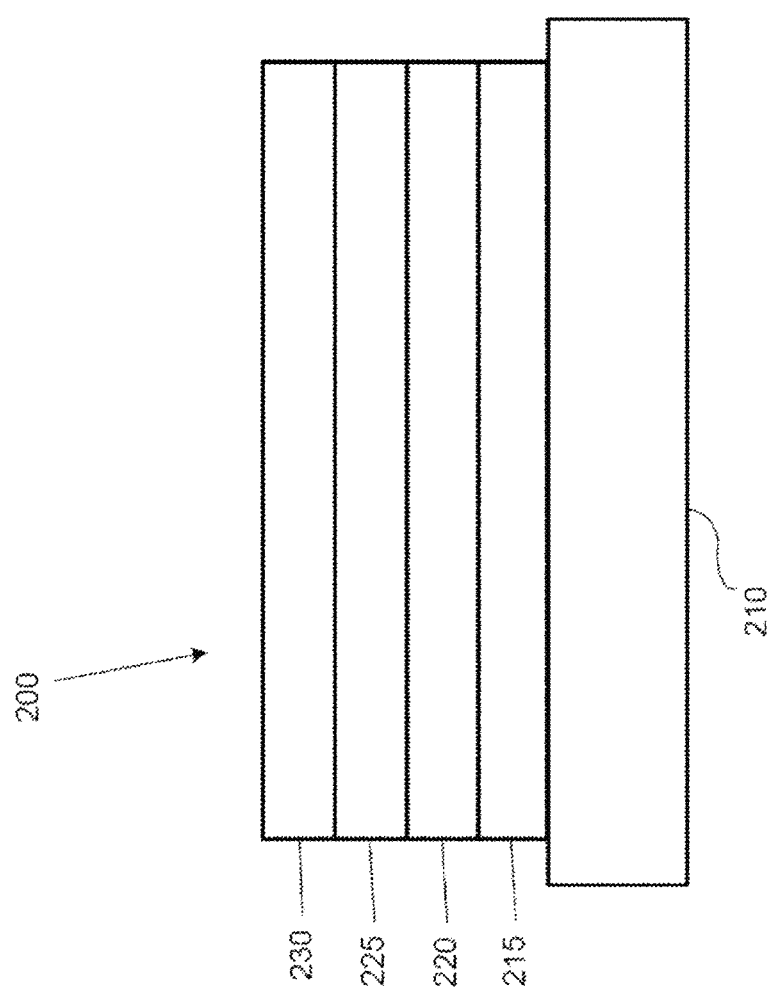
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —SR$_s$ radical.

The term "sulfinyl" refers to a —S(O)—R$_s$ radical.

The term "sulfonyl" refers to a —SO$_2$—R$_s$ radical.

The term "phosphino" refers to a —P(R$_s$)$_3$ radical, wherein each R$_s$ can be same or different.

The term "silyl" refers to a —Si(R$_s$)$_3$ radical, wherein each R$_s$ can be same or different.

In each of the above, R$_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred R$_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The term "substituted" refers to a substituent other than H that is bonded to the relevant position, e.g., a carbon. For example, where $R^1$ represents mono-substituted, then one $R^1$ must be other than H. Similarly, where $R^1$ represents di-substituted, then two of $R^1$ must be other than H. Similarly, where $R^1$ is unsubstituted, $R^1$ is hydrogen for all available positions. The maximum number of substitutions possible in a structure (for example, a particular ring or fused ring system) will depend on the number of atoms with available valencies.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Compounds of the Invention

A compound selected from the group consisting of Formulae BB, BC, BD, BE, BF, and BF. A person of ordinary skill recognizes that the dot represents the radical in the compound, and further understands that its respective stated position in the compound is not fixed at the one atom shown. Instead, the free-radical is more likely distributed among the overlapping molecular orbitals of the compound, which is known to provide the additional stability observed in the compounds.

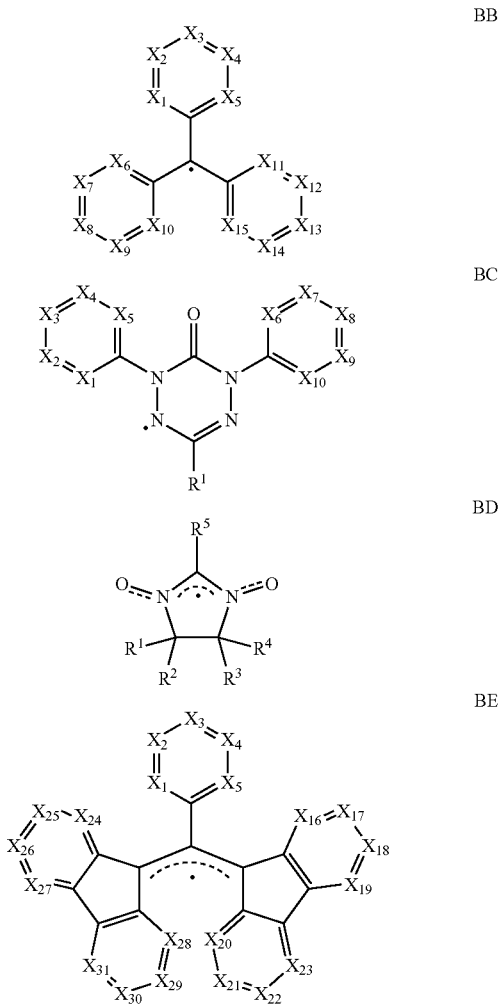

-continued

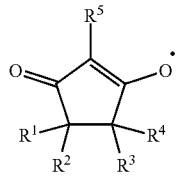
BF

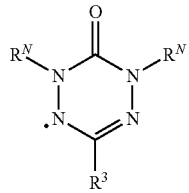
BG

For the respective compounds of Formulae BB, BC, BD, BE, BF, and BF:

$X_1$ to $X_5$ are independently selected from $CR^A$ or N;

$X_6$ to $X_{10}$ are independently selected from $CR^B$ or N;

$X_{11}$ to $X_{15}$ are independently selected from $CR^C$ or N;

$X_{16}$ to $X_{23}$ are independently selected from $CR^D$ or N;

$X_{24}$ to $X_{31}$ are independently selected from $CR^E$ or N;

$R^A$, $R^B$, $R^C$, $R^D$, and $R^E$ independently represent mono to the maximum allowable substitution, or no substitution;

each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;

$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;

wherein at least one of $R^1$ to $R^5$, $R^A$, $R^B$, $R^C$, $R^D$, or $R^E$ includes a polycyclic group selected from the group consisting of:

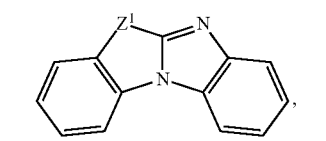

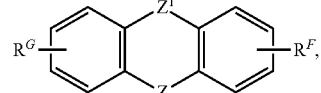

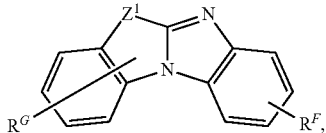

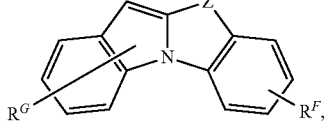

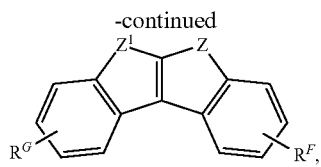

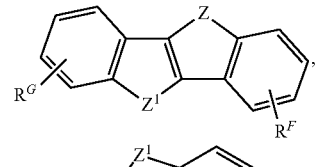

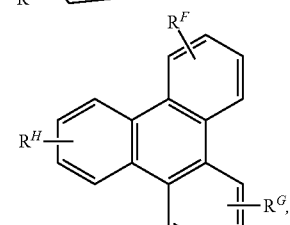

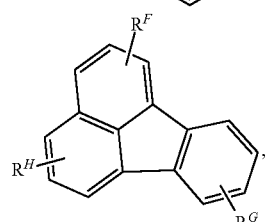

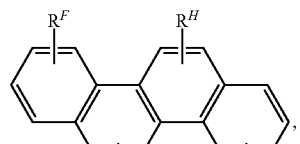

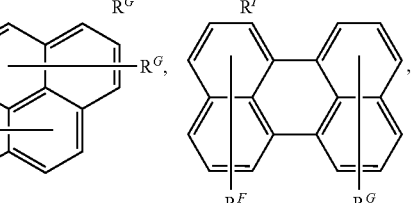

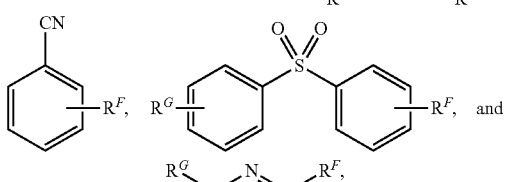

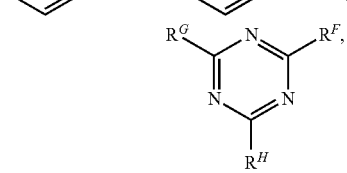

and any aza-analogue of each thereof, each of which is optionally substituted with $R^P$, wherein $R^P$ is selected from the group consisting of deuterium, fluorine, alkyl, cycloalkyl, amino, aryl, heteroaryl, silyl, nitrile, and combinations thereof;

wherein $R^F$ to $R^I$ are independently selected from the group consisting of deuterium, fluorine, alkyl, cycloalkyl, amino, aryl, heteroaryl, silyl, nitrile, and combinations thereof; and Z and $Z^1$ are independently selected from the group consisting of O, S, Se, $NR^N$, CR'CR", SiR'R", and GeR'R", wherein R' and R" are independently $R^N$;

with the proviso that the following compound is excluded

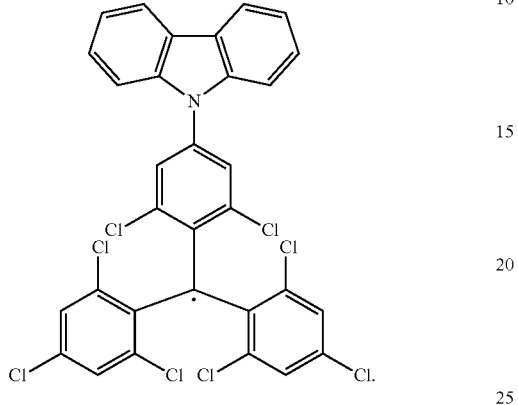

In one embodiment, each $R^1$ to $R^5$, and each $R^A$, $R^B$, $R^C$, $R^D$, and $R^E$ are independently selected from the group consisting of hydrogen, deuterium, fluorine, chlorine, alkyl, cycloalkyl, alkoxy, aryloxy, amino, silyl, aryl, heteroaryl, nitrile, and combinations thereof. In another embodiment, each $R^1$ to $R^5$, and each $R^A$, $R^B$, $R^C$, $R^D$, and $R^E$ are independently selected from the group consisting of hydrogen, deuterium, fluorine, chlorine, nitrile, alkyl, aryl, heteroaryl, and combinations thereof.

In one embodiment, at least one of $R^1$ to $R^5$, $R^A$, $R^B$, $R^C$, $R^D$, or $R^E$ comprise a structure capable of emitting light from a singlet excited state to a singlet ground state in an organic light emitting device with an internal quantum efficiency of greater than 3% at room temperature. In one embodiment, at least one of $R^1$ to $R^5$, $R^A$, $R^B$, $R^C$, $R^D$, or $R^E$ comprises a structure capable of emitting light from a singlet excited state to a singlet ground state in an organic light emitting device with an internal quantum efficiency of greater than 6% at room temperature. In one embodiment, at least one of $R^1$ to $R^5$, $R^A$, $R^B$, $R^C$, $R^D$, or $R^E$ comprises a structure capable of emitting light from a singlet excited state to a singlet ground state in an organic light emitting device with an internal quantum efficiency of greater than 9% at room temperature.

Polycyclic groups of interest are selected from the group consisting of

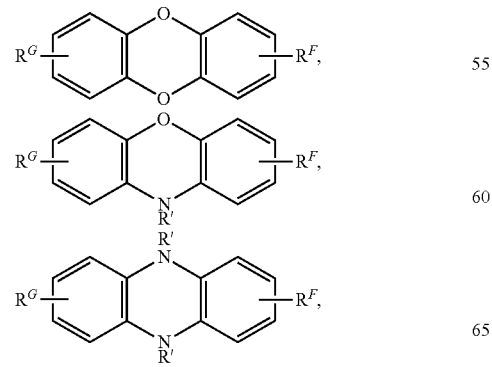

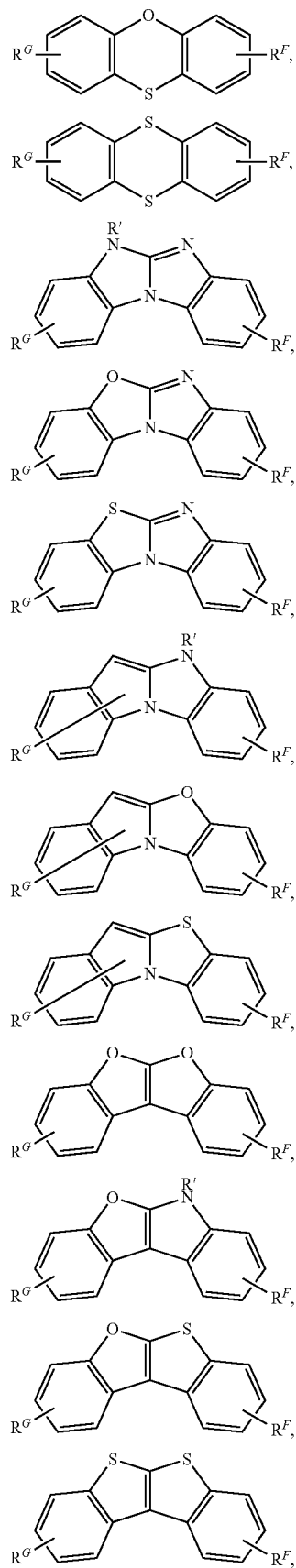

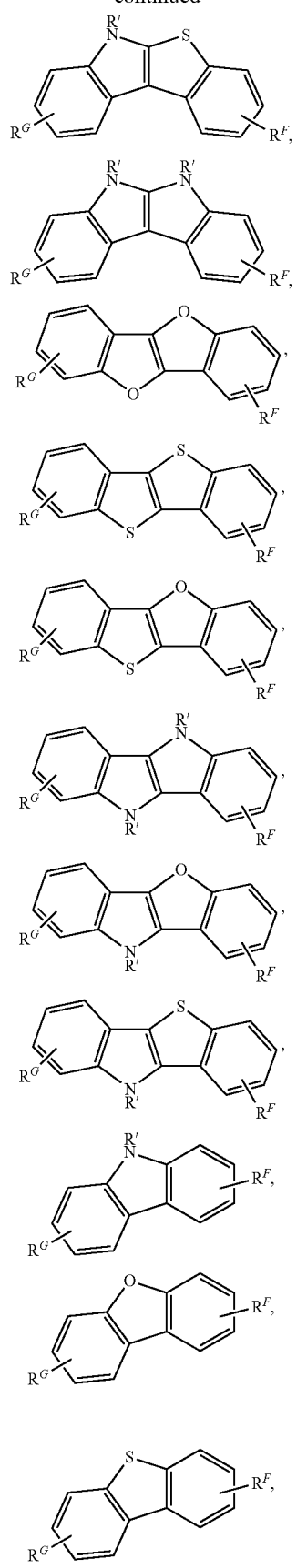
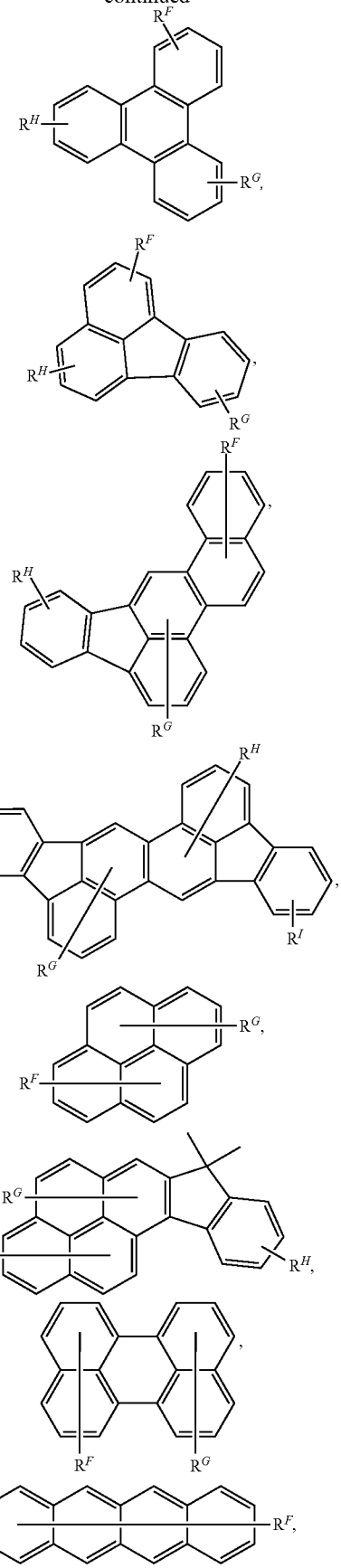

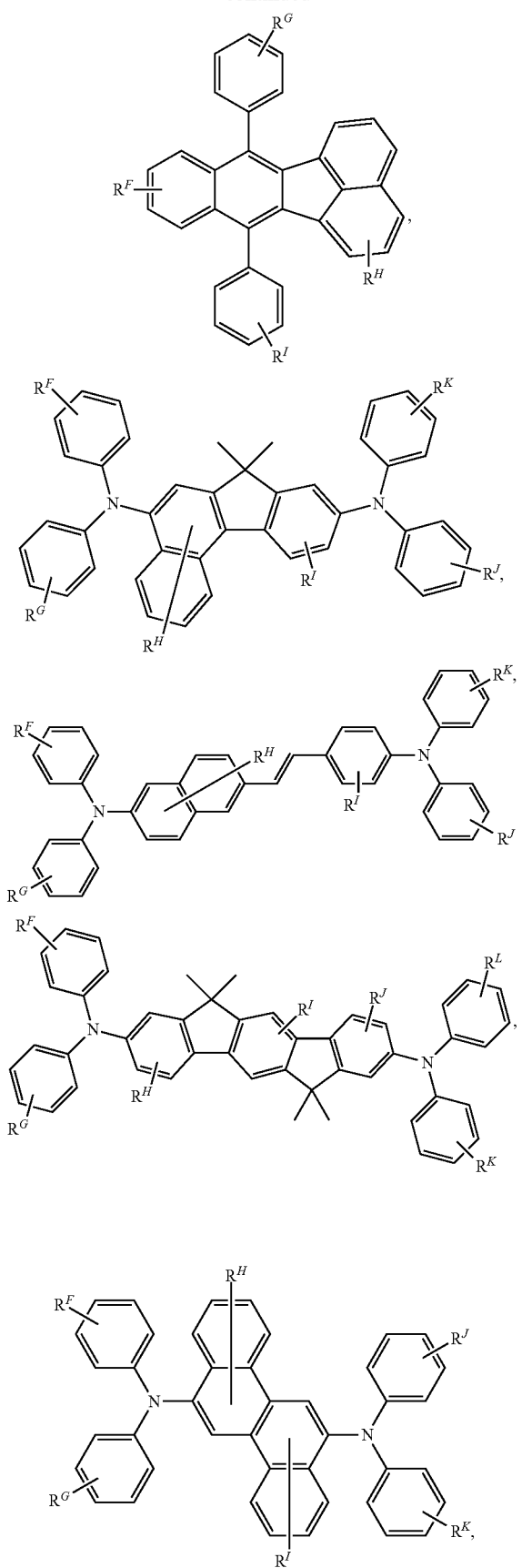
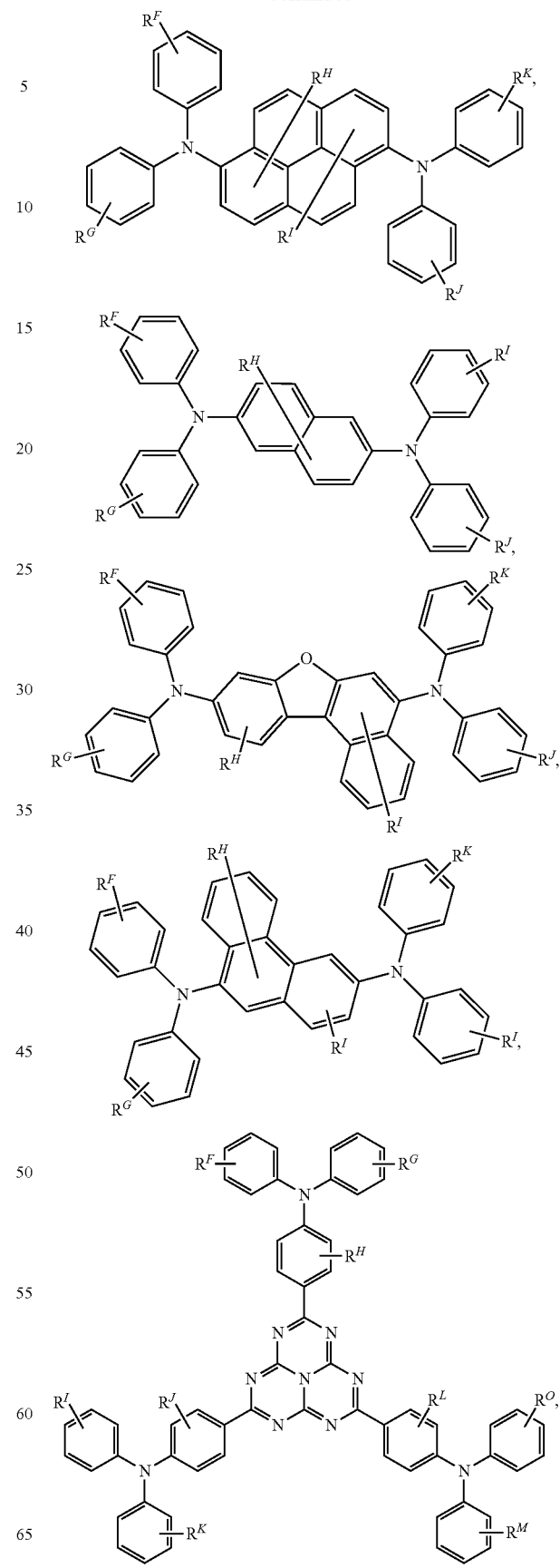

-continued

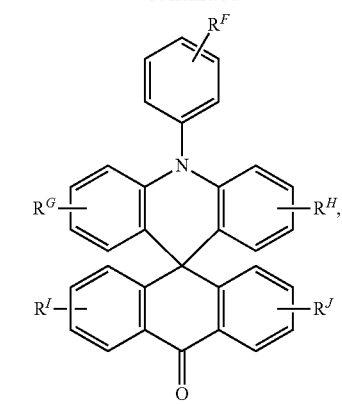

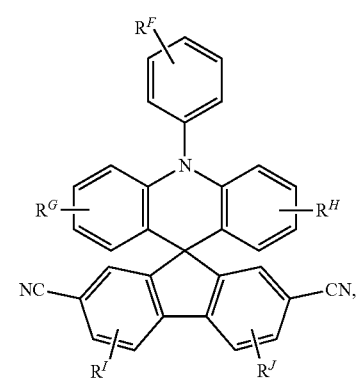

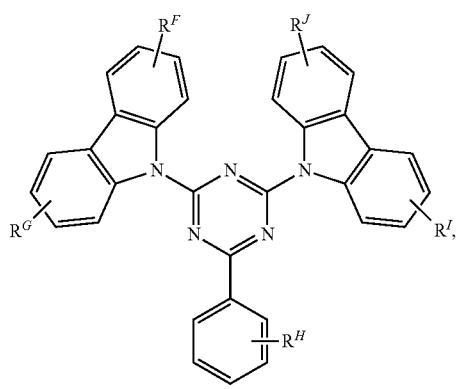

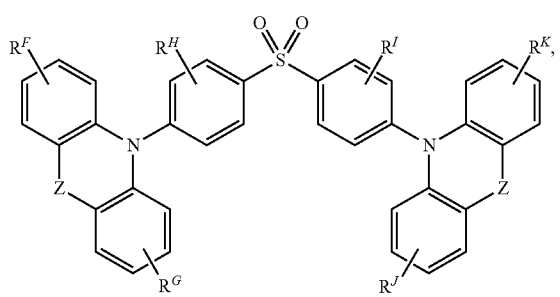

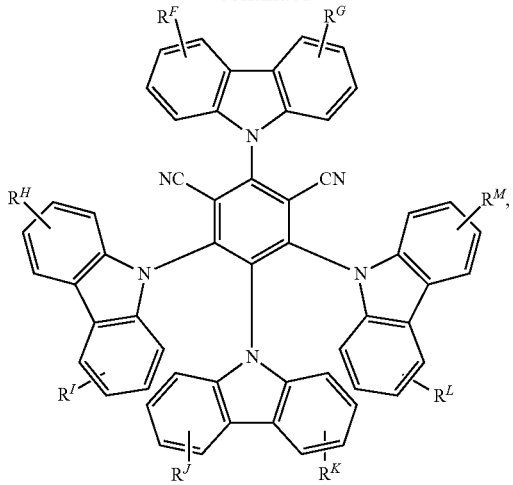

and aza-analogues thereof;
wherein $R^F$ to $R^M$ and $R^O$ are independently selected from the group consisting of deuterium, fluorine, alkyl, cycloalkyl, amino, aryl, heteroaryl, silyl, nitrile, and combinations thereof, and the polycyclic group is attached through one of $R^F$ to $R^M$, $R^O$ or R', wherein R' is $R^N$.

In one embodiment, the compound of Formula BB is selected from the group consisting of:

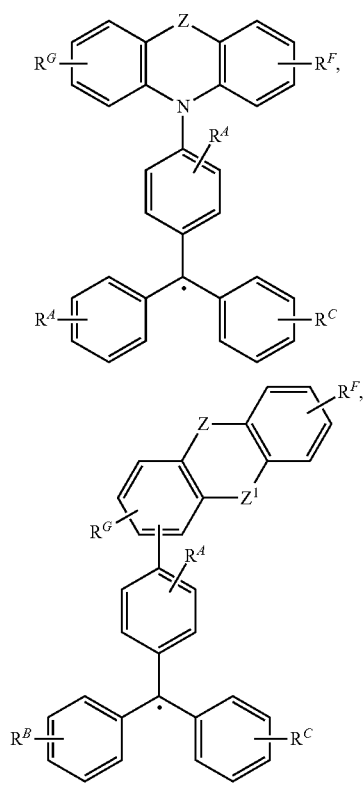
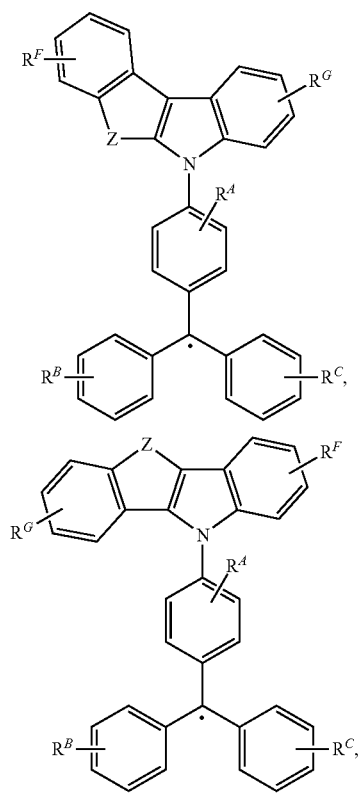
-continued
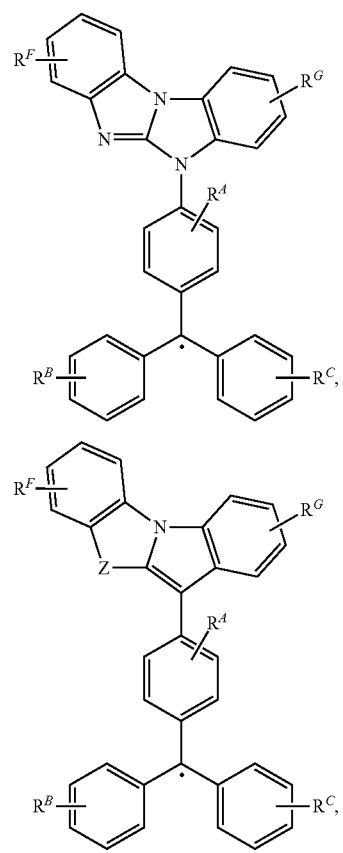
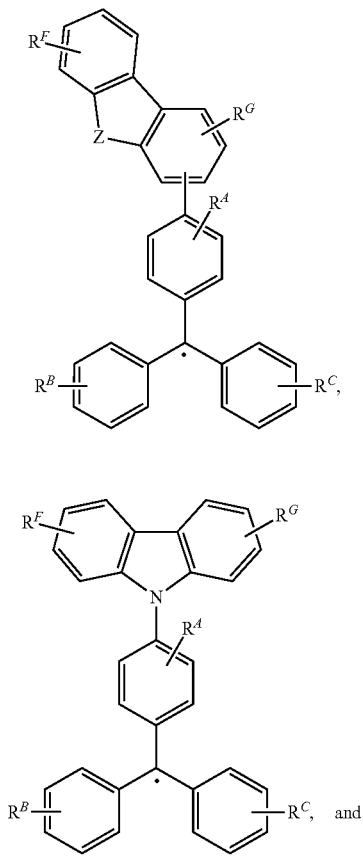

-continued
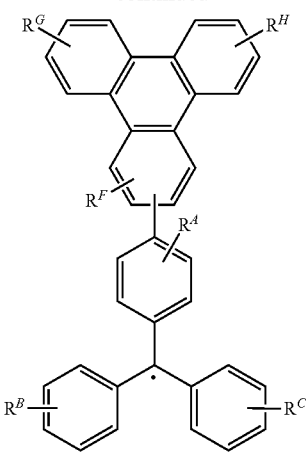
In one embodiment, the compound of Formula BE is selected from the group consisting of:
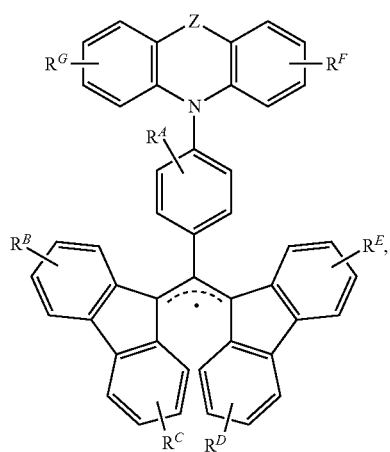
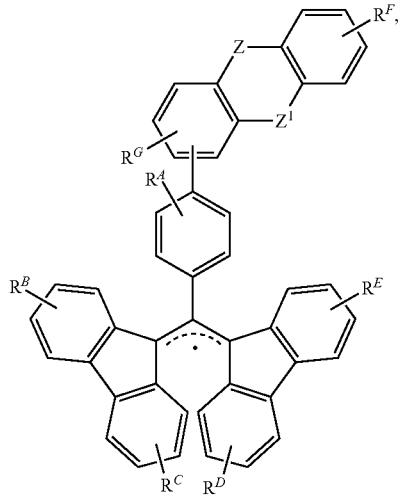
-continued
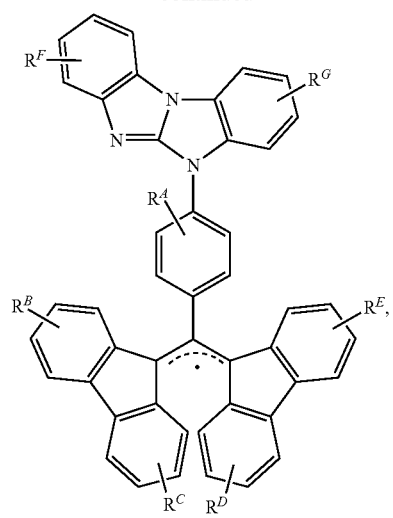
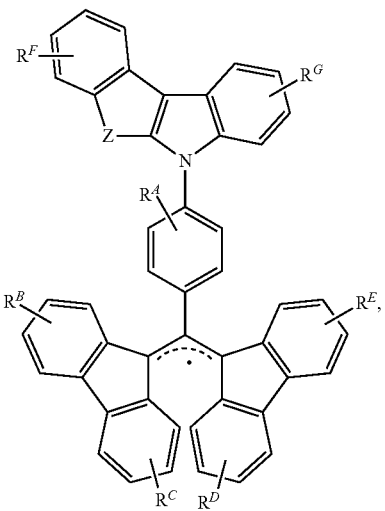
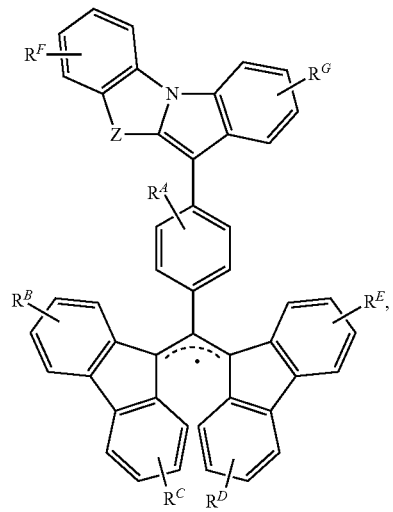

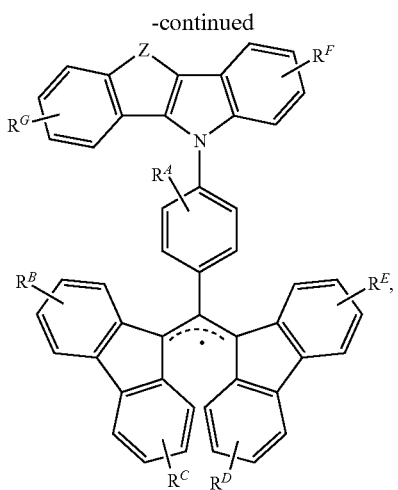
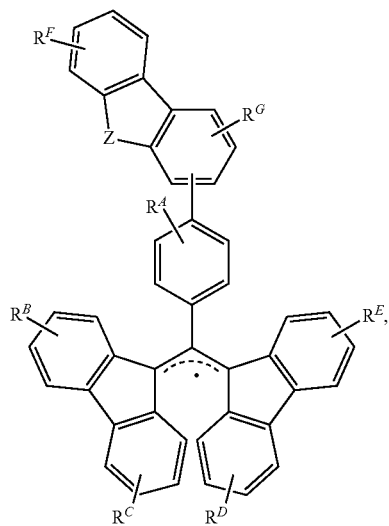
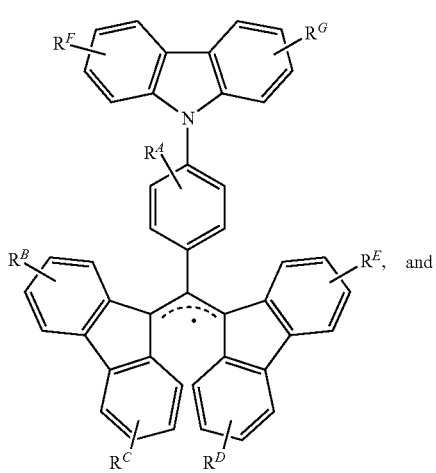
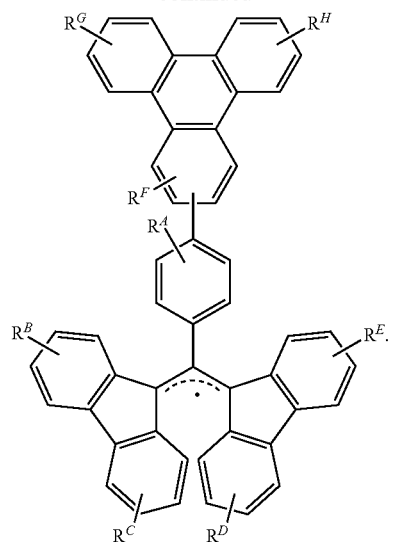
In one embodiment, the compound of Formula BD is selected from the group consisting of:
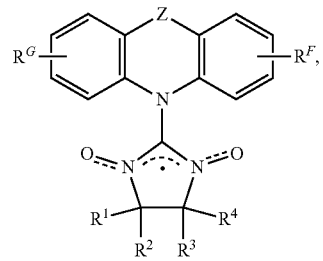
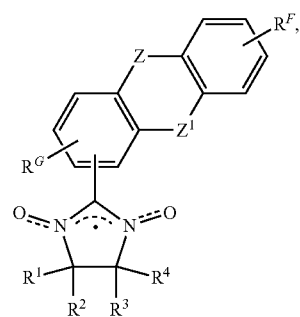
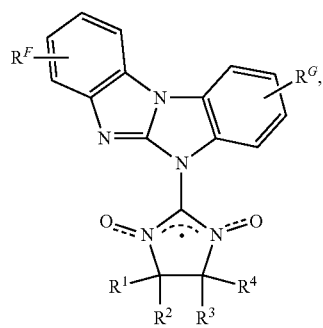

31
-continued
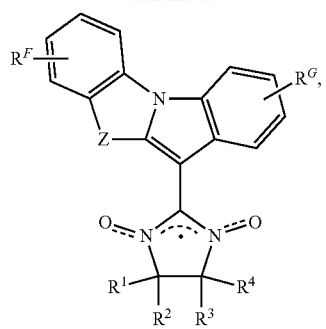
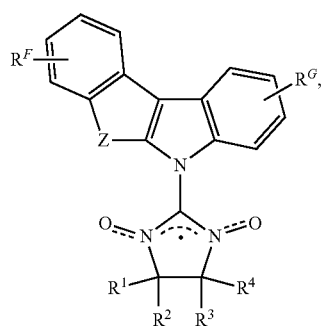
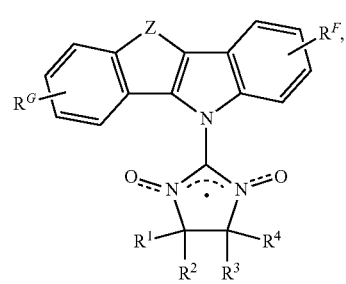
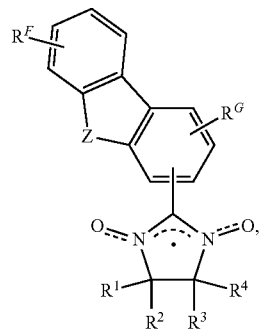
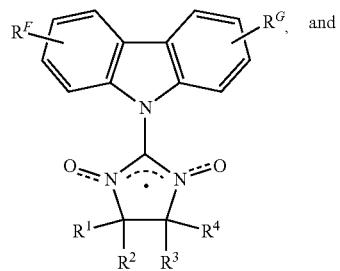 and
32
-continued
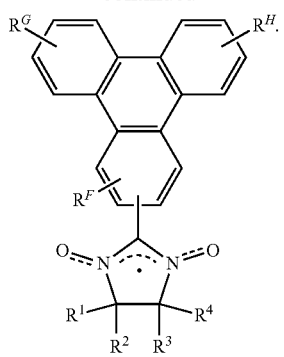
Select compounds of interest are selected from the group consisting of:
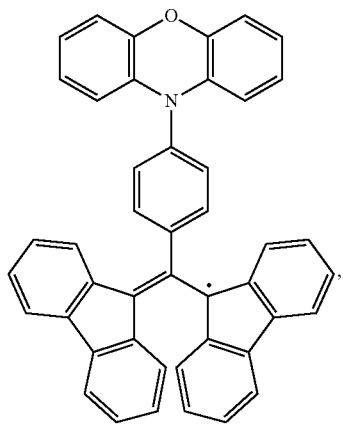
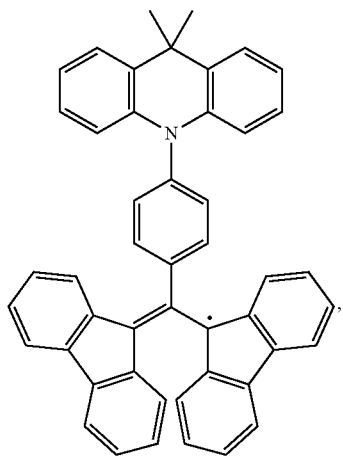

33
-continued
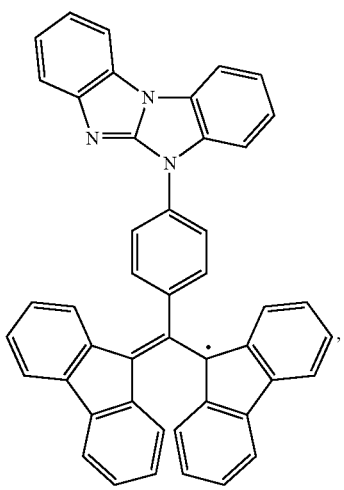
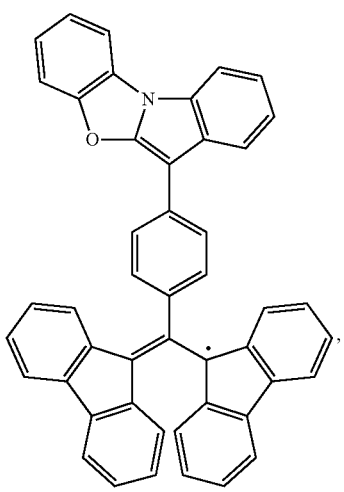
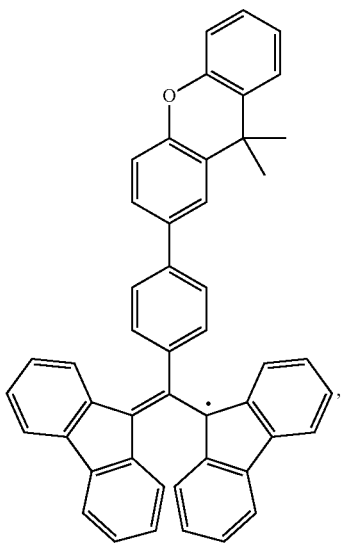
34
-continued
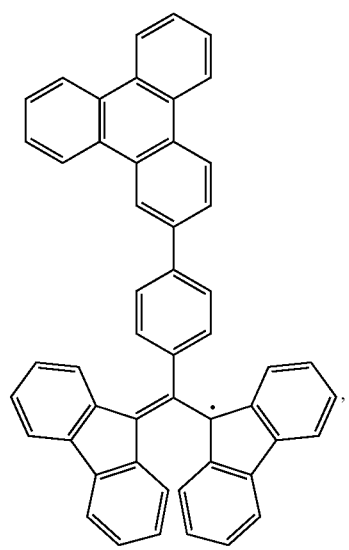
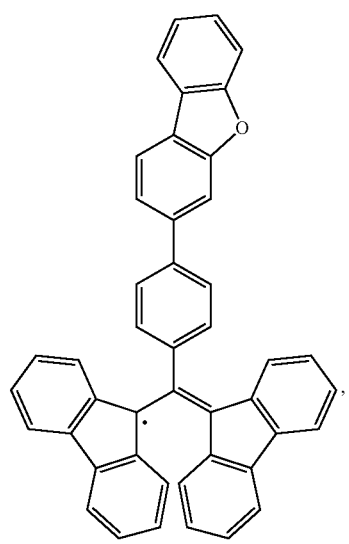
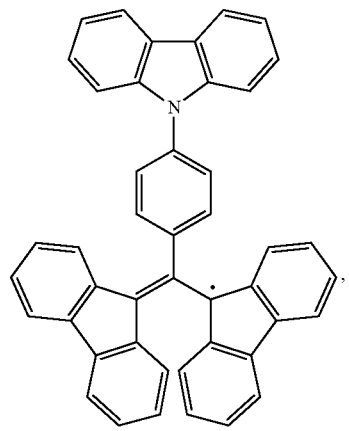

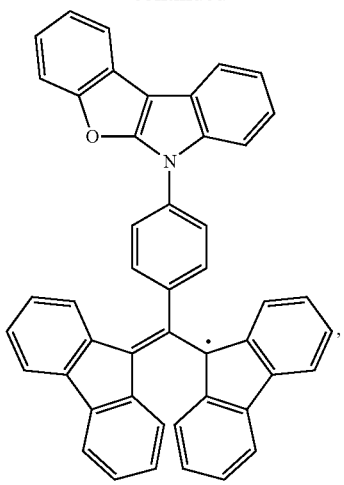
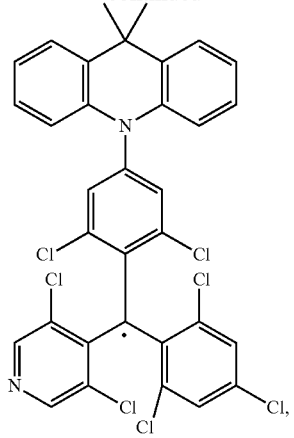
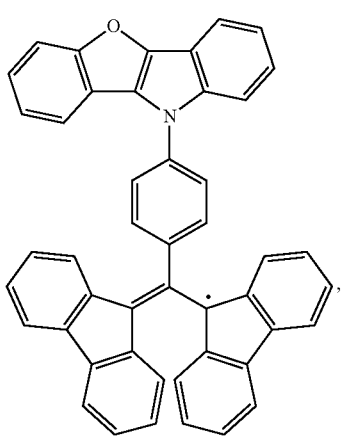
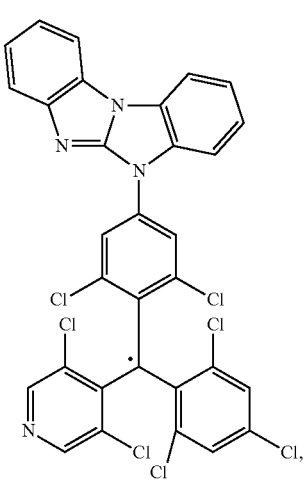
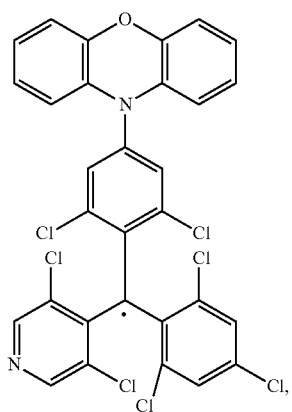
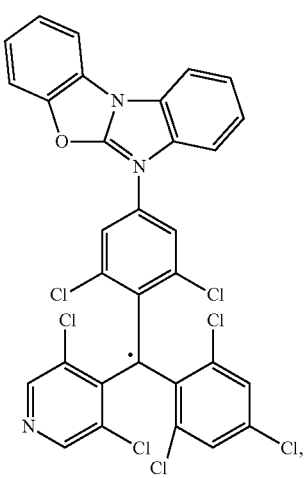

37
-continued
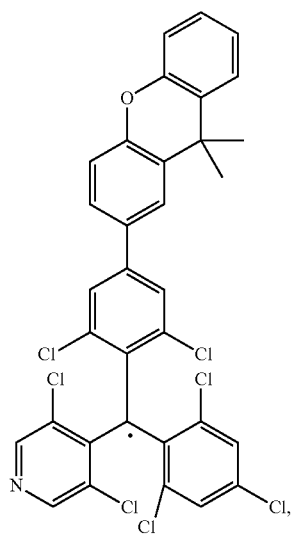
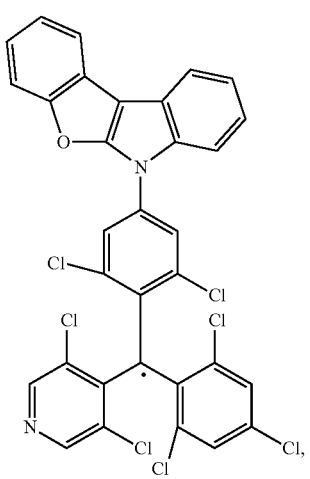
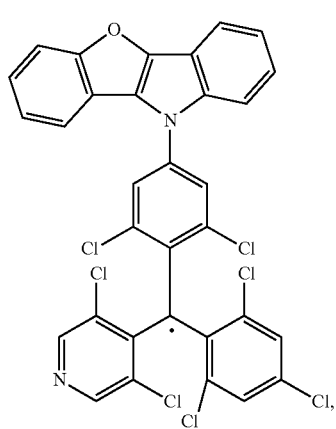
38
-continued
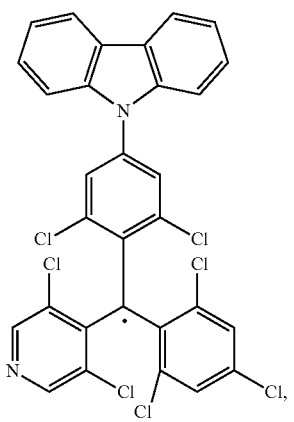
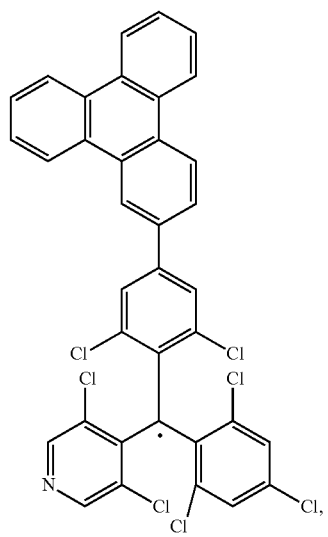
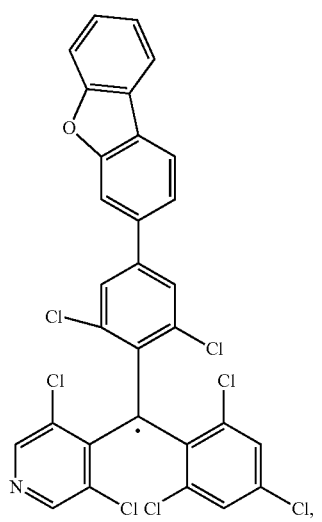

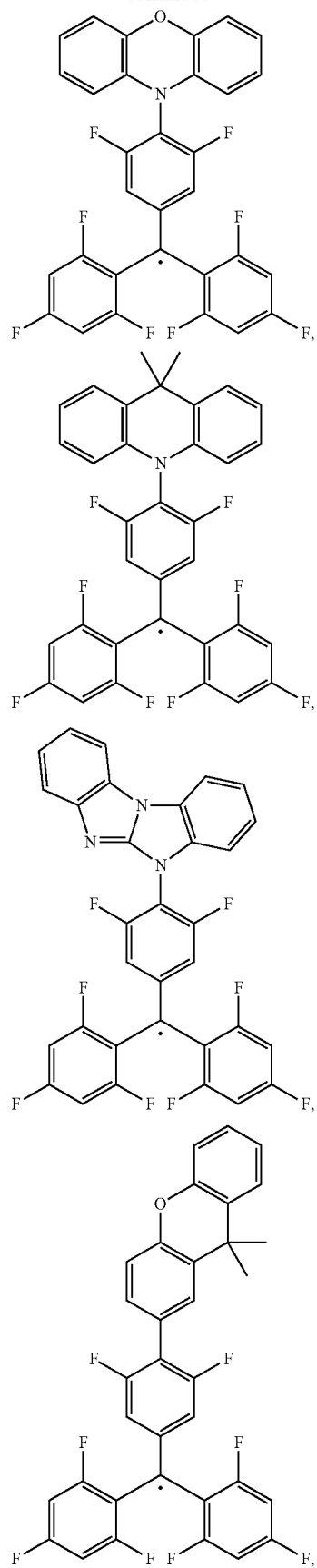
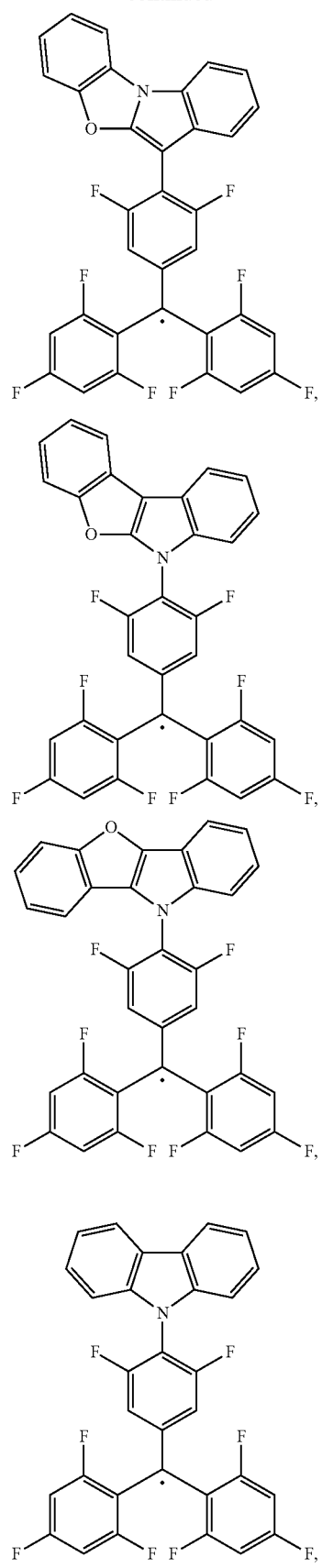

-continued
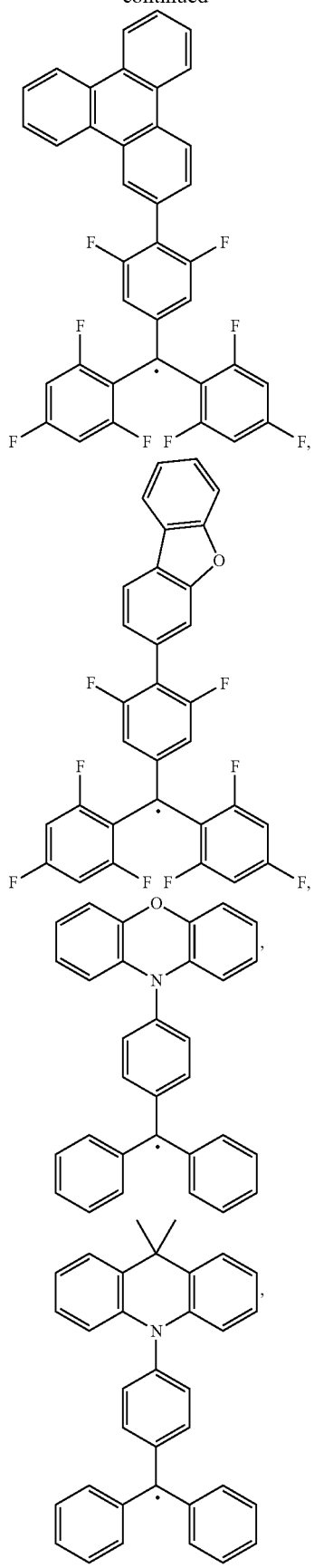
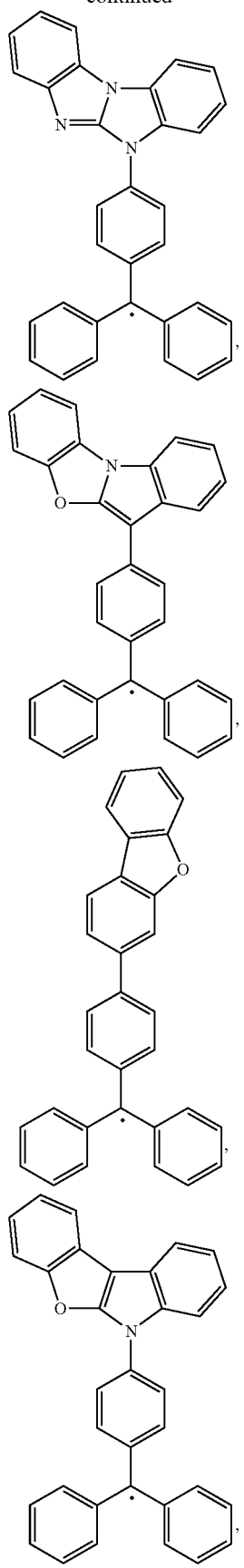

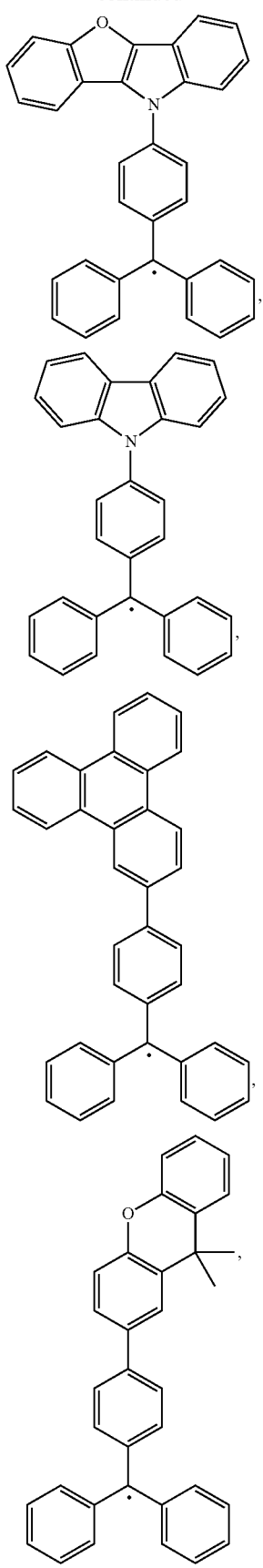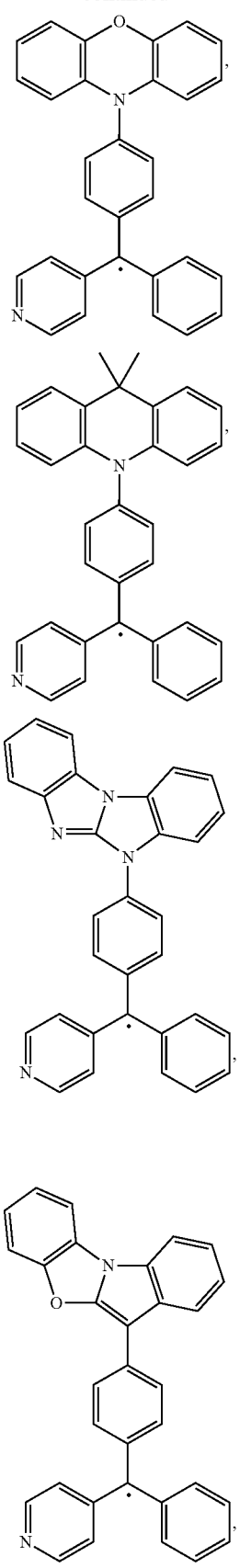

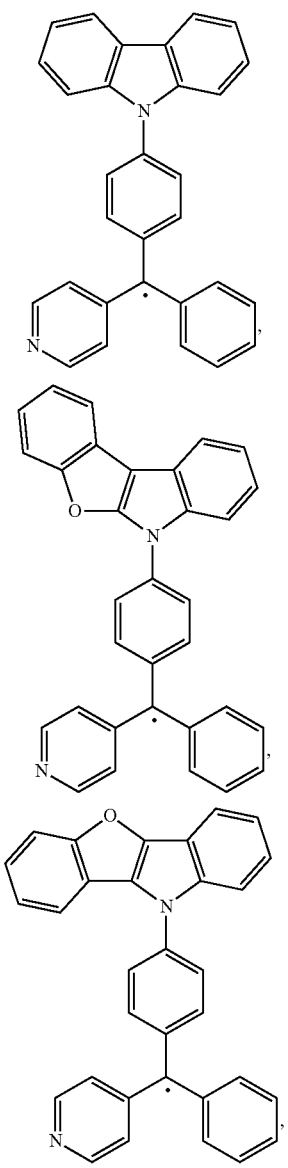
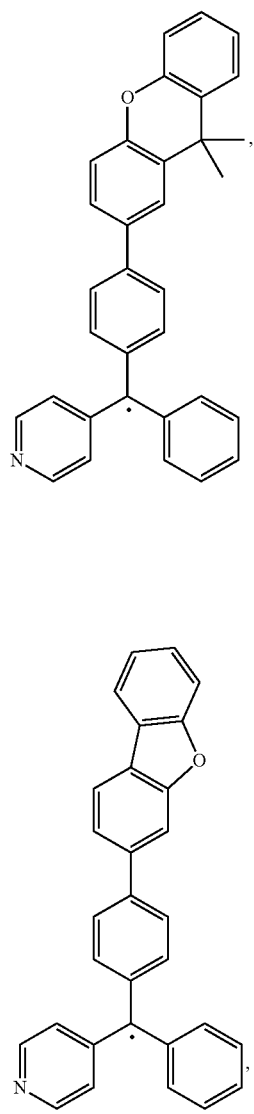
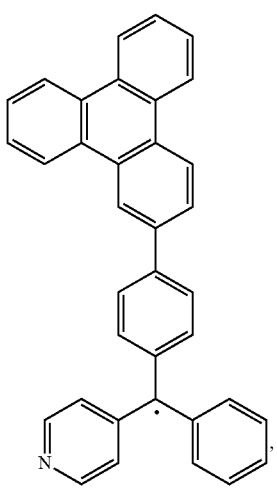
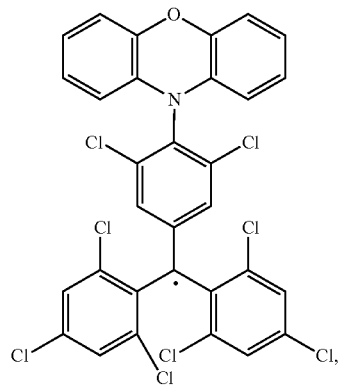

-continued

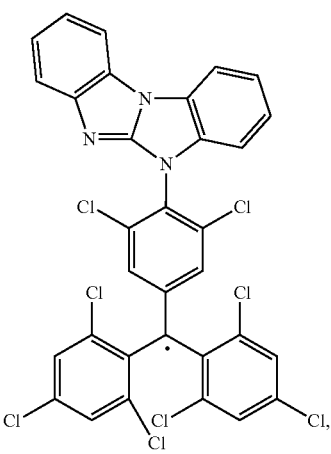
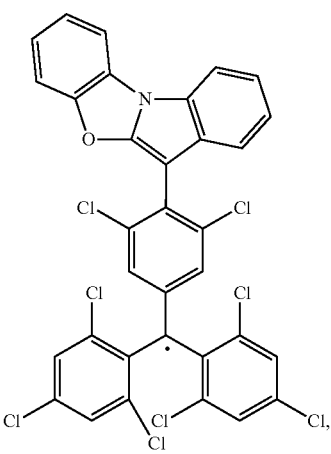
-continued
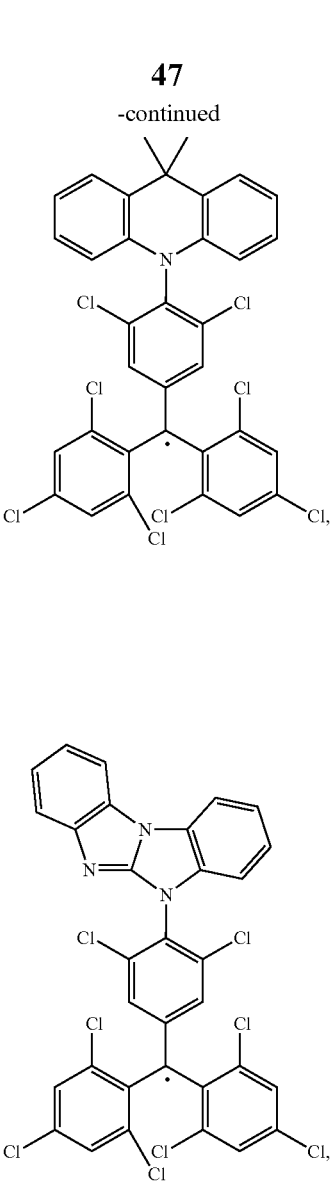

49
-continued
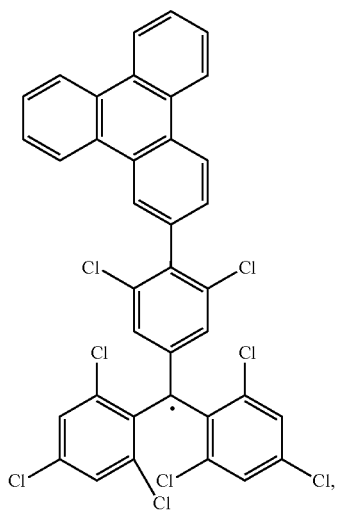
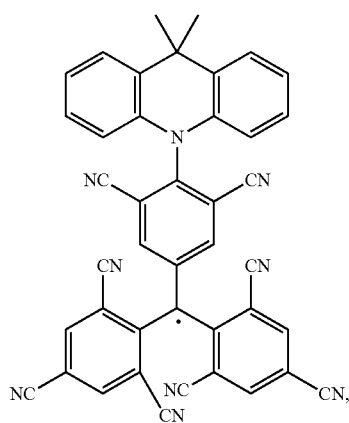
50
-continued
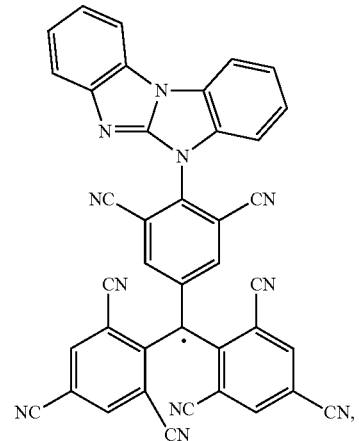
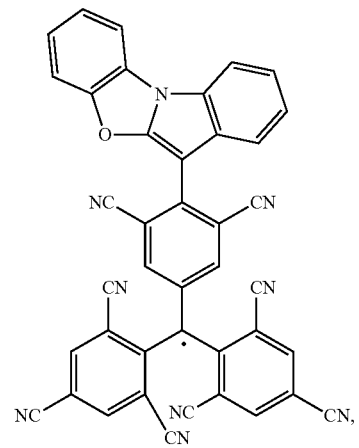
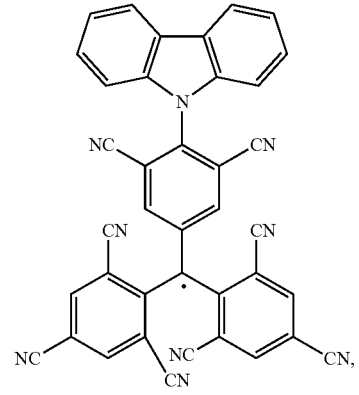
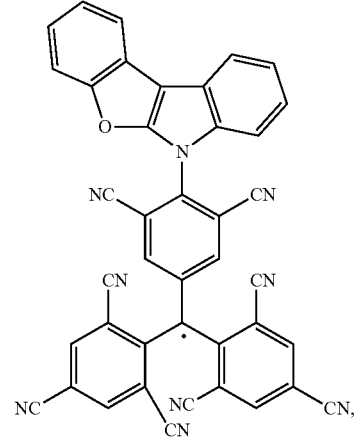

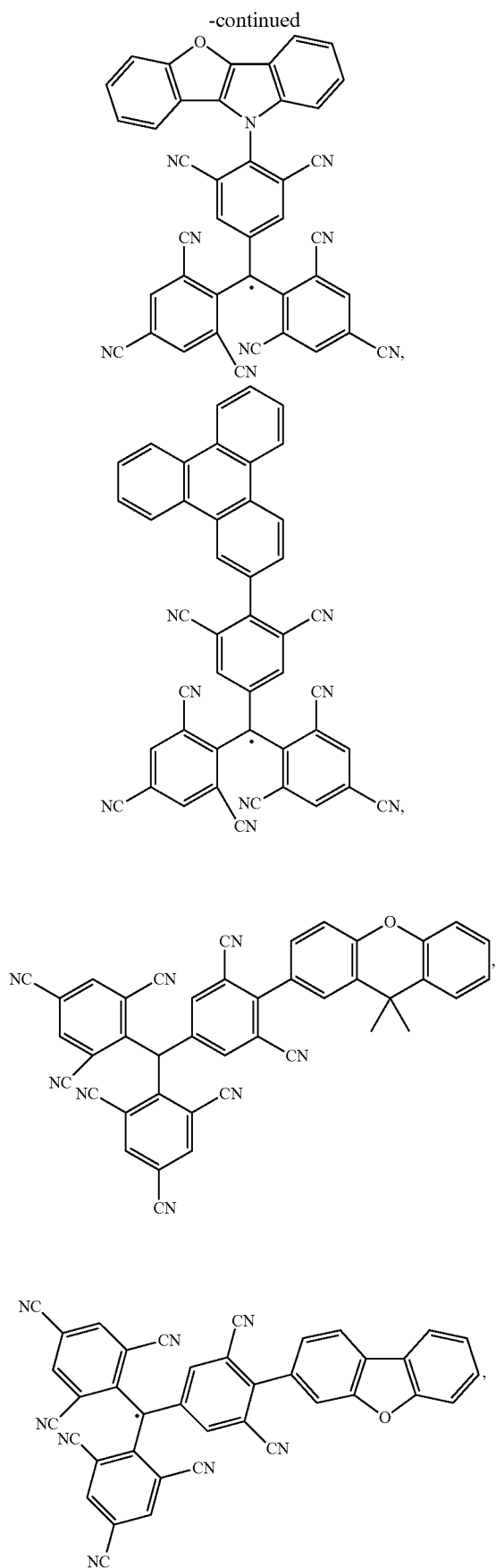
In one embodiment, the compounds of Formulae BB, BC, BD, BE, BF, and BF, will have a peak emission wavelength $\lambda_{max}$ in a range from 700 nm to 1100 nm. In one embodiment, the compound has a peak emission wavelength $\lambda_{max}$ in a range from 800 nm to 100 nm. In one embodiment, the compound has a peak emission wavelength $\lambda_{max}$ in a range from 825 nm to 950 nm.

The invention is also directed to a compound of formula A-L-B; wherein Component A is a fluorescent emitter, which includes fluorescent compounds that are known and referred to in the art as thermally-assisted delayed fluorescence emitters. Alternatively, Component A is a structure listed in Table 1 below. Component B comprises a structure selected from the group consisting of Formulae BB, BC, BD, BE, BF, and BF, above; and L is a direct bond or an organic linker. Alternatively, Component B is B1 to B10 listed in Table 1 below.

The invention is also directed to a formulation, or a mixture, of a Component A and a Component B. Component A is a fluorescent emitter that includes fluorescent compounds known and referred to in the art as thermally-assisted delayed fluorescence emitters. Alternatively, Component A is a structure listed in Table 1 below. Component B comprises a structure selected from the group consisting of Formulae BB, BC, BD, BE, BF, and BF, above; and L is a direct bond or an organic linker. Alternatively, Component B is B1 to B10 listed in Table 1 below.

In the two distinct embodiments above, that is, in a compound of formula A-L-B, or a mixture of Components A and B, Component A can include a structure or compound, respectively, selected from the group consisting of:

-continued

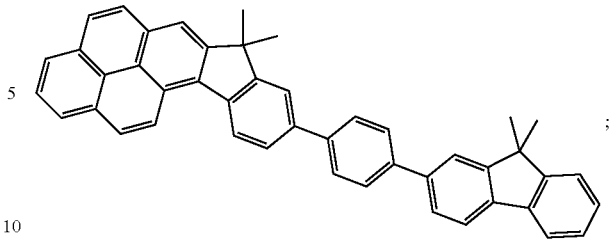

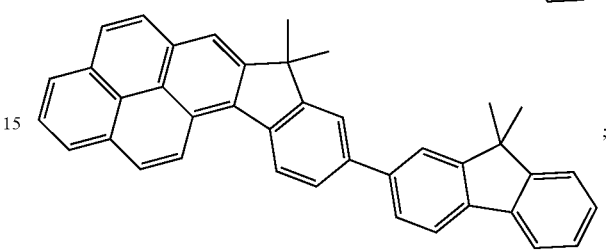

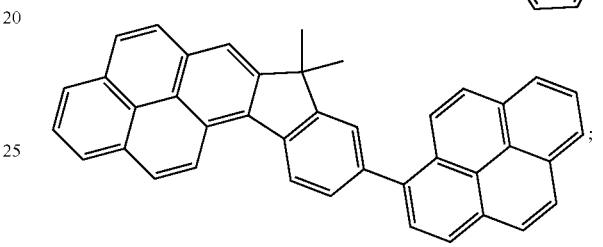

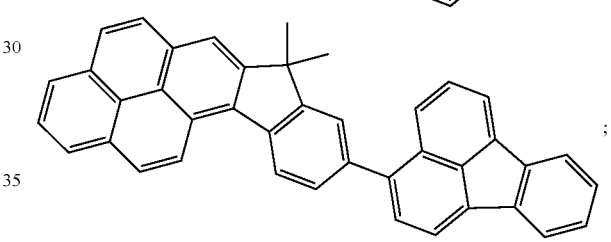

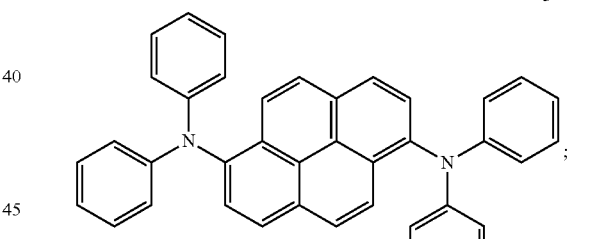

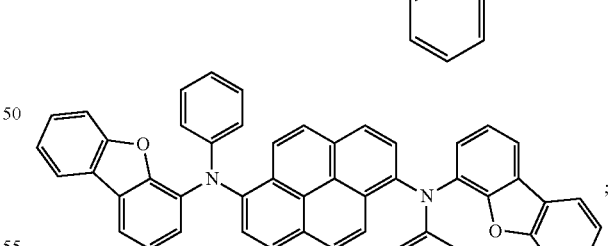

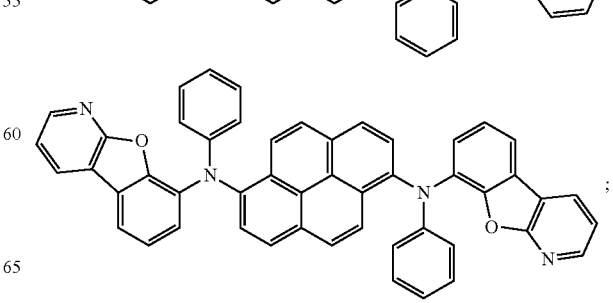

55
-continued
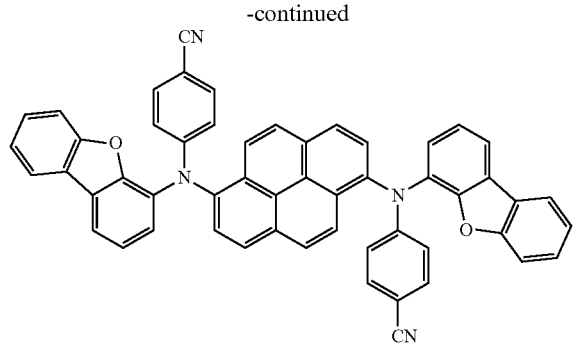
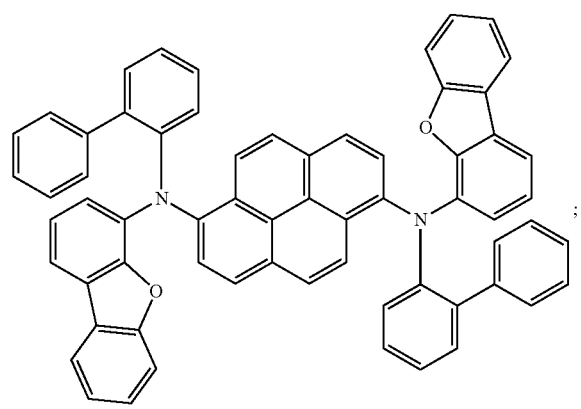
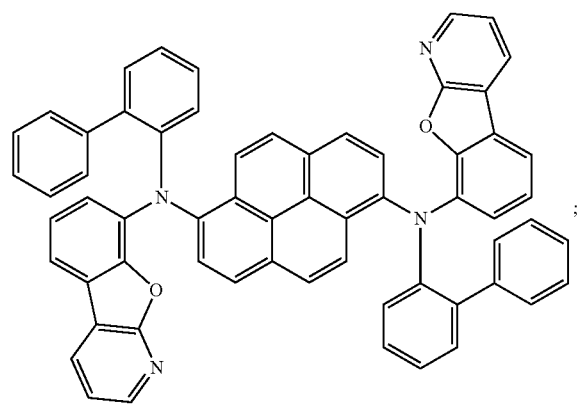
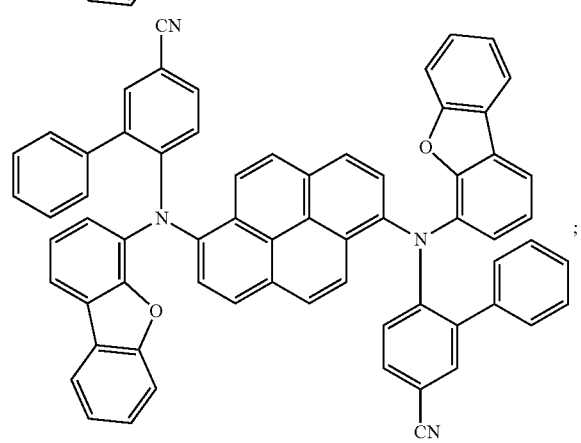
56
-continued
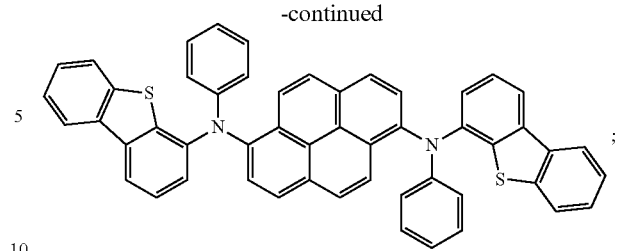
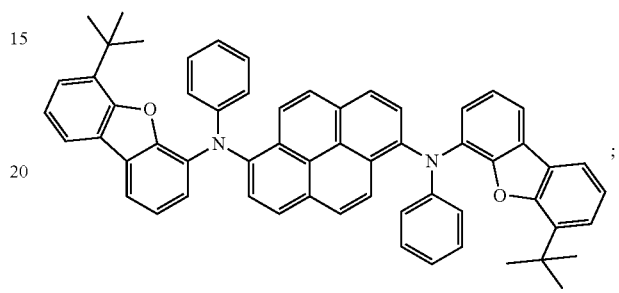
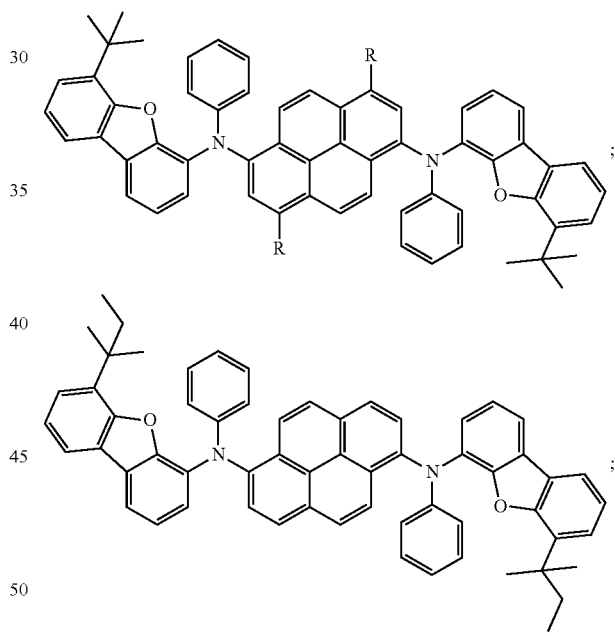
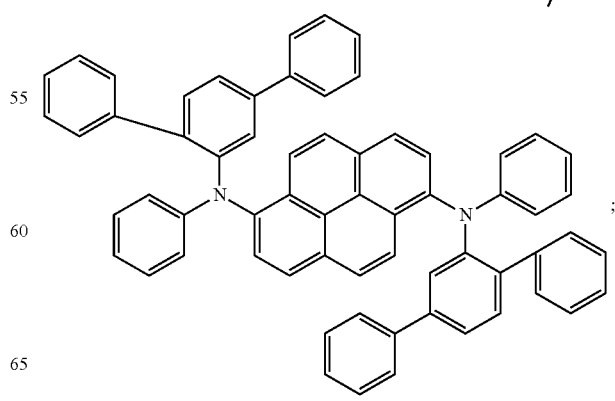

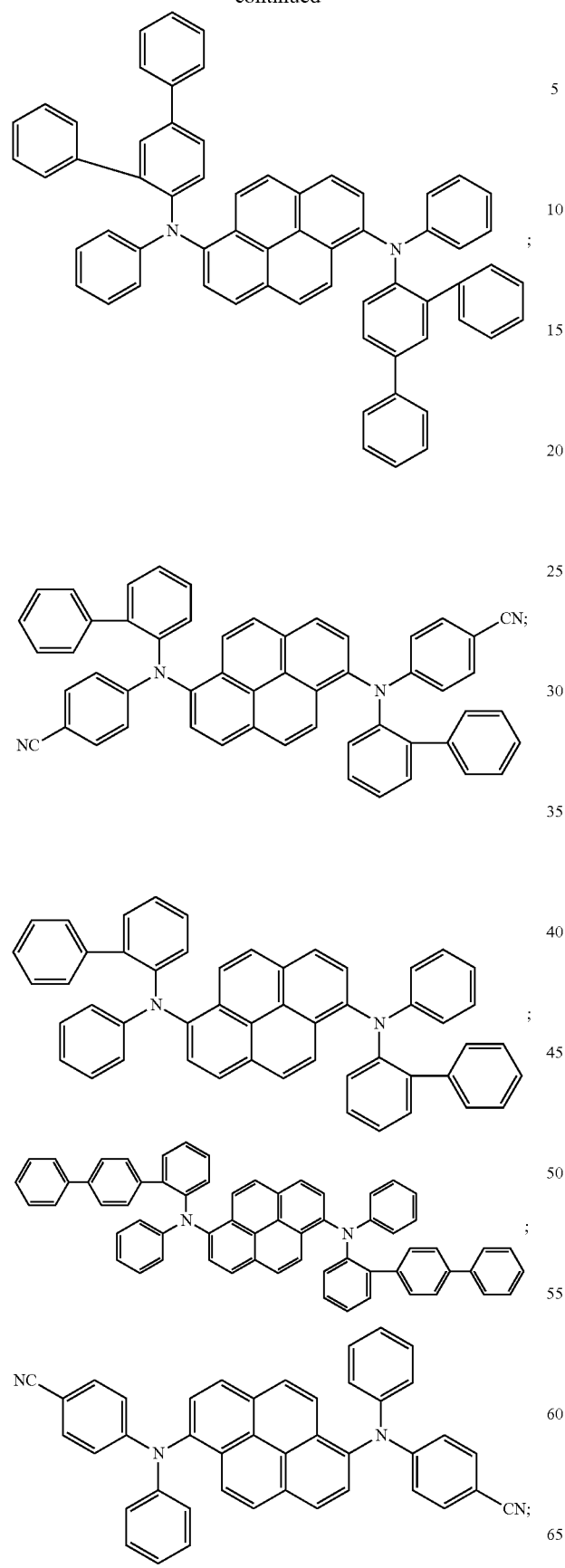

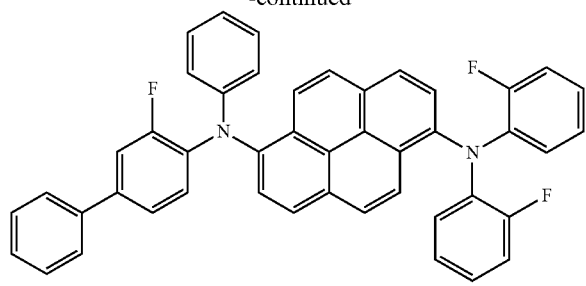
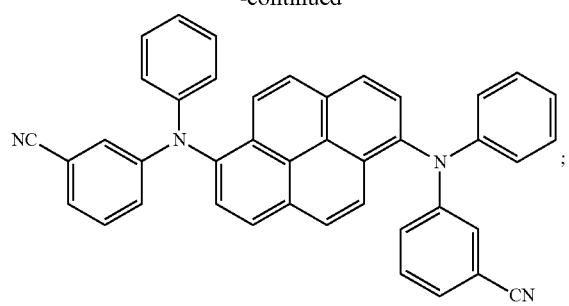
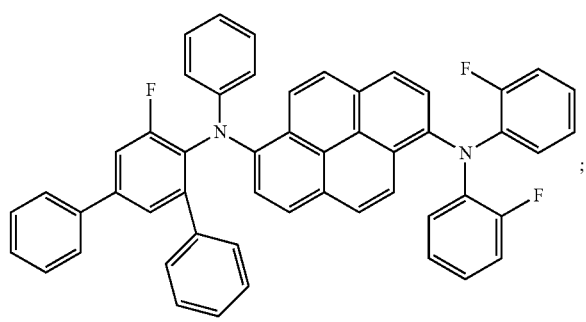
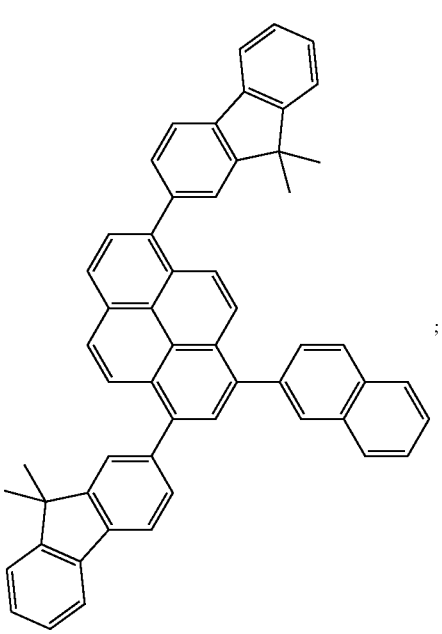
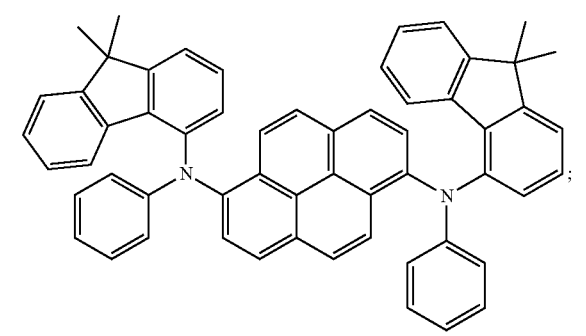
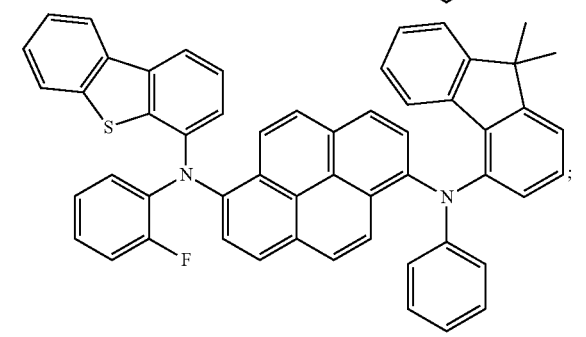
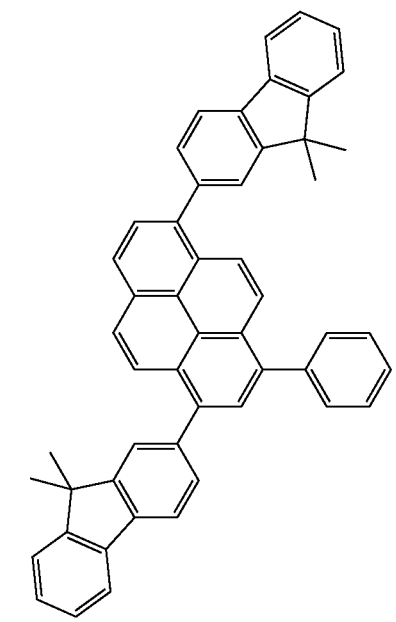
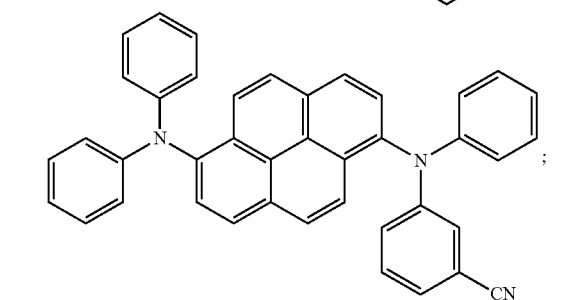

-continued
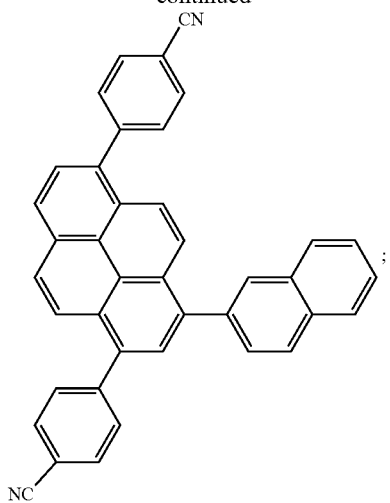
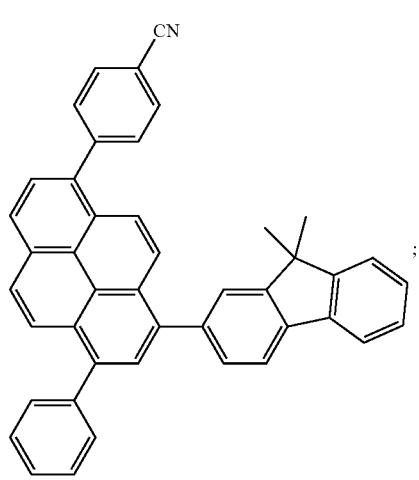
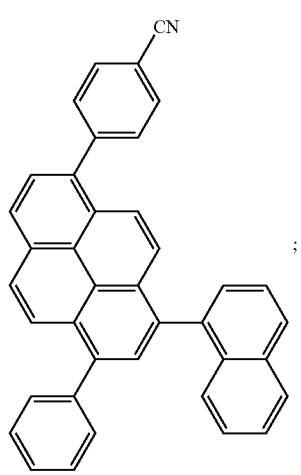
-continued
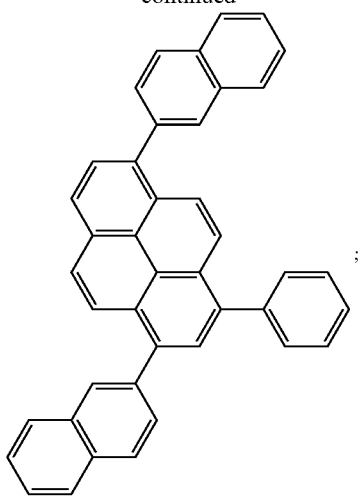
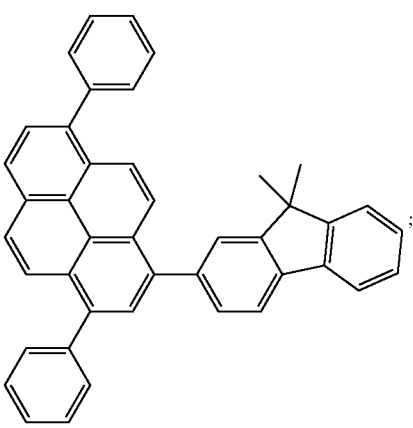
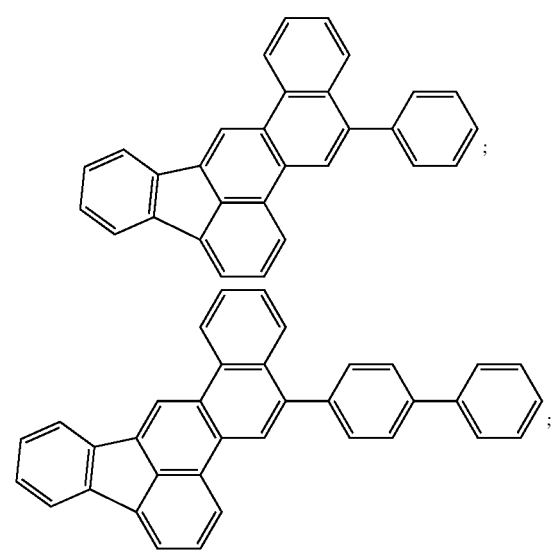

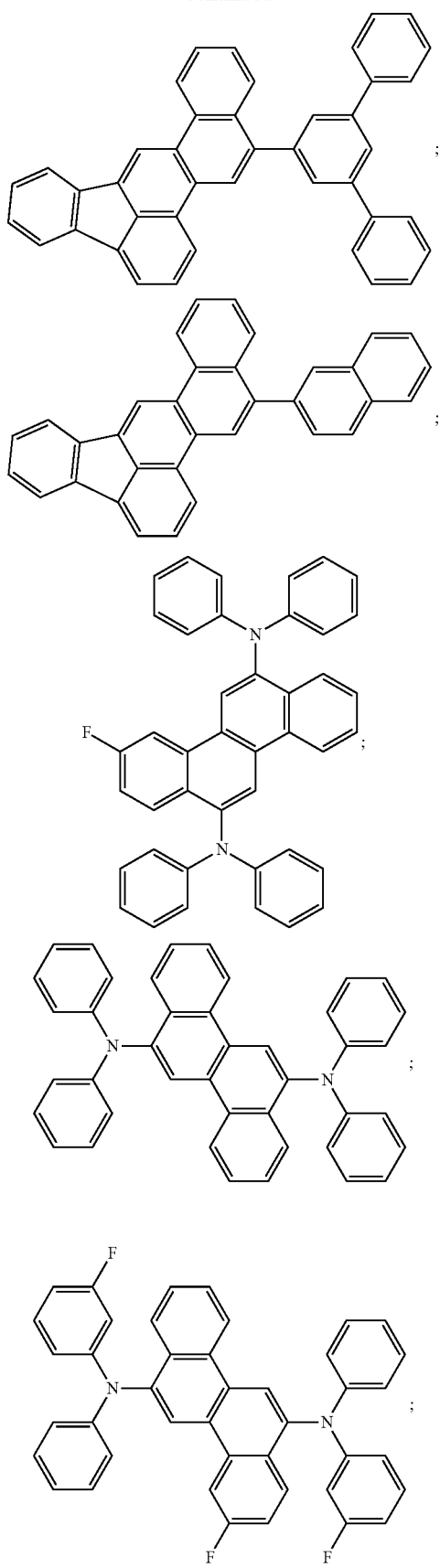
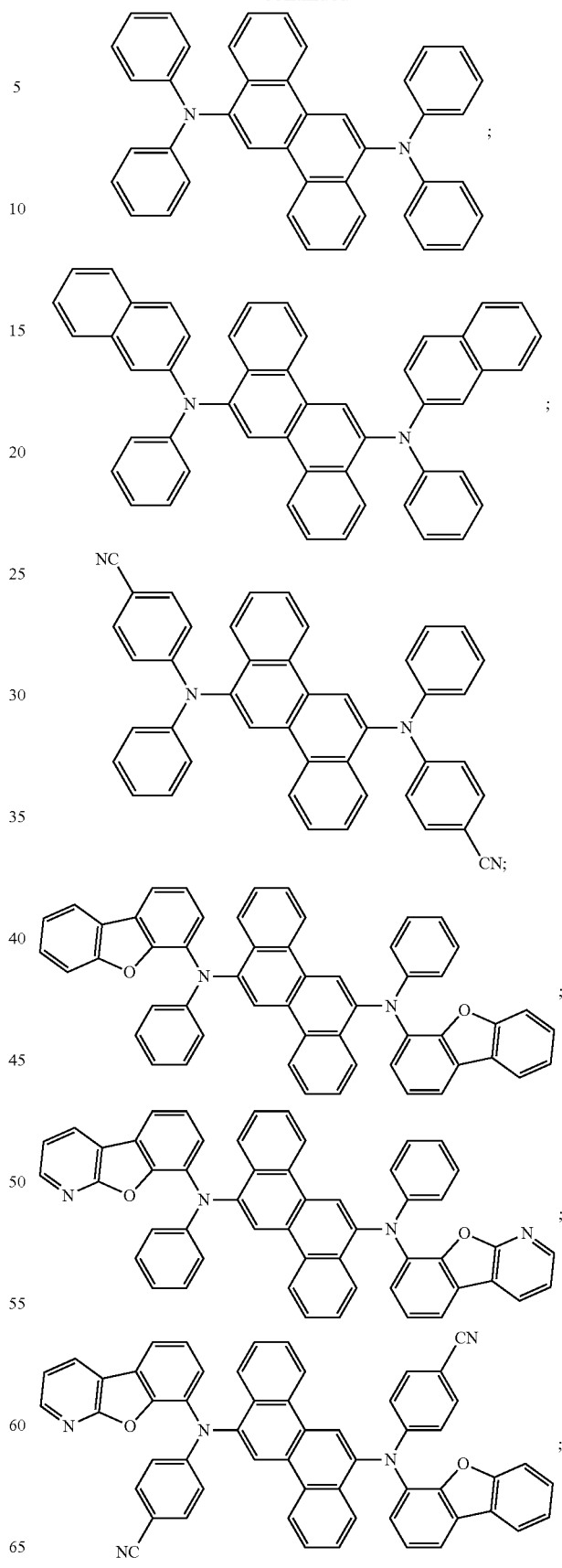

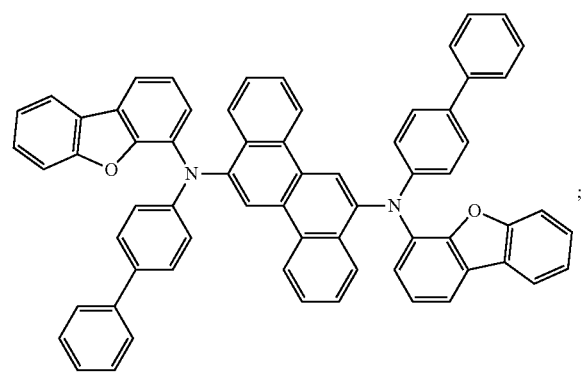
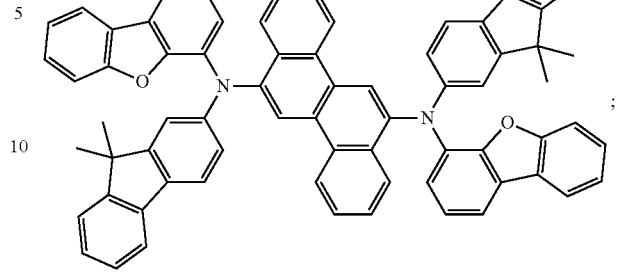
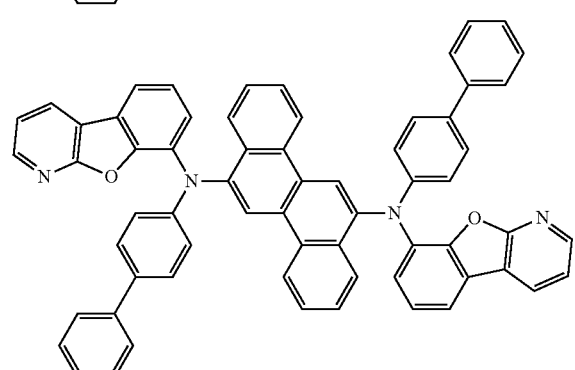
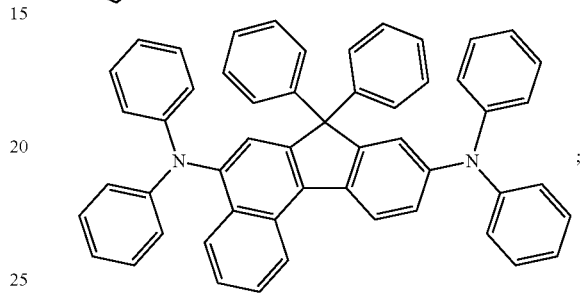
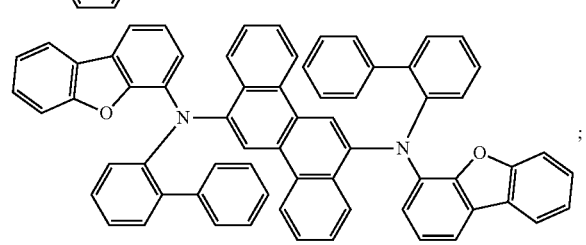
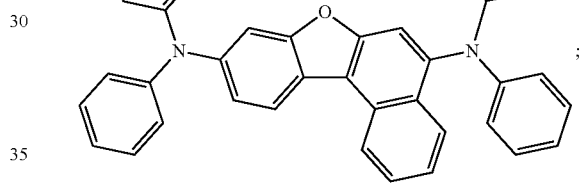
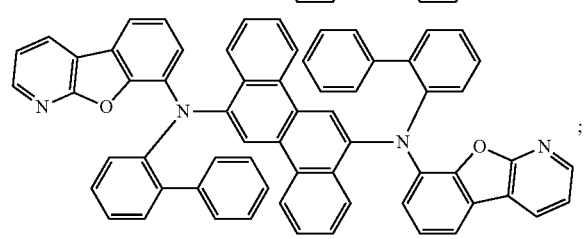
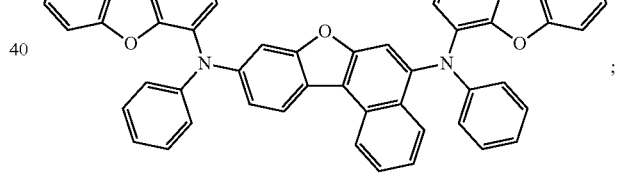
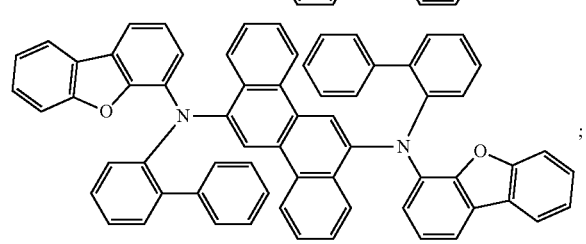
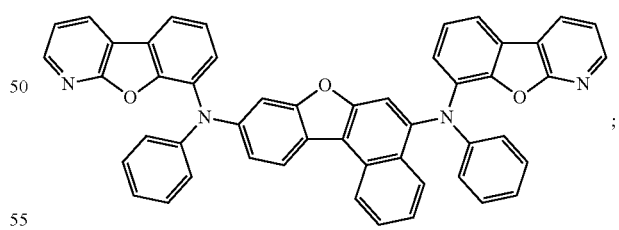
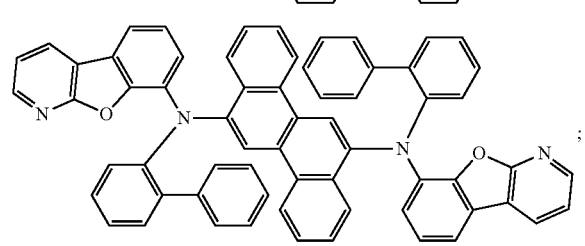
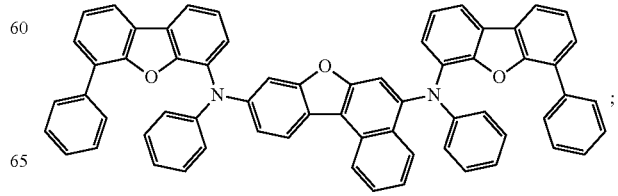

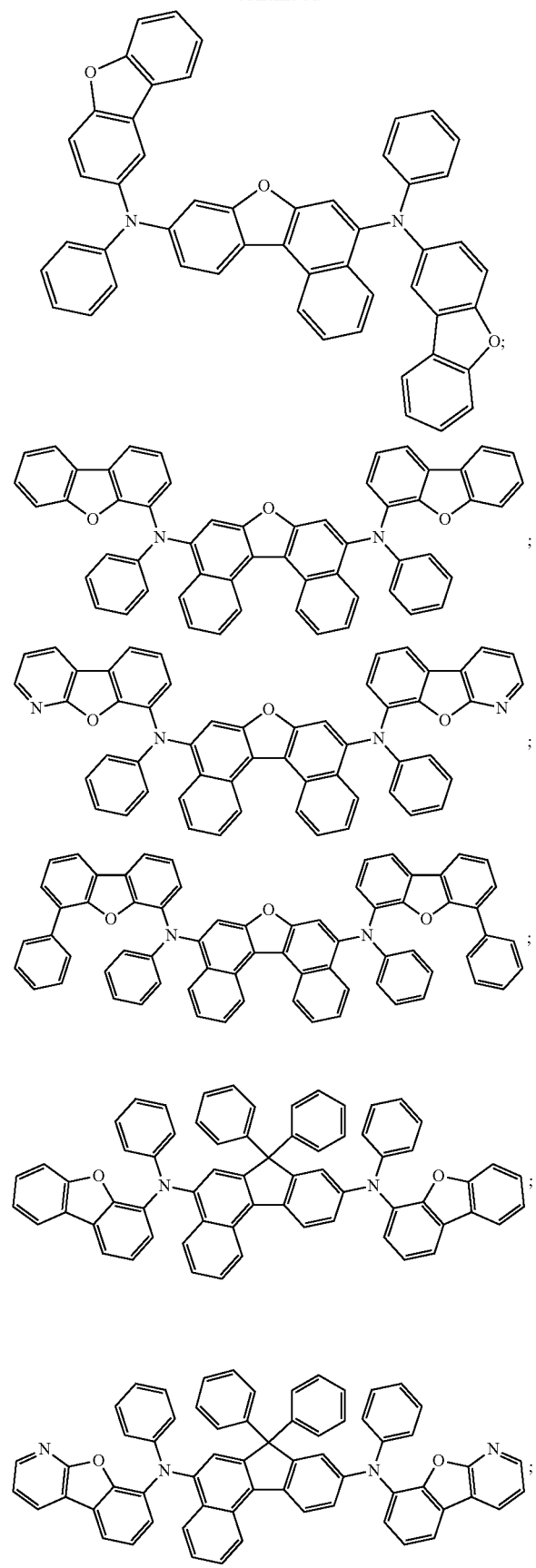
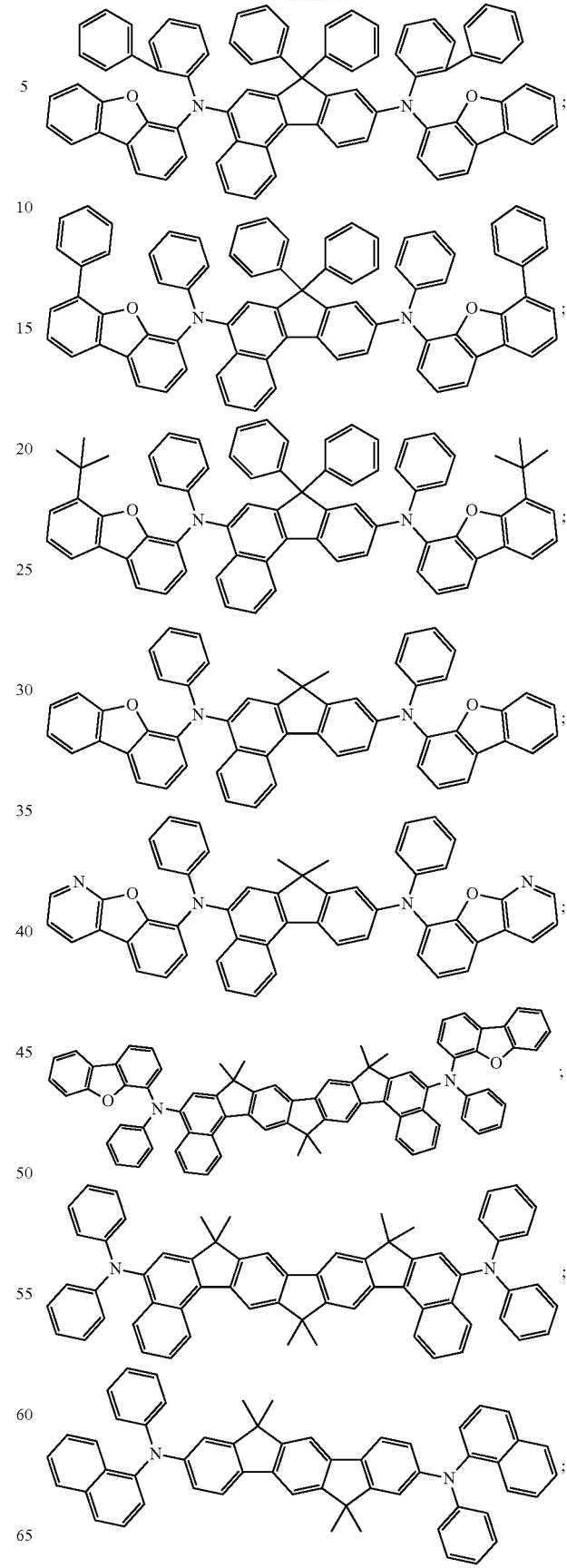

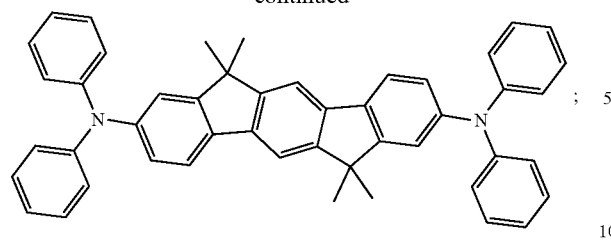
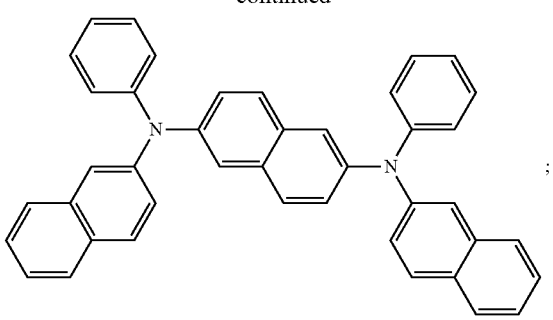
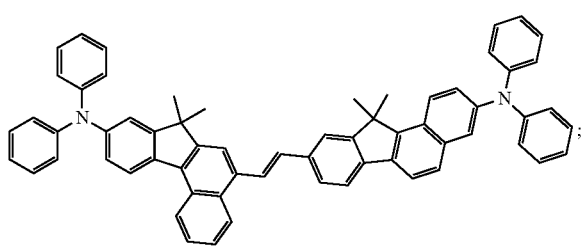
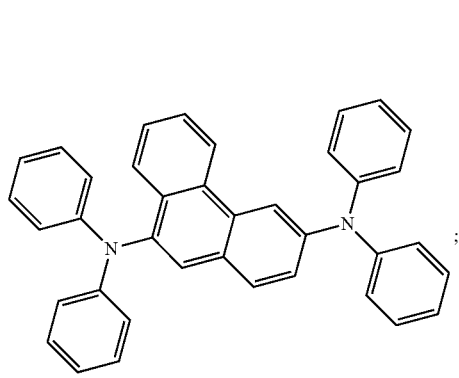
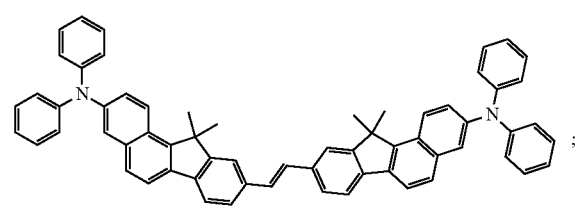
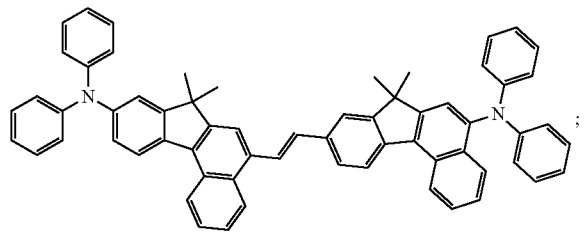
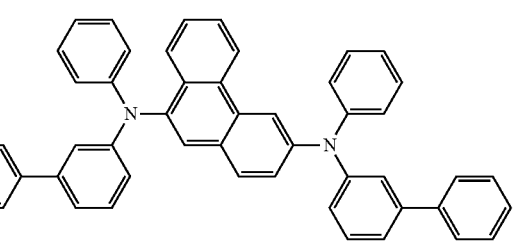
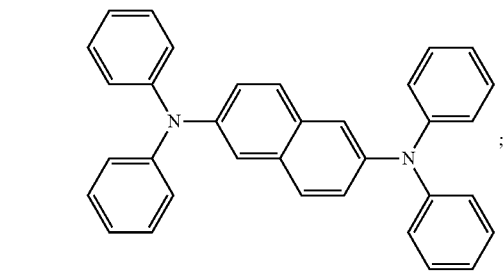
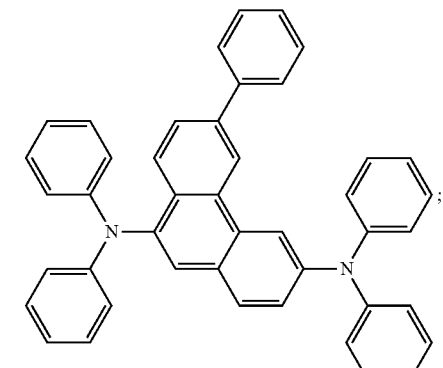
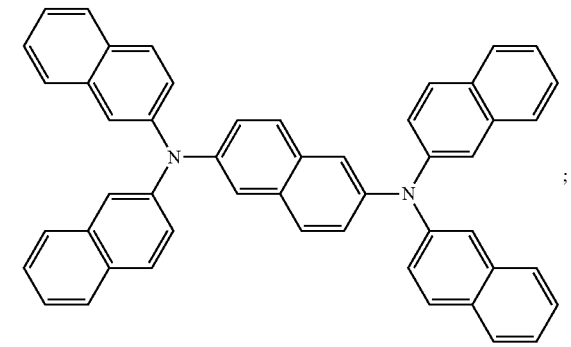
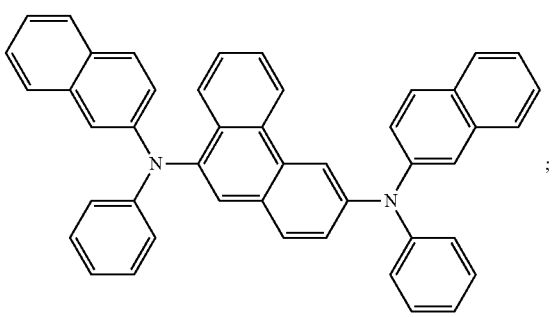

71
-continued
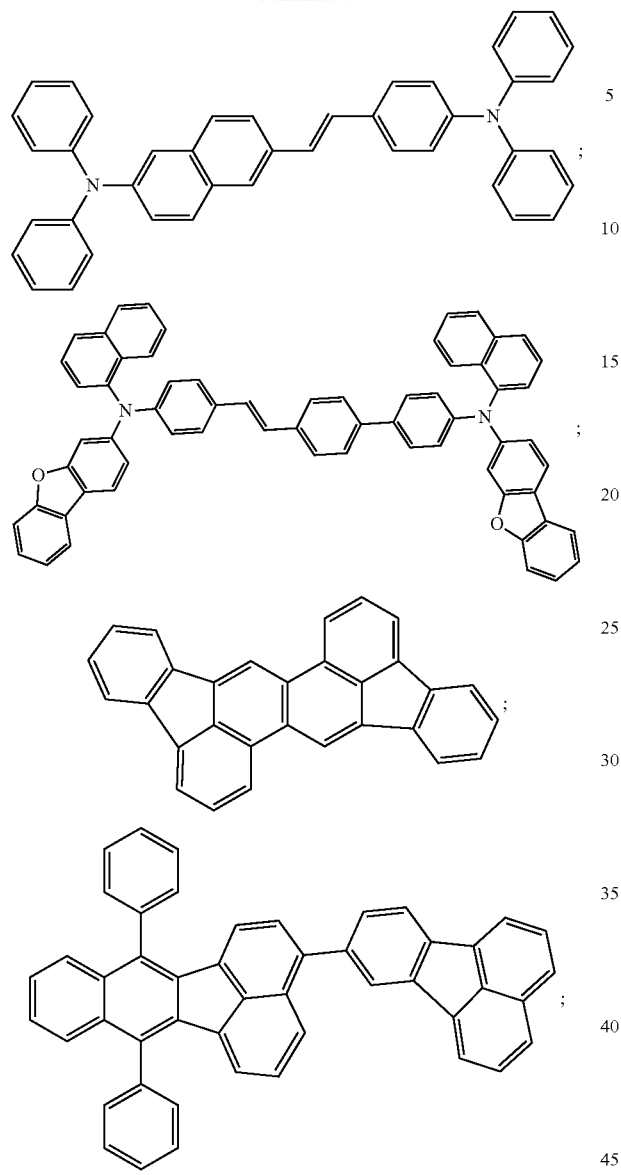
72
-continued
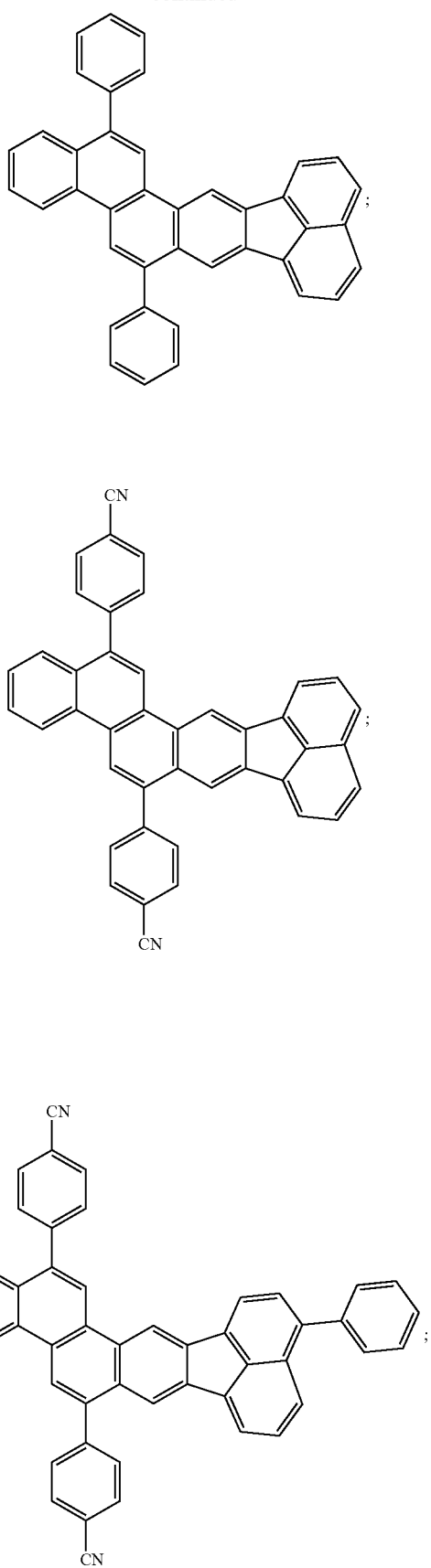

73
-continued
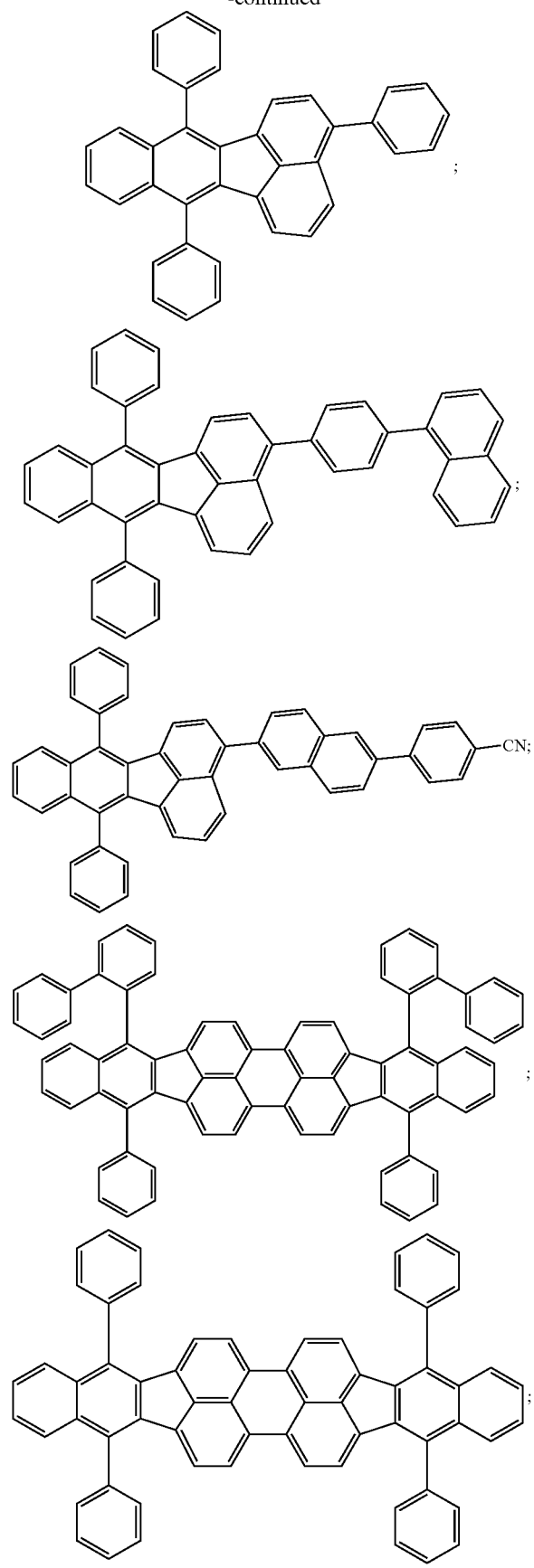
74
-continued
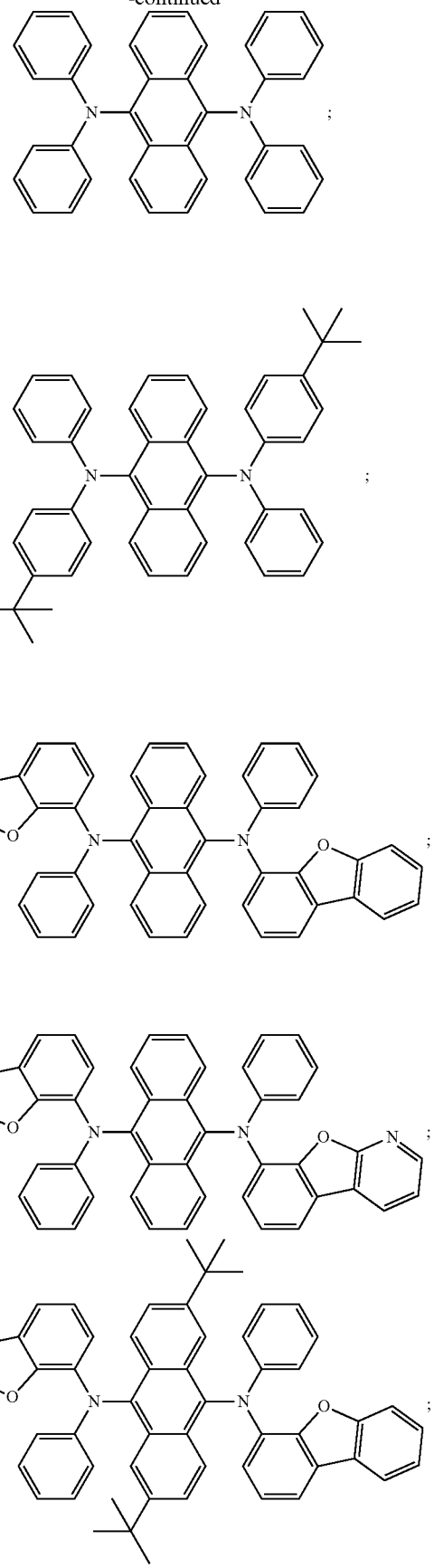

75
-continued
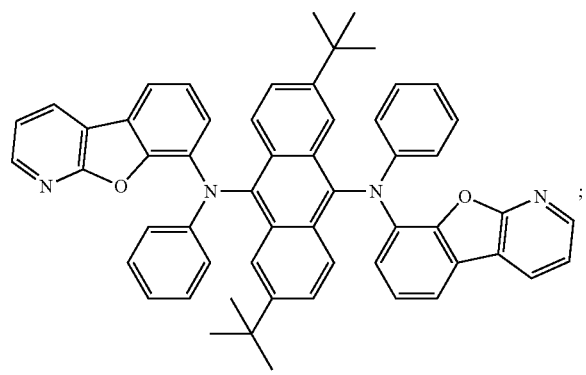
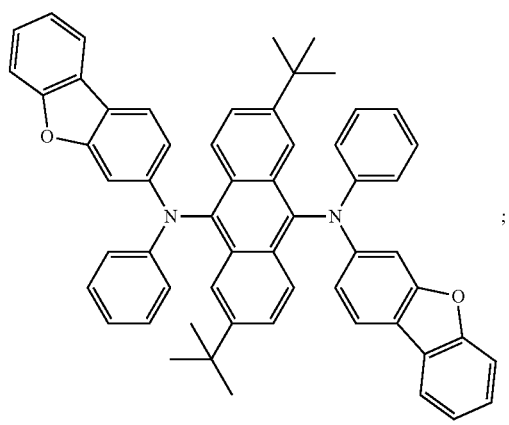
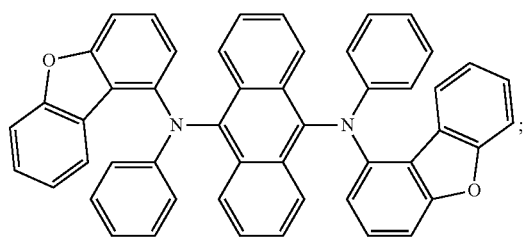
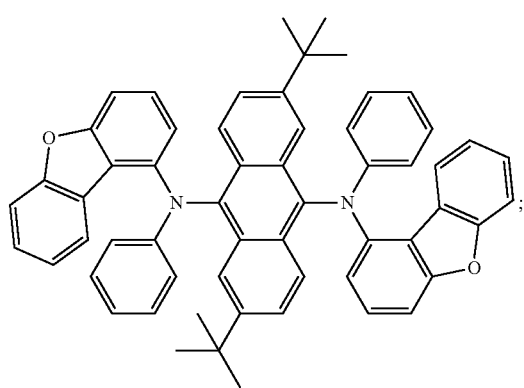
76
-continued
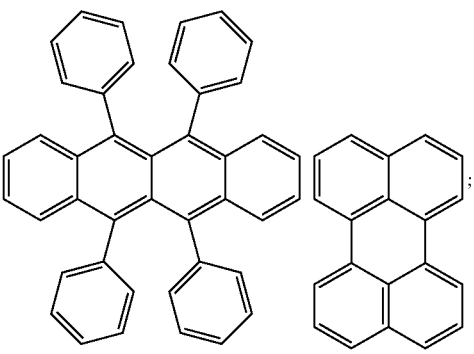
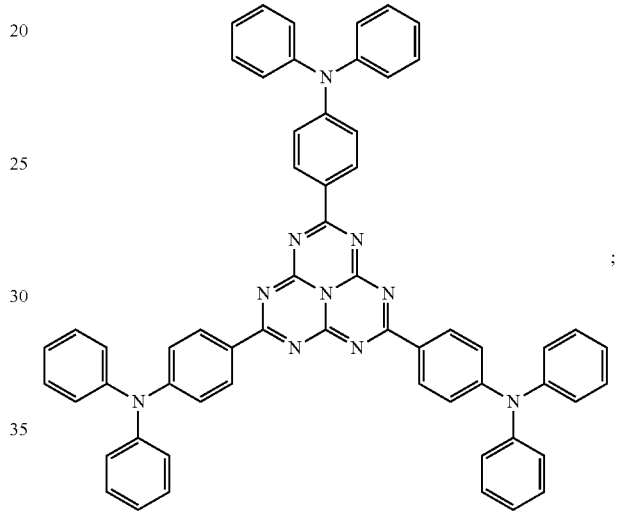
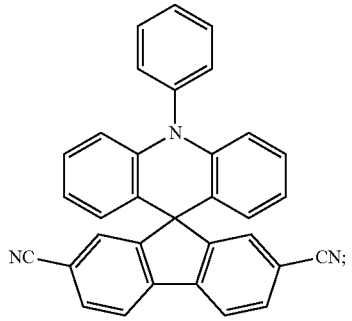
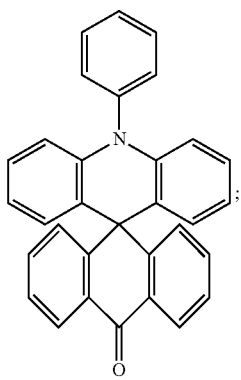

77
-continued
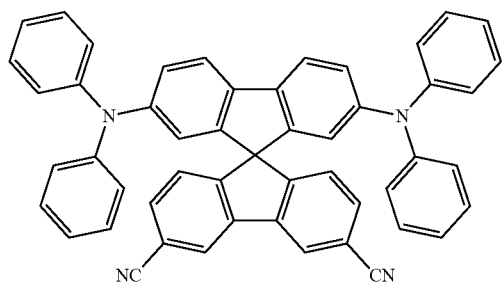
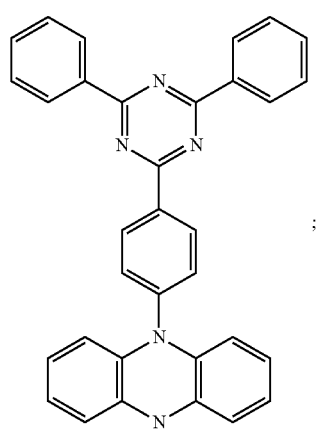
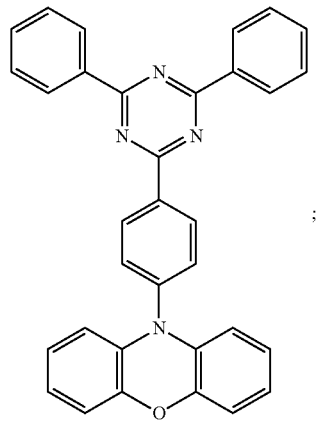
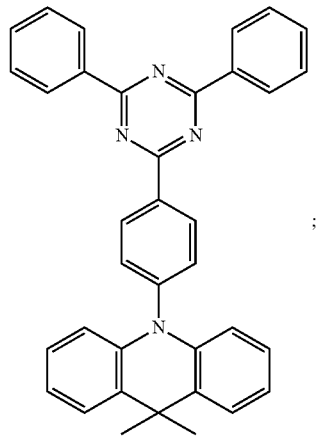
78
-continued
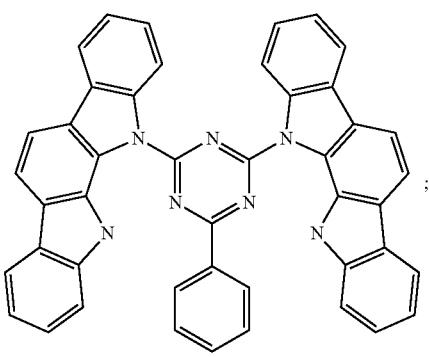
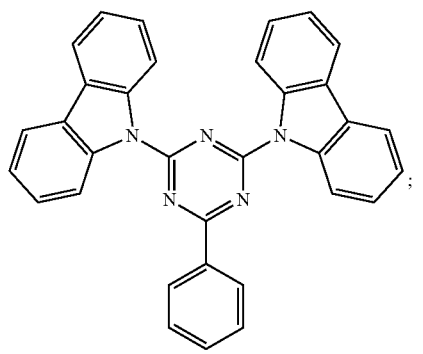
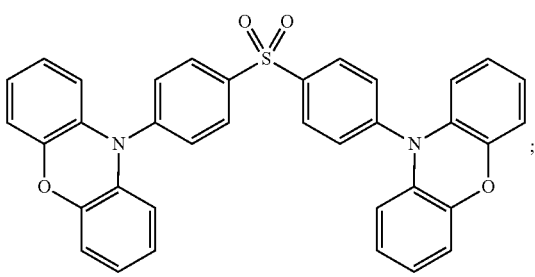
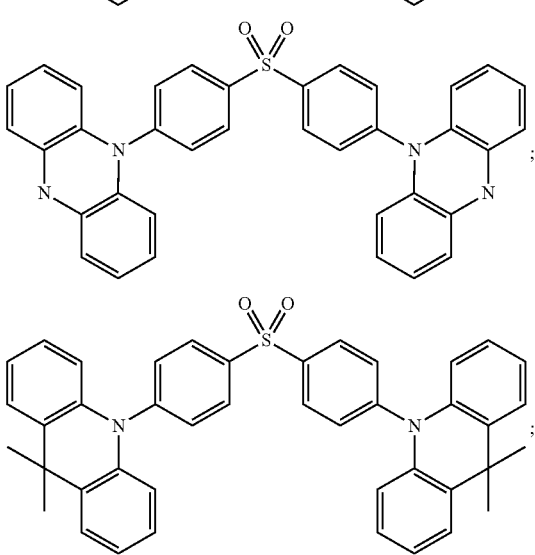

-continued

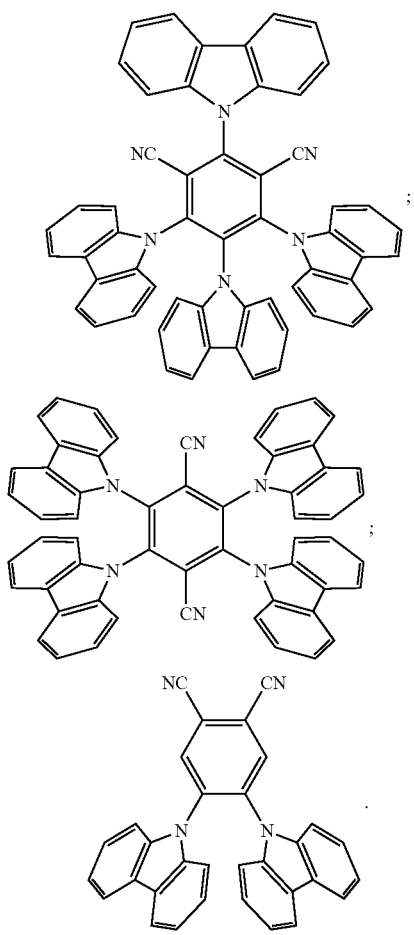
; and

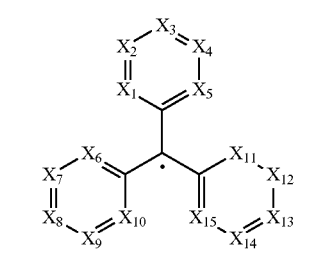

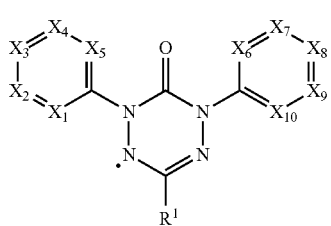

Component B may be a structure or compound, respectively, selected from the group consisting of Formulae BB, BC, BD, BE, BF, and BF:

BB

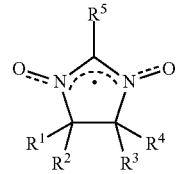

BC

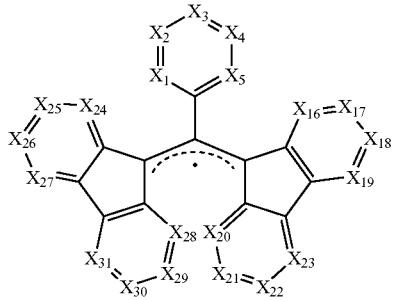

-continued

BD

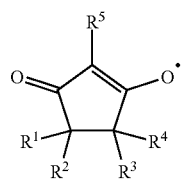

BE

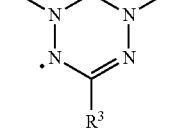

BF (structure)

BG (structure)

For the respective compounds of the Formulae BB, BC, BD, BE, BF, and BF:

$X_1$ to $X_5$ are independently selected from $CR^A$ or N;

$X_6$ to $X_{10}$ are independently selected from $CR^B$ or N;

$X_{11}$ to $X_{15}$ are independently selected from $CR^C$ or N;

$X_{16}$ to $X_{23}$ are independently selected from $CR^D$ or N;

$X_{24}$ to $X_{31}$ are independently selected from $CR^E$ or N;

$R^A$, $R^B$, $R^C$, $R^D$, and $R^E$ independently represent mono to the maximum allowable substitution, or no substitution;

each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;

$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;

wherein at least one of $R^1$ to $R^5$, $R^A$, $R^B$, $R^C$, $R^D$, or $R^E$ includes a polycyclic group selected from the group consisting of:

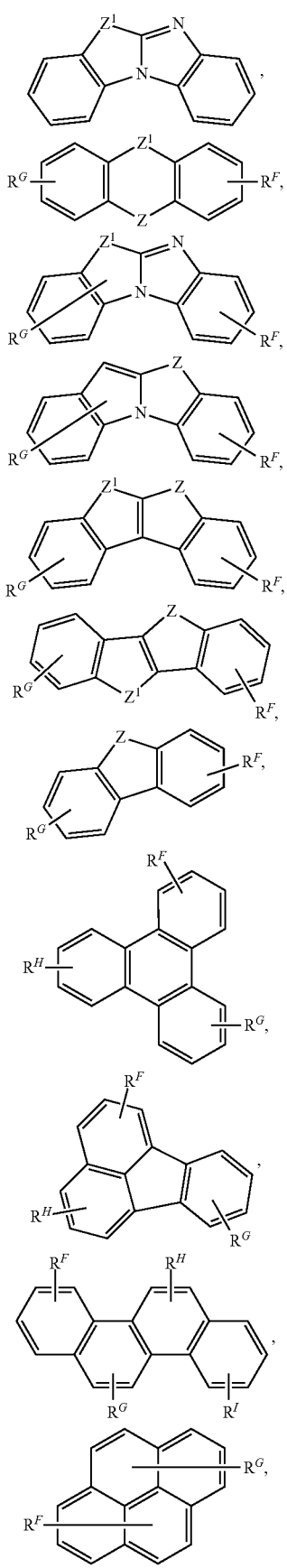

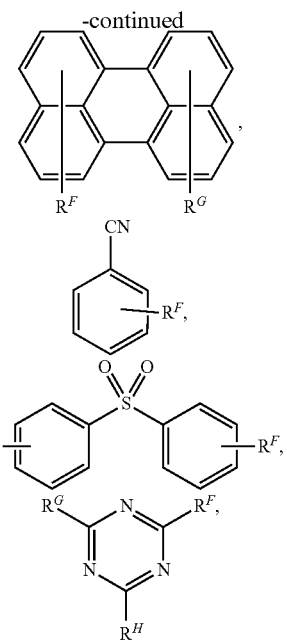

-continued

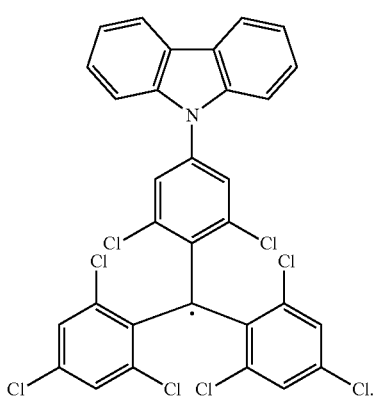

and any aza-analogue of each thereof, each of which is optionally substituted with $R^P$, wherein $R^P$ is selected from the group consisting of deuterium, fluorine, chlorine, alkyl, cycloalkyl, amino, aryl, heteroaryl, silyl, nitrile, and combinations thereof;

wherein $R^F$ to $R^I$ are independently selected from the group consisting of deuterium, fluorine, chlorine, alkyl, cycloalkyl, amino, aryl, heteroaryl, silyl, nitrile, and combinations thereof; and Z and $Z^1$ are independently selected from the group consisting of O, S, Se, $NR^N$, CR'CR", SiR'R", and GeR'R", wherein R' and R" are independently $R^N$;

with the proviso that the following compound is excluded

Alternatively, Component B is B1 to B10 listed in Table 1 below.

For the compounds, A-L-B, organic linkers of interest are selected from a direct bond, a divalent aryl, or a divalent heteroaryl. In one embodiment, L can include 2-36 carbon atoms or an aromatic group. In one embodiment, L comprises a carbocyclic group. Select organic linkers of interest can be selected from one of L1 to L17 below.

In one embodiment, the compound is a Compound X having the formula Ai-Lj-Bk.

Lj is selected from the group consisting of:
Direct bond — L1
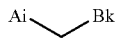 L2
 L3
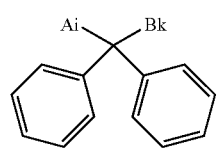 L4
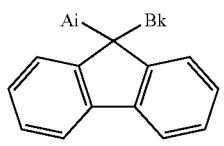 L5
 L6
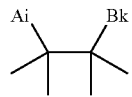 L7
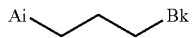 L8
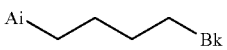 L9
 L10
 L11
 L12
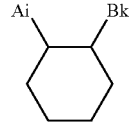 L13
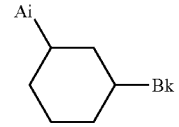 L14
 L15
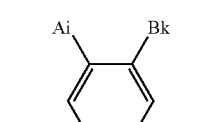 L16
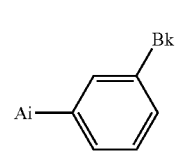
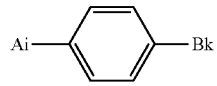 L17
Bk is selected from the group consisting of:
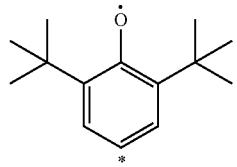 B1
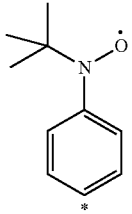 B2
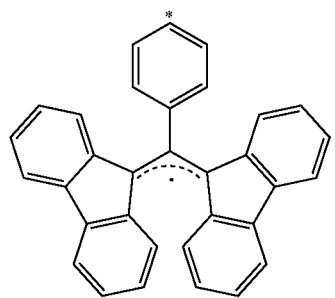 B3
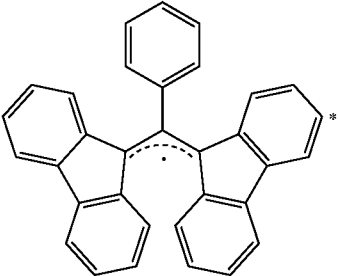 B4
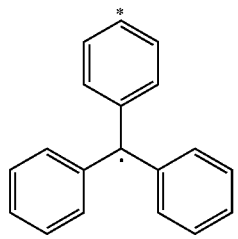 B5

-continued

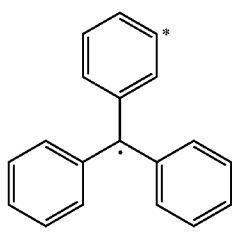
B6

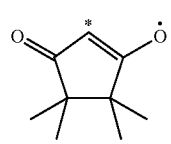
B7

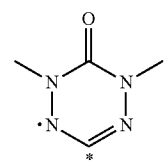
B8

-continued

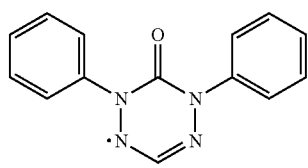
B9

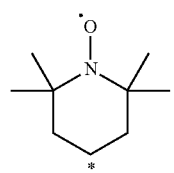
B10

* attaches to Lj

* represents the point of attachment of Bk to the linker Li; and Ai is indicated below to provide the following compounds listed in Table 1.

TABLE 1

| Ai | Ci | Lj | Bk | x equals to | Compound x |
|---|---|---|---|---|---|
| (structure 1) | i is an integer from 1 to 19 | j is an integer from 1 to 17 | k is an integer from 1 to 10 | $17(i-1)+j+323(k-1)$ | Compound 1 - 3230 |
| (structure 2) | i is an integer from 1 to 17 | j is an integer from 1 to 17 | k is an integer from 1 to 10 | $17(i-1)+j+289(k-1)+3230$ | Compound 3231 - 6120 |
| (structure 3) | i is an integer from 1 to 22 | j is an integer from 1 to 17 | k is an integer from 1 to 10 | $17(i-1)+j+374(k-1)+6120$ | Compound 6121 - 9860 |
| (structure 4) | i is an integer from 1 to 20 | j is an integer from 1 to 17 | k is an integer from 1 to 10 | $17(i-1)+j+340(k-1)+9860$ | Compound 9861 - 13260 |

TABLE 1-continued

| Ai | Ci | Lj | Bk | x equals to | Compound x |
|---|---|---|---|---|---|
| (structure) | i is an integer from 1 to 21 | j is an integer from 1 to 17 | k is an integer from 1 to 10 | 17(i − 1) + j + 357(k − 1) + 13260 | Compound 13261 - 16830 |
| (structure) | i is an integer from 1 to 21 | j is an integer from 1 to 17 | k is an integer from 1 to 10 | 17(i − 1) + j + 357(k − 1) + 16830 | Compound 16831 - 20400 |
| (structure) | i is an integer from 1 to 21 | j is an integer from 1 to 17 | k is an integer from 1 to 10 | 17(i − 1) + j + 357(k − 1) + 20400 | Compound 20401 - 23970 |
| (structure) | i is an integer from 1 to 7 | j is an integer from 1 to 17 | k is an integer from 1 to 10 | 17(i − 1) + j + 119(k − 1) + 23970 | Compound 23971 - 25160 |
| (structure) | i is an integer from 1 to 14 | j is an integer from 1 to 17 | k is an integer from 1 to 10 | 17(i − 1) + j + 238(k − 1) + 25160 | Compound 25161 - 27540 |
| (structure) | i is an integer from 1 to 11 | j is an integer from 1 to 17 | k is an integer from 1 to 10 | 17(i − 1) + j + 187(k − 1) + 27540 | Compound 27541 - 29410 |

TABLE 1-continued

| Ai | Ci | Lj | Bk | x equals to | Compound x |
|---|---|---|---|---|---|
| (structure) | i = 1 | j is an integer from 1 to 17 | k is an integer from 1 to 10 | j + 17(k − 1) + 29410 | Compound 29411 - 29580 |
| (structure) | i is an integer from 1 to 16 | j is an integer from 1 to 17 | k is an integer from 1 to 10 | 17(i − 1) + j + 272(k − 1) + 29580 | Compound 29581 - 32300 |
| (structure) | i is an integer from 1 to 13 | j is an integer from 1 to 17 | k is an integer from 1 to 10 | 17(i − 1) + j + 221(k − 1) + 32300 | Compound 32301 - 34510 |
| (structure) | i = 1 | j is an integer from 1 to 17 | k is an integer from 1 to 10 | j + 17(k − 1) + 34510 | Compound 34511 - 34680 |
| (structure) | i is an integer from 1 to 13 | j is an integer from 1 to 17 | k is an integer from 1 to 10 | 17(i − 1) + j + 221(k − 1) + 34680 | Compound 34681 - 36890 |

TABLE 1-continued

| Ai | Ci | Lj | Bk | x equals to | Compound x |
|---|---|---|---|---|---|
| (structure with pyridofuran, cyclohexyl-N, naphthalene, cyclohexyl-N, furopyridine) | i is an integer from 1 to 10 | j is an integer from 1 to 17 | k is an integer from 1 to 10 | 17(i − 1) + j + 17(k − 1) + 36890 | Compound 36891 - 38590 |
| (structure with pyridofuran-N(Lj-Bk), pyrene, N(phenyl), pyridofuran) | i = 1 | j is an integer from 1 to 17 | k is an integer from 1 to 10 | j + 17(k − 1) + 38590 | Compound 38591 - 38760 |
| (structure with benzofuran, CN-phenyl-N, naphthalene, N(CN-phenyl), furan) | i is an integer from 1 to 13 | j is an integer from 1 to 17 | k is an integer from 1 to 10 | 17(i − 1) + j + 221(k − 1) + 38760 | Compound 38761 - 40970 |
| (structure with phenyl-dibenzofuran, CN-phenyl-N, naphthalene, N(CN-phenyl), phenyl-furan) | i is an integer from 1 to 15 | j is an integer from 1 to 17 | k is an integer from 1 to 10 | 17(i − 1) + j + 255(k − 1) + 40970 | Compound 40971 - 43520 |
| (structure with pyridofuran, CN-phenyl-N, naphthalene, N(CN-phenyl), furopyridine) | i is an integer from 1 to 12 | j is an integer from 1 to 17 | k is an integer from 1 to 10 | 17(i − 1) + j + 204(k − 1) + 43520 | Compound 43521 - 45560 |

TABLE 1-continued

| Ai | Ci | Lj | Bk | x equals to | Compound x |
|---|---|---|---|---|---|
| 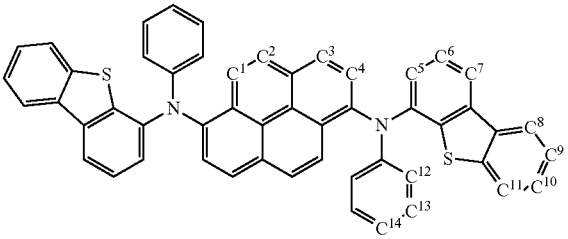 | i is an integer from 1 to 14 | j is an integer from 1 to 17 | k is an integer from 1 to 10 | $17(i-1) + j + 238(k-1) + 45560$ | Compound 45561 - 47940 |
| 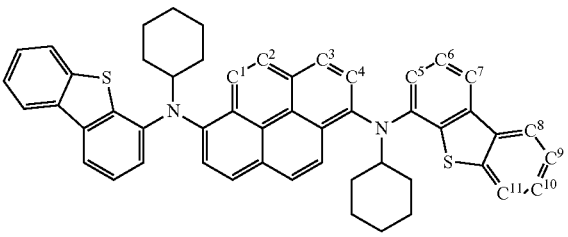 | i is an integer from 1 to 11 | j is an integer from 1 to 17 | k is an integer from 1 to 10 | $17(i-1) + j + 187(k-1) + 47940$ | Compound 47941 - 49810 |
| 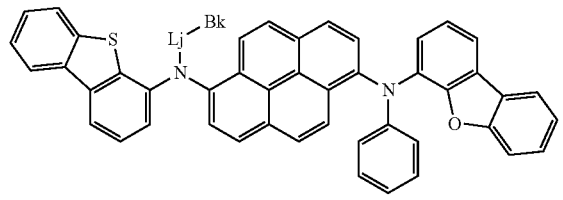 | i = 1 | j is an integer from 1 to 17 | k is an integer from 1 to 10 | $j + 17(k-1) + 49810$ | Compound 49811 - 49980 |
| 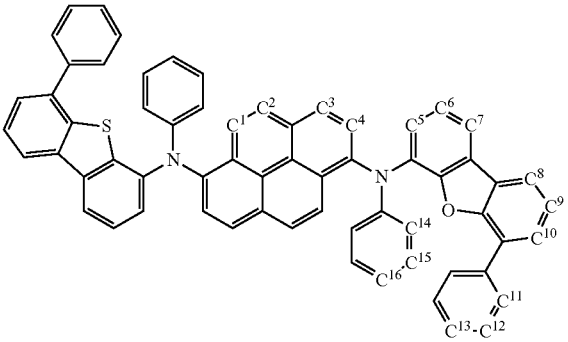 | i is an integer from 1 to 16 | j is an integer from 1 to 17 | k is an integer from 1 to 10 | $17(i-1) + j + 272(k-1) + 49980$ | Compound 49981 - 52700 |
| 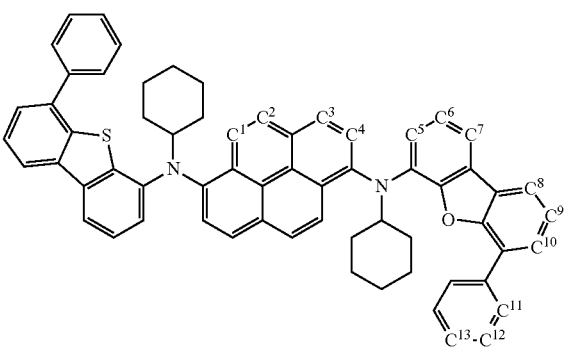 | i is an integer from 1 to 13 | j is an integer from 1 to 17 | k is an integer from 1 to 10 | $17(i-1) + j + 221(k-1) + 52700$ | Compound 52701 - 54910 |

TABLE 1-continued

| Ai | Ci | Lj | Bk | x equals to | Compound x |
|---|---|---|---|---|---|
| (structure: phenyl-dibenzothiophene-N(Lj-Bk)-pyrene-N(phenyl)(phenyl-dibenzothiophene)) | i = 1 | j is an integer from 1 to 17 | k is an integer from 1 to 10 | j + 17(k − 1) + 54910 | Compound 54911 - 55080 |
| (structure: pyridine-benzothiophene-N(phenyl)-(C1-C4 ring)-N-(thienopyridine with C5-C10)-with C11-C13 substituent) | i is an integer from 1 to 13 | j is an integer from 1 to 17 | k is an integer from 1 to 10 | 17(i − 1) + j + 221(k − 1) + 55080 | Compound 55081 - 57290 |
| (structure: pyridine-benzothiophene-N(cyclohexyl)-(C1-C4 ring)-N(cyclohexyl)-(thienopyridine with C5-C10)) | i is an integer from 1 to 10 | j is an integer from 1 to 17 | k is an integer from 1 to 10 | 17(i − 1) + j + 170(k − 1) + 57290 | Compound 57291 - 58990 |
| (structure: pyridine-benzothiophene-N(Lj-Bk)-pyrene-N(phenyl)(pyridine-benzothiophene)) | i = 1 | j is an integer from 1 to 17 | k is an integer from 1 to 10 | j + 17(k − 1) + 58990 | Compound 58991 - 59160 |
| (structure: dibenzothiophene-N(CN-phenyl)-(C1-C4 ring)-N(CN-phenyl with C12,C13)-(thiophene with C5-C10)) | i is an integer from 1 to 13 | j is an integer from 1 to 17 | k is an integer from 1 to 10 | 17(i − 1) + j + 221 (k − 1) + 59160 | Compound 59161 - 61370 |

TABLE 1-continued

| Ai | Ci | Lj | Bk | x equals to | Compound x |
|---|---|---|---|---|---|
| (structure with dibenzothiophene-phenyl, CN-phenyl, naphthalene core, thiophene with phenyl) | i is an integer from 1 to 15 | j is an integer from 1 to 17 | k is an integer from 1 to 10 | 17(i − 1) + j + 255(k − 1) + 61370 | Compound 61371 - 63920 |
| (structure with pyridine-furan, CN-phenyl, naphthalene, furopyrimidine) | i is an integer from 1 to 12 | j is an integer from 1 to 17 | k is an integer from 1 to 10 | 17(i − 1) + j + 204(k − 1) + 63920 | Compound 63921 - 65960 |
| (structure with NC-phenyl, naphthalene, phenyl substituents) | i is an integer from 1 to 9 | j is an integer from 1 to 17 | k is an integer from 1 to 10 | 17(i − 1) + j + 153(k − 1) + 65960 | Compound 65961 - 67490 |
| (structure with m-CN-phenyl, naphthalene, m-CN-phenyl) | i is an integer from 1 to 9 | j is an integer from 1 to 17 | k is an integer from 1 to 10 | 17(i − 1) + j + 153(k − 1) + 67490 | Compound 67491 - 69020 |
| (structure with naphthyl-phenyl-N, naphthalene, phenyl-N-phenyl) | i is an integer from 1 to 14 | j is an integer from 1 to 17 | k is an integer from 1 to 10 | 17(i − 1) + j + 238(k − 1) + 69020 | Compound 69021 - 71400 |

TABLE 1-continued

| Ai | Ci | Lj | Bk | x equals to | Compound x |
|---|---|---|---|---|---|
| (structure with naphthyl, phenyl amine groups on pyrene core, labeled $C^1$–$C^{14}$) | i is an integer from 1 to 14 | j is an integer from 1 to 17 | k is an integer from 1 to 10 | 17(i − 1) + j + 238(k − 1) + 71400 | Compound 71401 - 73780 |
| (structure with two indene/fluorene-type groups and phenyl group on pyrene core, labeled $C^1$–$C^{25}$) | i is an integer from 1 to 25 | j is an integer from 1 to 17 | k is an integer from 1 to 10 | 17(i − 1) + j + 425(k − 1) + 73780 | Compound 73781 - 78030 |
| (structure with two indene/fluorene-type groups and phenyl group on pyrene core, labeled $C^1$–$C^{21}$) | i is an integer from 1 to 21 | j is an integer from 1 to 17 | k is an integer from 1 to 10 | 17(i − 1) + j + 357(k − 1) + 78030 | Compound 78031 - 81600 |

TABLE 1-continued

| Ai | Ci | Lj | Bk | x equals to | Compound x |
|---|---|---|---|---|---|
| (structure with C1–C17) | i is an integer from 1 to 17 | j is an integer from 1 to 17 | k is an integer from 1 to 10 | 17(i − 1) + j + 289(k − 1) + 81600 | Compound 81601 - 84490 |
| (structure with C1–C17) | i is an integer from 1 to 13 | j is an integer from 1 to 17 | k is an integer from 1 to 10 | 17(i − 1) + j + 221(k − 1) + 84490 | Compound 84491 - 86700 |
| (structure with C1–C21) | i is an integer from 1 to 21 | j is an integer from 1 to 17 | k is an integer from 1 to 10 | 17(i − 1) + j + 357(k − 1) + 86700 | Compound 86701 - 90270 |

TABLE 1-continued

| Ai | Ci | Lj | Bk | x equals to | Compound x |
|---|---|---|---|---|---|
| (structure) | i is an integer from 1 to 25 | j is an integer from 1 to 17 | k is an integer from 1 to 10 | 17(i − 1) + j + 425(k − 1) + 90270 | Compound 90271 - 94520 |
| (structure) | i is an integer from 1 to 16 | j is an integer from 1 to 17 | k is an integer from 1 to 10 | 17(i − 1) + j + 272(k − 1) + 94520 | Compound 94521 - 97240 |
| (structure) | i is an integer from 1 to 20 | j is an integer from 1 to 17 | k is an integer from 1 to 10 | 17(i − 1) + j + 340(k − 1) + 97240 | Compound 97241 - 100640 |
| (structure) | i is an integer from 1 to 8 | j is an integer from 1 to 17 | k is an integer from 1 to 10 | 17(i − 1) + j + 136(k − 1) + 100640 | Compound 100641 - 102000 |
| (structure) | i is an integer from 1 to 15 | j is an integer from 1 to 17 | k is an integer from 1 to 10 | 17(i − 1) + j + 255(k − 1) + 102000 | Compound 102001 - 104550 |

TABLE 1-continued

| Ai | Ci | Lj | Bk | x equals to | Compound x |
|---|---|---|---|---|---|
| (structure) | i is an integer from 1 to 15 | j is an integer from 1 to 17 | k is an integer from 1 to 10 | 17(i − 1) + j + 255(k − 1) + 104550 | Compound 104551 - 107100 |
| (structure) | i is an integer from 1 to 10 | j is an integer from 1 to 17 | k is an integer from 1 to 10 | 17(i − 1) + j + l70(k − 1) + 107100 | Compound 107101 - 108800 |
| (structure) | i is an integer from 1 to 15 | j is an integer from 1 to 17 | k is an integer from 1 to 10 | 17(i − 1) + j + 255(k − 1) + 108800 | Compound 108801 - 111350 |
| (structure) | i is an integer from 1 to 14 | j is an integer from 1 to 17 | k is an integer from 1 to 10 | 17(i − 1) + j + 238(k − 1) + 111350 | Compound 111351 - 113730 |
| (structure) | i is an integer from 1 to 14 | j is an integer from 1 to 17 | k is an integer from 1 to 10 | 17(i − 1) + j + 238(k − 1) + 113730 | Compound 113731 - 116110 |

TABLE 1-continued

| Ai | Ci | Lj | Bk | x equals to | Compound x |
|---|---|---|---|---|---|
| (structure) | i is an integer from 1 to 17 | j is an integer from 1 to 17 | k is an integer from 1 to 10 | 17(i − 1) + j + 289(k − 1) + 116110 | Compound 116111 - 119000 |
| (structure) | i is an integer from 1 to 14 | j is an integer from 1 to 17 | k is an integer from 1 to 10 | 17(i − 1) + j + 238(k − 1) + 119000 | Compound 119001 - 121380 |
| (structure) | i is an integer from 1 to 17 | j is an integer from 1 to 17 | k is an integer from 1 to 10 | 17(i − 1) + j + 289(k − 1) + 121380 | Compound 121381 - 124270 |
| (structure) | i is an integer from 1 to 31 | j is an integer from 1 to 17 | k is an integer from 1 to 10 | 17(i − 1) + j + 527(k − 1) + 124270 | Compound 124271 - 129540 |
| (structure) | i is an integer from 1 to 29 | j is an integer from 1 to 17 | k is an integer from 1 to 10 | 17(i − 1) + j + 493(k − 1) + 129540 | Compound 129541 - 134470 |
| (structure) | i is an integer from 1 to 29 | j is an integer from 1 to 17 | k is an integer from 1 to 10 | 17(i − 1) + j + 493(k − 1) + 134470 | Compound 134471 - 139400 |

TABLE 1-continued

| Ai | Ci | Lj | Bk | x equals to | Compound x |
|---|---|---|---|---|---|
| (structure) | i is an integer from 1 to 35 | j is an integer from 1 to 17 | k is an integer from 1 to 10 | 17(i − 1) + j + 595(k − 1) + 139400 | Compound 139401 - 145350 |
| (structure) | i is an integer from 1 to 29 | j is an integer from 1 to 17 | k is an integer from 1 to 10 | 17(i − 1) + j + 493(k − 1) + 145350 | Compound 145351 - 150280 |
| (structure) | i is an integer from 1 to 14 | j is an integer from 1 to 17 | k is an integer from 1 to 10 | 17(i − 1) + j + 238(k − 1) + 150280 | Compound 150281 - 152660 |
| (structure) | i is an integer from 1 to 24 | j is an integer from 1 to 17 | k is an integer from 1 to 10 | 17(i − 1) + j + 408(k − 1) + 152660 | Compound 152661 - 156740 |
| (structure) | i is an integer from 1 to 22 | j is an integer from 1 to 17 | k is an integer from 1 to 10 | 17(i − 1) + j + 374(k − 1) + 156740 | Compound 156741 - 160480 |
| (structure) | i is an integer from 1 to 22 | j is an integer from 1 to 17 | k is an integer from 1 to 10 | 17(i − 1) + j + 374(k − 1) + 160480 | Compound 160481 - 164220 |

TABLE 1-continued

| Ai | Ci | Lj | Bk | x equals to | Compound x |
|---|---|---|---|---|---|
| [structure] | i is an integer from 1 to 28 | j is an integer from 1 to 17 | k is an integer from 1 to 10 | 17(i − 1) + j + 476(k − 1) + 164220 | Compound 164221 - 168980 |
| [structure] | i is an integer from 1 to 22 | j is an integer from 1 to 17 | k is an integer from 1 to 10 | 17(i − 1) + j + 374(k − 1) + 168980 | Compound 168981 - 172720 |
| [structure] | i is an integer from 1 to 7 | j is an integer from 1 to 17 | k is an integer from 1 to 10 | 17(i − 1) + j + 119(k − 1) + 172720 | Compound 172721 - 173910 |
| [structure] | i is an integer from 1 to 14 | j is an integer from 1 to 17 | k is an integer from 1 to 10 | 17(i − 1) + j + 238(k − 1) + 173910 | Compound 173911 - 176290 |
| [structure] | i is an integer from 1 to 13 | j is an integer from 1 to 17 | k is an integer from 1 to 10 | 17(i − 1) + j + 221(k − 1) + 176290 | Compound 176291 - 178500 |
| [structure] | i is an integer from 1 to 13 | j is an integer from 1 to 17 | k is an integer from 1 to 10 | 17(i − 1) + j + 221(k − 1) + 178500 | Compound 178501 - 180710 |

TABLE 1-continued

| Ai | Ci | Lj | Bk | x equals to | Compound x |
|---|---|---|---|---|---|
| (structure) | i is an integer from 1 to 16 | j is an integer from 1 to 17 | k is an integer from 1 to 10 | 17(i − 1) + j + 272(k − 1) + 180710 | Compound 180711 - 183430 |
| (structure) | i is an integer from 1 to 13 | j is an integer from 1 to 17 | k is an integer from 1 to 10 | 17(i − 1) + j + 221(k − 1) + 183430 | Compound 183431 - 185640 |
| (structure) | i is an integer from 1 to 6 | j is an integer from 1 to 17 | k is an integer from 1 to 10 | 17(i − 1) + j + 102(k − 1) + 185640 | Compound 185641 - 186660 |
| (structure) | i is an integer from 1 to 13 | j is an integer from 1 to 17 | k is an integer from 1 to 10 | 17(i − 1) + j + 221(k − 1) + 186660 | Compound 186661 - 188870 |
| (structure) | i is an integer from 1 to 10 | j is an integer from 1 to 17 | k is an integer from 1 to 10 | 17(i − 1) + j + 170(k − 1) + 188870 | Compound 188871 - 190570 |

TABLE 1-continued

| Ai | Ci | Lj | Bk | x equals to | Compound x |
|---|---|---|---|---|---|
| (structure with C1–C20) | i is an integer from 1 to 17 | j is an integer from 1 to 17 | k is an integer from 1 to 10 | 17(i − 1) + j + 289(k − 1) + 190570 | Compound 190571 - 193460 |
| (structure with CN, C1–C19) | i is an integer from 1 to 16 | j is an integer from 1 to 17 | k is an integer from 1 to 10 | 17(i − 1) + j + 272(k − 1) + 193460 | Compound 193461 - 196180 |
| (structure with C1–C9) | i is an integer from 1 to 9 | j is an integer from 1 to 17 | k is an integer from 1 to 10 | 17(i − 1) + j + 153(k − 1) + 196180 | Compound 196181 - 197710 |
| (structure with C1–C5, N,N-diphenyl) | i is an integer from 1 to 5 | j is an integer from 1 to 17 | k is an integer from 1 to 10 | 17(i − 1) + j + 85(k − 1) + 197710 | Compound 197711 - 198560 |

TABLE 1-continued

| Ai | Ci | Lj | Bk | x equals to | Compound x |
|---|---|---|---|---|---|
| (structure) | i is an integer from 1 to 12 | j is an integer from 1 to 17 | k is an integer from 1 to 10 | 17(i − 1) + j + 204(k − 1) + 198560 | Compound 198561 - 200600 |
| (structure) | i is an integer from 1 to 11 | j is an integer from 1 to 17 | k is an integer from 1 to 10 | 17(i − 1) + j + 187(k − 1) + 200600 | Compound 200601 - 202470 |
| (structure) | i is an integer from 1 to 11 | j is an integer from 1 to 17 | k is an integer from 1 to 10 | 17(i − 1) + j + 187(k − 1) + 202470 | Compound 202471 - 204340 |
| (structure) | i is an integer from 1 to 14 | j is an integer from 1 to 17 | k is an integer from 1 to 10 | 17(i − 1) + j + 238(k − 1) + 204340 | Compound 204341 - 206720 |
| (structure) | i is an integer from 1 to 11 | j is an integer from 1 to 17 | k is an integer from 1 to 10 | 17(i − 1) + j + 187(k − 1) + 206720 | Compound 206721 - 208590 |

TABLE 1-continued

| Ai | Ci | Lj | Bk | x equals to | Compound x |
|---|---|---|---|---|---|
| (structure) | i is an integer from 1 to 5 | j is an integer from 1 to 17 | k is an integer from 1 to 10 | 17(i − 1) + j + 85(k − 1) + 208590 | Compound 208591 - 209440 |
| (structure) | i is an integer from 1 to 3 | j is an integer from 1 to 17 | k is an integer from 1 to 10 | 17(i − 1) + j + 51(k − 1) + 209440 | Compound 209441 - 209950 |
| (structure) | i is an integer from 1 to 9 | j is an integer from 1 to 17 | k is an integer from 1 to 10 | 17(i − 1) + j + 153(k − 1) + 209950 | Compound 209951 - 211480 |

TABLE 1-continued

| Ai | Ci | Lj | Bk | x equals to | Compound x |
|---|---|---|---|---|---|
| (structure) | i is an integer from 1 to 5 | j is an integer from 1 to 17 | k is an integer from 1 to 10 | 17(i − 1) + j + 85(k − 1) + 211480 | Compound 211481 - 212330 |
| (structure) | i is an integer from 1 to 10 | j is an integer from 1 to 17 | k is an integer from 1 to 10 | 17(i − 1) + j + 170(k − 1) + 212330 | Compound 212331 - 214030 |
| (structure) | i is an integer from 1 to 11 | j is an integer from 1 to 17 | k is an integer from 1 to 10 | 17(i − 1) + j + 187(k − 1) + 214030 | Compound 214031 - 215900 |
| (structure) | i is an integer from 1 to 9 | j is an integer from 1 to 17 | k is an integer from 1 to 10 | 17(i − 1) + j + 153(k − 1) + 215900 | Compound 215901 - 217430 |

TABLE 1-continued

| Ai | Ci | Lj | Bk | x equals to | Compound x |
|---|---|---|---|---|---|
| (structure with triazine, phenoxazine) | i is an integer from 1 to 9 | j is an integer from 1 to 17 | k is an integer from 1 to 10 | 17(i − 1) + j + 153(k − 1) + 217430 | Compound 217431 - 218960 |
| (structure with triazine, dicarbazole) | i is an integer from 1 to 7 | j is an integer from 1 to 17 | k is an integer from 1 to 10 | 17(i − 1) + j + 119(k − 1) + 218960 | Compound 218961 - 220150 |
| (structure with sulfone, phenoxazines) | i is an integer from 1 to 6 | j is an integer from 1 to 17 | k is an integer from 1 to 10 | 17(i − 1) + j + 102(k − 1) + 220150 | Compound 220151 - 221170 |
| (structure with dicyanobenzene, carbazoles) | i is an integer from 1 to 12 | j is an integer from 1 to 17 | k is an integer from 1 to 10 | 17(i − 1) + j + 204(k − 1) + 221170 | Compound 221171 - 223210 |

TABLE 1-continued

| Ai | Ci | Lj | Bk | x equals to | Compound x |
|---|---|---|---|---|---|
| | i is an integer from 1 to 4 | j is an integer from 1 to 17 | k is an integer from 1 to 10 | 17(i − 1) + j + 68(k − 1) + 223210 | Compound 223211 - 223890 |
| | i is an integer from 1 to 5 | j is an integer from 1 to 17 | k is an integer from 1 to 10 | 17(i − 1) + j + 85(k − 1) + 223890 | Compound 223891 - 224740 |
| | i is an integer from 1 to 23 | j is an integer from 1 to 17 | k is an integer from 1 to 10 | 17(i − 1) + j + 391 (k − 1) + 224740 | Compound 224741 - 228650 |
| | i = 1 | j is an integer from 1 to 17 | k is an integer from 1 to 10 | j + 17(k − 1) + 228650 | Compound 228651 - 228820 |

TABLE 1-continued
| Ai | Ci | Lj | Bk | x equals to | Compound x |
|---|---|---|---|---|---|
| 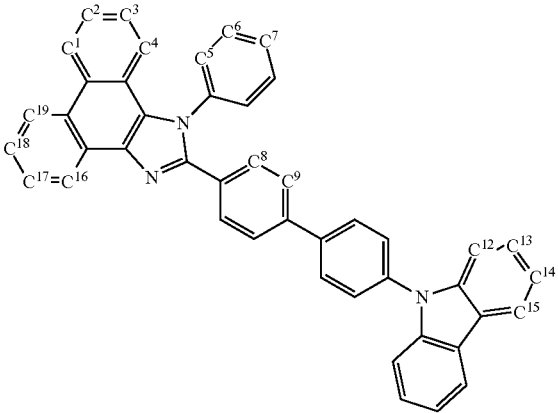 | i is an integer from 1 to 19 | j is an integer from 1 to 17 | k is an integer from 1 to 10 | 17(i − 1) + j + 323(k − 1) + 228820 | Compound 228821 - 232050 |
| 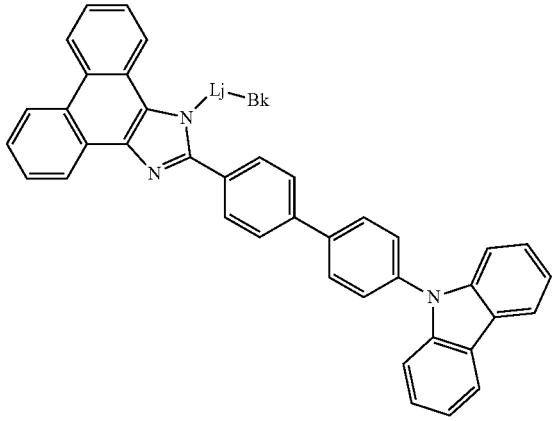 | i = 1 | j is an integer from 1 to 17 | k is an integer from 1 to 10 | j + 17(k − 1) + 232050 | Compound 232051 - 232220 |
| 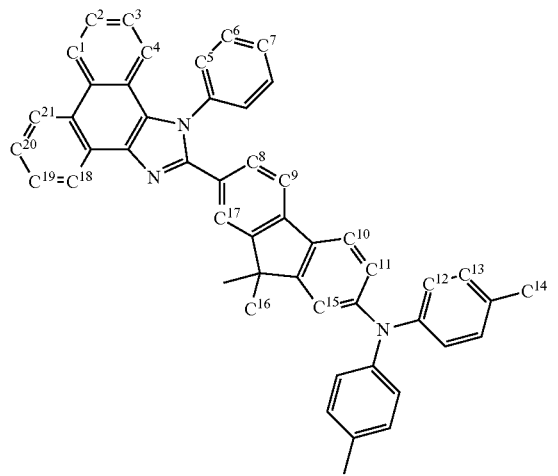 | i is an integer from 1 to 21 | j is an integer from 1 to 17 | k is an integer from 1 to 10 | 17(i − 1) + j + 357(k − 1) + 232220 | Compound 232221 - 235790 |

TABLE 1-continued

| Ai | Ci | Lj | Bk | x equals to | Compound x |
|---|---|---|---|---|---|
| 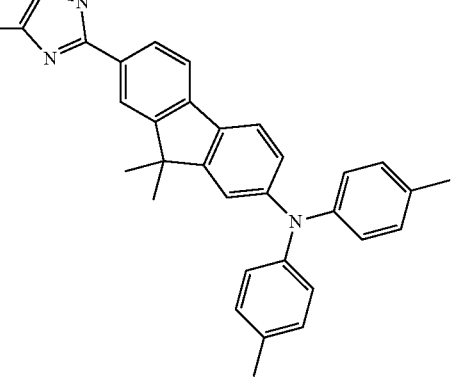 | i = 1 | j is an integer from 1 to 17 | k is an integer from 1 to 10 | j + 17(k − 1) + 235790 | Compound 235791 - 235960 |
| 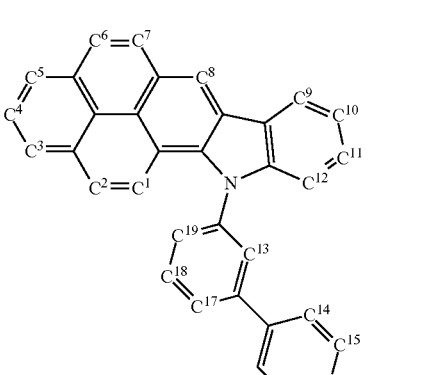 | i is an integer from 1 to 19 | j is an integer from 1 to 17 | k is an integer from 1 to 10 | 17(i − 1) + j + 323(k − 1) + 235960 | Compound 235961 - 239190 |
| 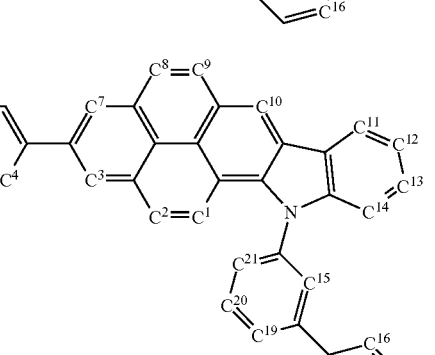 | i is an integer from 1 to 21 | j is an integer from 1 to 17 | k is an integer from 1 to 10 | 17(i − 1) + j + 357(k − 1) + 239190 | Compound 239191 - 242760 |
| 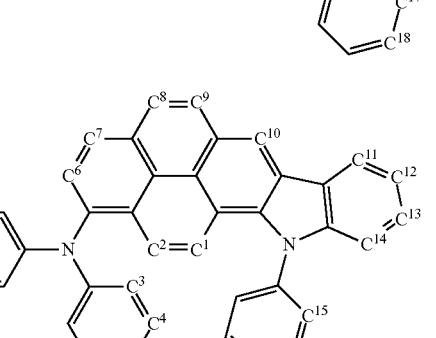 | i is an integer from 1 to 17 | j is an integer from 1 to 17 | k is an integer from 1 to 10 | 17(i − 1) + j + 289(k − 1) + 242760 | Compound 242761 - 245650 |

131 132

TABLE 1-continued

| Ai | Ci | Lj | Bk | x equals to | Compound x |
|---|---|---|---|---|---|
| (structure) | i is an integer from 1 to 17 | j is an integer from 1 to 17 | k is an integer from 1 to 10 | 17(i − 1) + j + 289(k − 1) + 245650 | Compound 245651 - 248540 |
| (structure) | i is an integer from 1 to 19 | j is an integer from 1 to 17 | k is an integer from 1 to 10 | 17(i − 1) + j + 323(k − 1) + 248540 | Compound 248541 - 251770 |

In one embodiment, A is capable of emitting light by fluorescence or what is referred to in the art as thermally activated delayed fluorescence (TADF). Of particular interest are fluorescent or TADF emitters with emission in the blue to green region of the visible spectrum.

Of particular interest are compounds A-L-B that have a peak emission wavelength $\lambda_{max}$ in a range from 400 nm to 550 nm. The different embodiments of compounds A-L-B are described above. In another embodiment, the compounds A-L-B have a peak emission wavelength $\lambda_{max}$ in a range from 425 nm to 500 nm, a have a peak emission wavelength $\lambda_{max}$ in a range from 440 nm to 480 nm.

Of particular interest are mixtures of a Component A and a Component B, each of which is described above, that have a peak emission wavelength $\lambda_{max}$ in a range from 425 nm to 500 nm, a have a peak emission wavelength $\lambda_{max}$ in a range from 440 nm to 480 nm.

The invention is also directed to an organic light emitting device (OLED) comprising an anode; a cathode; and an organic layer disposed between the anode and the cathode. The organic layer includes a compound selected from the group consisting of Formulae BB, BC, BD, BE, BF, and BF:

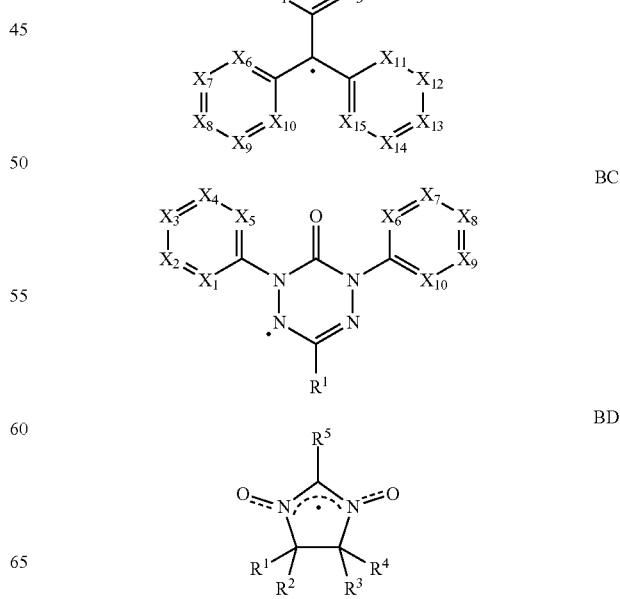

BE

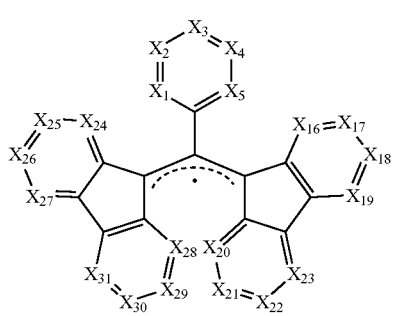

BF

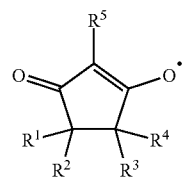

BG

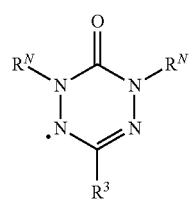

For the respective compounds of the Formulae BB, BC, BD, BE, BF, and BF:
wherein
$X_1$ to $X_5$ are independently selected from $CR^A$ or N;
$X_6$ to $X_{10}$ are independently selected from $CR^B$ or N;
$X_{11}$ to $X_{15}$ are independently selected from $CR^C$ or N;
$X_{16}$ to $X_{23}$ are independently selected from $CR^D$ or N;
$X_{24}$ to $X_{31}$ are independently selected from $CR^E$ or N;
$R^A$, $R^B$, $R^C$, $R^D$, and $R^E$ independently represent mono to the maximum allowable substitution, or no substitution;
each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;
$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;
wherein at least one of $R^1$ to $R^5$, $R^A$, $R^B$, $R^C$, $R^D$, or $R^E$ includes a polycyclic group selected from the group consisting of:

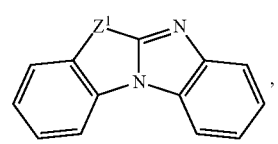

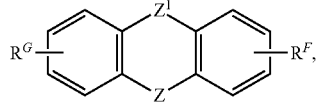

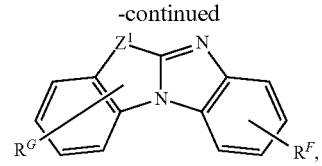

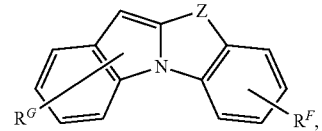

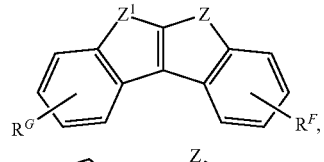

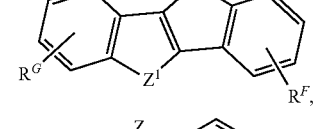

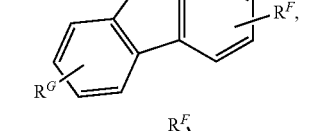

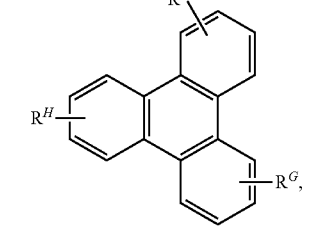

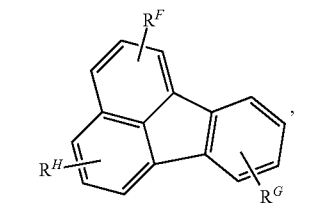

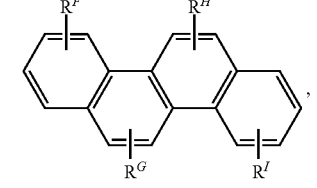

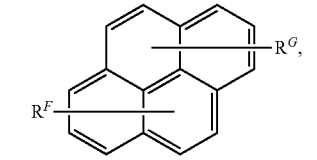

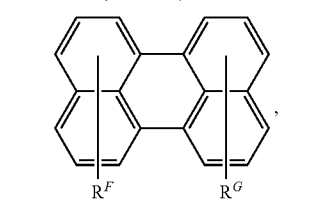

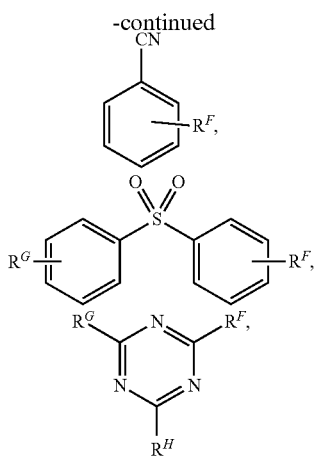

and any aza-analogue of each thereof, each of which is optionally substituted with $R^P$, wherein $R^P$ is selected from the group consisting of deuterium, fluorine, alkyl, cycloalkyl, amino, aryl, heteroaryl, silyl, nitrile, and combinations thereof, wherein $R^F$ to $R^I$ are independently selected from the group consisting of deuterium, fluorine, alkyl, cycloalkyl, amino, aryl, heteroaryl, silyl, nitrile, and combinations thereof, and Z and $Z^1$ are independently selected from the group consisting of O, S, Se, $NR^N$, CR'CR", SiR'R", and GeR'R", wherein R' and R" are independently $R^N$;

with the proviso that the following compound is excluded

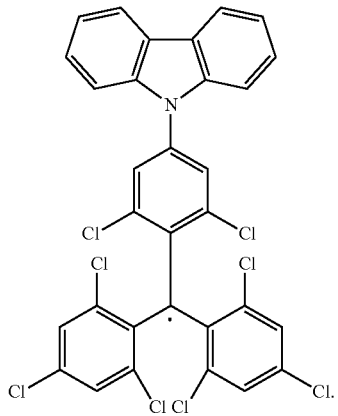

The present invention also includes an organic light emitting device (OLED) comprising an anode; a cathode; and an organic layer disposed between the anode and the cathode. In one embodiment, the organic layer includes one of the compound of formula A-L-B or select compounds of formula Ai-Li-Bk of Table 1. Component A described above is capable of emitting light from a singlet excited state to a singlet ground state in an organic light emitting device. Component B is an organic radical selected from the group consisting of Formulae BB, BC, BD, BE, BF, and BF as defined above. L is selected from the group consisting of a direct bond and an organic linker. Alternatively, L can be one of the select organic linkers L2 to L17.

In one embodiment, Component A is capable of emitting light from a singlet excited state to a singlet ground state in an organic light emitting device with an internal quantum efficiency of greater than 3% at room temperature. In one embodiment, Component A is capable of emitting light from a singlet excited state to a singlet ground state in an organic light emitting device with an internal quantum efficiency of greater than 6% at room temperature. In one embodiment, Component A is capable of emitting light from a singlet excited state to a singlet ground state in an organic light emitting device with an internal quantum efficiency of greater than 9% at room temperature.

In one embodiment, L is a direct bond. In one embodiment, L is a divalent aryl or heteroaryl. In one embodiment, L comprises 2-36 carbon atoms. In one embodiment, L comprises an aromatic group. In one embodiment, L comprises a carbocyclic group.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

E-type delayed fluorescence does not rely on the collision of two triplets, but rather on the thermal population between the triplet states and the singlet excited states. Compounds that are capable of generating E-type delayed fluorescence are required to have very small singlet-triplet gaps. Thermal energy can activate the transition from the triplet state back to the singlet state. This type of delayed fluorescence is also known as thermally activated delayed fluorescence (TADF). A distinctive feature of TADF is that the delayed component increases as temperature rises due to the increased thermal energy. If the reverse intersystem crossing rate is fast enough to minimize the non-radiative decay from the triplet state, the fraction of back populated singlet excited states can potentially reach 75%. The total singlet fraction can be 100%, far exceeding the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic ring.

In one embodiment, the organic layer further comprises a host, wherein the host comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In one embodiment, the organic layer further comprises a host, wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

In one embodiment, the host is selected from the group consisting of:

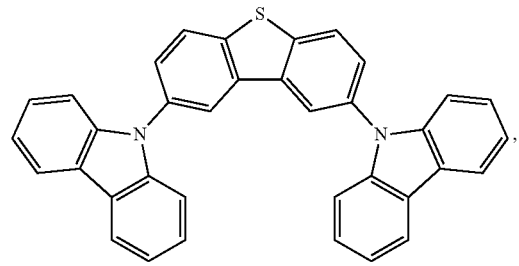

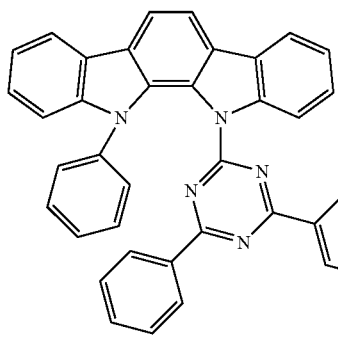

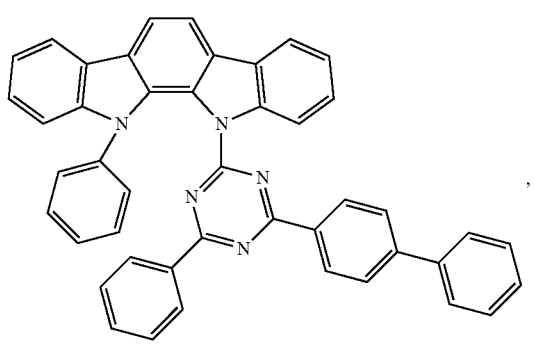

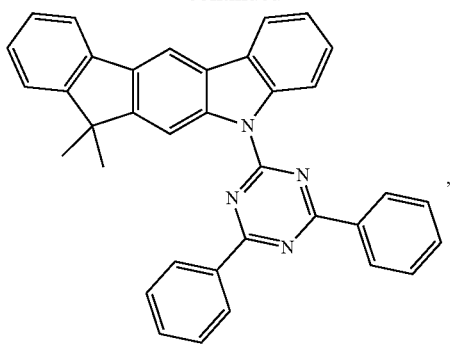

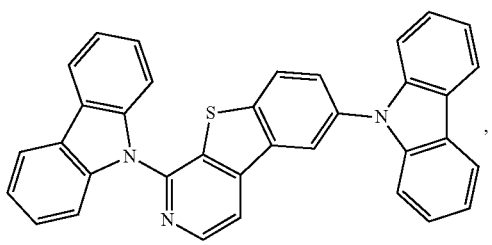

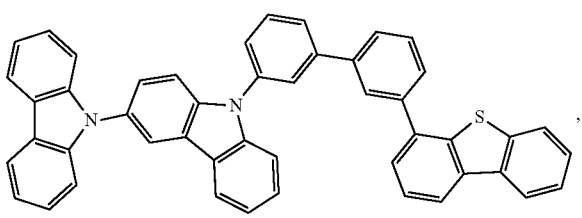

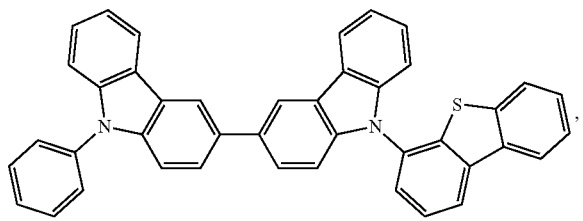

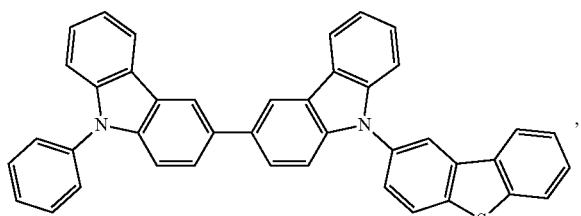

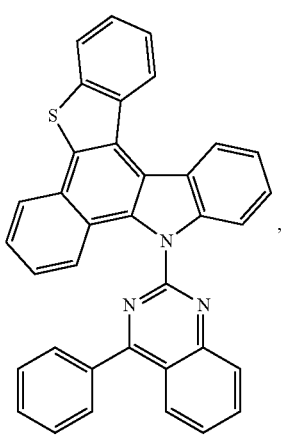

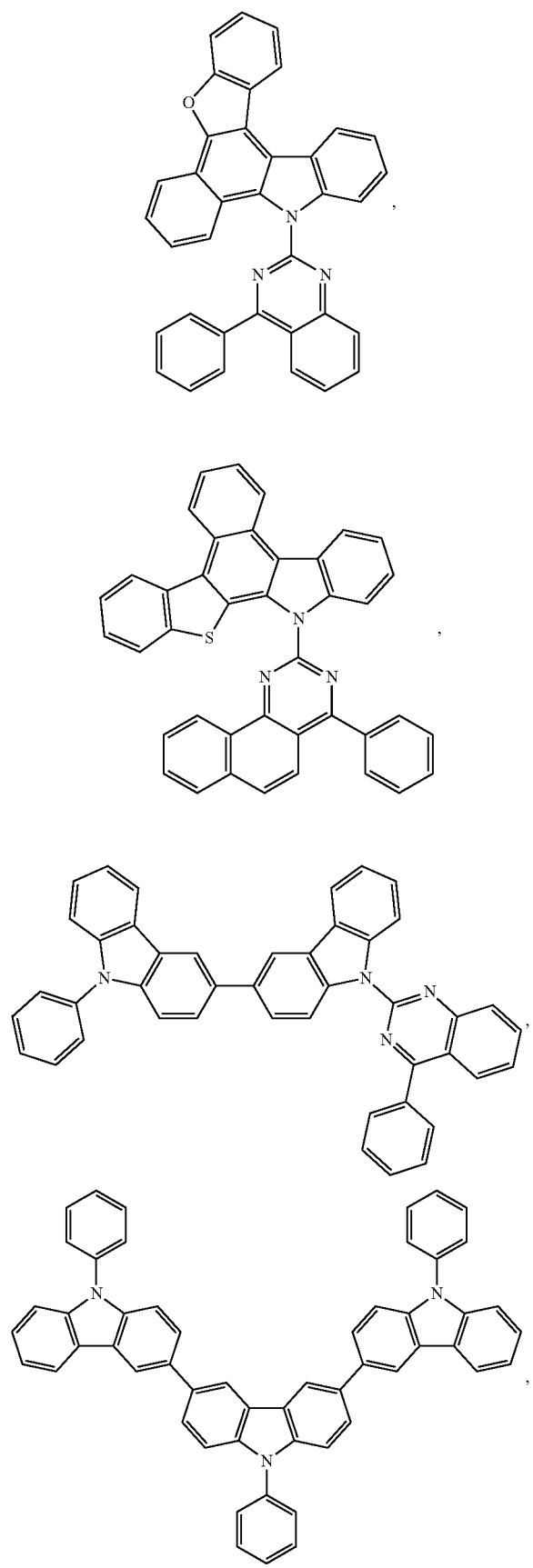
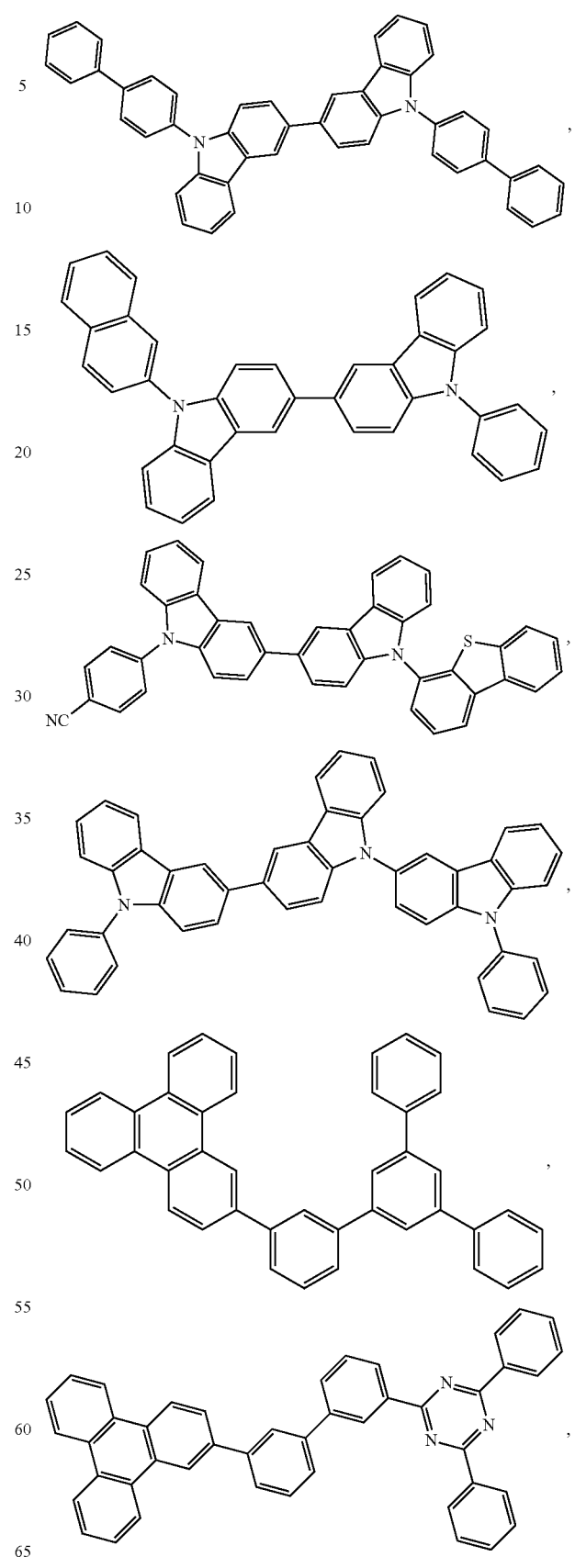

-continued

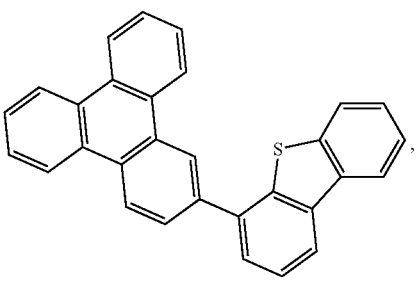

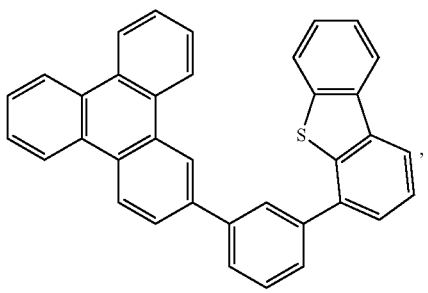

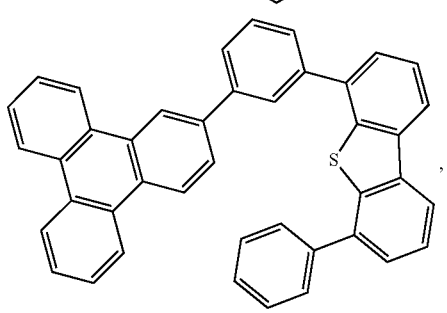

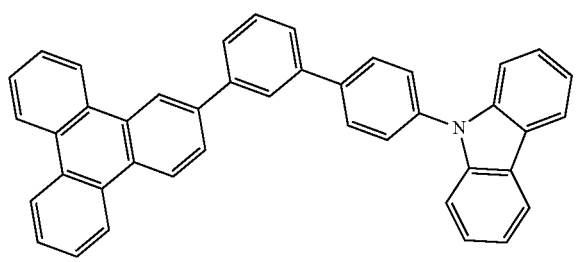

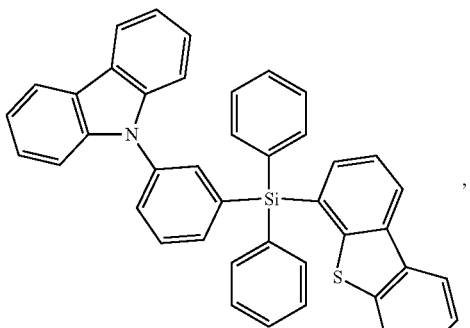

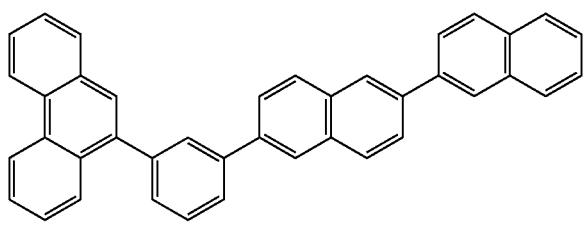

-continued

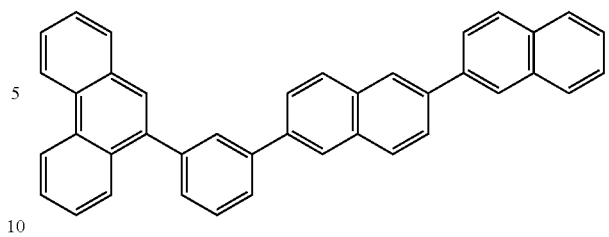

and combinations thereof.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The invention is also directed to a consumer product comprising an organic light emitting device (OLED) described above. The OLED comprises an anode; a cathode; and an organic layer, disposed between the anode and the cathode. In one embodiment, the organic layer includes a compound selected from the group consisting of Formulae BB, BC, BD, BE, BF, and BF:

BB
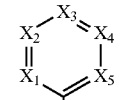

BC
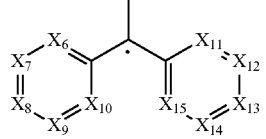

BD
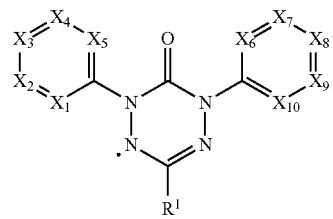

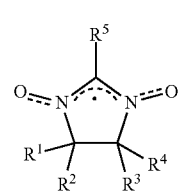

-continued

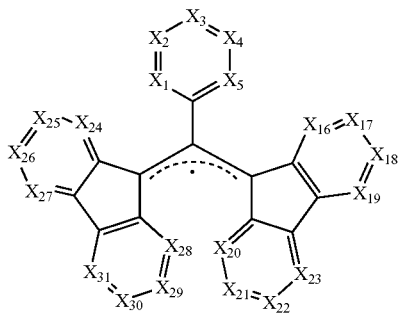
BE

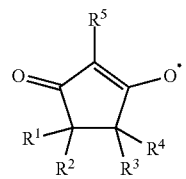
BF

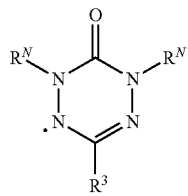
BG wherein $X_1$ to $X_5$ are independently selected from $CR^A$ or N;
$X_6$ to $X_{10}$ are independently selected from $CR^B$ or N;
$X_{11}$ to $X_{15}$ are independently selected from $CR^C$ or N;
$X_{16}$ to $X_{23}$ are independently selected from $CR^D$ or N;
$X_{24}$ to $X_{31}$ are independently selected from $CR^E$ or N;
$R^A$, $R^B$, $R^C$, $R^D$, and $R^E$ independently represent mono to the maximum allowable substitution, or no substitution;

each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;

$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;

wherein at least one of $R^1$ to $R^5$, $R^A$, $R^B$, $R^C$, $R^D$, or $R^E$ includes a polycyclic group selected from the group consisting of:

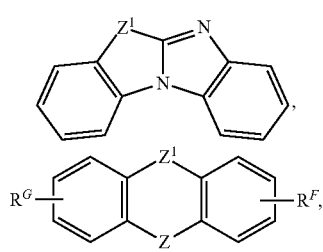

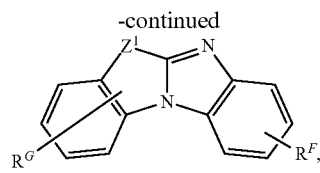

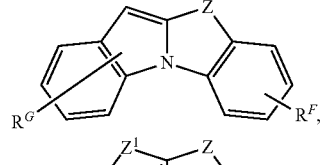

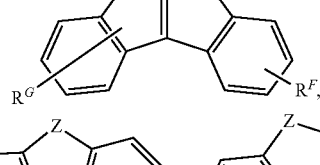

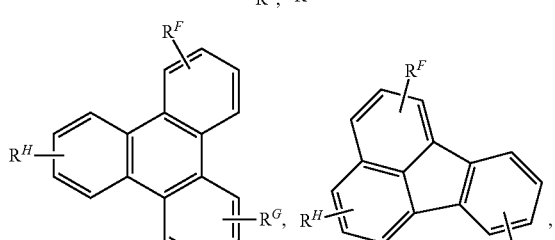

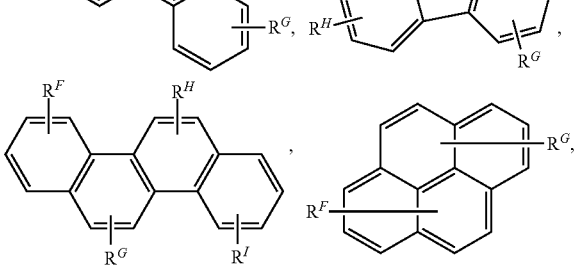

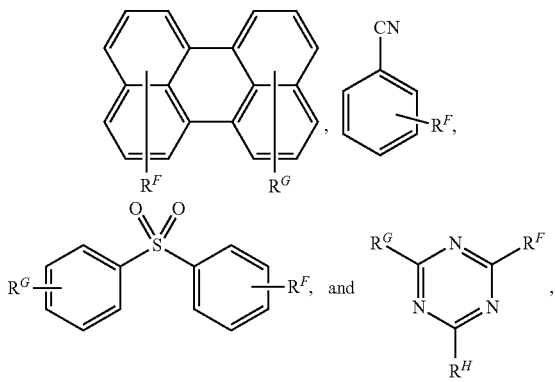

and any aza analogue of each thereof, each of which is optionally substituted with $R^P$, wherein $R^P$ is selected from the group consisting of deuterium, fluorine, alkyl, cycloalkyl, amino, aryl, heteroaryl, silyl, nitrile, and combinations thereof;

wherein $R^F$ to $R^I$ are independently selected from the group consisting of deuterium, fluorine, alkyl, cycloalkyl, amino, aryl, heteroaryl, silyl, nitrile, and combinations thereof, and Z and $Z^1$ are independently selected from the group consisting of O, S, Se, $NR^N$, $CR^1CR^2$, $SiR^1R^2$, and $GeR^1R^2$;

with the proviso that the following compound is excluded

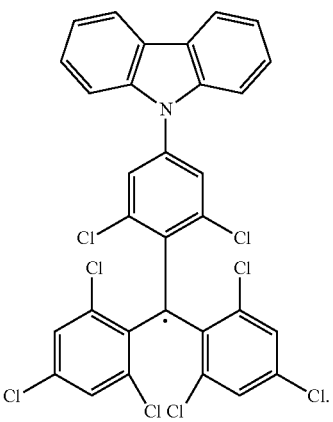

The present invention also includes a consumer product comprising an organic light emitting device (OLED) comprising an anode; a cathode; and an organic layer disposed between the anode and the cathode. In one embodiment, the organic layer includes a compound of formula A-L-B or Ai-Li-Bk described above. Alternatively, the OLED comprises an organic layer with a mixture of a Component A and a Component B as described above.

The present invention also includes a consumer product comprising an organic light emitting device (OLED) comprising an anode; a cathode; and an organic layer disposed between the anode and the cathode. In one embodiment, the organic layer includes a formulation comprising a Component A that functions as a fluorescent emitter in an organic light emitting device at room temperature; and a Component B. Component A is a fluorescent emitter that includes fluorescent compounds known and referred to in the art as thermally-assisted delayed fluorescence emitters. Alternatively, Component A is a structure listed in Table 1 below. Component B comprises a structure selected from the group consisting of Formulae BB, BC, BD, BE, BF, and BF, above; and L is a direct bond or an organic linker. Alternatively, Component B is B1 to B10 listed in Table 1 above. For the more preferred formulations, the molar ratio of Component A to Component B in the formulation is from 95:5 to 60:40, e.g., from 95:15 to 80:20, from 90:10 to 70:30.

In one embodiment, the consumer product is selected from the group consisting of a flat panel display, a curved display, a computer monitor, a medical monitor, a television, a billboard, a light for interior or exterior illumination and/or signaling, a heads-up display, a fully or partially transparent display, a flexible display, a rollable display, a foldable display, a stretchable display, a laser printer, a telephone, a mobile phone, a tablet, a phablet, a personal digital assistant (PDA), a wearable device, a laptop computer, a digital camera, a camcorder, a viewfinder, a micro-display less than 2 inches diagonal), a 3-D display, a virtual reality or augmented reality display, a vehicle, a video wall comprising multiple displays tiled together, a theater or stadium screen, and a sign.

In one embodiment, the consumer product is a virtual reality or augmented reality display.

The organic layer can also include a host. In some embodiments, two or more hosts are preferred. In some embodiments, the hosts used may be a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

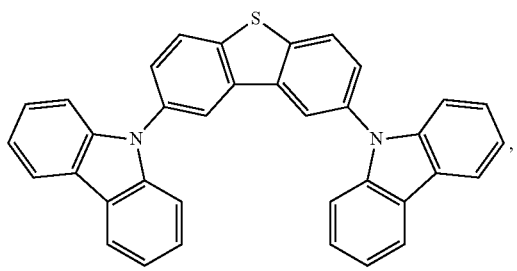

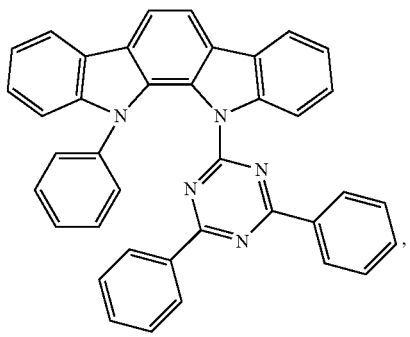

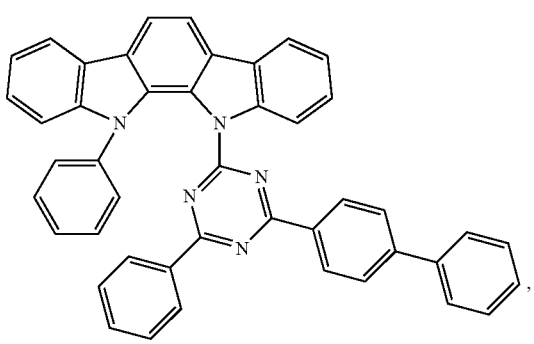

147
-continued
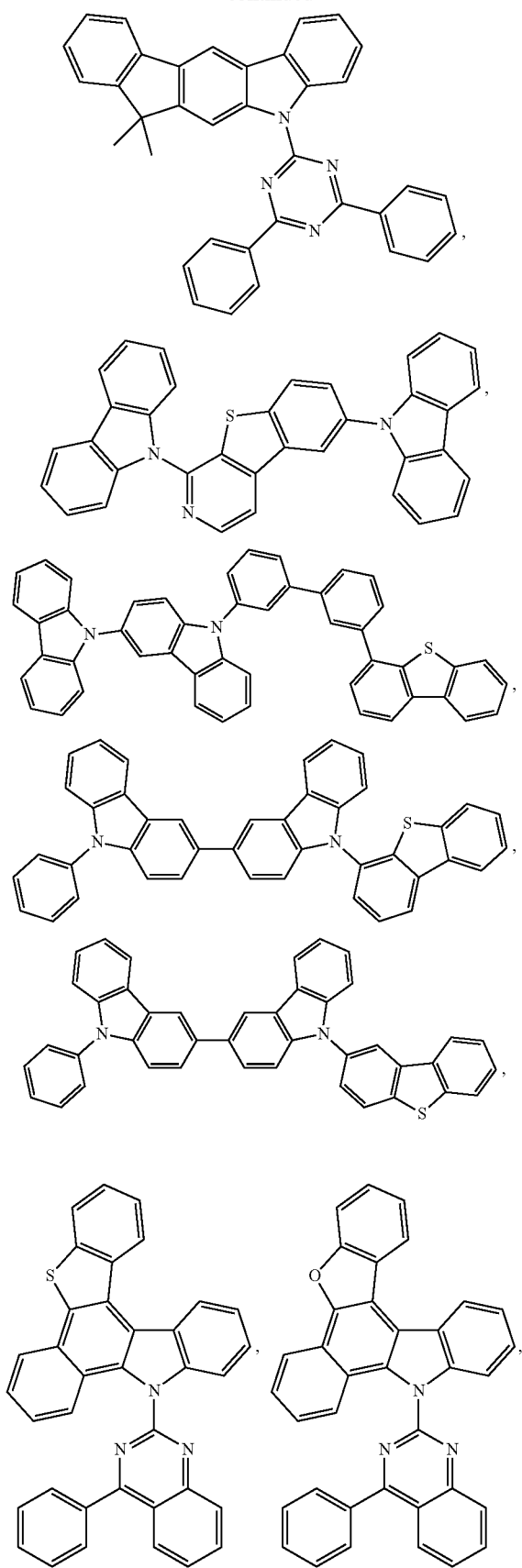
148
-continued
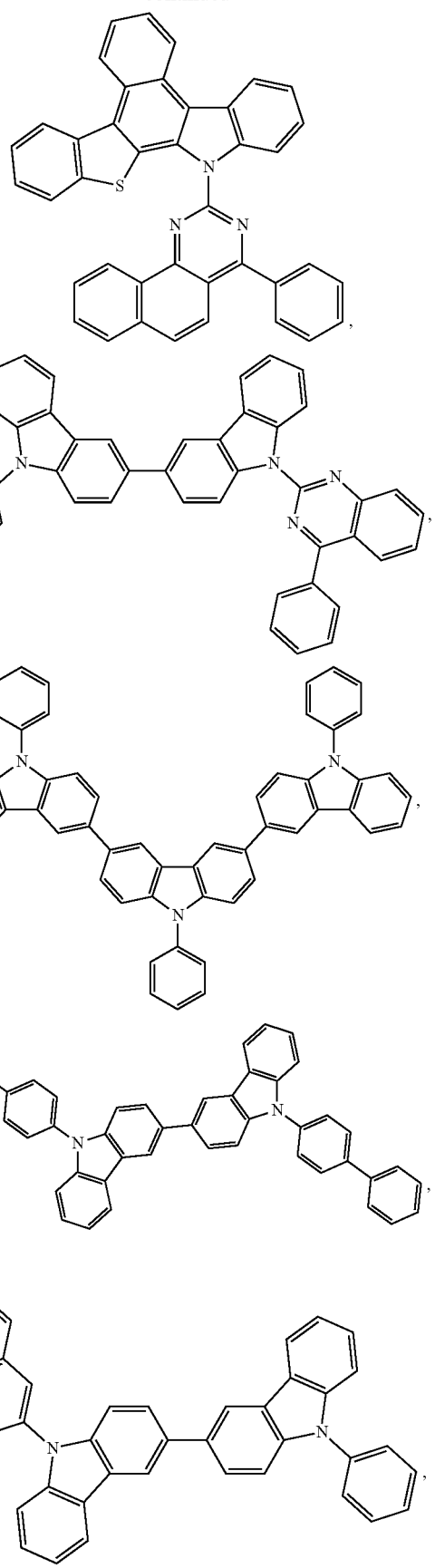

149
-continued

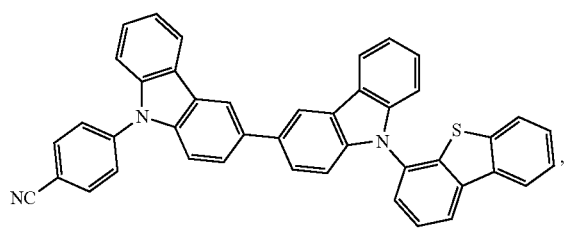

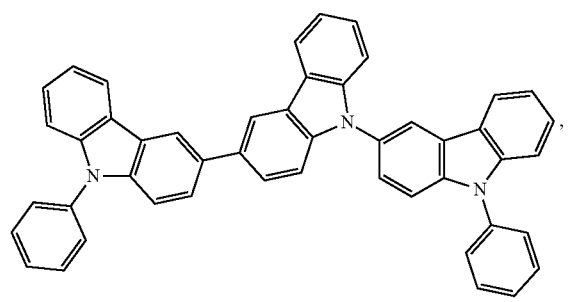

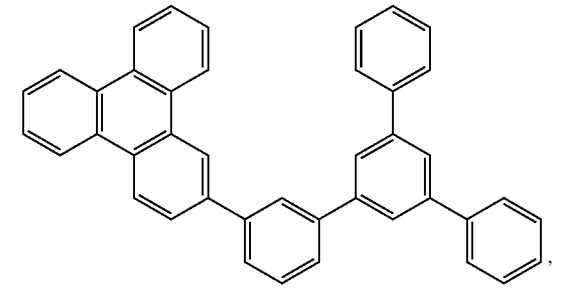

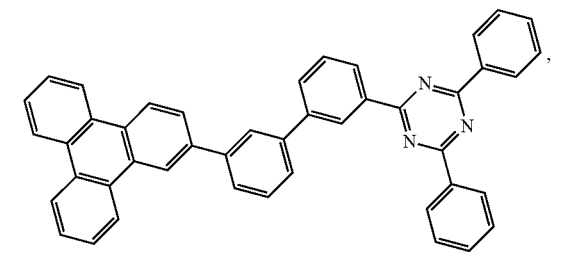

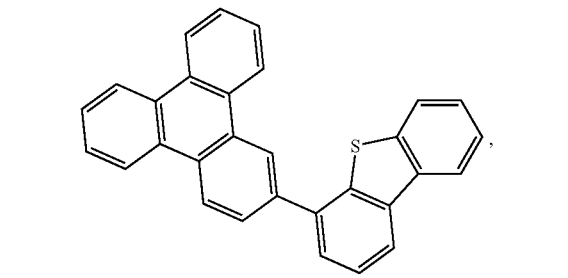

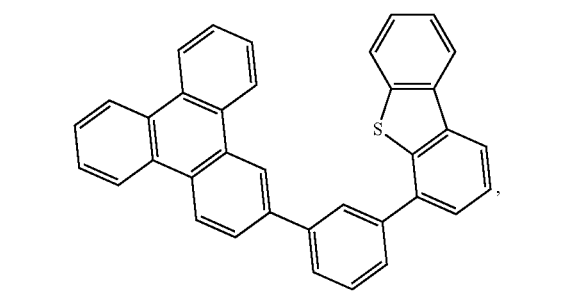

150
-continued

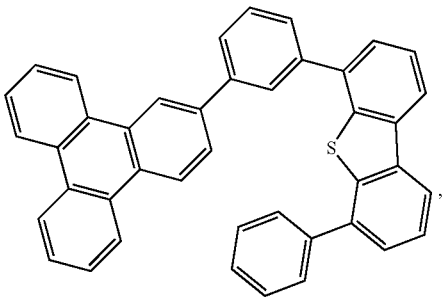

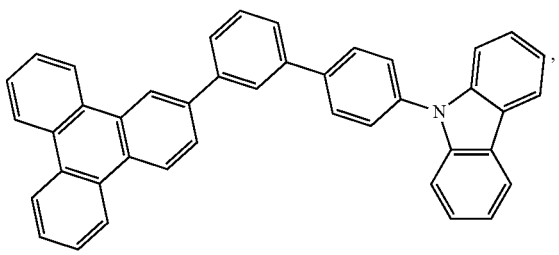

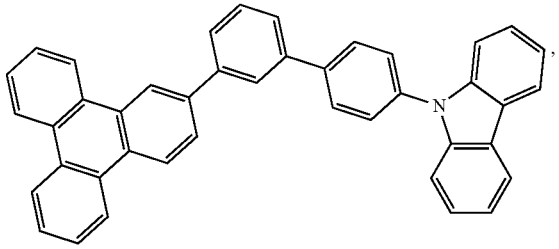

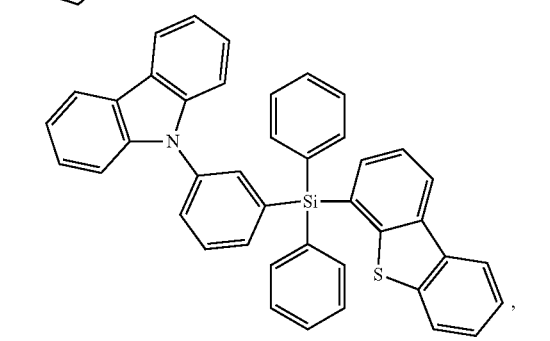

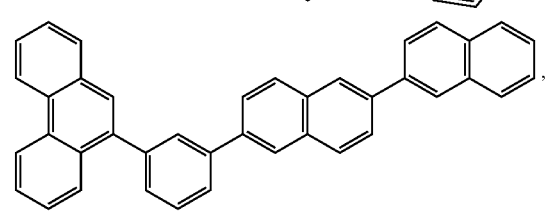

and combinations thereof.

Additional information on possible hosts is provided below.

The invention is also directed to a formulation that comprises one or more of the compounds described herein. The formulation can include one or more components selected from the group consisting of a solvent, a host, a hole injection material, hole transport material, electron blocking material, hole blocking material, and an electron transport material, disclosed herein.

In one embodiment. Component A comprises one or more structures selected from the group consisting of:

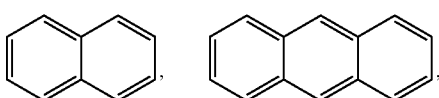
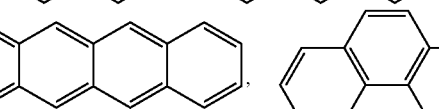

151

-continued

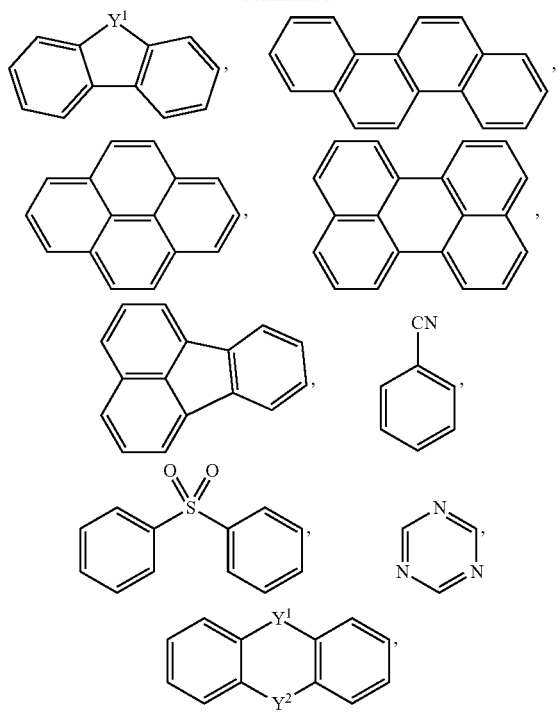

and aza-analogues thereof;

wherein $Y^1$ and $Y^2$ are each independently selected from the group consisting of O, S, Se, NR' and CR'R"; wherein R' and R" are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent substituents of R' and R" can join to form a ring.

In one embodiment, Component A comprises one or more structures selected from the group consisting of:

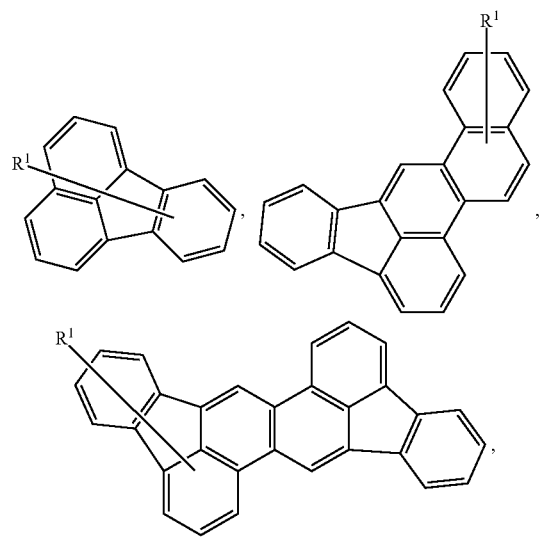

152

-continued

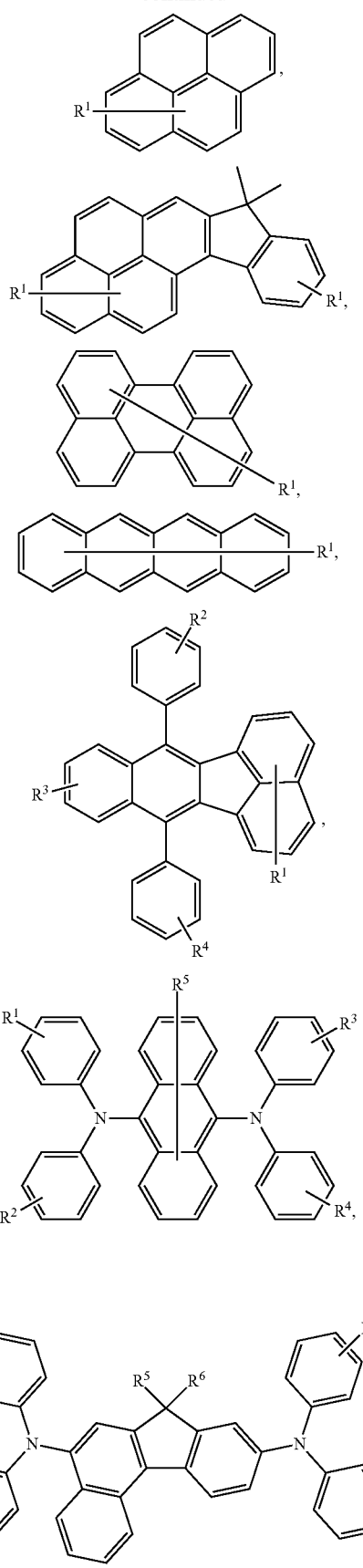

153
-continued
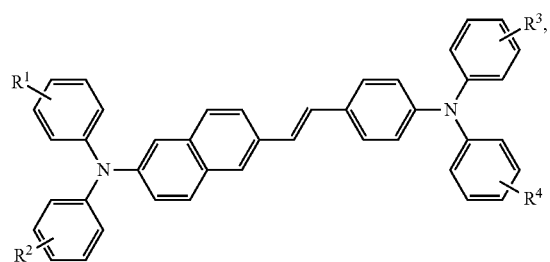
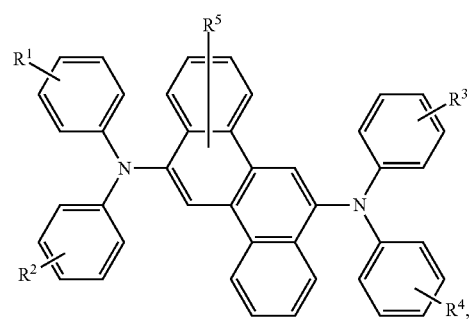
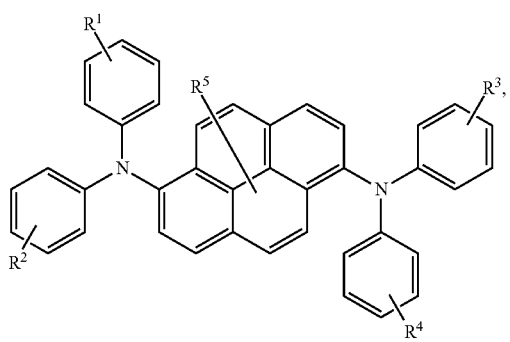
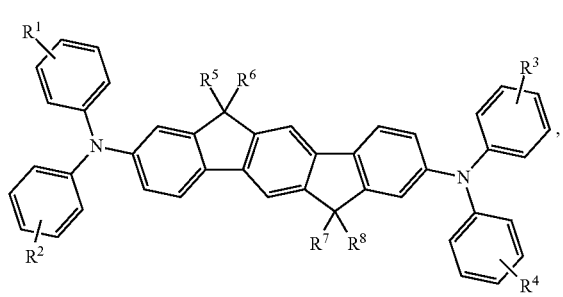
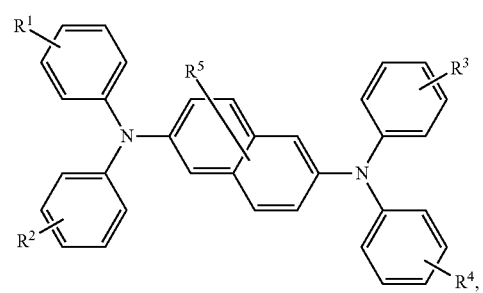
154
-continued
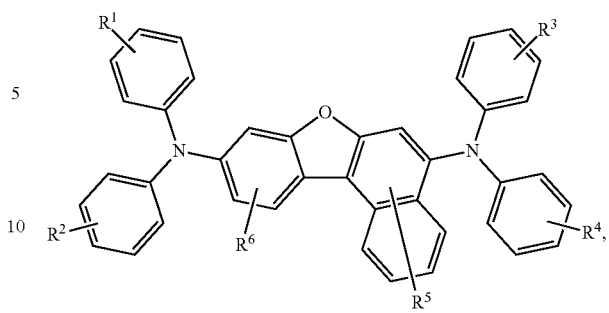
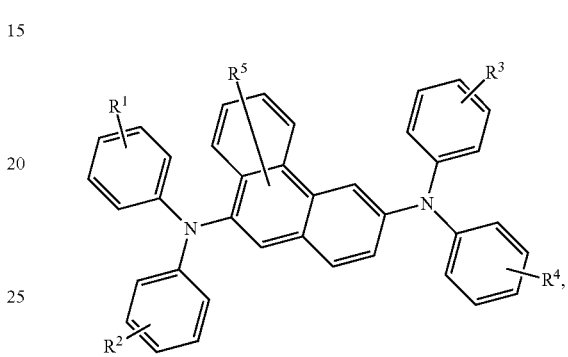
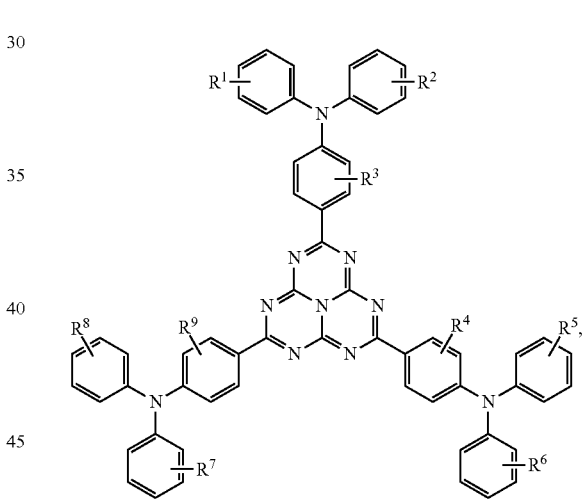
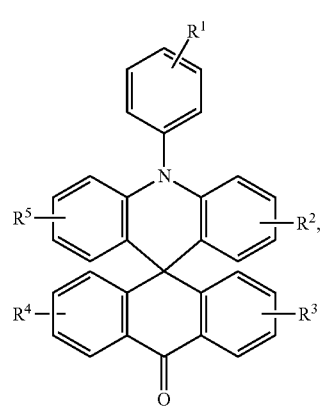

-continued

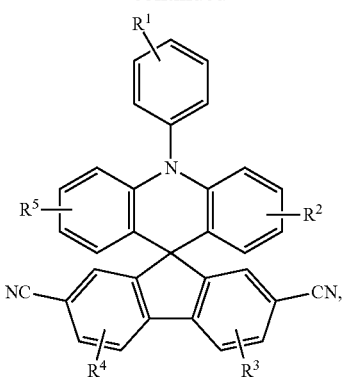

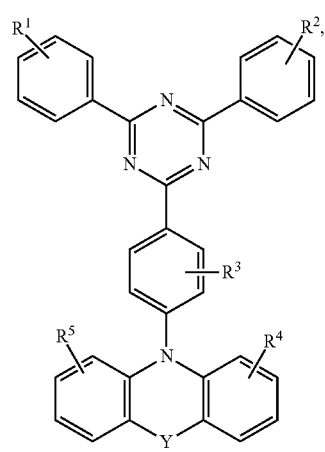

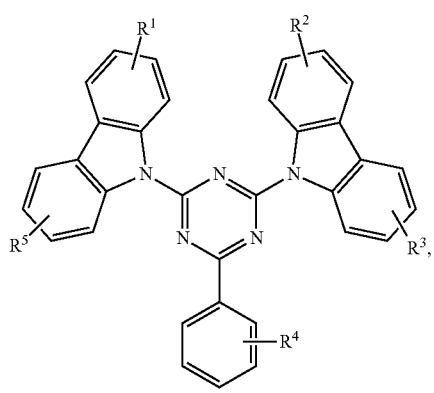

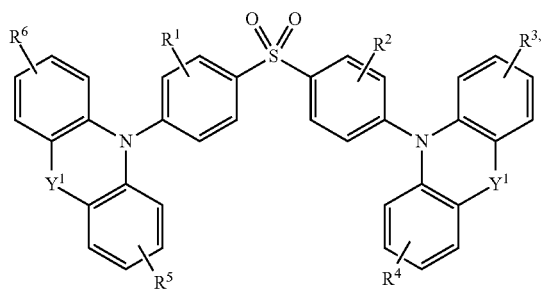

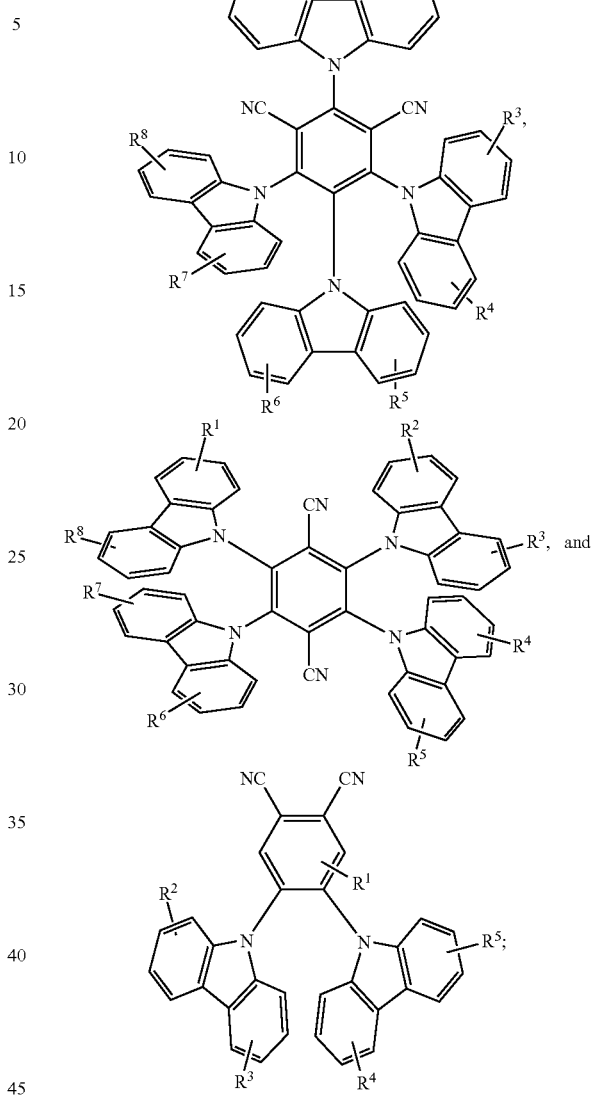

wherein $R^1$ to $R^9$ each independently represent from mono to maximum number of substitutions they can have, or no substitution; wherein $R^1$ to $R^9$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein each $Y^1$ is the same or different and is selected from the group consisting of O, S, Se, $NR_N$ and CR'R"; wherein $R^N$, R', and R" are defined above.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

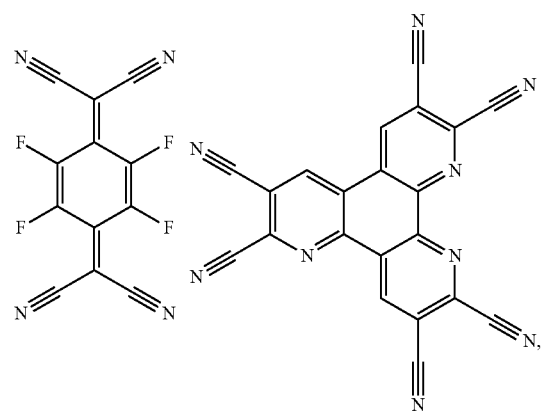

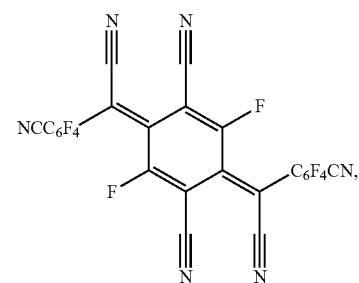

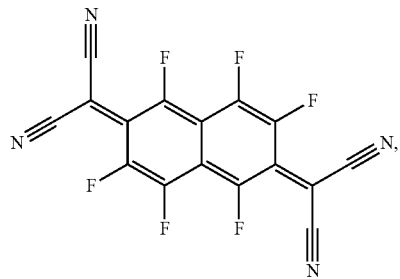

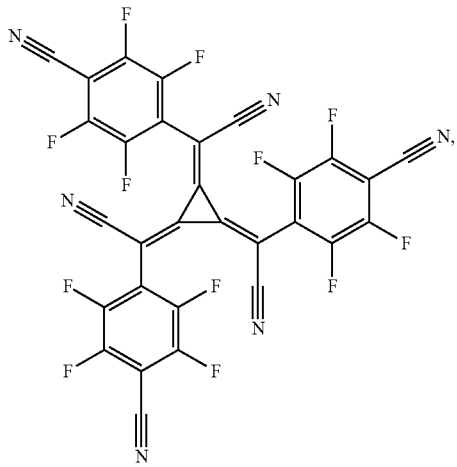

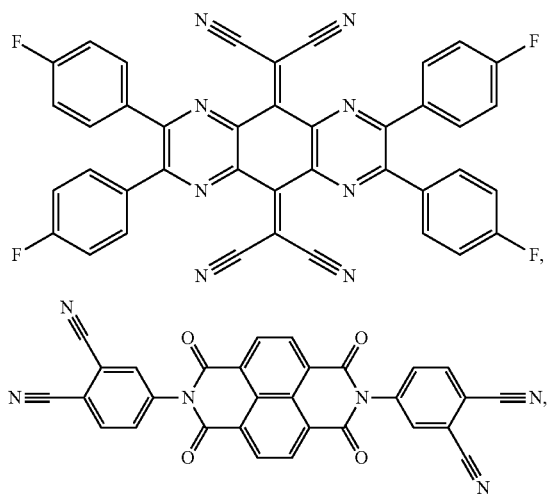

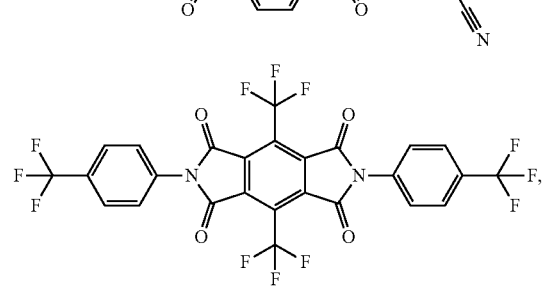

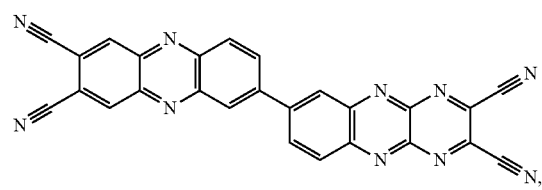

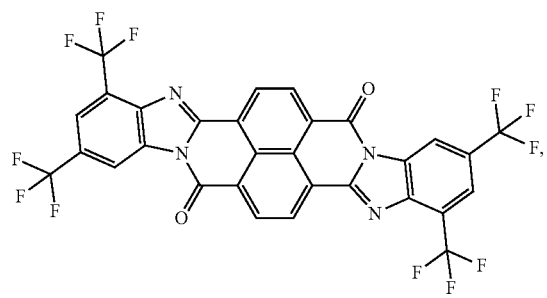

-continued

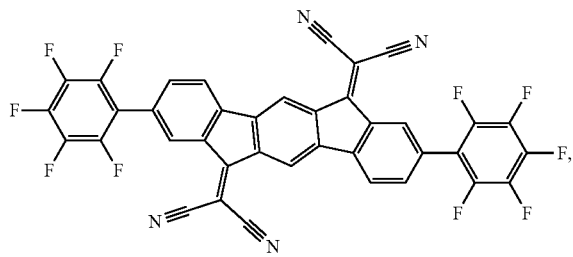

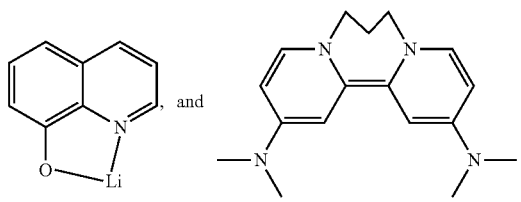

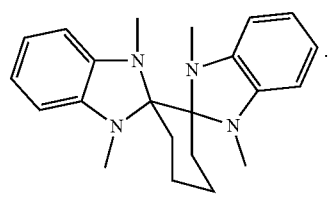

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

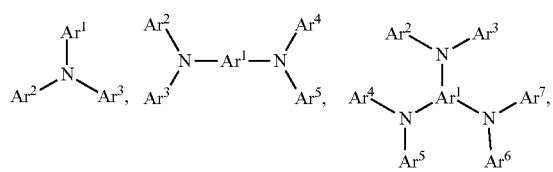

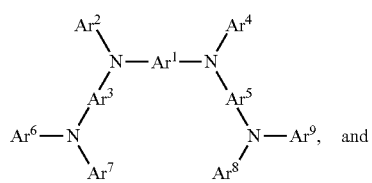

-continued

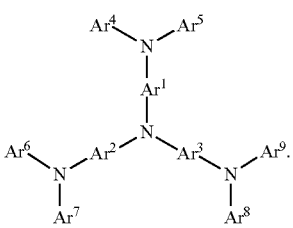

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

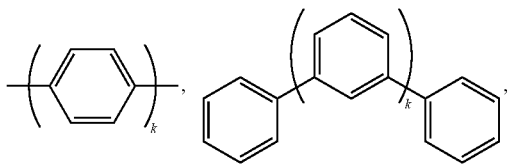

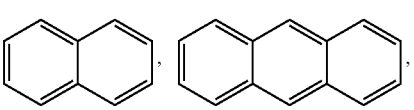

-continued

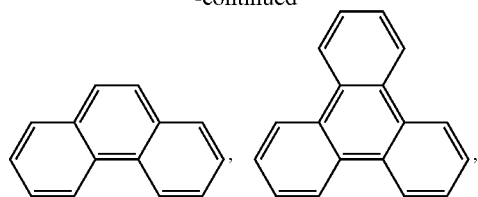

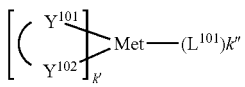

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

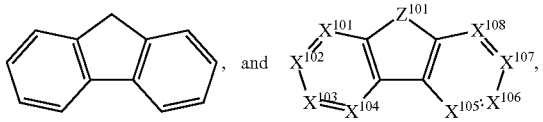

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

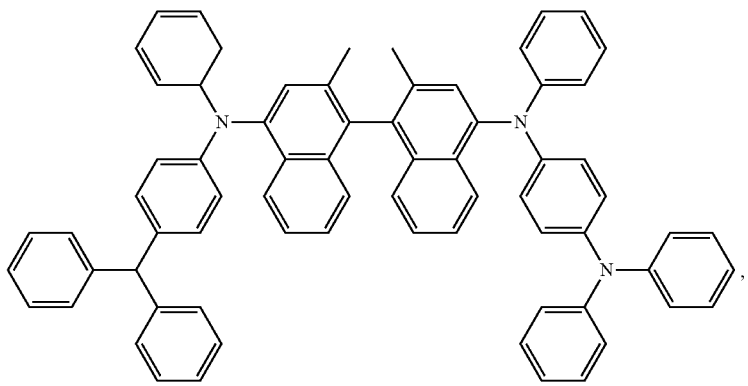

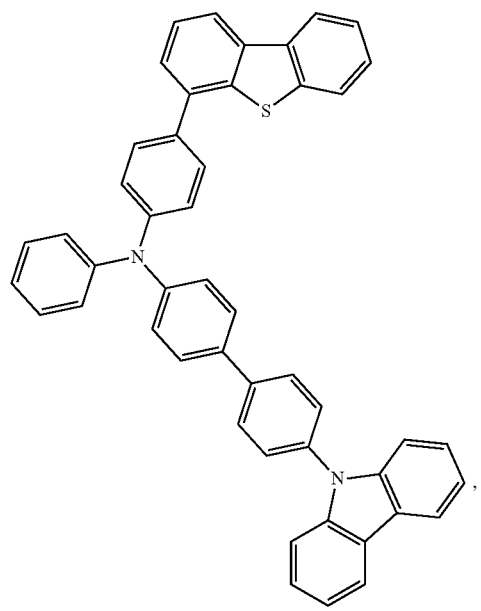
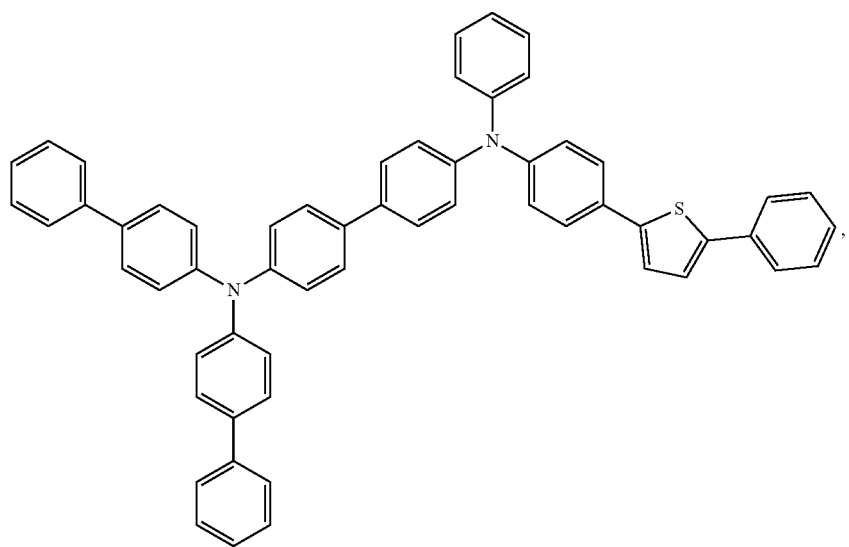
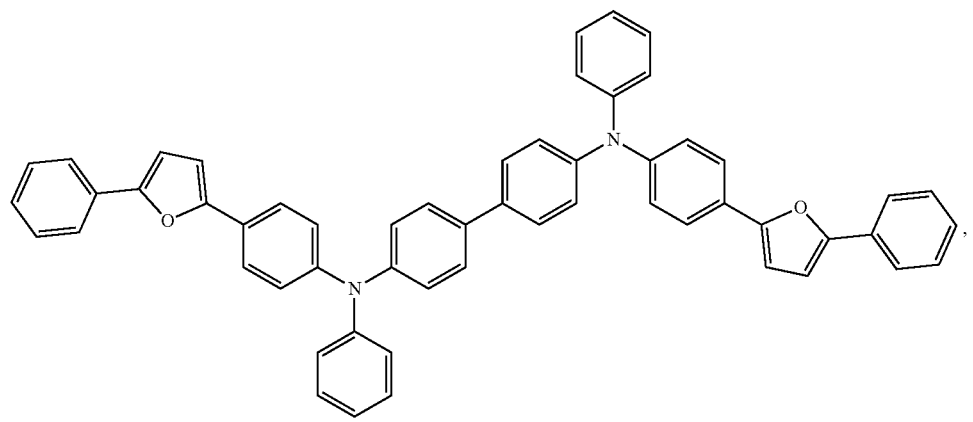

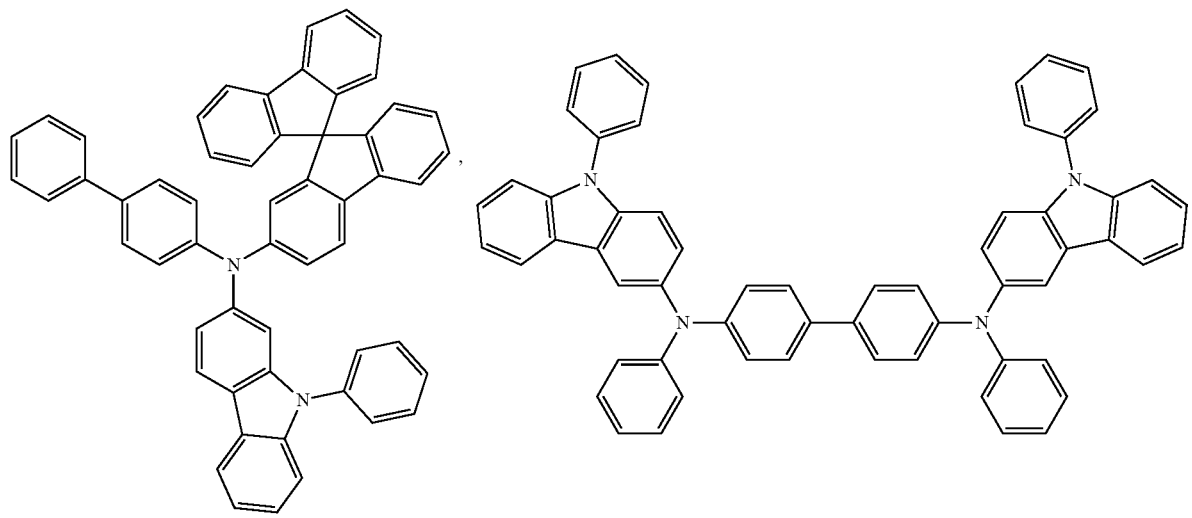
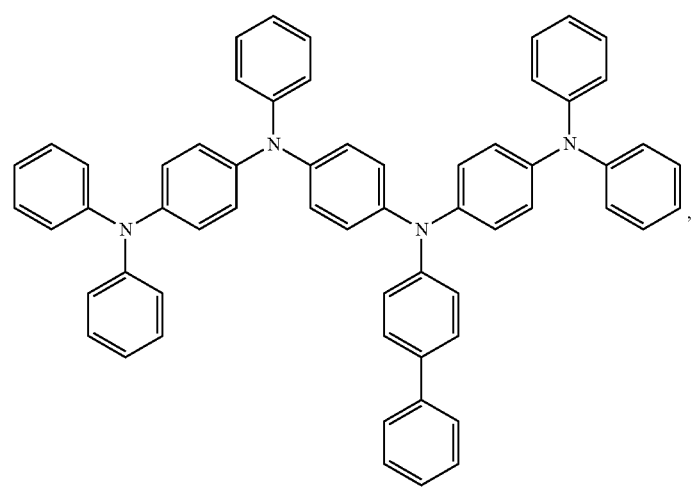
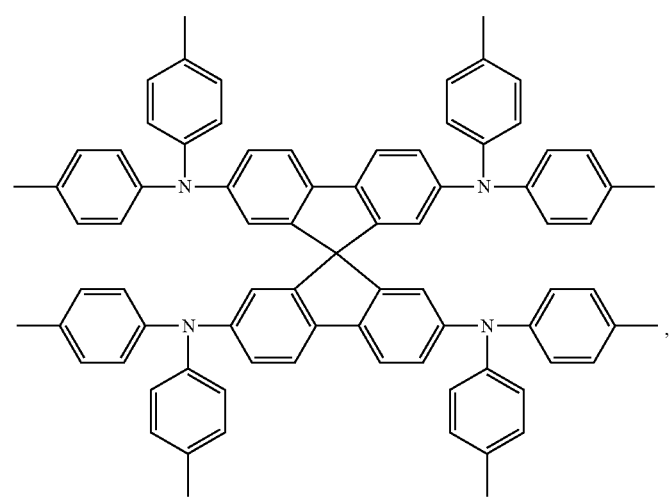

-continued
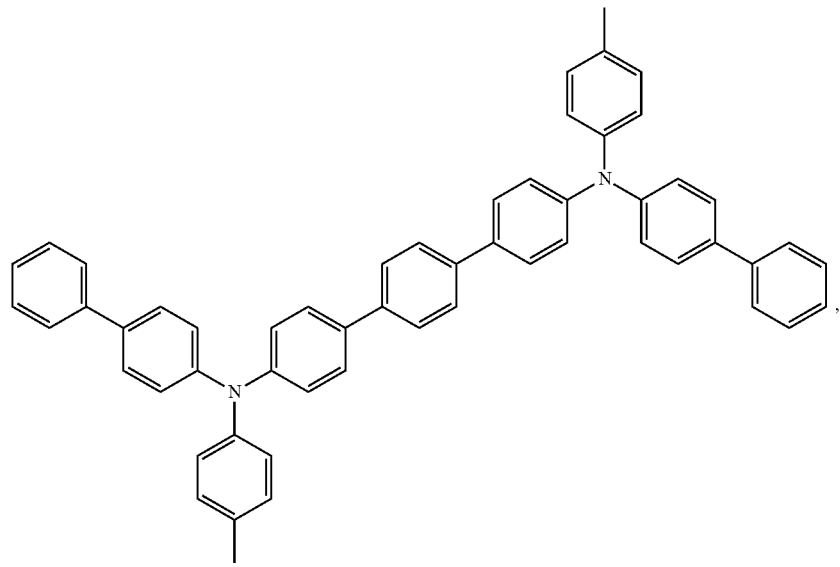
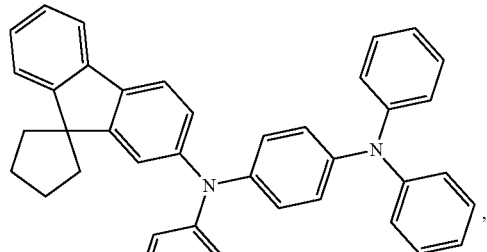
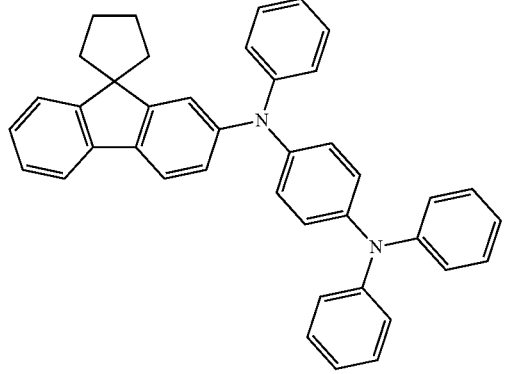
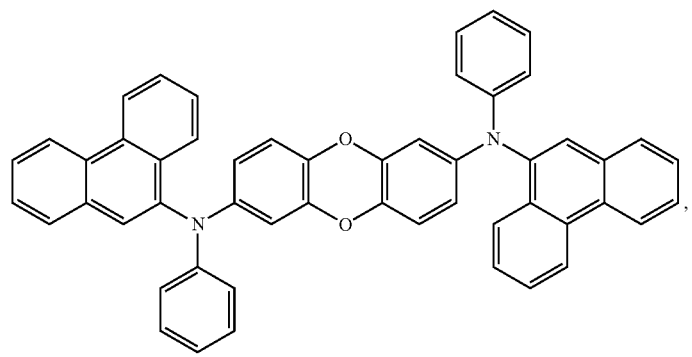

-continued
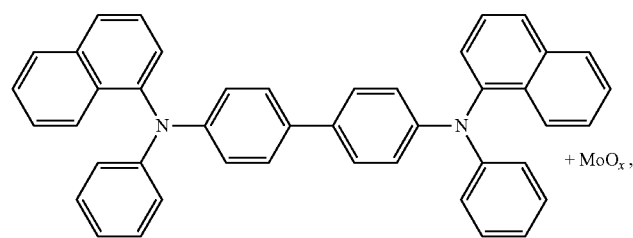
+MoOx,
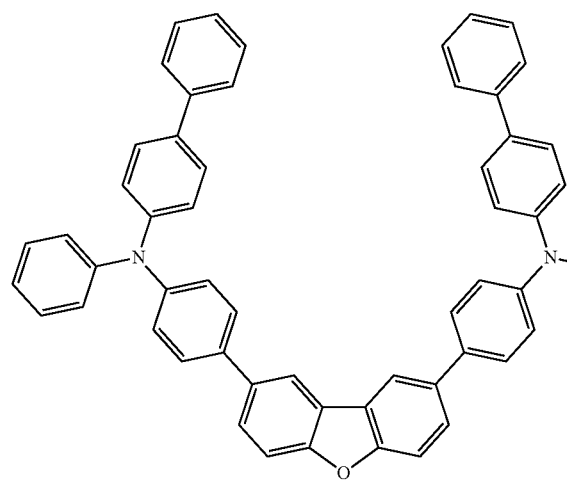
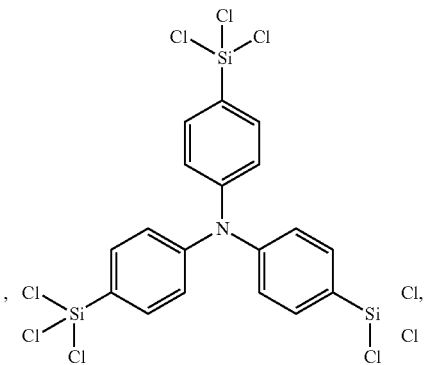
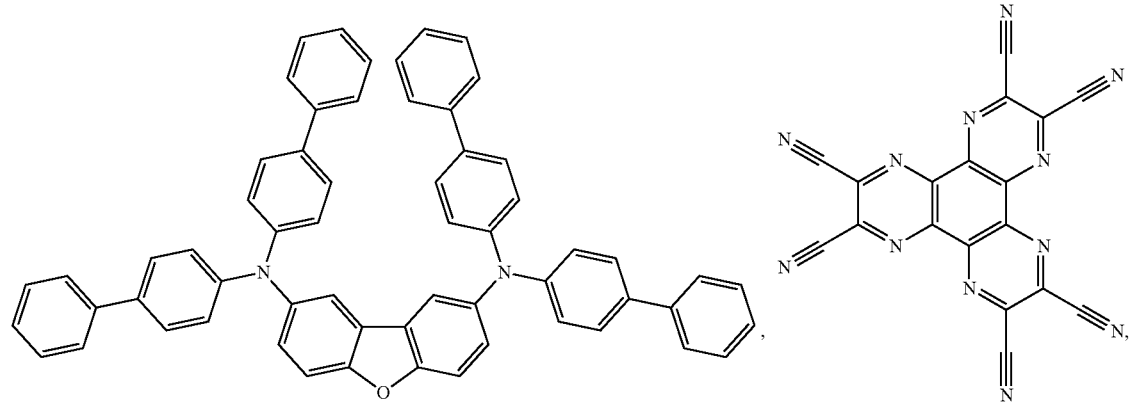
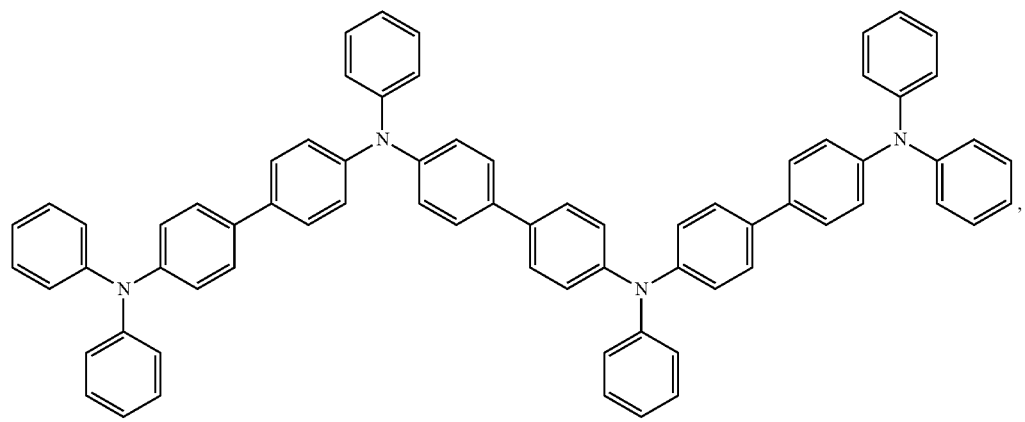

-continued
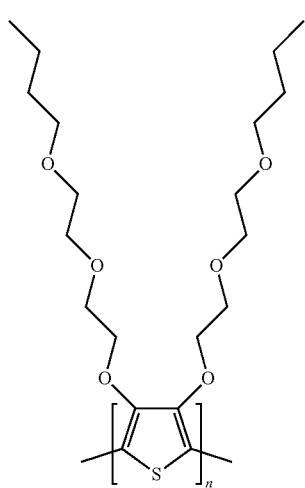 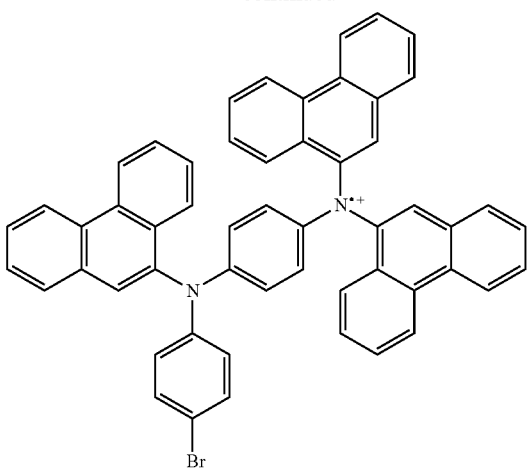
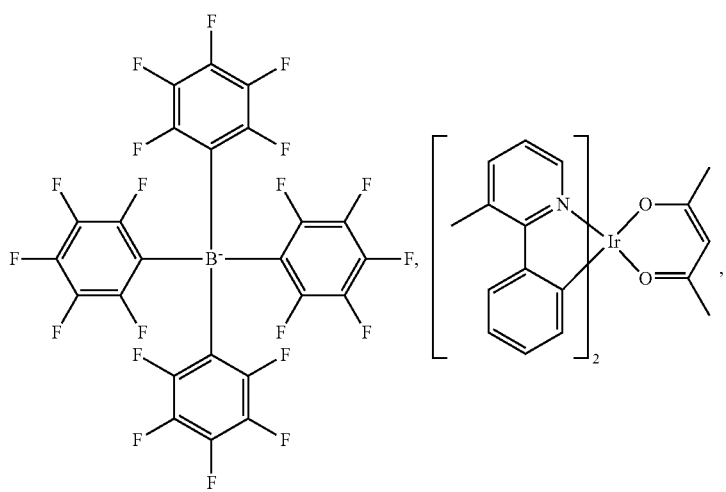
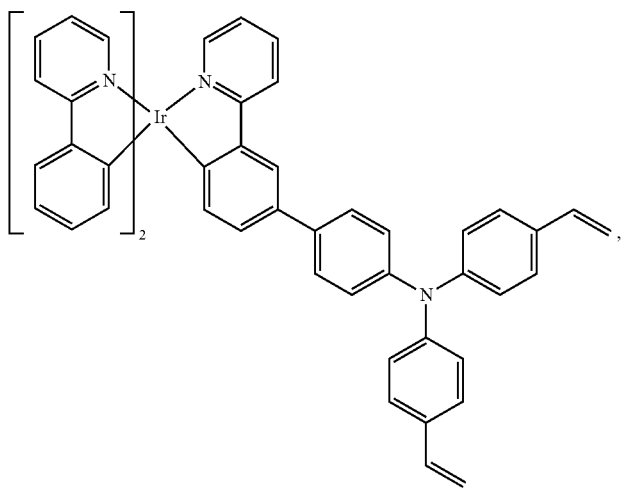

-continued
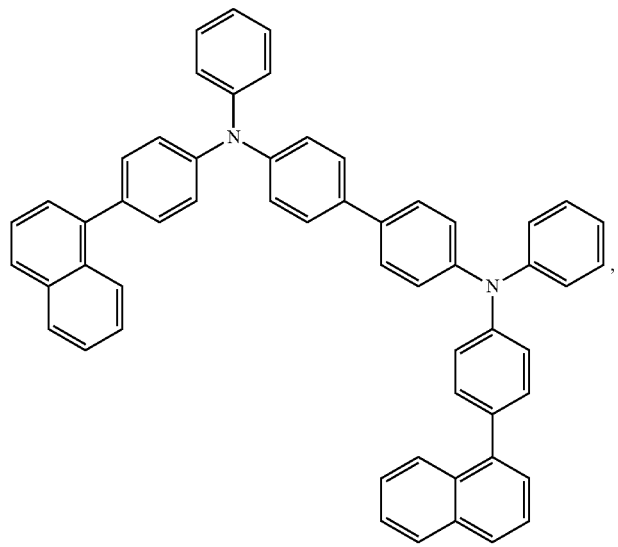
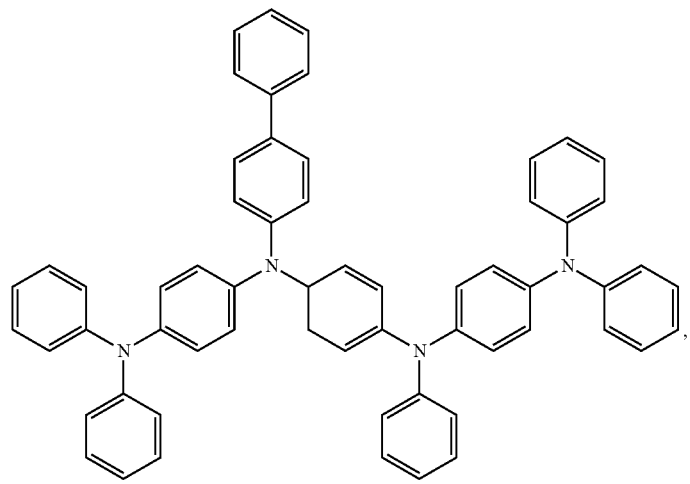
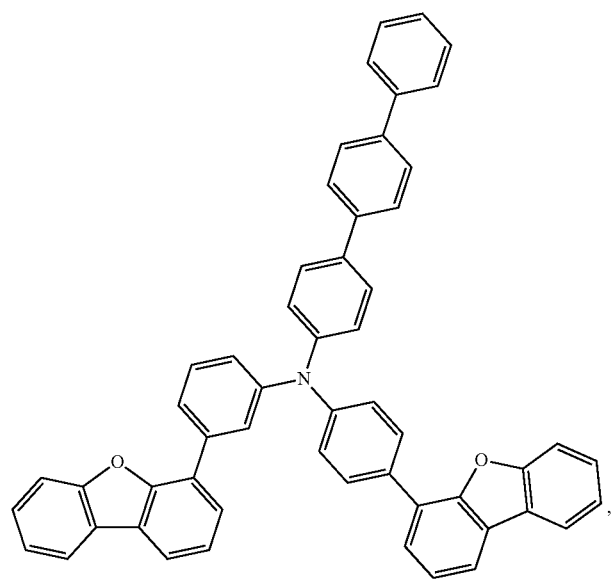

-continued
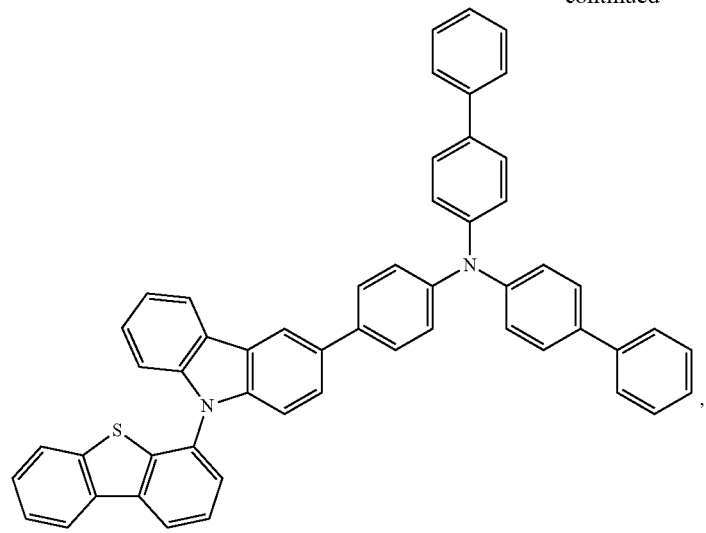
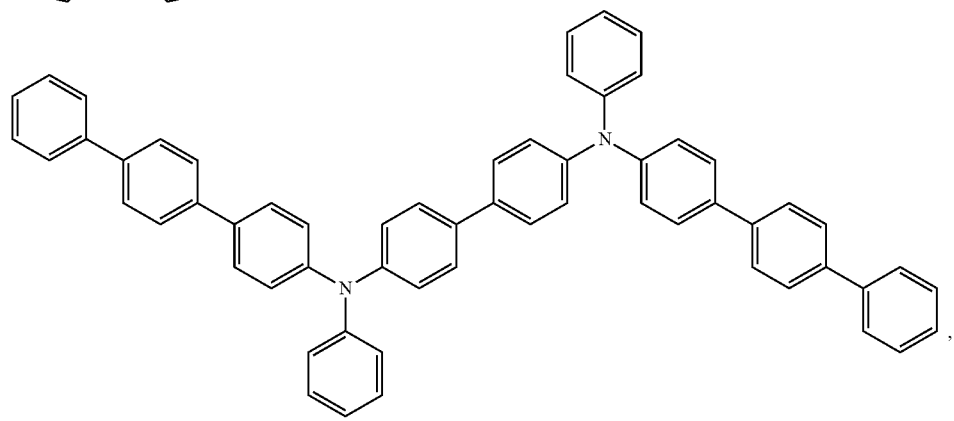
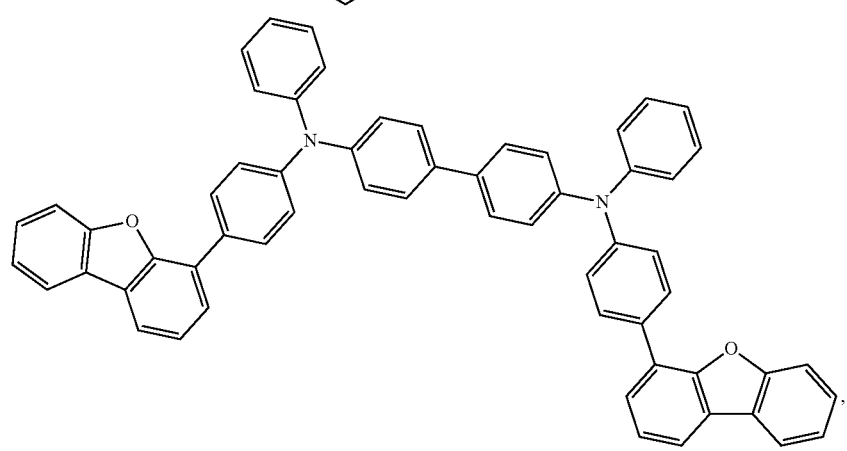
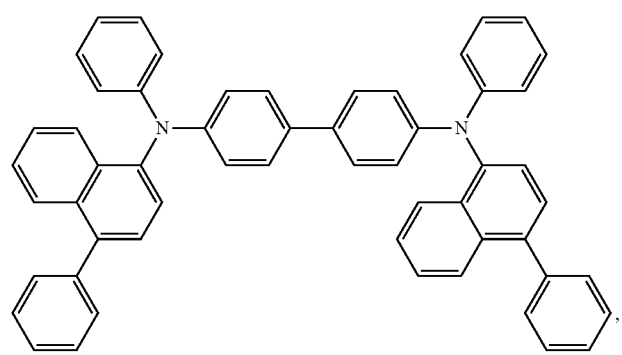

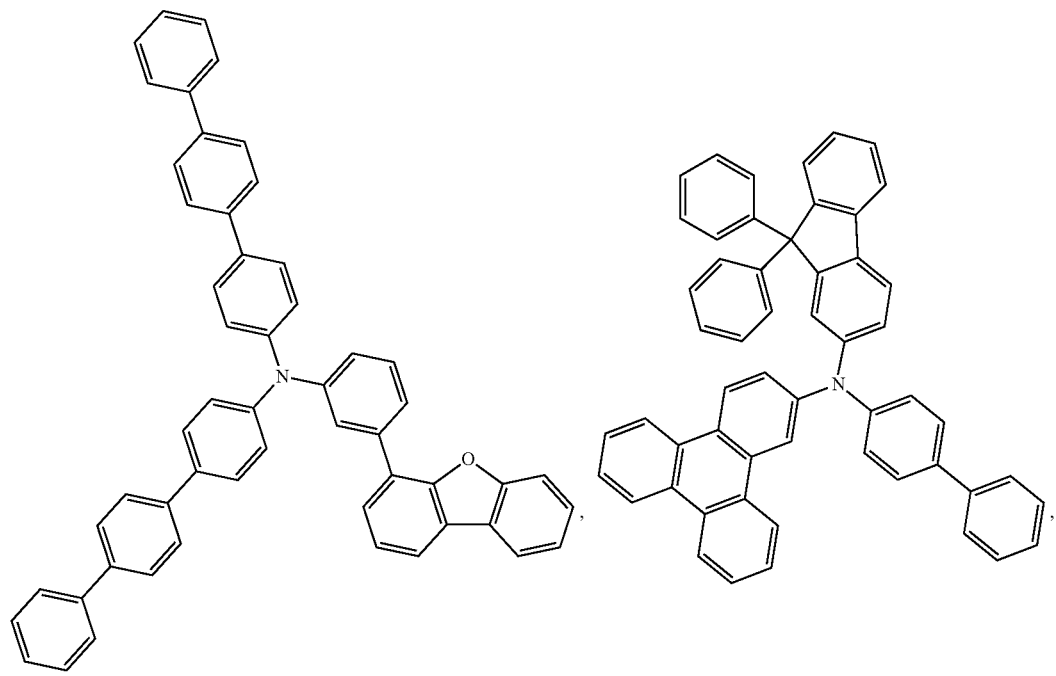
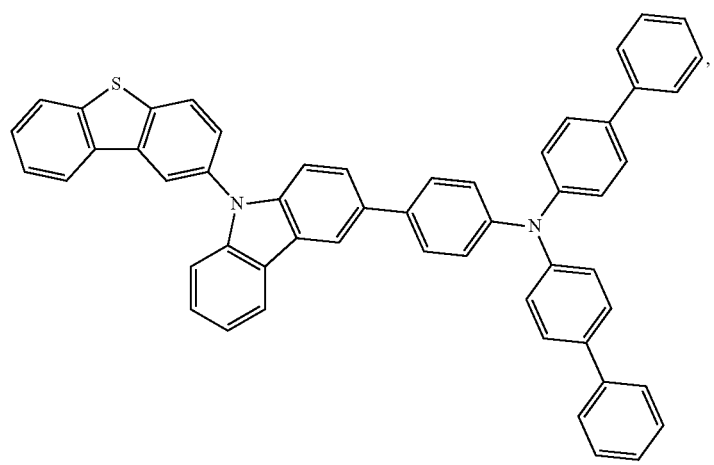
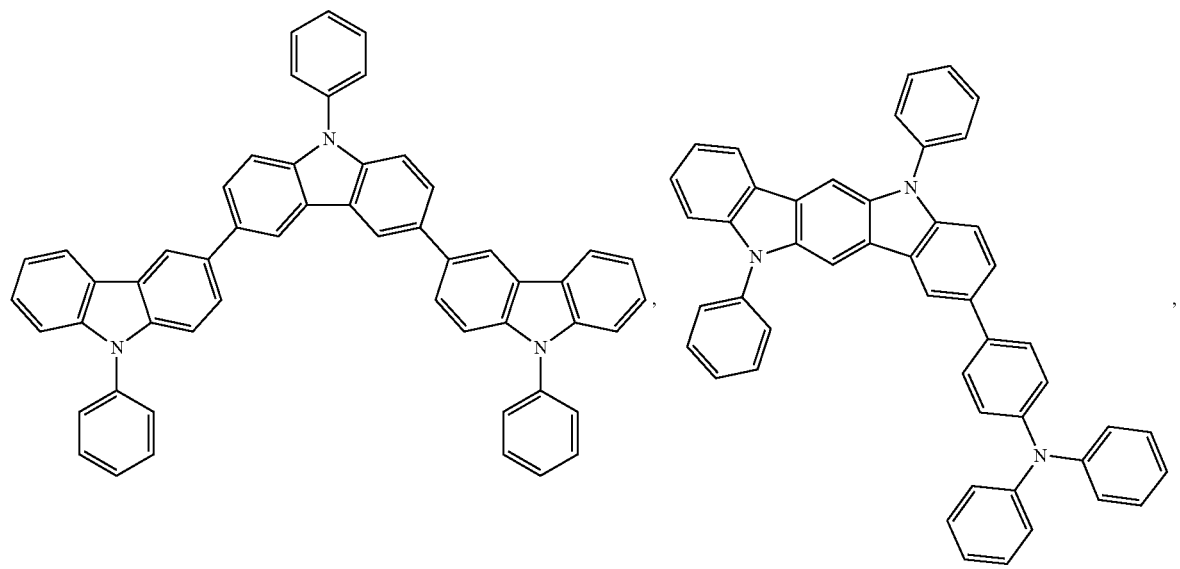

-continued
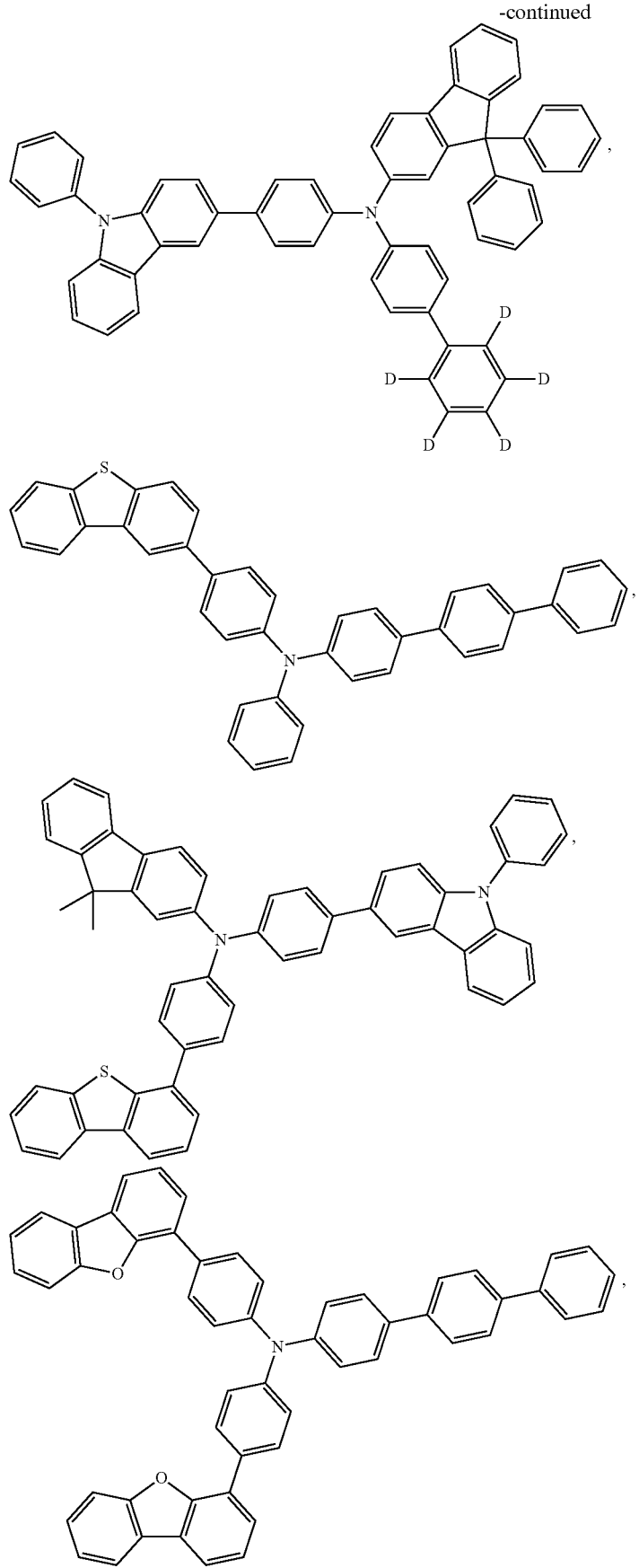

181 182
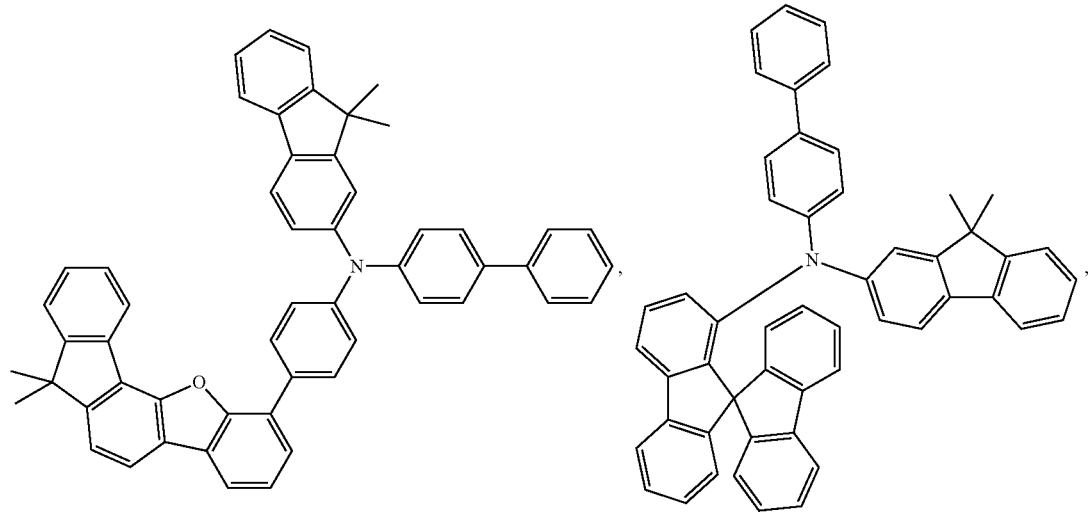
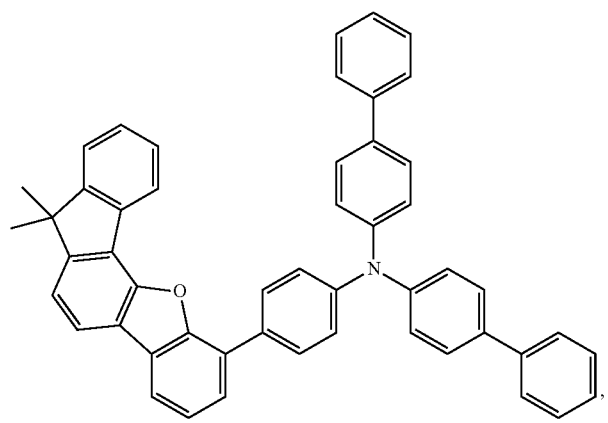
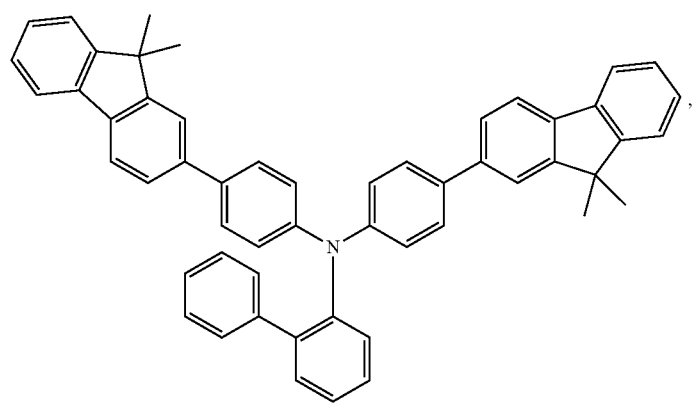

-continued
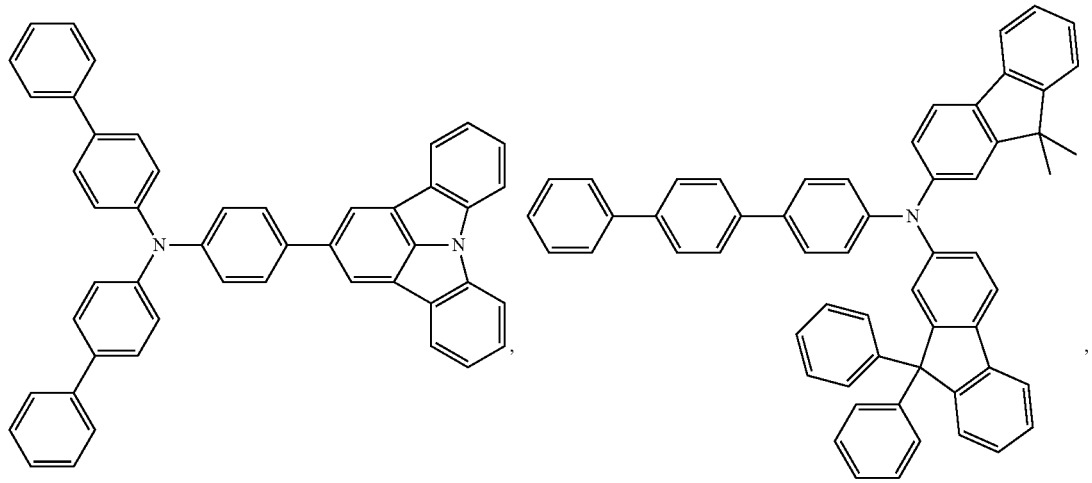
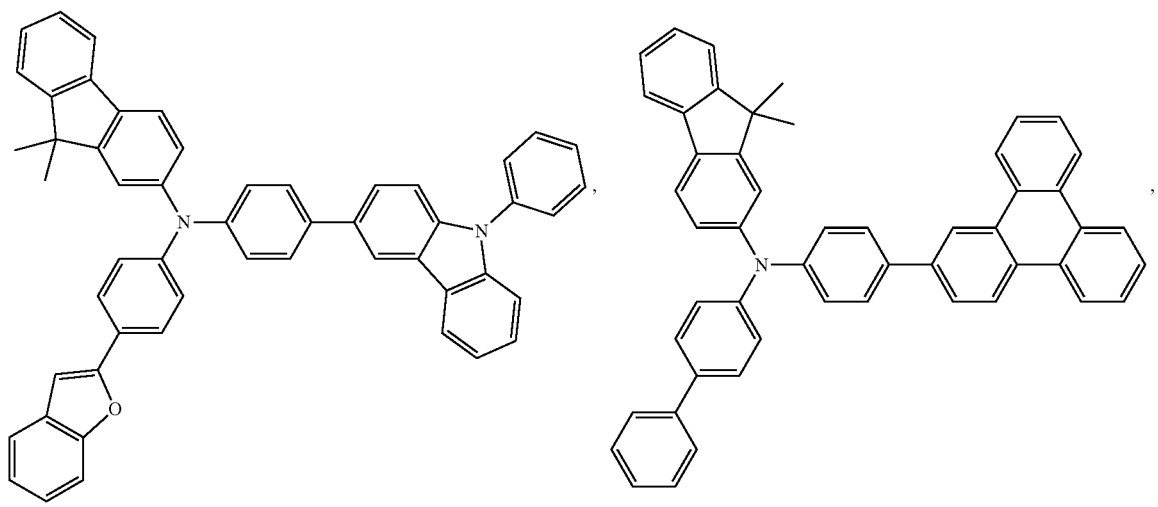
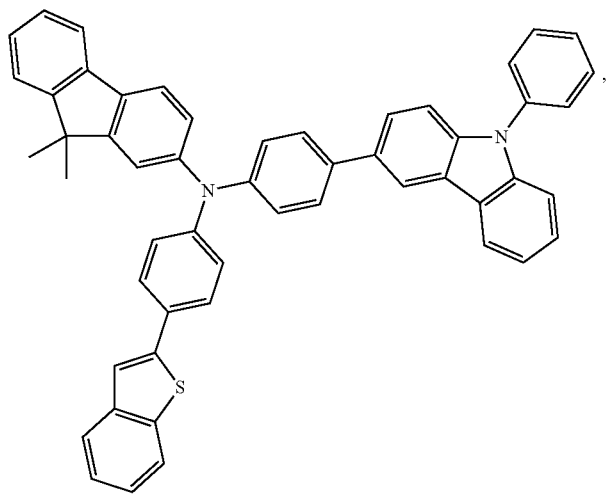

-continued
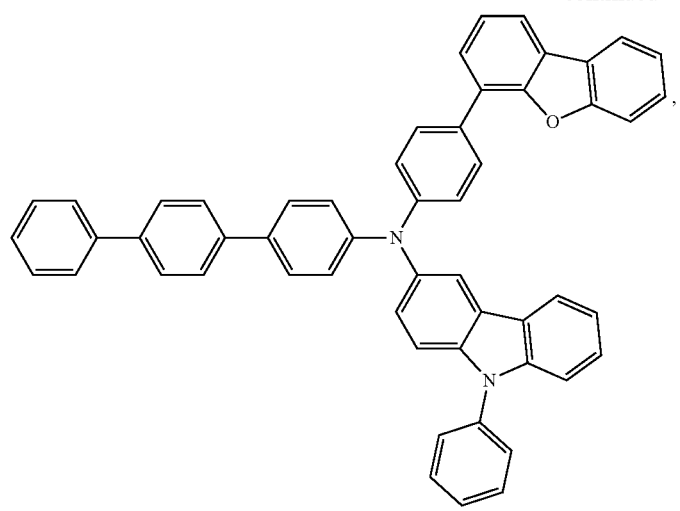
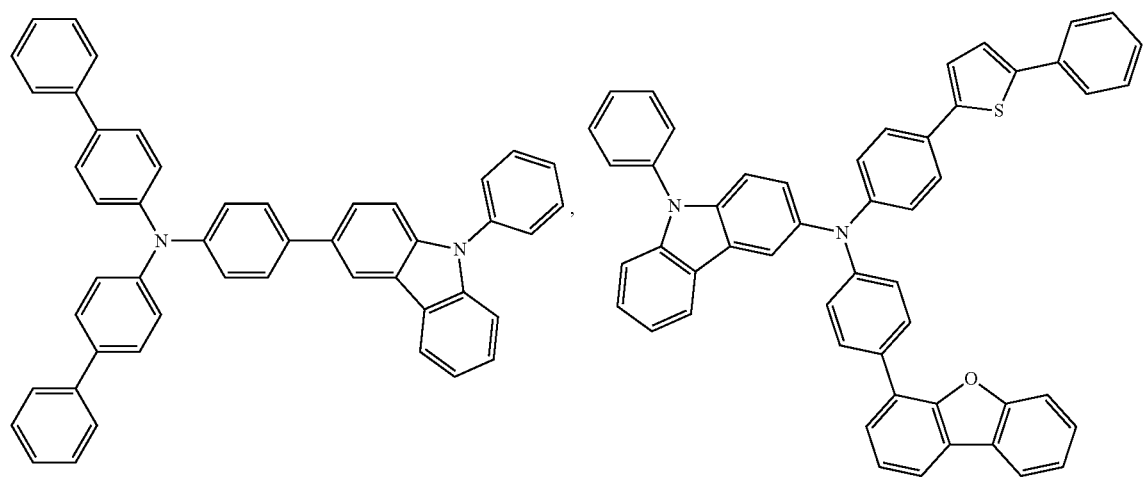
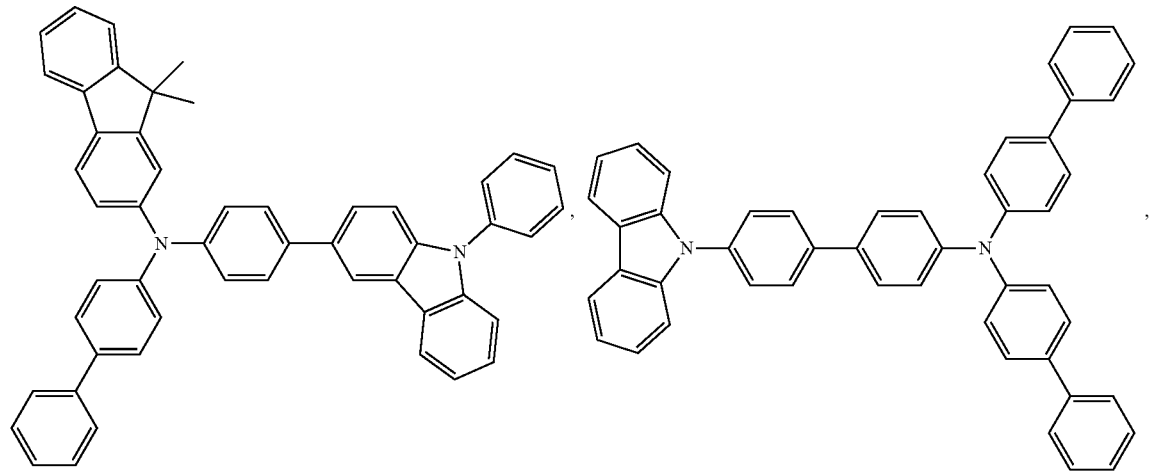

-continued
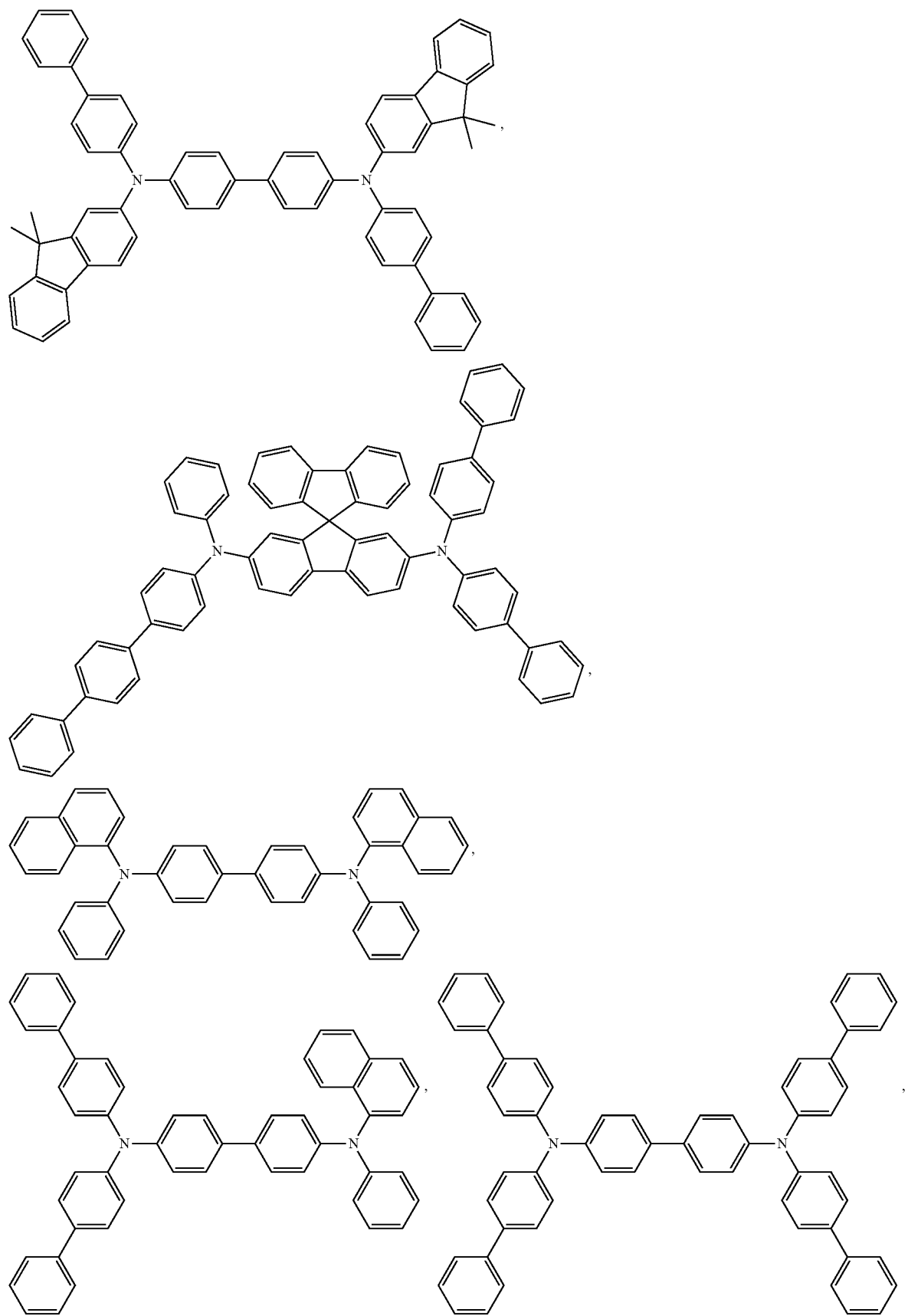

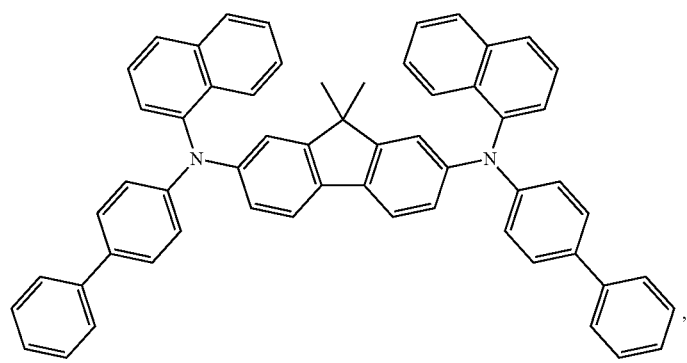
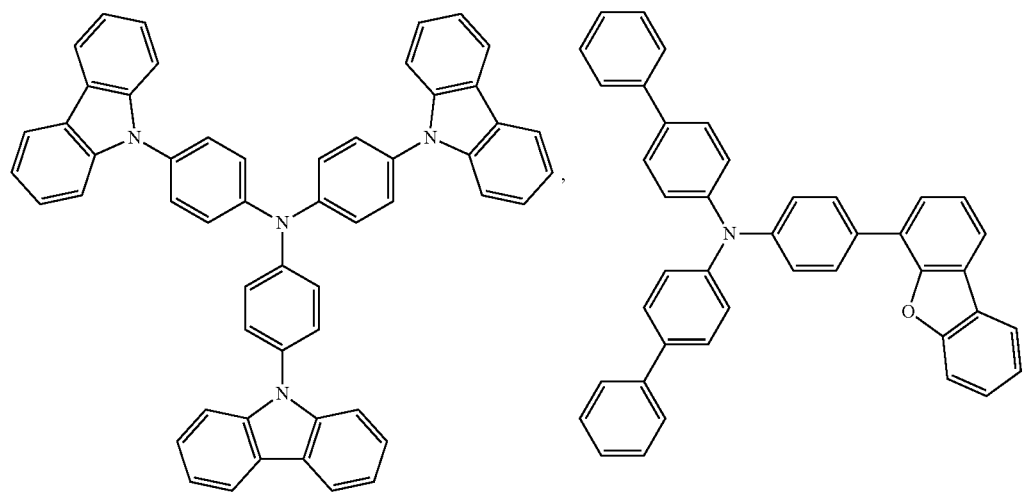
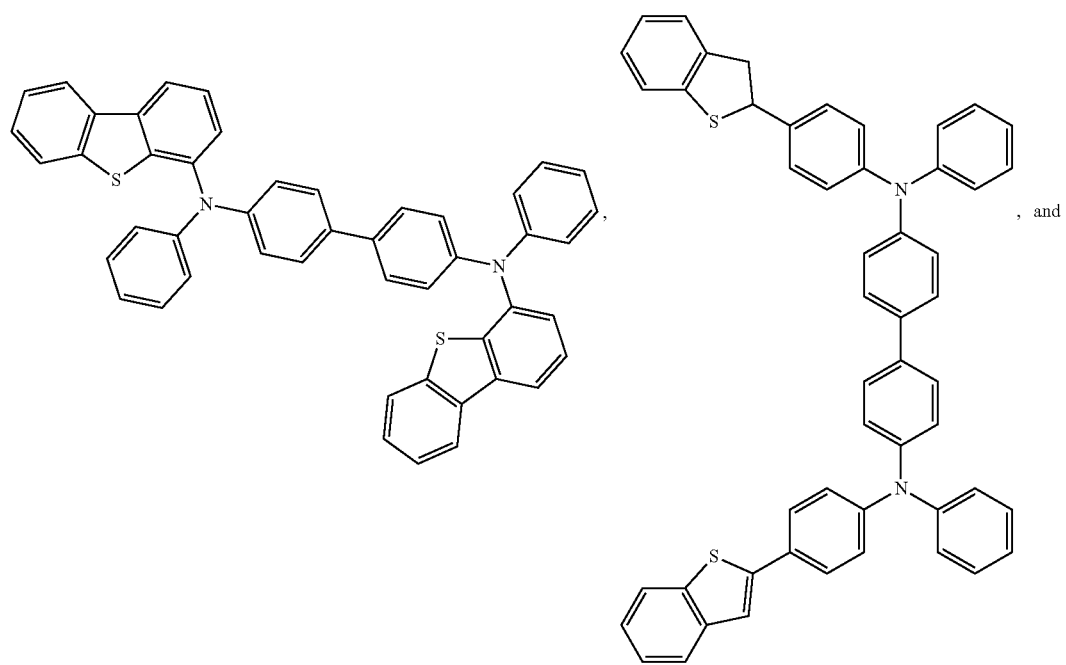

-continued

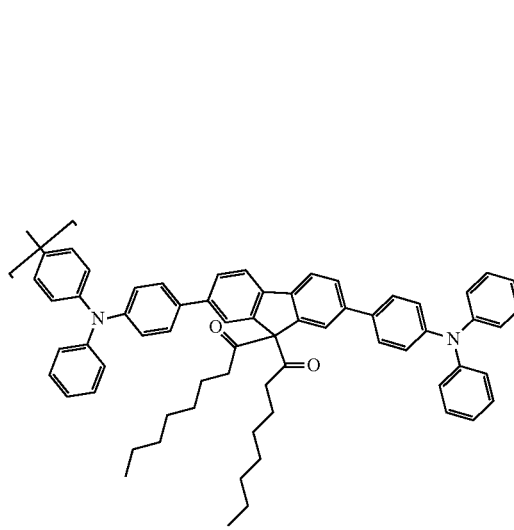

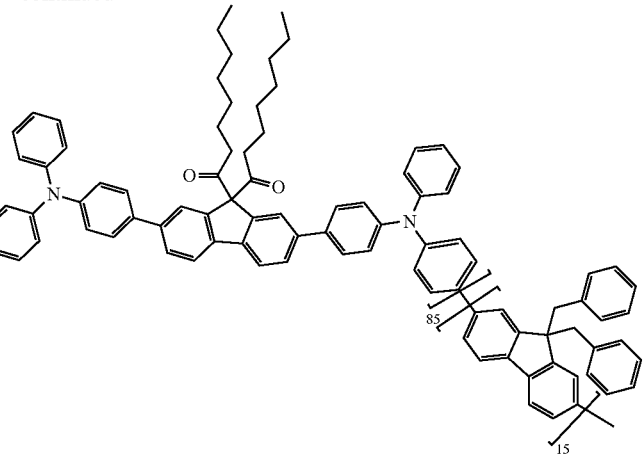

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

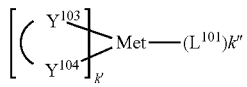

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

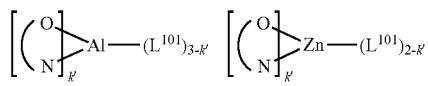

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of other organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

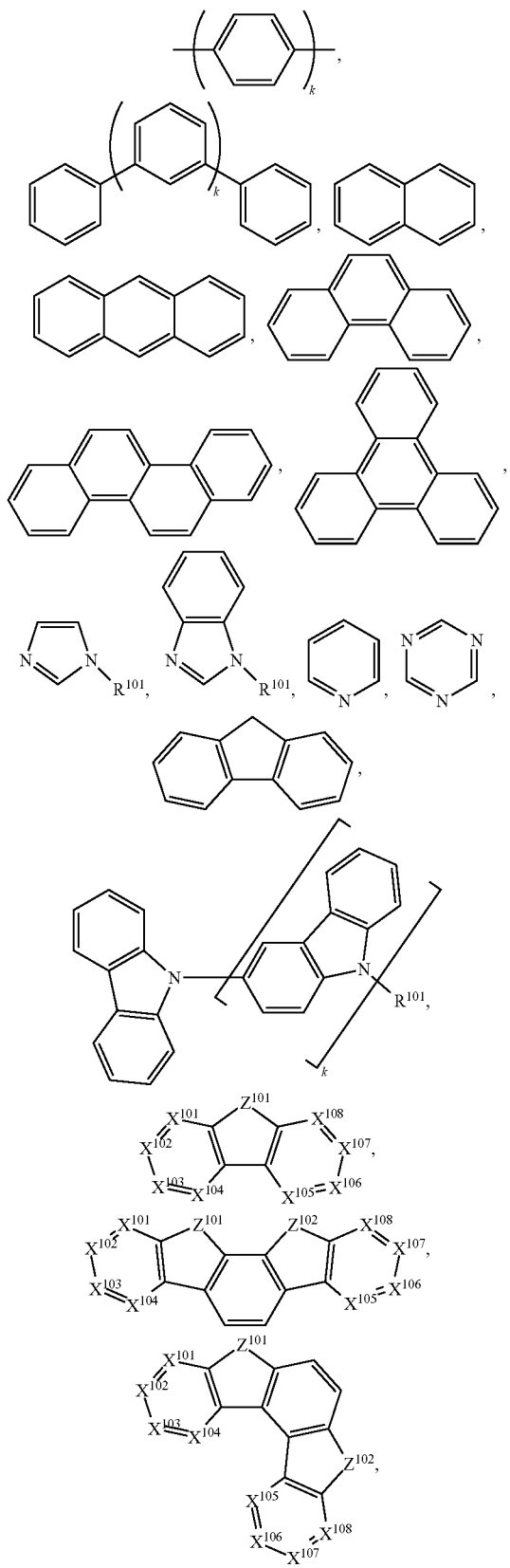

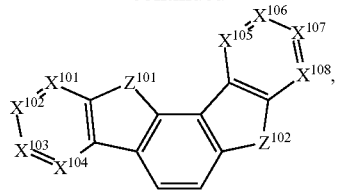

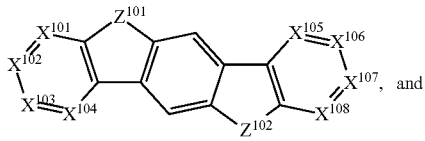

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

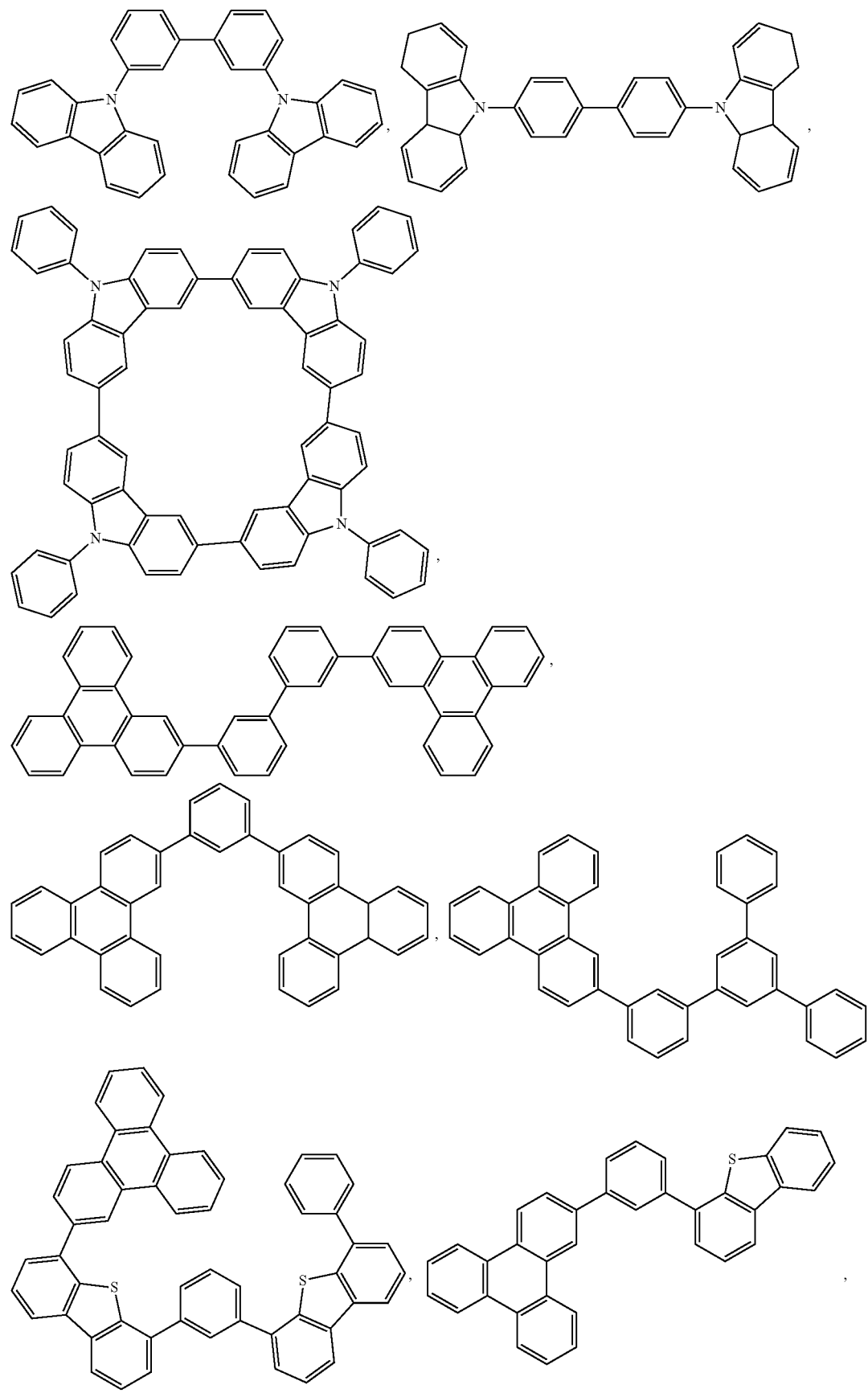

-continued
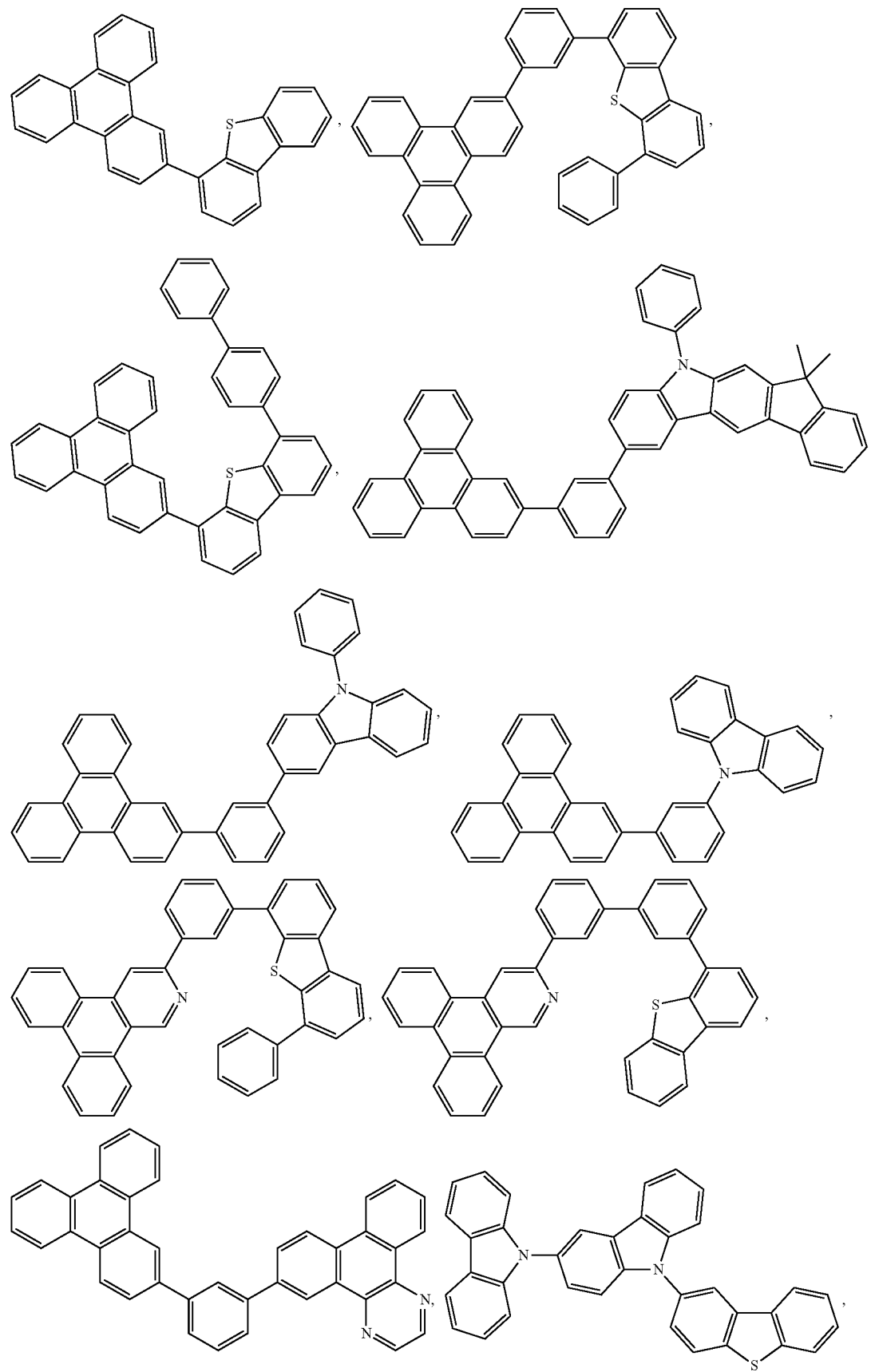

-continued
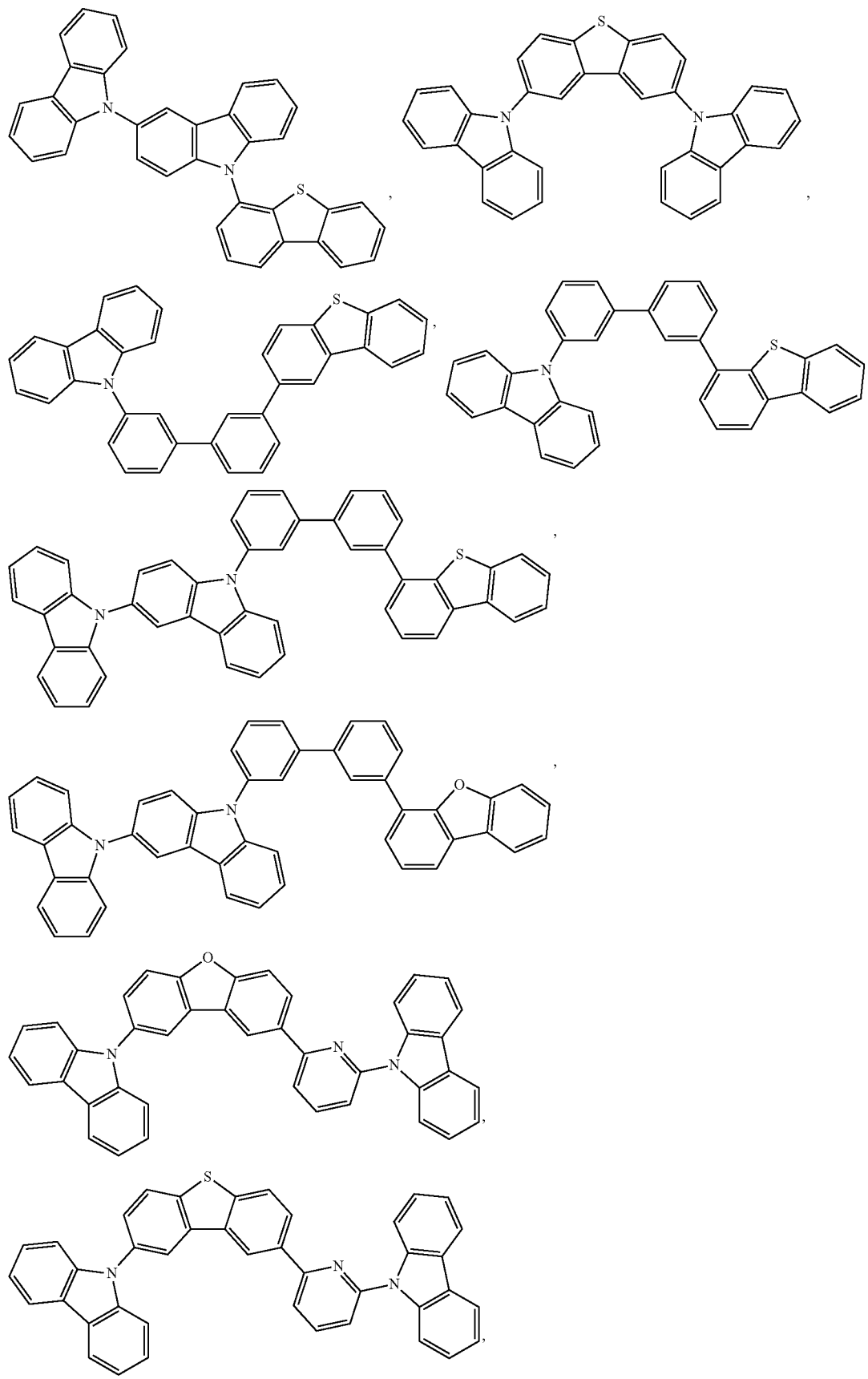

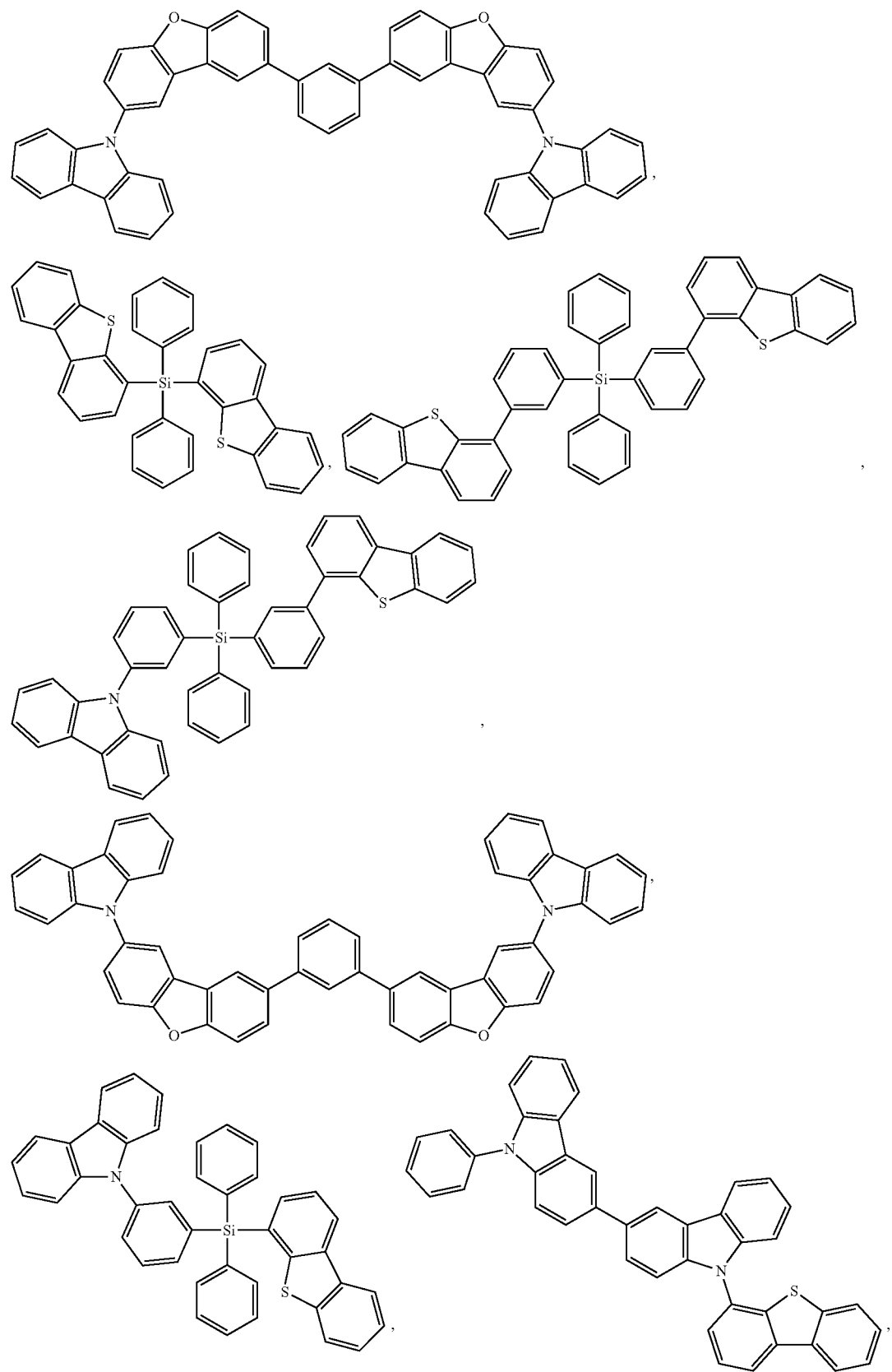

-continued
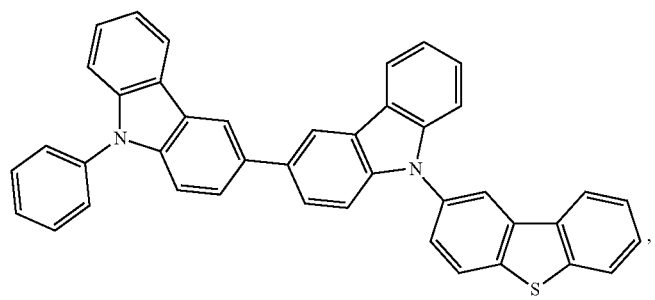
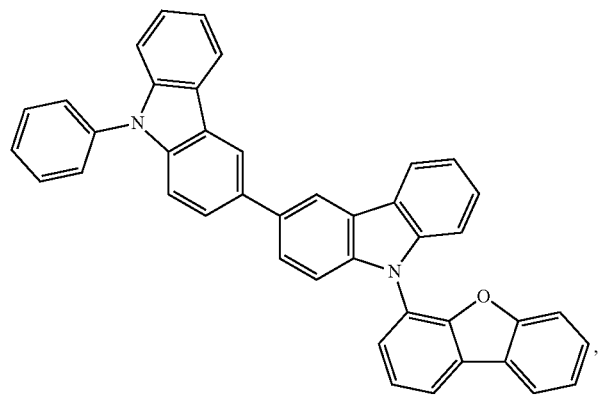
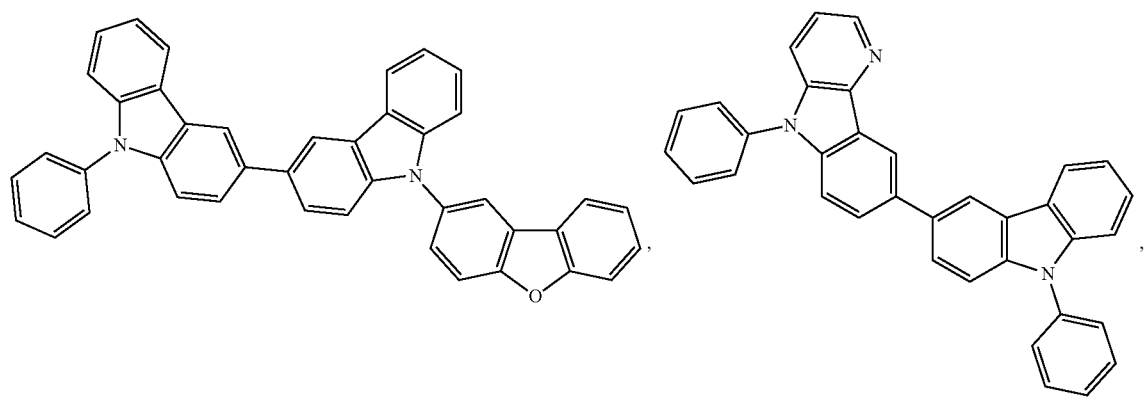
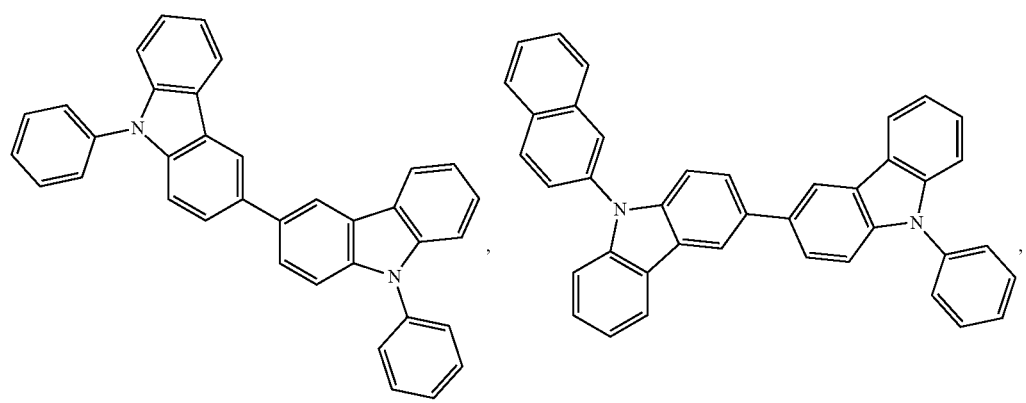

205 206
-continued
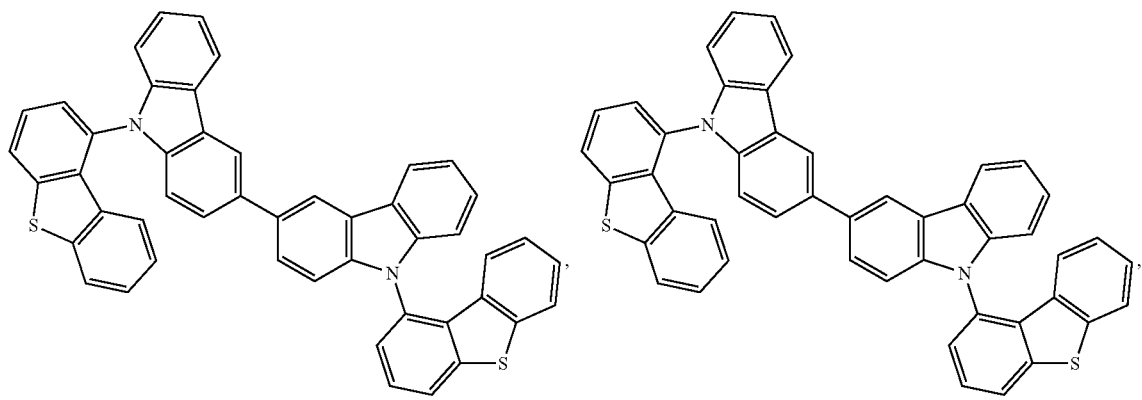
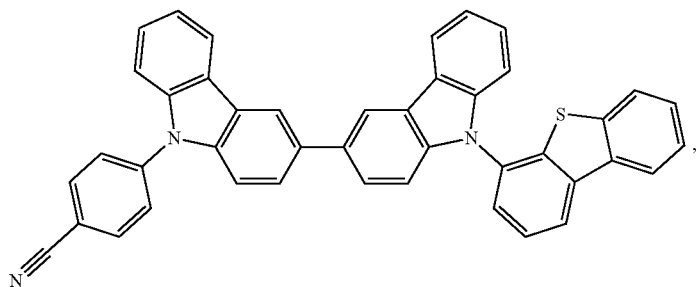
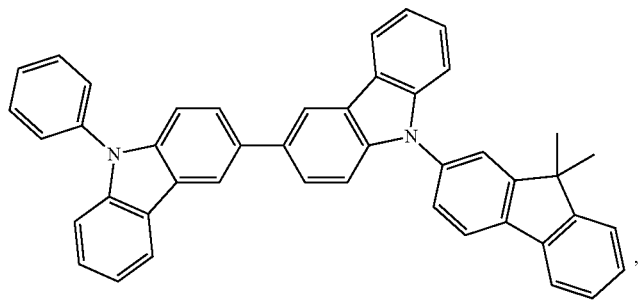
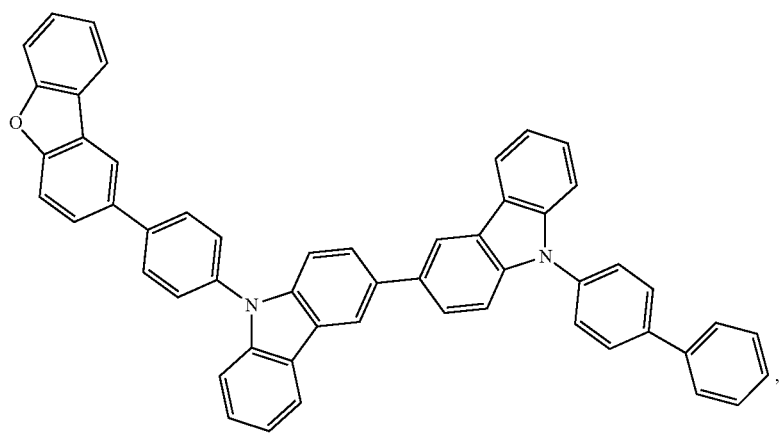

-continued
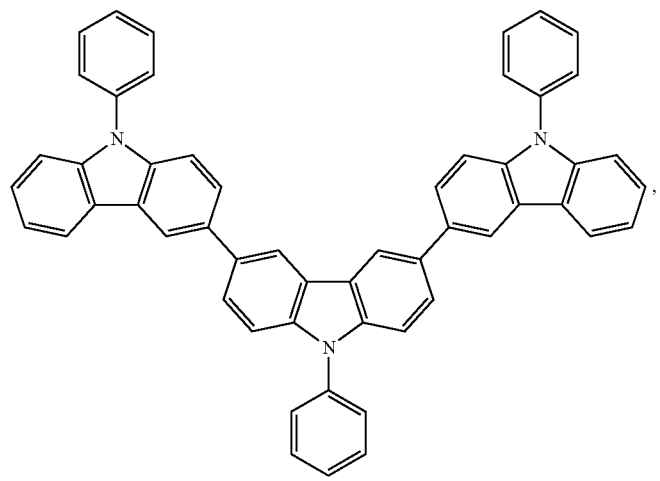
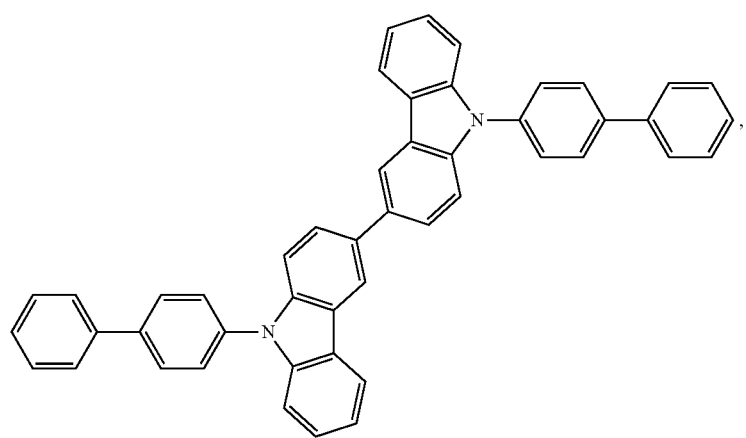
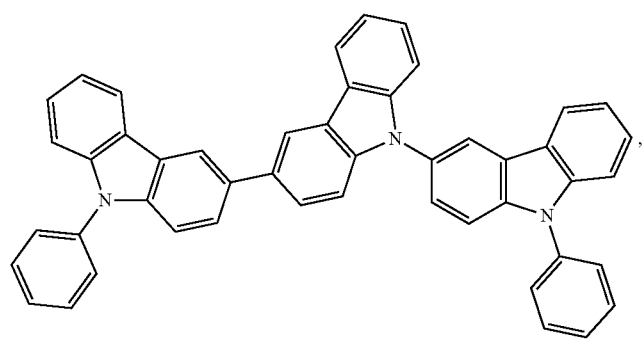
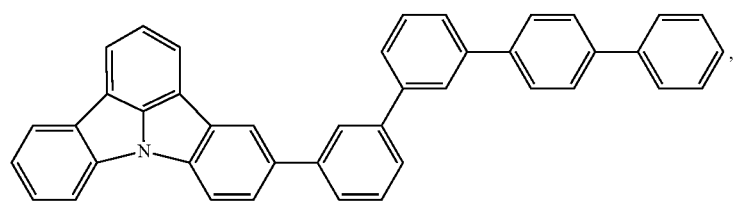

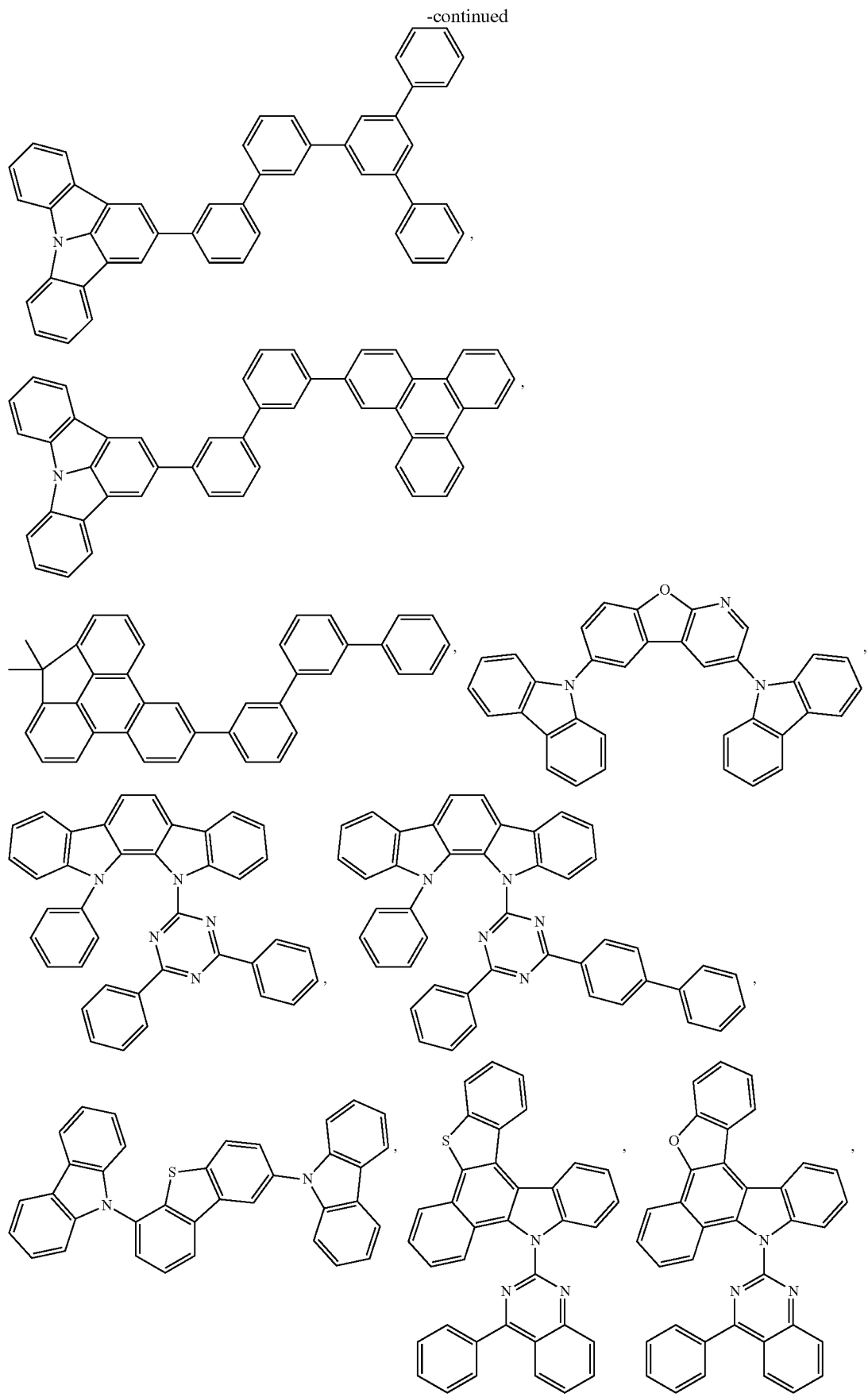

-continued
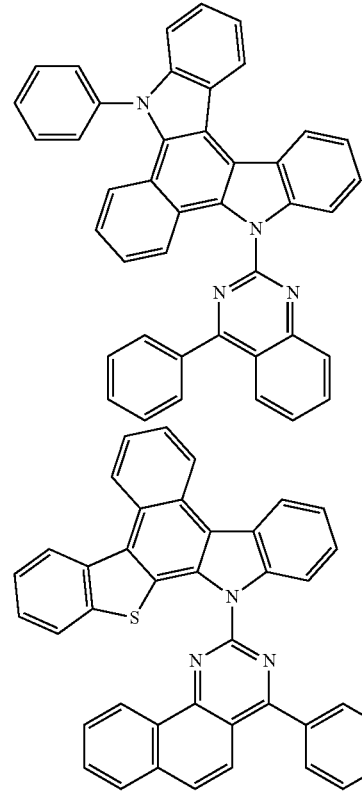
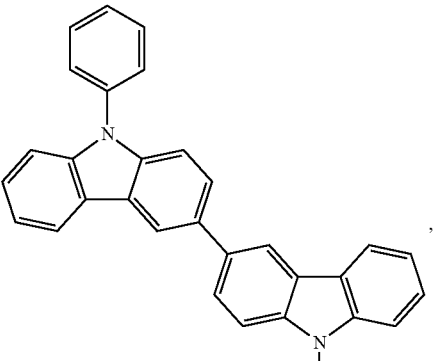
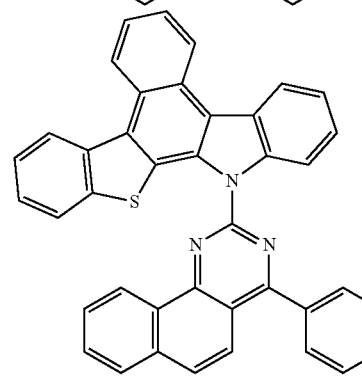
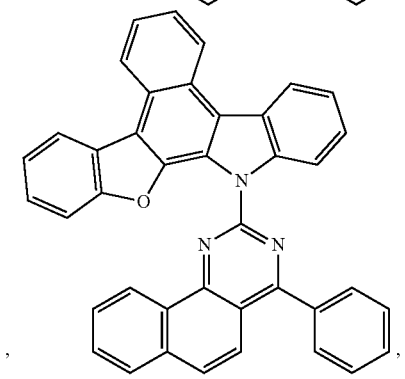
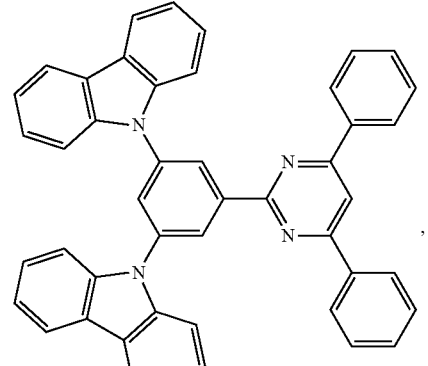
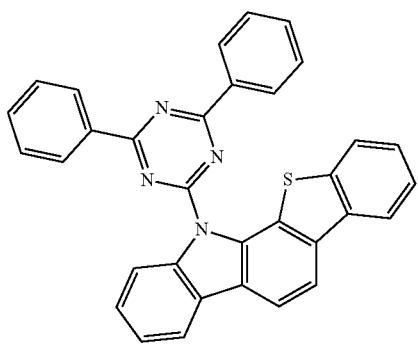
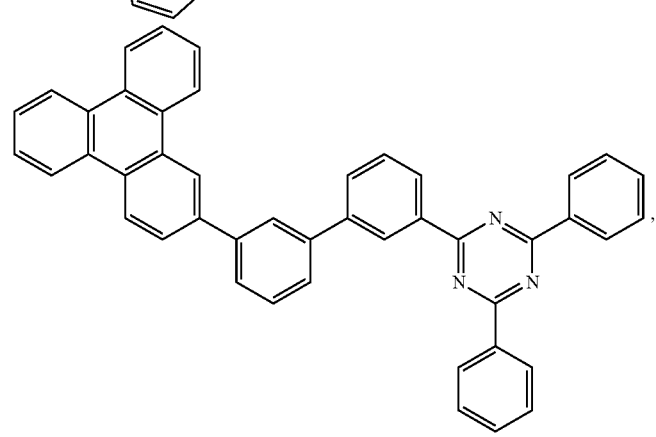

-continued
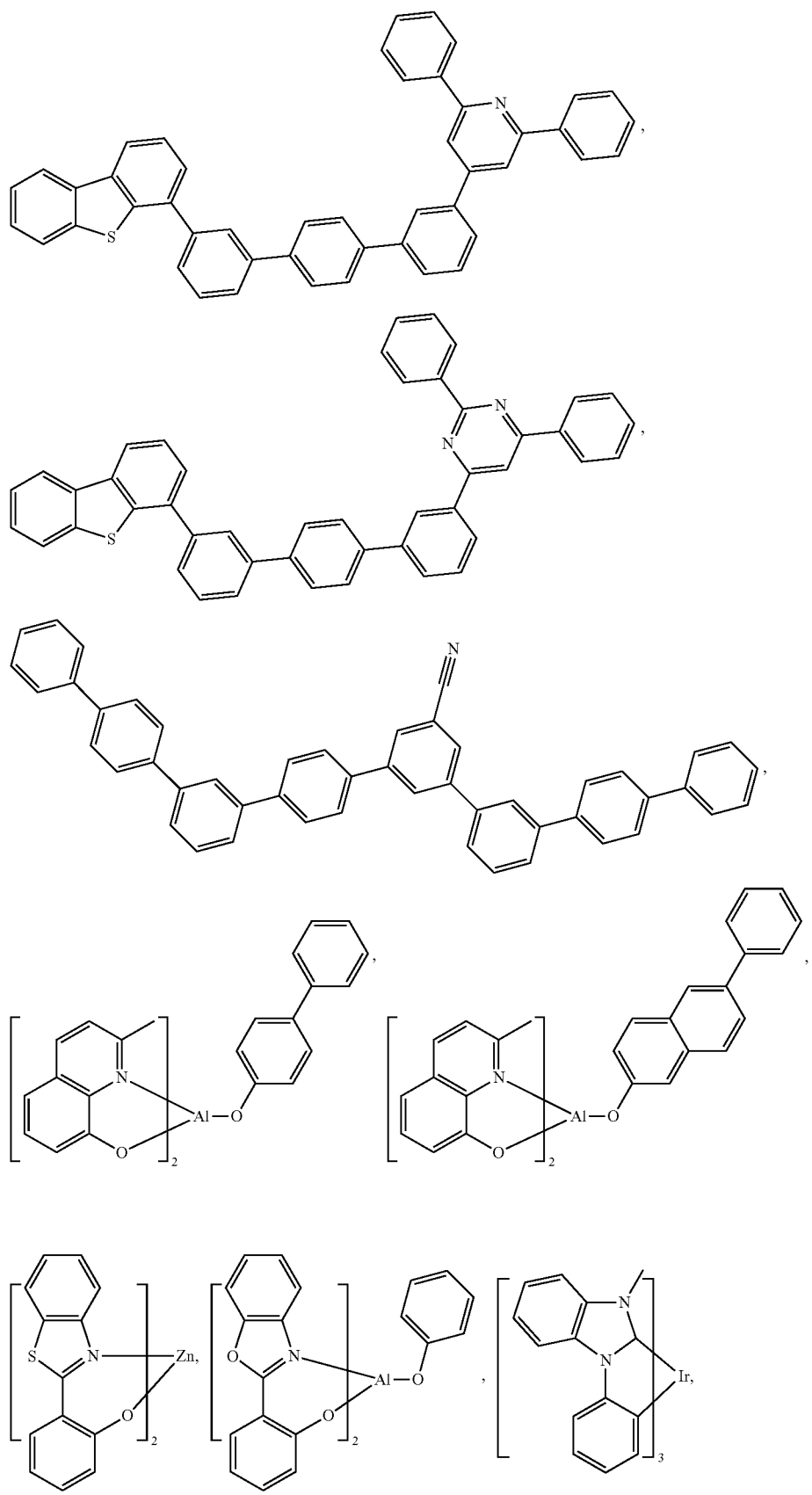

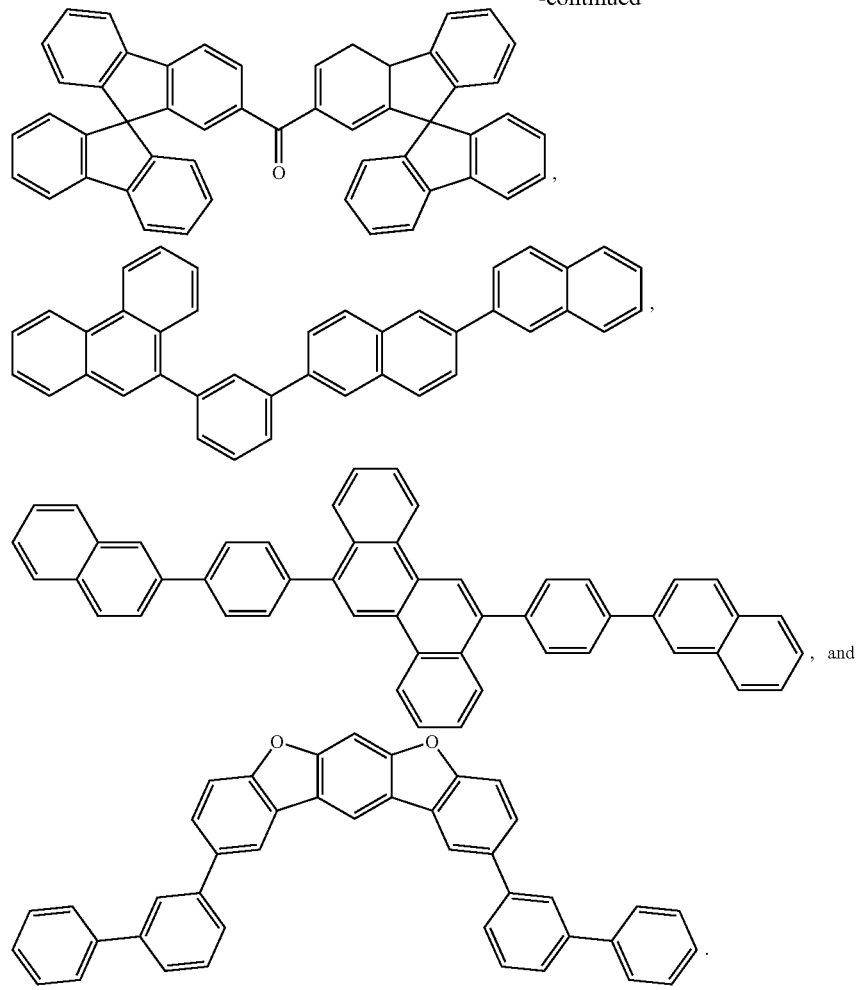

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO006081973, WO06121811, WO07018067, WO07108362, WO07115970, WO007115981, WO008035571, WO2002015645, WO2003040257, WO2005019373, WO2006056418, WO2008054584, WO2008078800, WO2008096609, WO2008101842, WO2009000673, WO2009050281, WO2009100991,
WO2010028151, WO2010054731, WO2010086089,
WO2010118029, WO2011044988, WO2011051404,
WO2011107491, WO2012020327, WO2012163471,
WO2013094620, WO2013107487, WO2013174471,
WO2014007565, WO2014008982, WO2014023377,
WO2014024131, WO2014031977, WO2014038456,
WO2014112450.
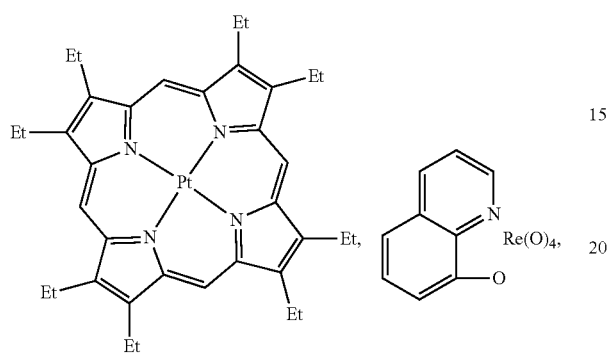
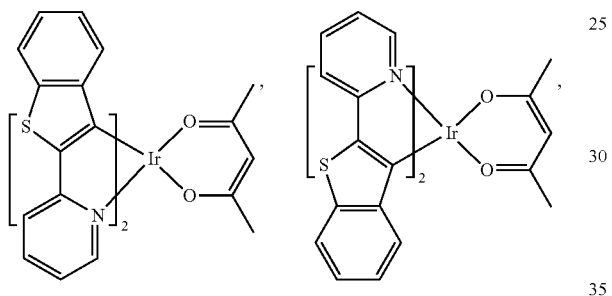
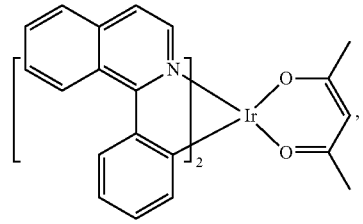
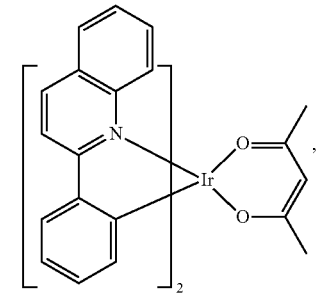
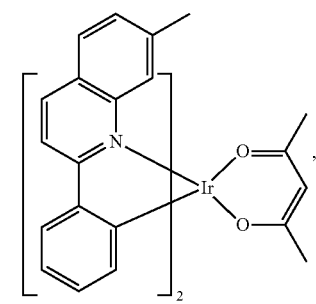
-continued
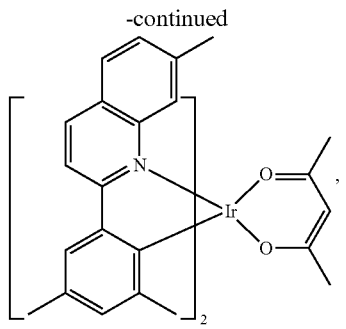
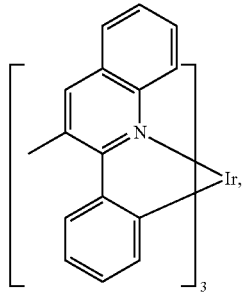
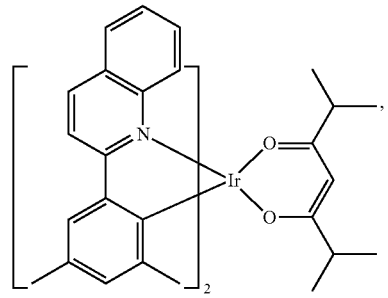
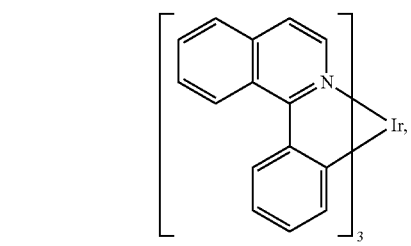
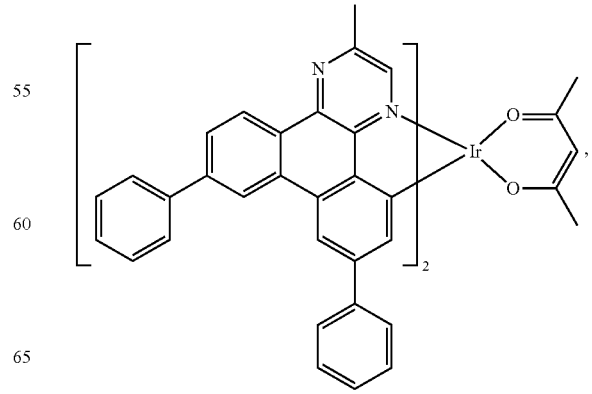

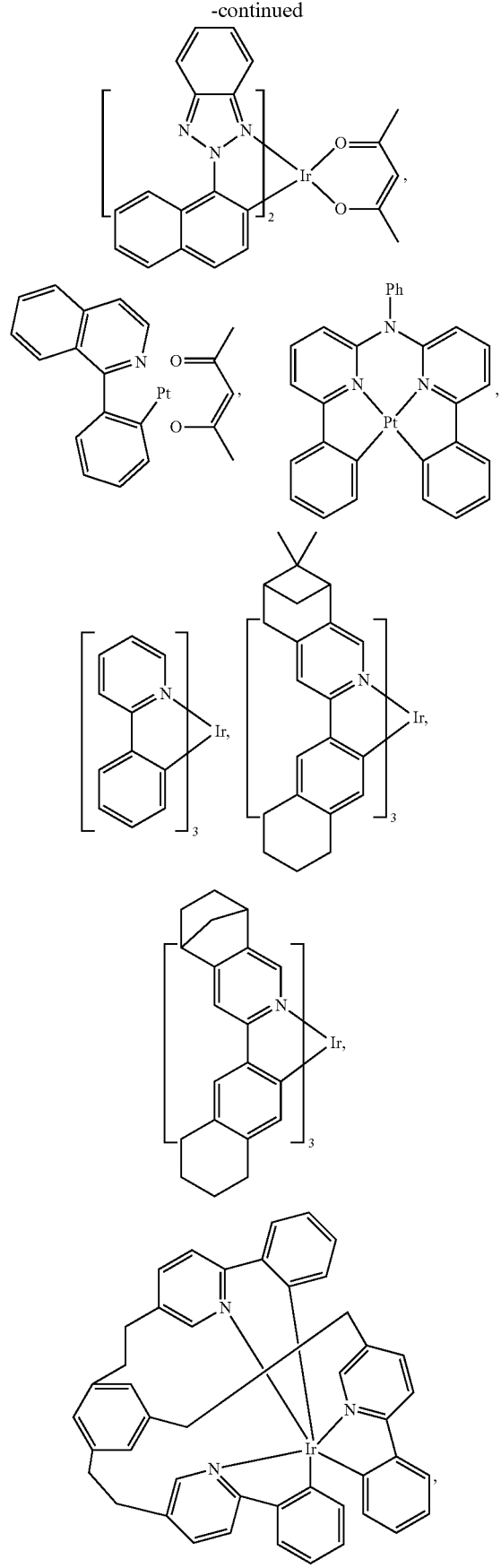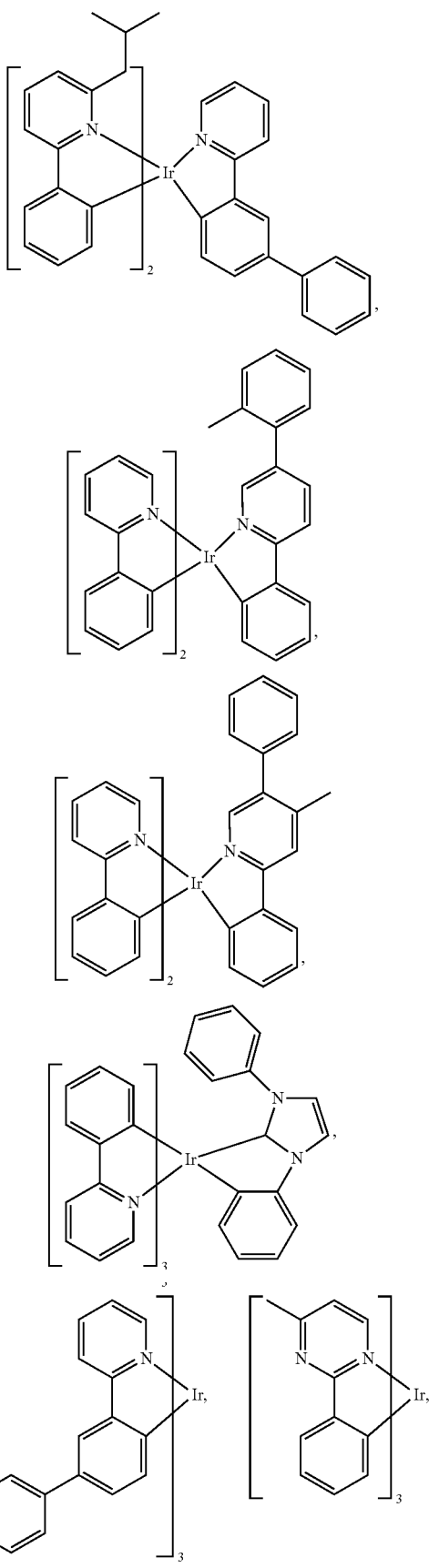

221
-continued
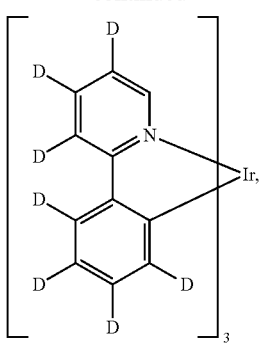
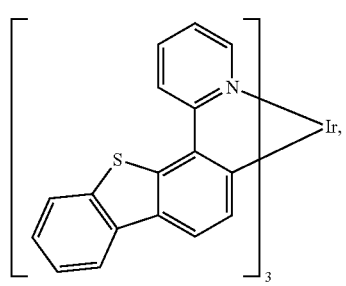
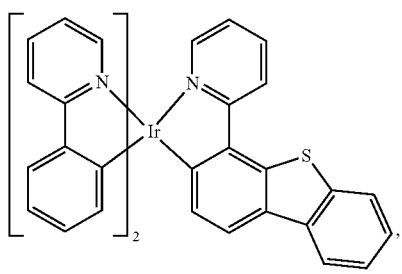
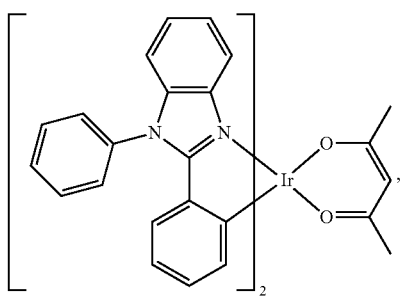
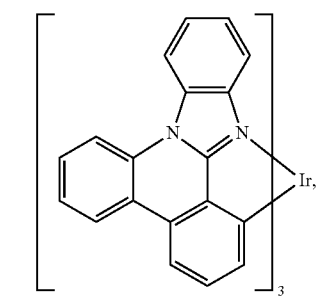
222
-continued
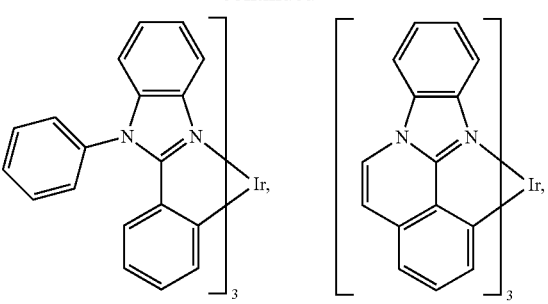
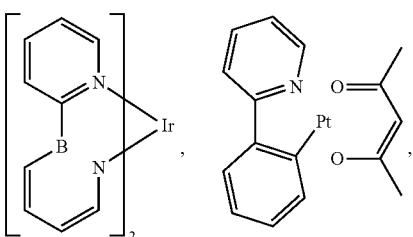
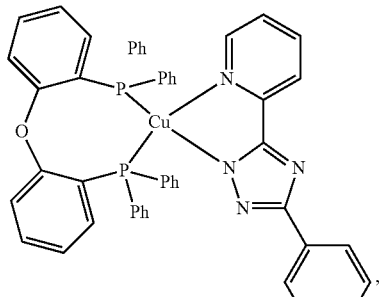
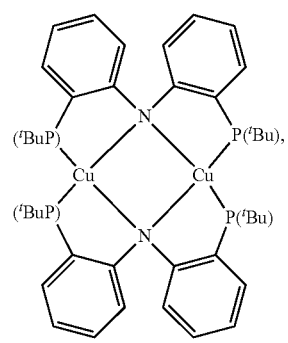
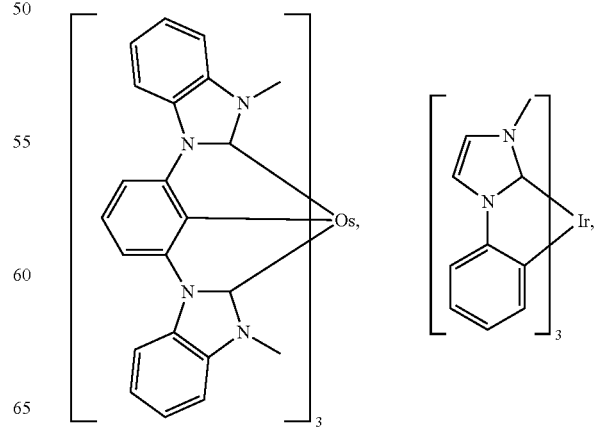

223
-continued
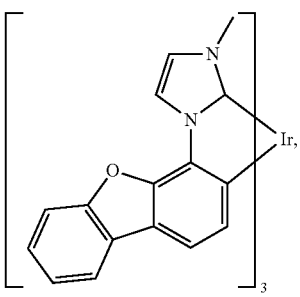
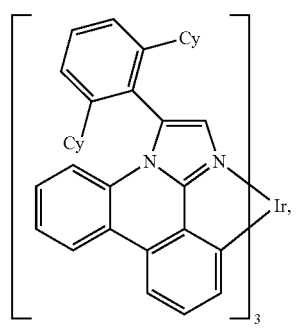
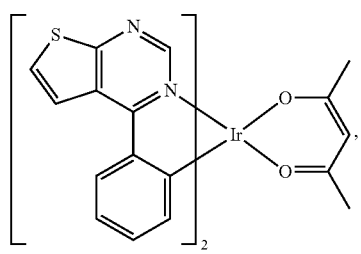
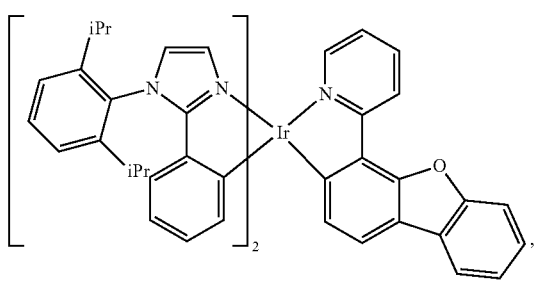
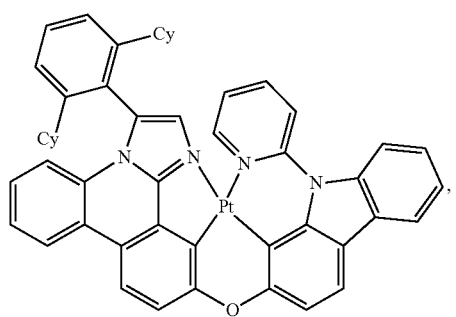
224
-continued
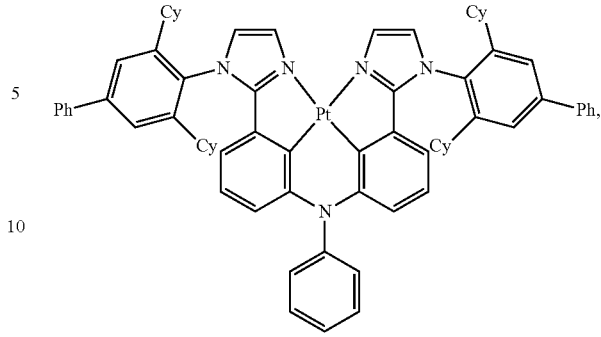
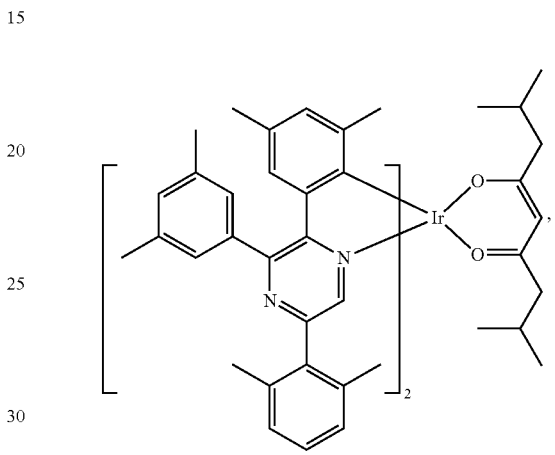
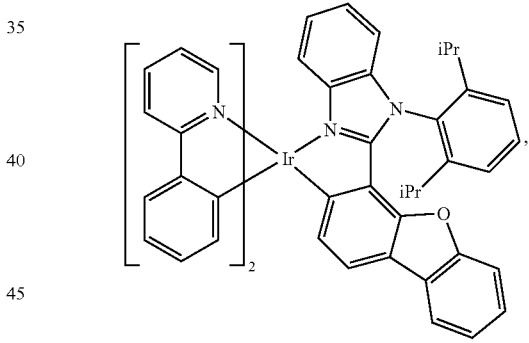
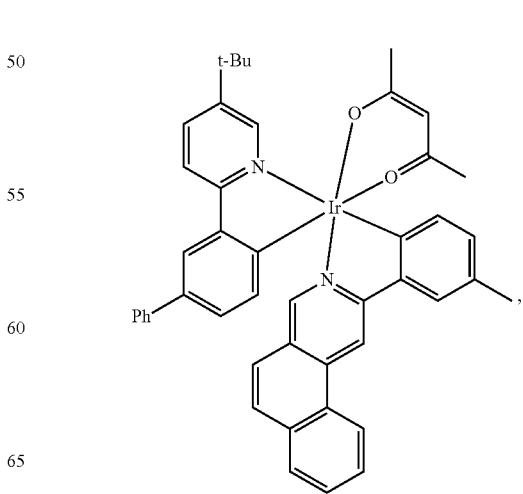

225
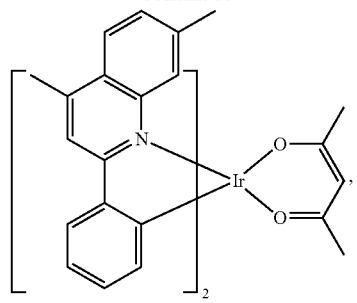
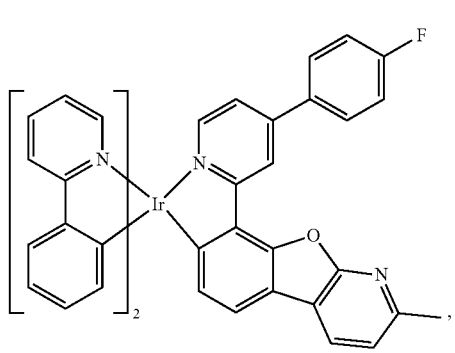
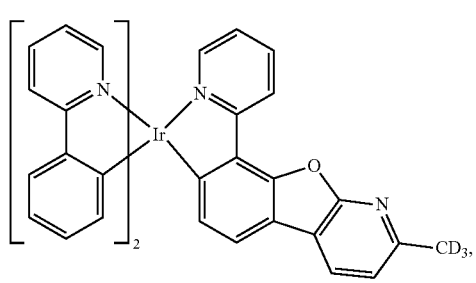
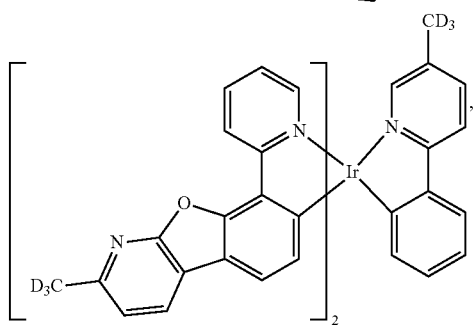
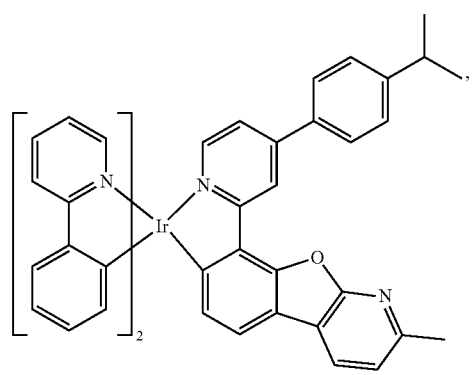
226
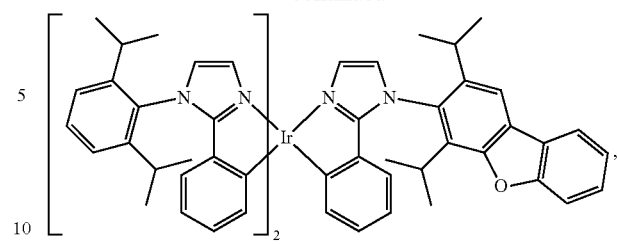
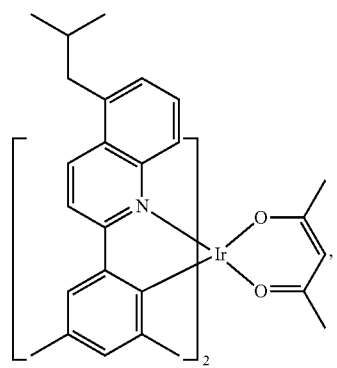
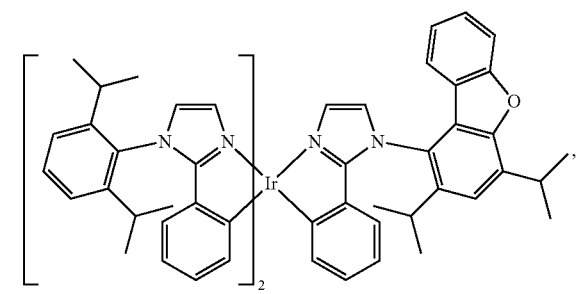
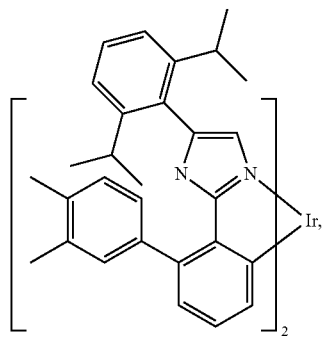
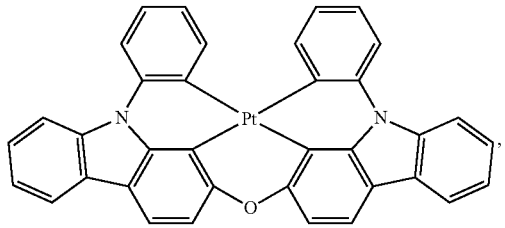

227
-continued
228
-continued
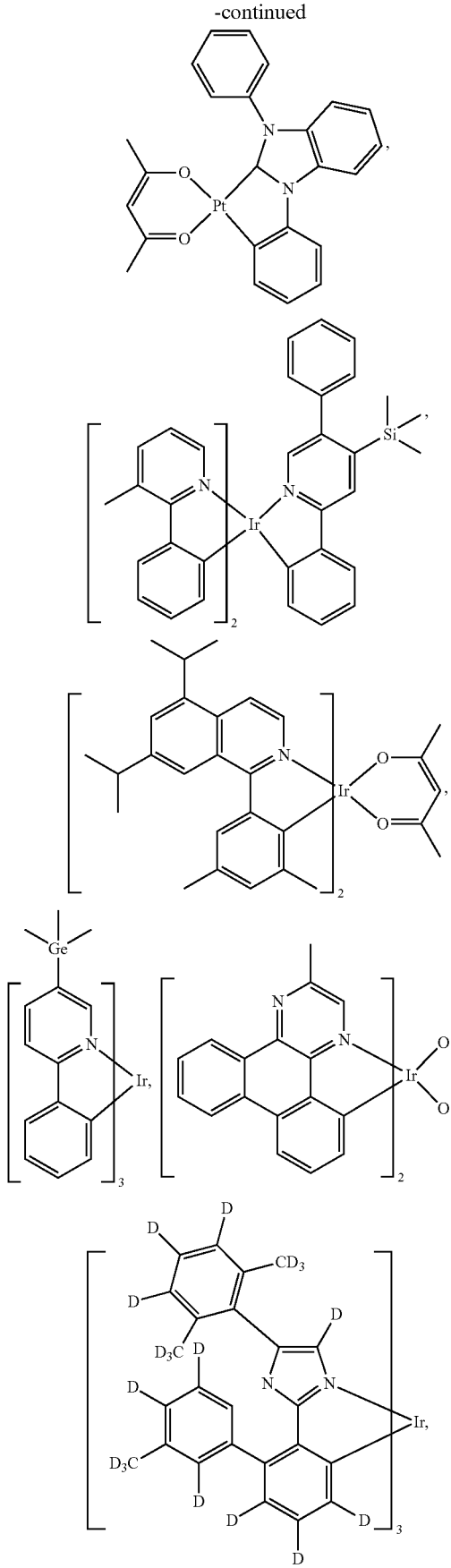
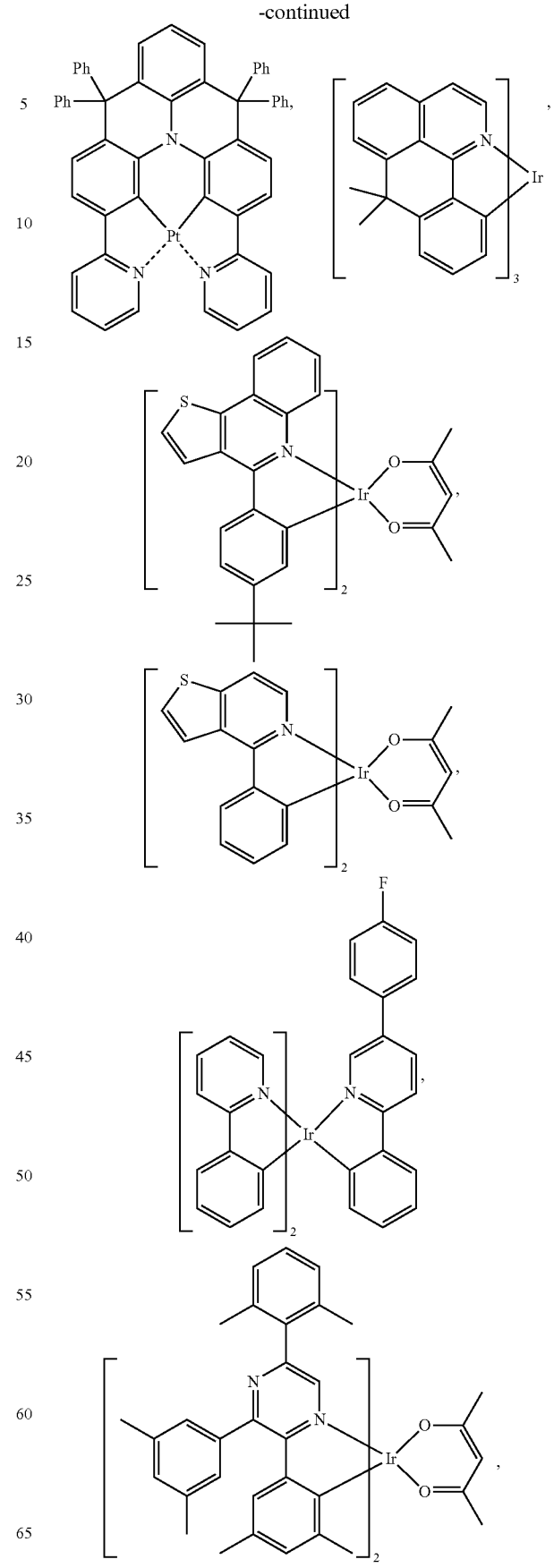

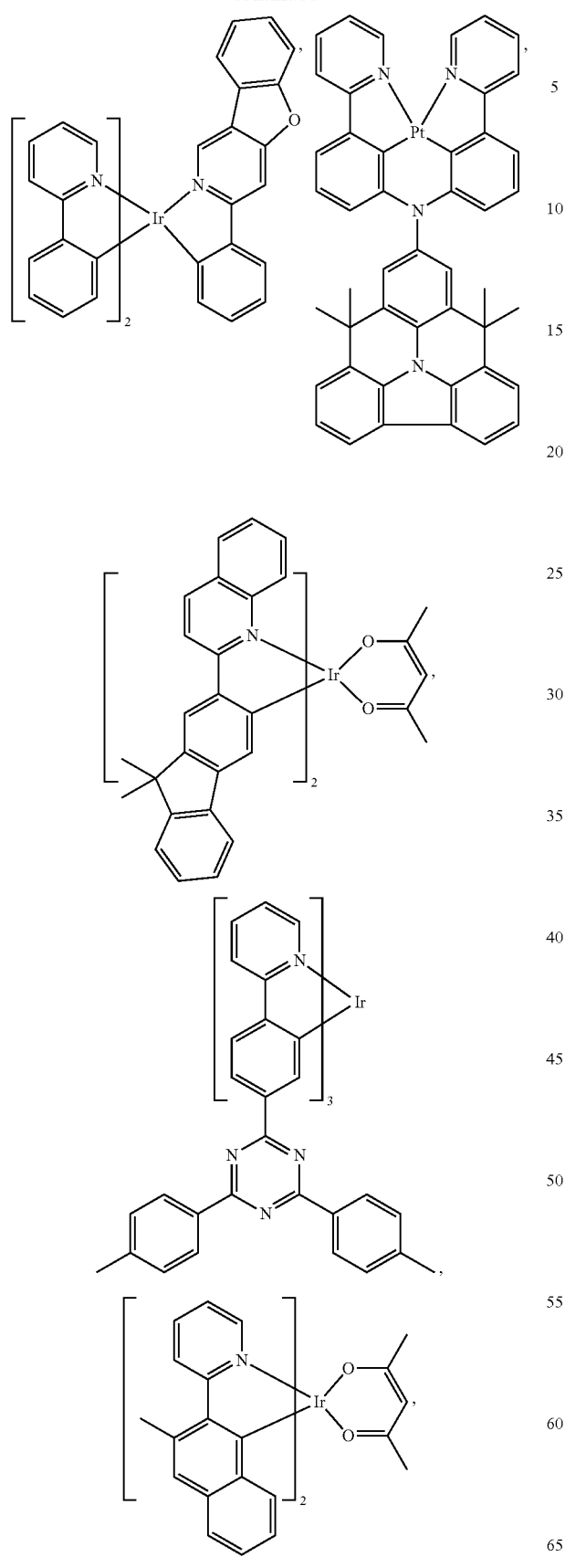
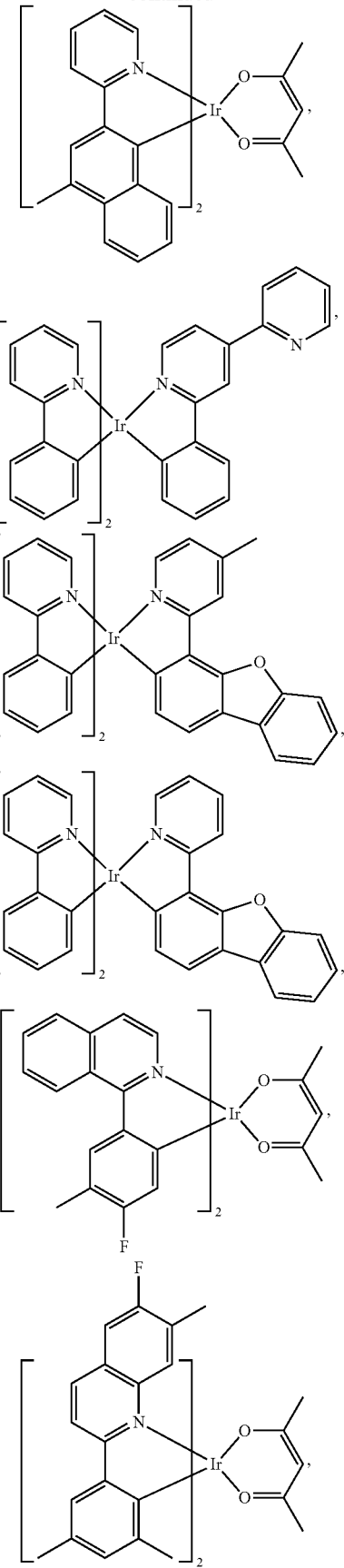

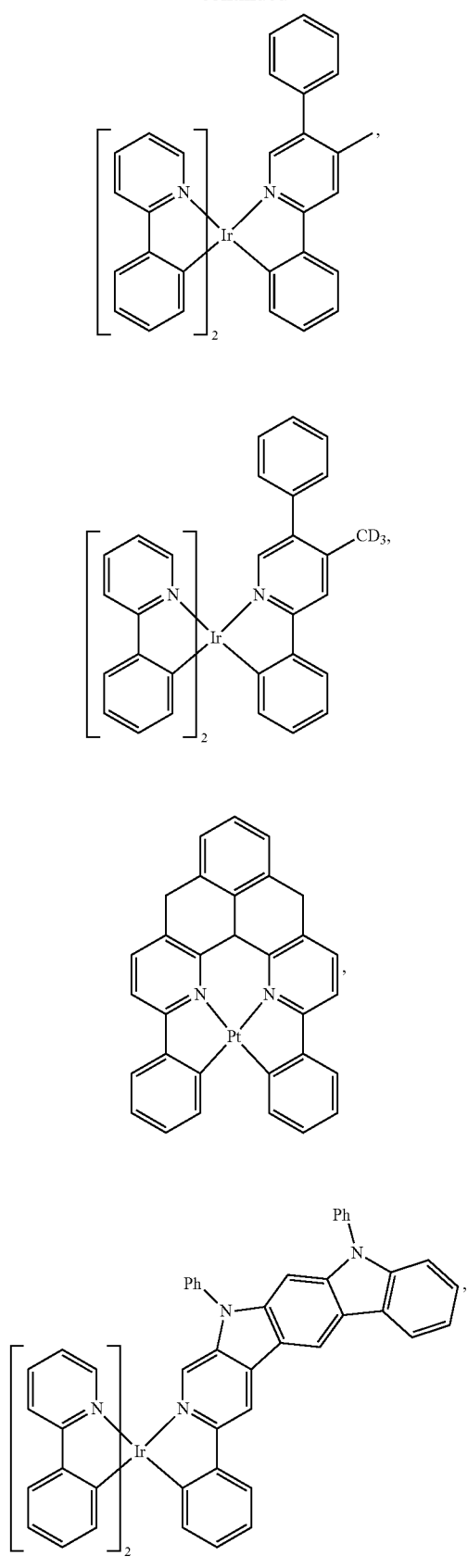
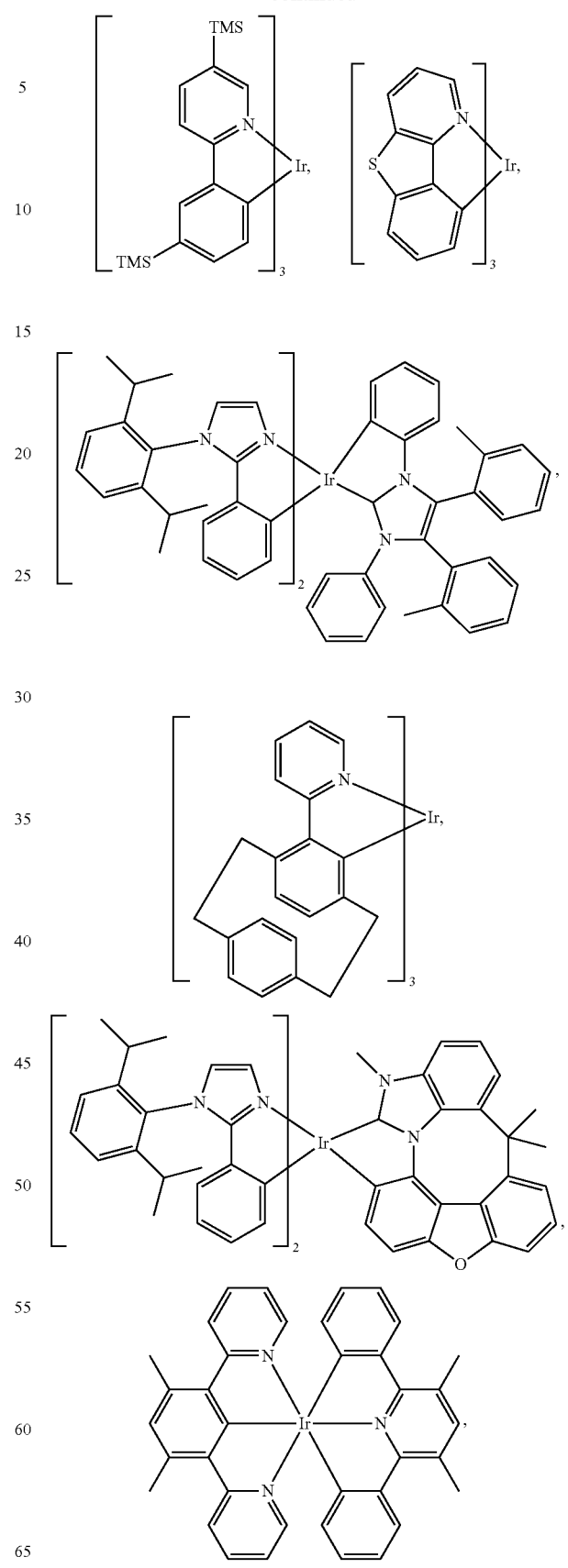

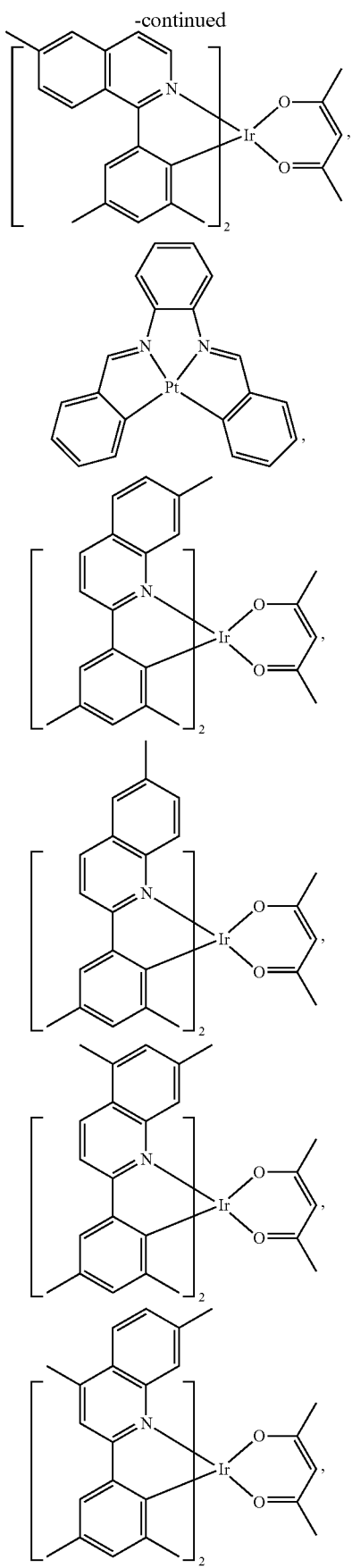
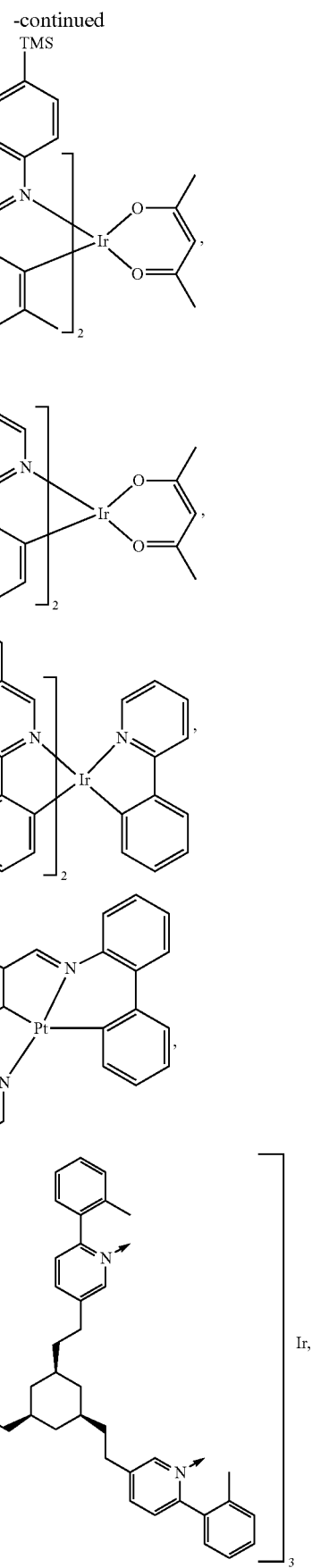

-continued
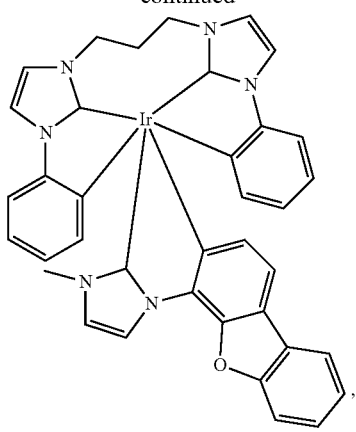
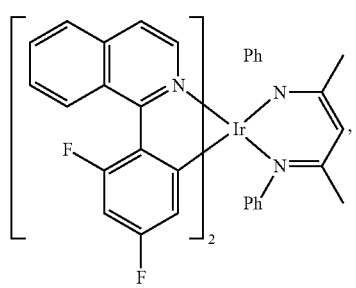
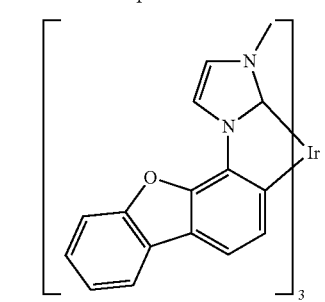
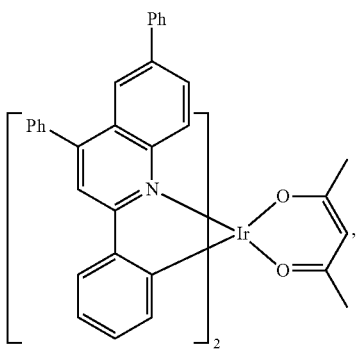
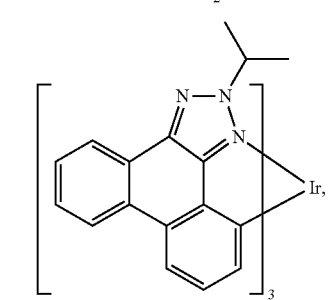
-continued
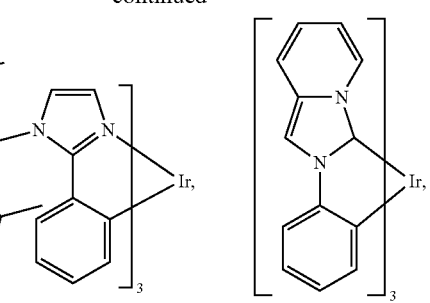

-continued

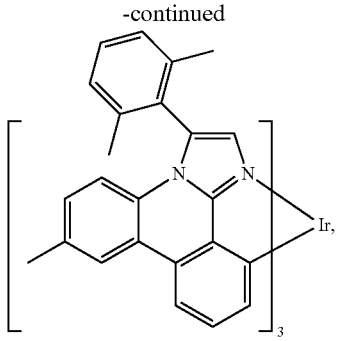

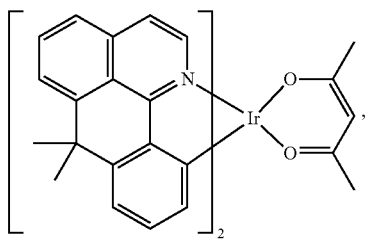

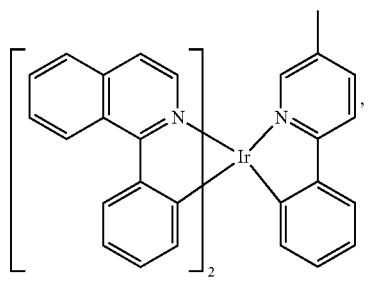

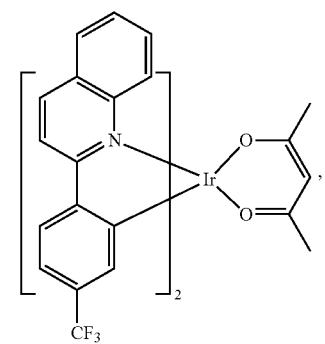

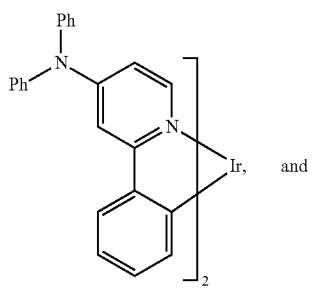

-continued

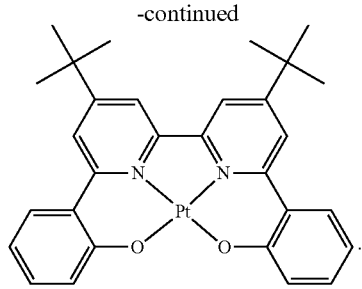

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

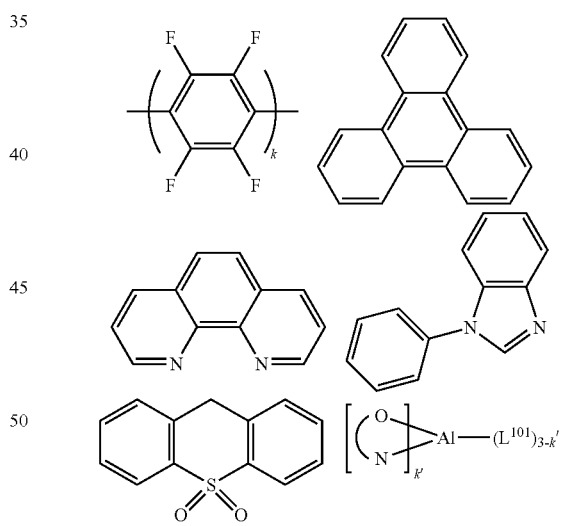

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

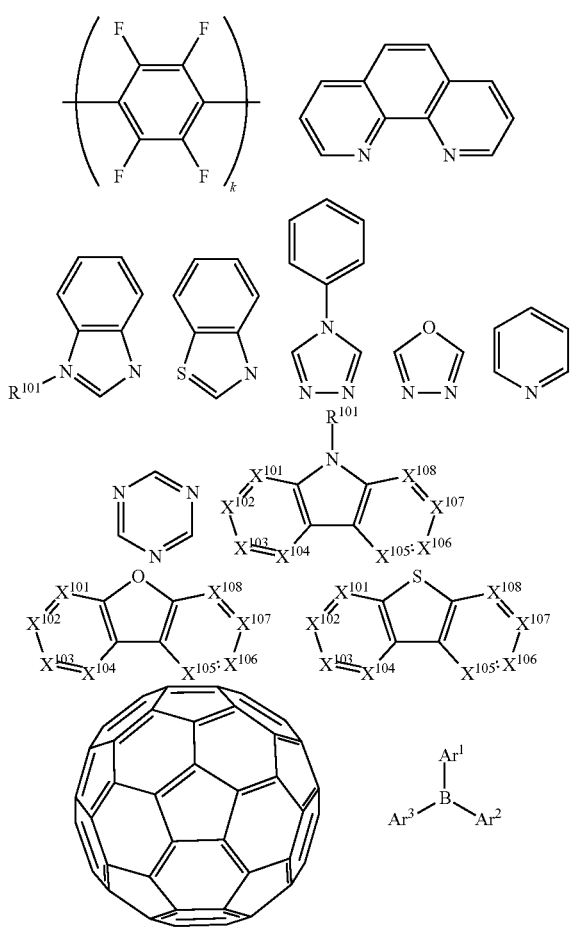

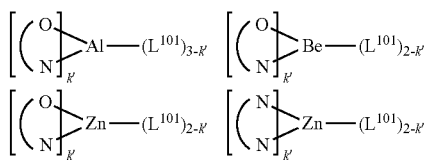

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar_1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

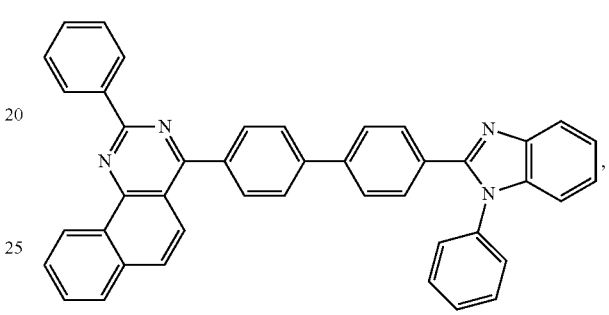

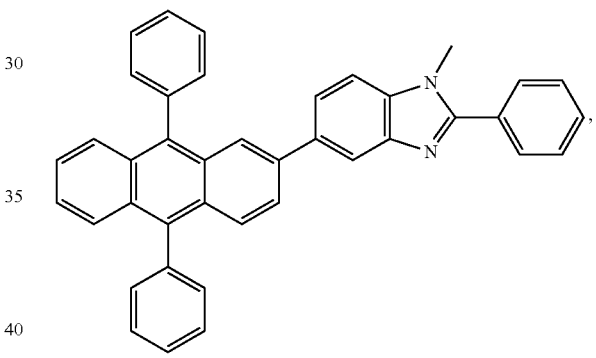

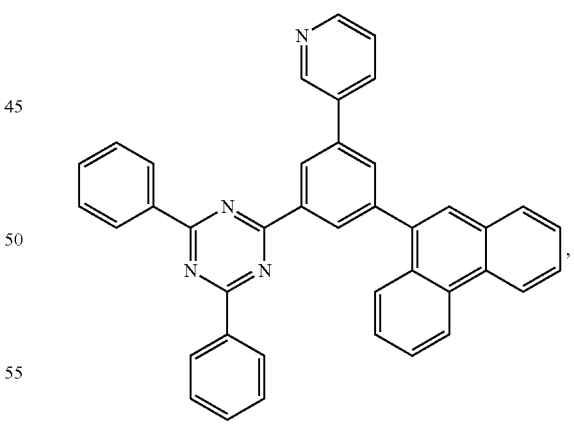

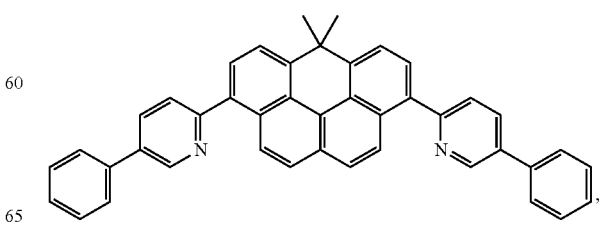

241
-continued
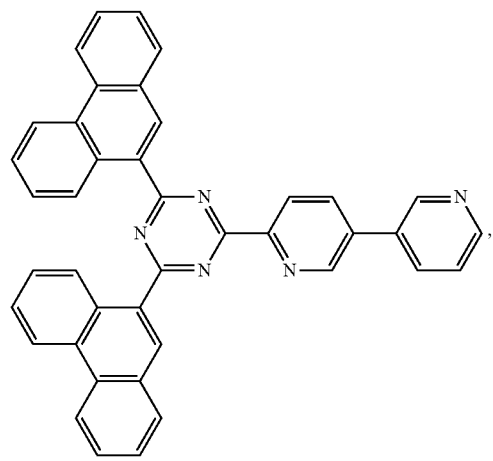
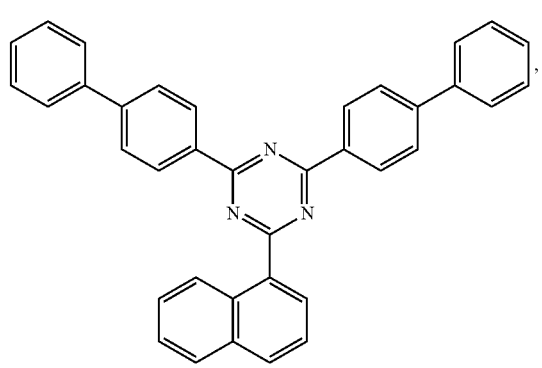
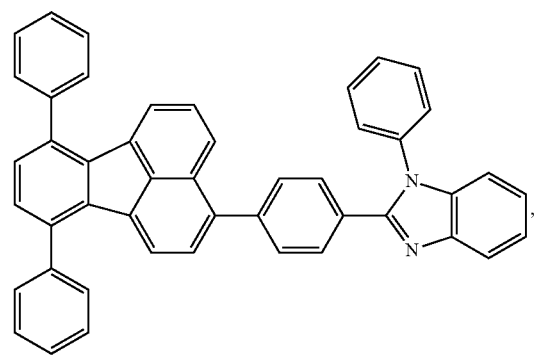
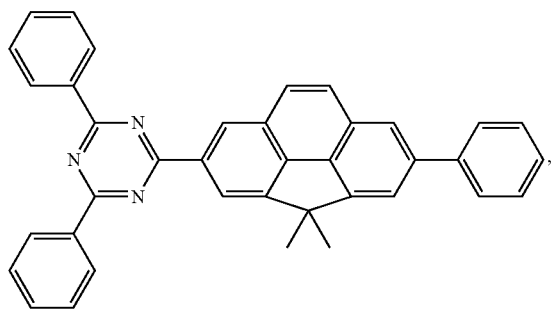
242
-continued
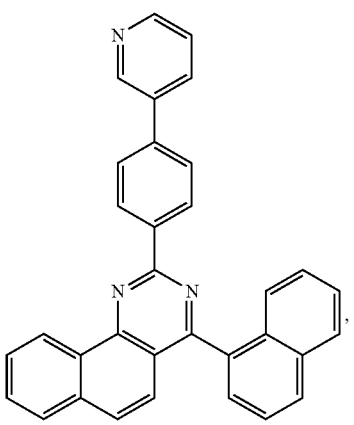
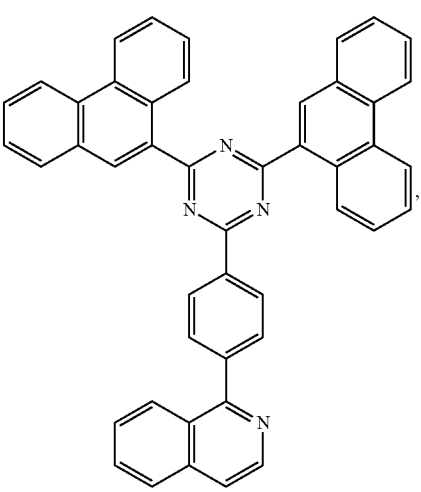
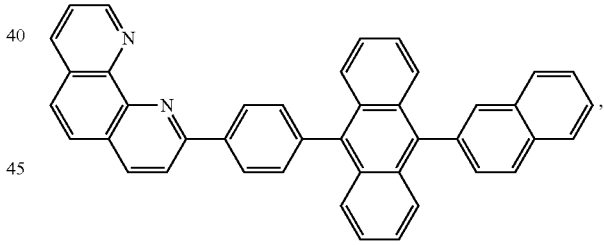
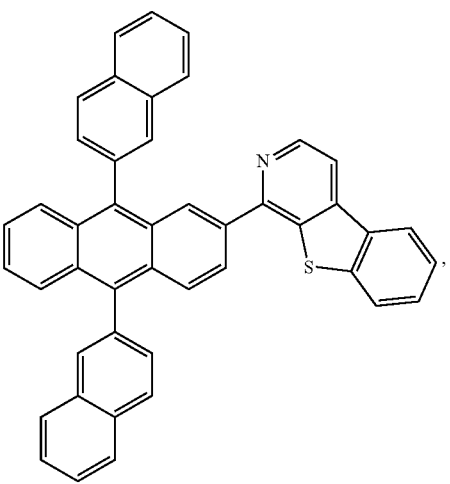

243
-continued
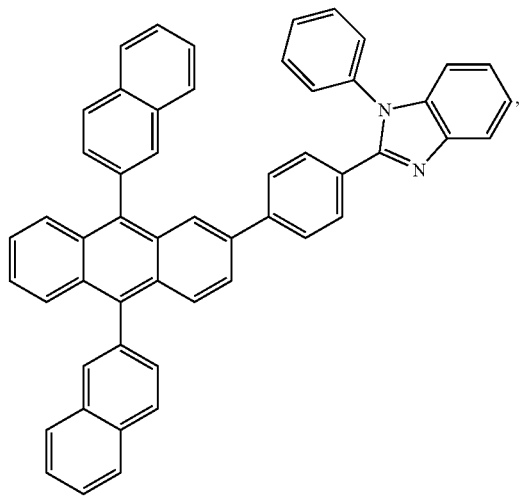
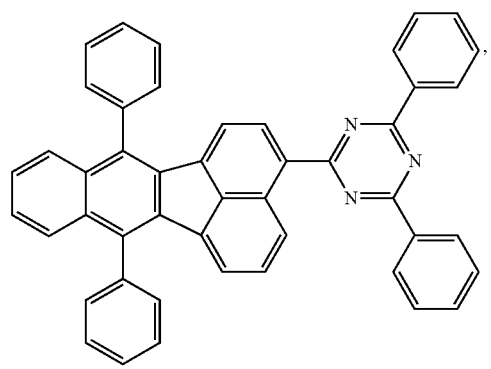
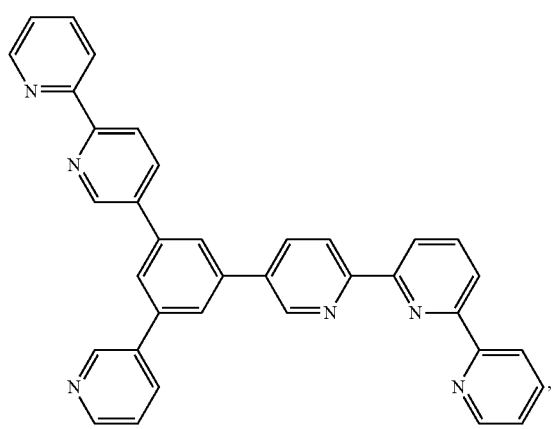
244
-continued
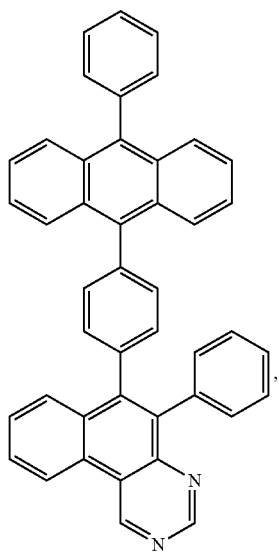
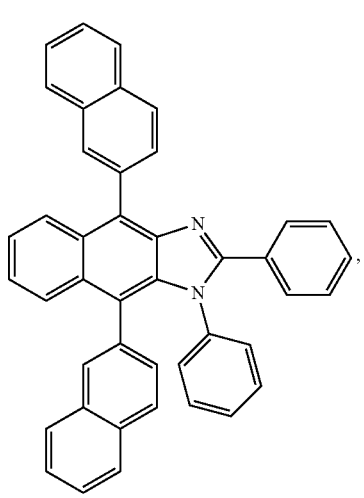
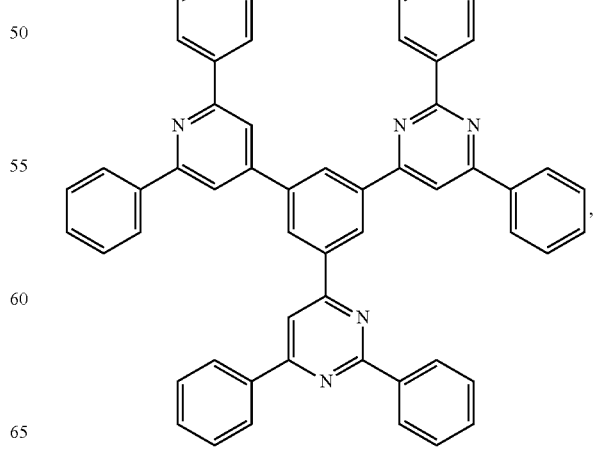

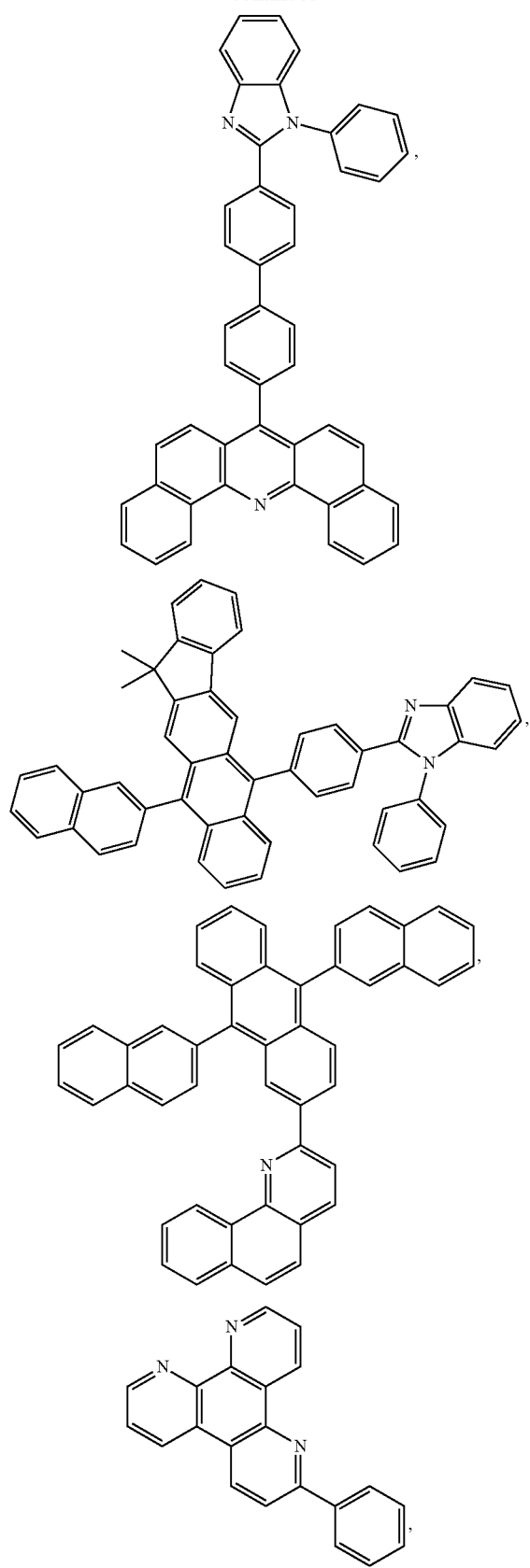
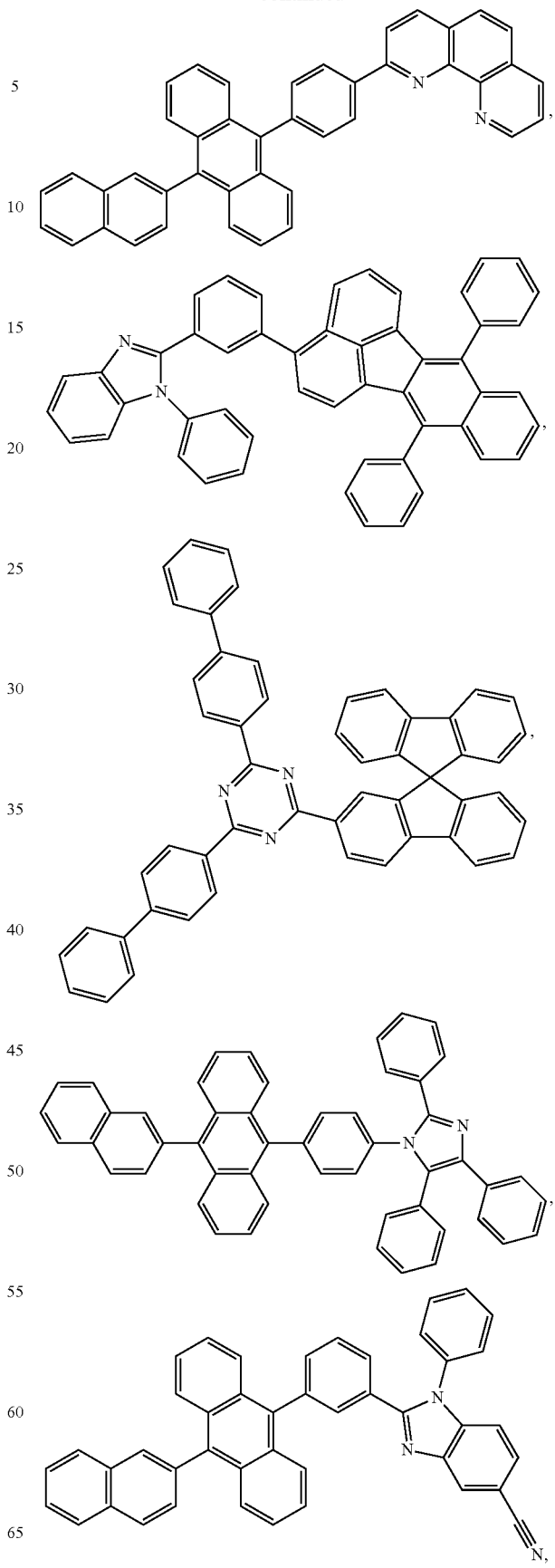

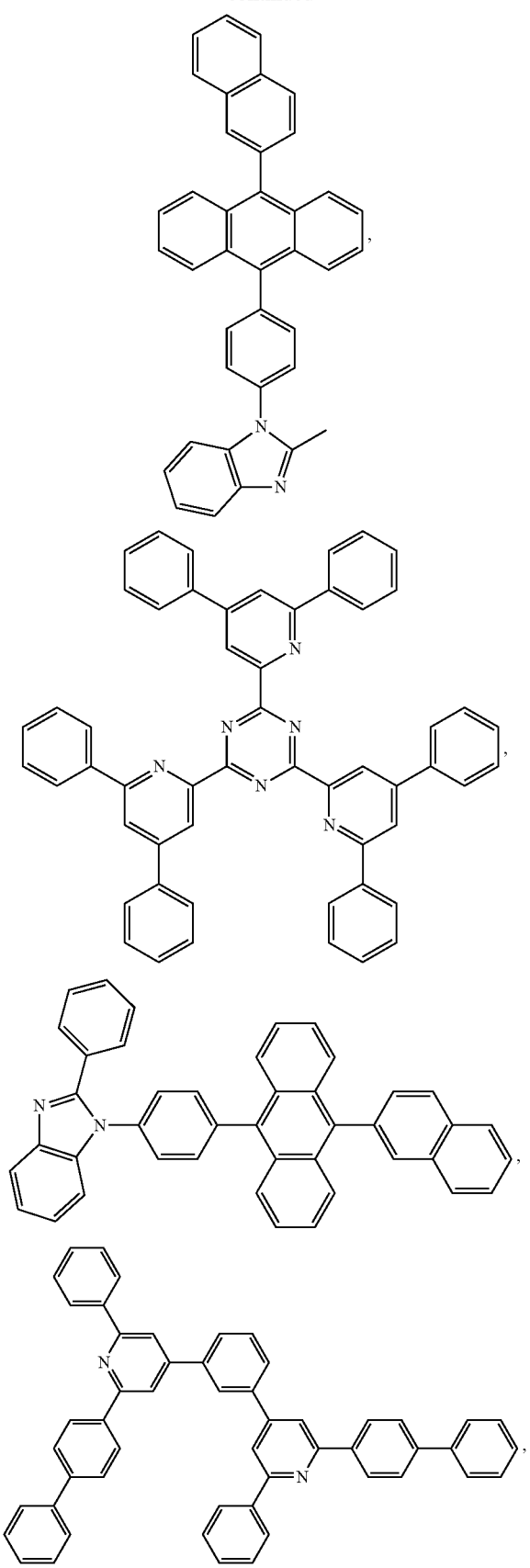

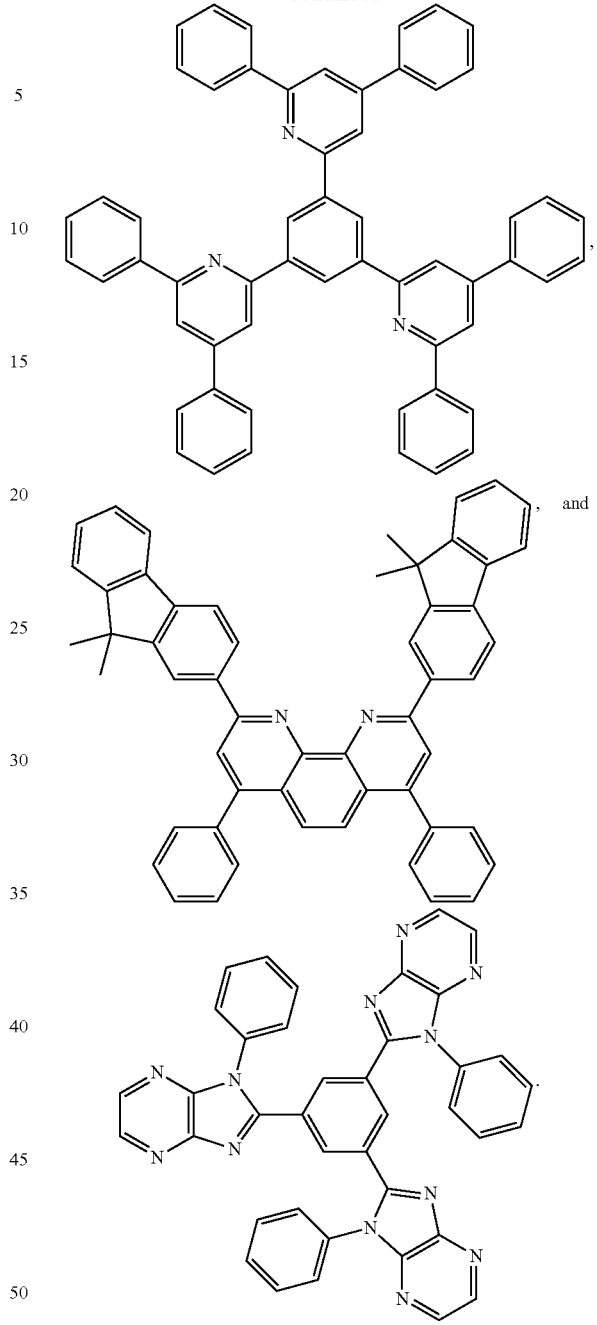

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

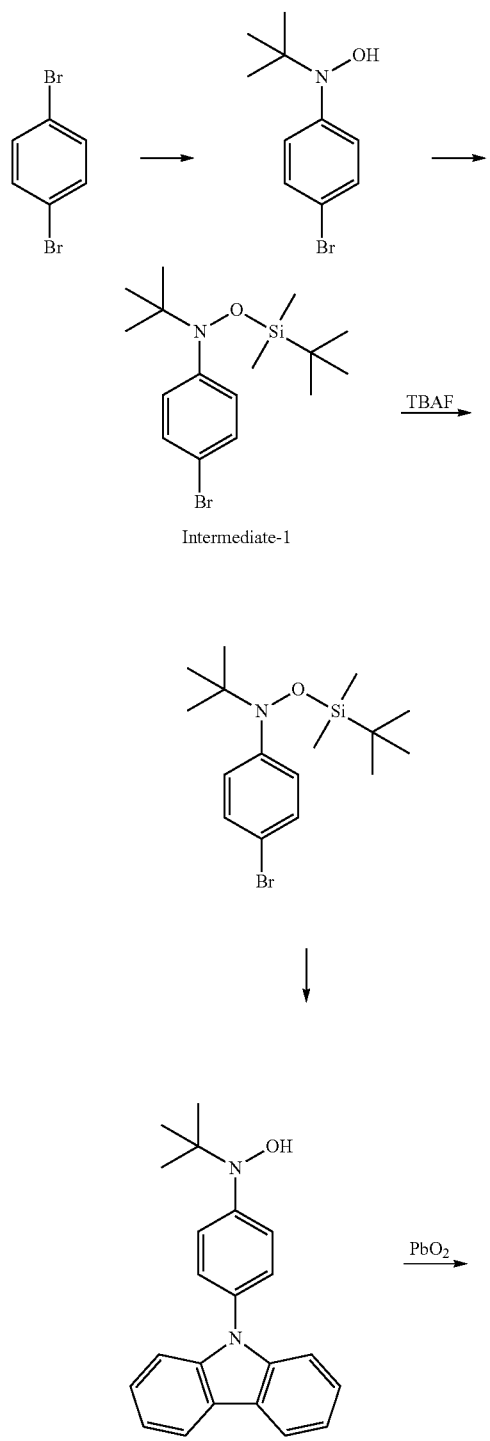

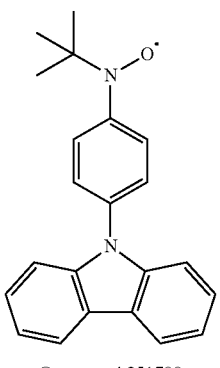

Compound 251788

Intermediate-1 is synthesized according to reported procedure (*Synth. Met.* 2001, 122, 485-493). Compound 251788 is obtained by deprotection of Intermediate-1 by TBAF, followed by transition metal catalyzed C—N coupling between Intermediate-1 and carbazole and oxidation in the presence of PbO$_2$ (*J. Am. Chem. Soc.* 2009, 131, 3700-3712).

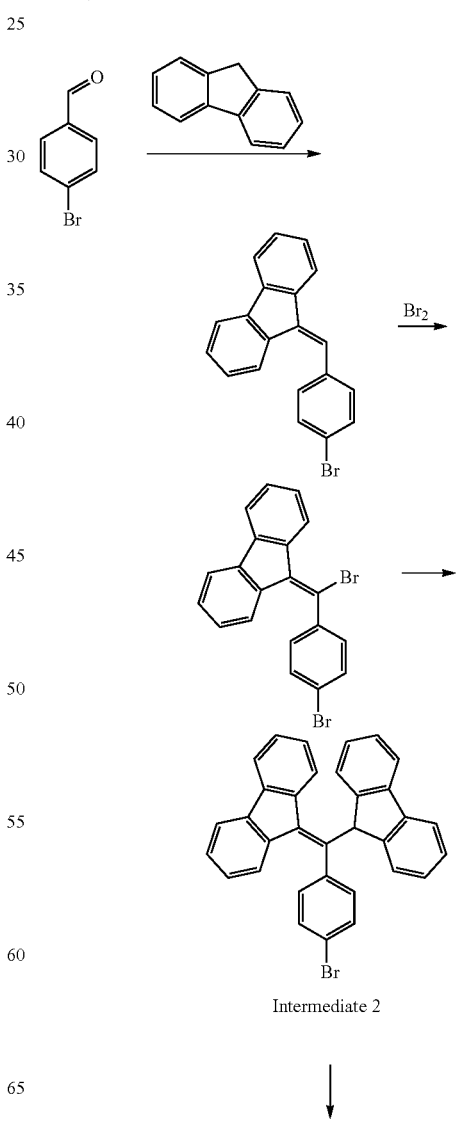

Intermediate 2

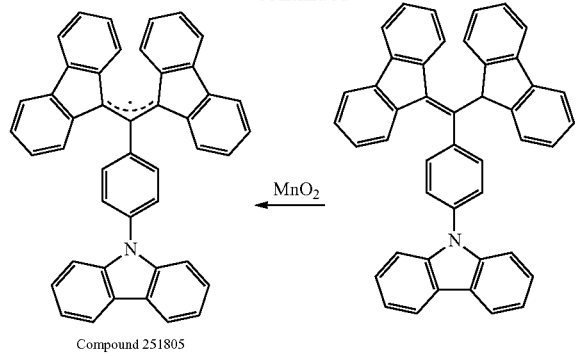

Compound 251805

Intermediate-2 is synthesized according to reported procedure (PCT Int. Appl. 2013022046). Compound 251805 is obtained by transition metal catalyzed C—N coupling between Intermediate-1 and carbazole, followed by a literature oxidation procedure in the presence of MnO₂ (*J. Phys. Chem. A*, 2016, 120, 2841-2853).

Time Dependent Density Functional Theory (TDDFT) calculations were used to predict the emission properties of select compounds described herein. The emission wavelength was calculated within the Gaussian software package using the B3LYP-D3 hybrid functional set and 6-31G* basis set, and derived from the relative energy of the first vertical excited doublet state compared to the corresponding ground state. A continuum solvent model was applied to simulate tetrahydrofuran solvent. The DFT calculations are summarized in Table 2.

The DFT calculations demonstrate that how substituent effects may be used to tune the emission properties of stable radical emitters over a wide range of wavelengths. For example, the α-nitronyl nitroxide compounds 1-4 vary over an emission range of 518-579 nm (green to yellow). These are useful wavelengths for the fabrication of organic light-emitting devices. Compounds 5-19 are all constructed around the triphenylmethyl radical, and exhibit emission over a very wide range of wavelengths—from yellow (e.g. compound 5) to red (e.g. compound 10) to near IR (e.g. compound 17)—depending on substitution. It may therefore be anticipated that these compounds will find application in organic light-emitting devices, including night-vision and virtual reality displays.

TABLE 2

| Representative Compound No. | Structure | Emission Wavelength (nm) |
|---|---|---|
| 1 | 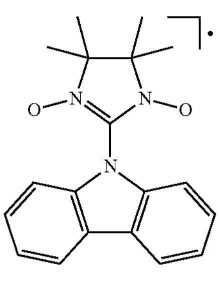 | 528 |
| 2 | 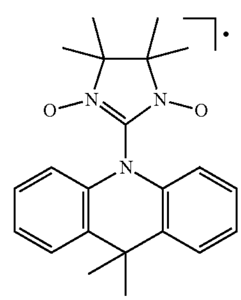 | 544 |
| 3 | 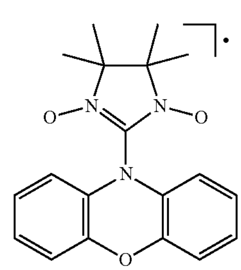 | 579 |

TABLE 2-continued

| Representative Compound No. | Structure | Emission Wavelength (nm) |
|---|---|---|
| 4 | 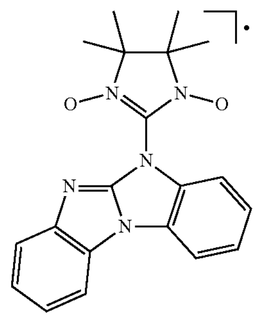 | 518 |
| 5 | 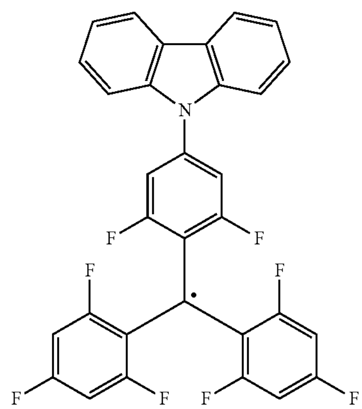 [SMILES: Fc1cc(F)c(C(c2c(F)cc(F)cc2F)c2c(F)cc(-n3c4ccccc4c4ccccc43)cc2F)c(F)c1] | 581 |
| 6 | 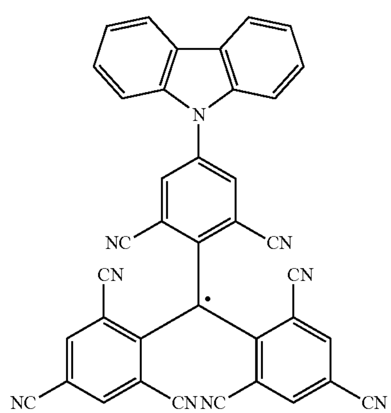 [SMILES: N#Cc1cc(C#N)c(C(c2c(C#N)cc(C#N)cc2C#N)c2c(C#N)cc(-n3c4ccccc4c4ccccc43)cc2C#N)c(C#N)c1] | 1081 |
| 7 | 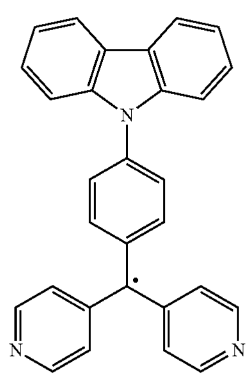 [SMILES: c1ccc2c(c1)c1ccccc1n2-c1ccc(C(c2ccncc2)c2ccncc2)cc1] | 610 |

TABLE 2-continued

| Representative Compound No. | Structure | Emission Wavelength (nm) |
|---|---|---|
| 8 | 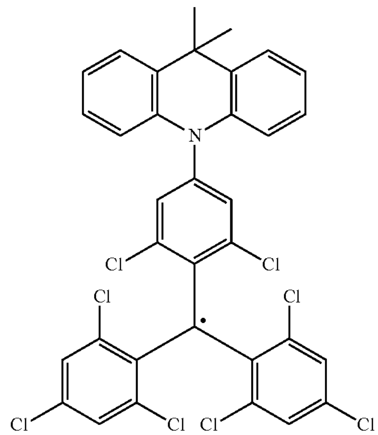 [SMILES: CC1(C)c2ccccc2N(c2cc(Cl)c(C(c3c(Cl)cc(Cl)cc3Cl)c3c(Cl)cc(Cl)cc3Cl)c(Cl)c2)c2ccccc21] | 1015 |
| 9 | 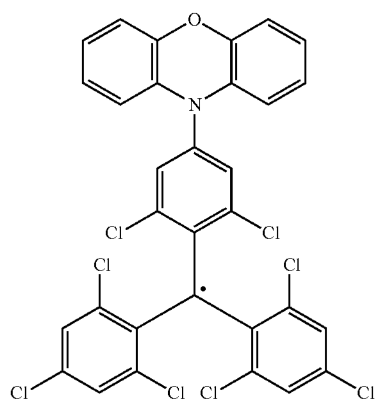 [SMILES: Clc1cc(Cl)c(C(c2c(Cl)cc(Cl)cc2Cl)c2c(Cl)cc(N3c4ccccc4Oc4ccccc43)cc2Cl)c(Cl)c1] | 1279 |
| 10 | 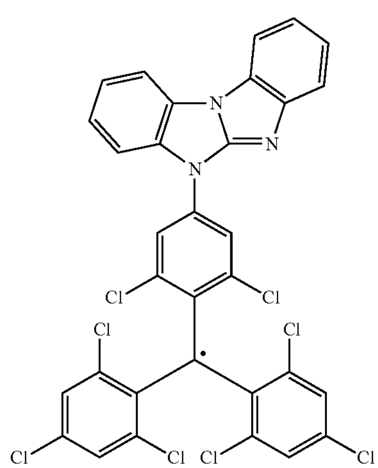 [SMILES: Clc1cc(Cl)c(C(c2c(Cl)cc(Cl)cc2Cl)c2c(Cl)cc(-n3c4ccccc4n4c5ccccc5nc34)cc2Cl)c(Cl)c1] | 644 |

TABLE 2-continued

| Representative Compound No. | Structure | Emission Wavelength (nm) |
|---|---|---|
| 11 | 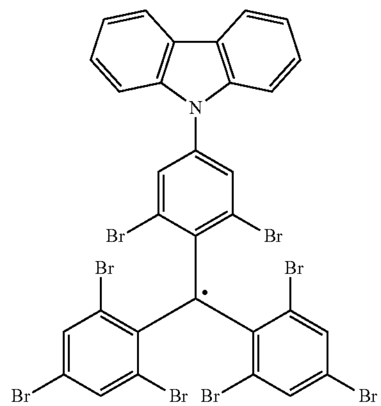 [SMILES: Brc1cc(Br)c(C(c2c(Br)cc(Br)cc2Br)c2c(Br)cc(-n3c4ccccc4c4ccccc43)cc2Br)c(Br)c1] | 687 |
| 12 | 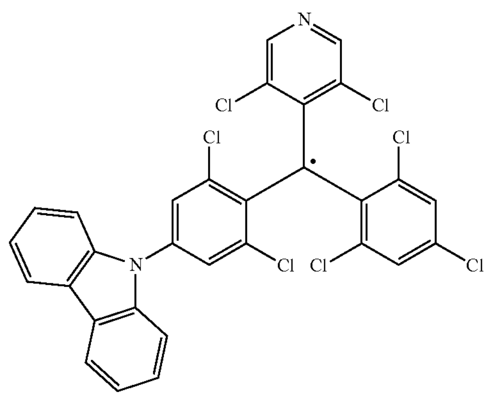 [SMILES: Clc1cc(Cl)c(C(c2c(Cl)cncc2Cl)c2c(Cl)cc(-n3c4ccccc4c4ccccc43)cc2Cl)c(Cl)c1] | 693 |
| 13 | 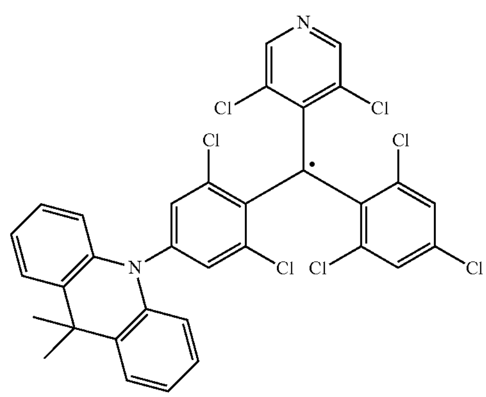 [SMILES: CC1(C)c2ccccc2N(c2cc(Cl)c(C(c3c(Cl)cncc3Cl)c3c(Cl)cc(Cl)cc3Cl)c(Cl)c2)c2ccccc21] | 1170 |
| 14 | 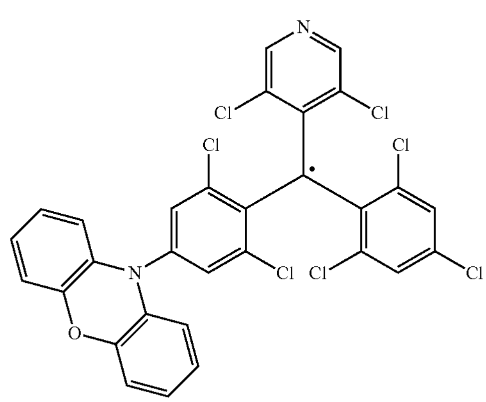 [SMILES: Clc1cc(Cl)c(C(c2c(Cl)cncc2Cl)c2c(Cl)cc(N3c4ccccc4Oc4ccccc43)cc2Cl)c(Cl)c1] | 1322 |

TABLE 2-continued
| Representative Compound No. | Structure | Emission Wavelength (nm) |
|---|---|---|
| 15 | 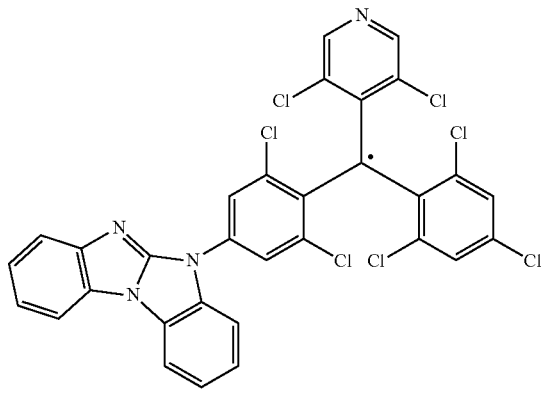 [SMILES: Clc1cc(Cl)c(C(c2c(Cl)cncc2Cl)c2c(Cl)cc(-n3c4ccccc4n4c5ccccc5nc34)cc2Cl)c(Cl)c1] | 670 |
| 16 | 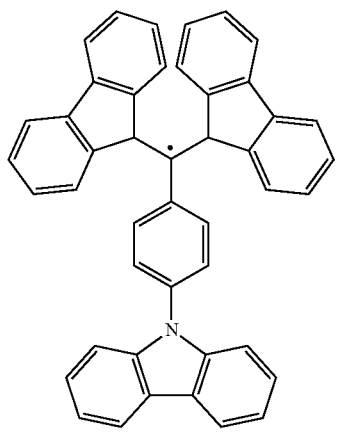 [SMILES: c1ccc2c(c1)-c1ccccc1C2C(c1ccc(-n2c3ccccc3c3ccccc32)cc1)C1c2ccccc2-c2ccccc21] | 769 |
| 17 | 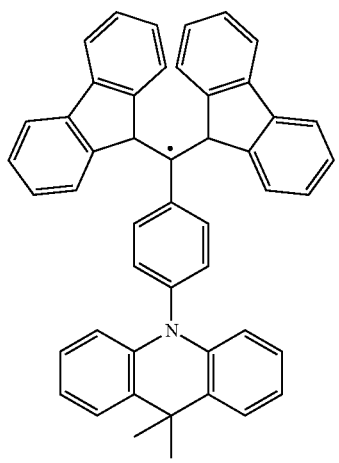 [SMILES: CC1(C)c2ccccc2N(c2ccc(C(C3c4ccccc4-c4ccccc43)C3c4ccccc4-c4ccccc43)cc2)c2ccccc21] | 982 |

TABLE 2-continued

| Representative Compound No. | Structure | Emission Wavelength (nm) |
|---|---|---|
| 18 | 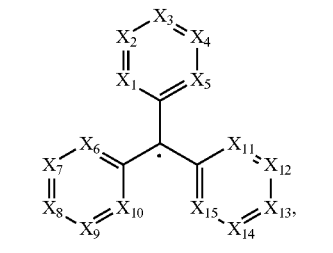 | 1485 |
| 19 | 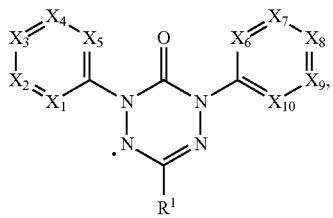 | 771 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound selected from the group consisting of Formulae BB, BC, BD, BE, BF, and BG 263
-continued

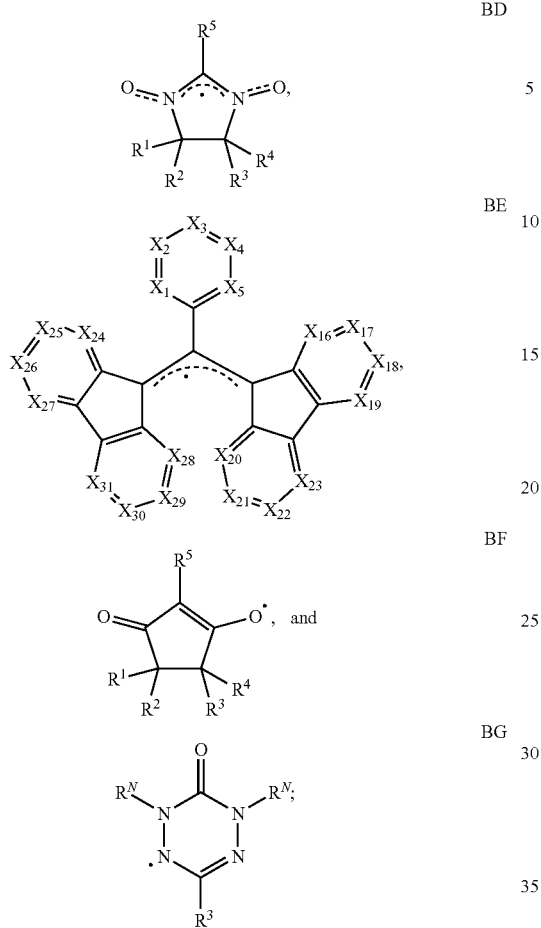

BD

BE

BF

BG wherein

X₁ to X₅ are independently selected from $CR^A$ or N;

X₆ to X₁₀ are independently selected from $CR^B$ or N;

X₁₁ to X₁₅ are independently selected from $CR^C$ or N;

X₁₆ to X₂₃ are independently selected from $CR^D$ or N;

X₂₄ to X₃₁ are independently selected from $CR^E$ or N;

$R^A$, $R^B$, $R^C$, $R^D$, and $R^E$ independently represent mono to the maximum allowable substitution, or no substitution;

each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;

$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;

wherein at least one of $R^1$ to $R_5$, $R^A$, $R_B$, $R^C$, $R^D$, or $R^E$ includes a polycyclic group selected from the group consisting of:

264

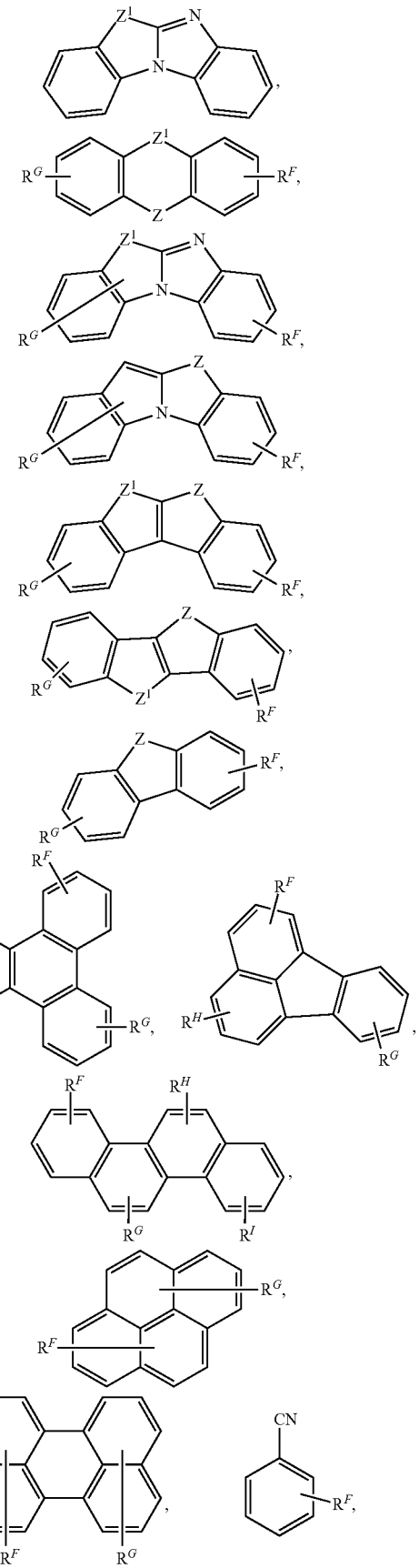

-continued

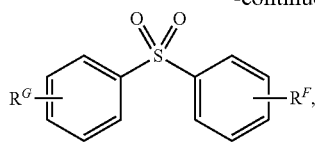 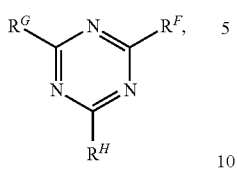

and any aza-analogue of each thereof, each of which is optionally substituted with R$^P$, wherein R$^P$ is selected from the group consisting of deuterium, fluorine, alkyl, cycloalkyl, amino, aryl, heteroaryl, silyl, nitrile, and combinations thereof;

wherein R$^F$ to R$^I$ independently represent mono to the maximum allowable substitution, or no substitution and are independently selected from the group consisting of hydrogen, deuterium, fluorine, alkyl, cycloalkyl, amino, aryl, heteroaryl, silyl, and nitrile and combinations thereof; and Z and Z$^1$ are independently selected from the group consisting of O, S, Se, NR$^N$, CR'R", SiR'R", and GeR'R", wherein R' and R" are independently R$^N$;

with the proviso that R$^5$ in BD does not include both a pyrazole group and a pyrene group;

with the proviso that, in Formula BB, X$_1$ and X$_5$ are not CR$^A$, wherein R$^A$ is halide, at the same time; and with the proviso that, in Formula BE, at least one of X$_1$ to X$_5$ is CR$^A$, wherein R$^A$ is selected from the group consisting of

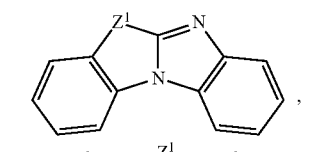

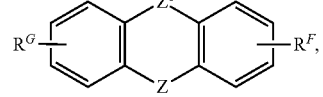

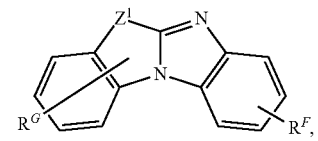

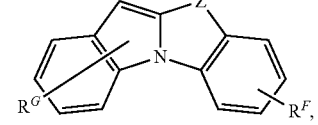

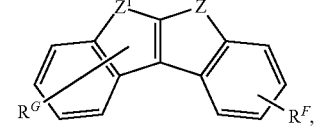

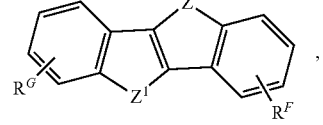

-continued

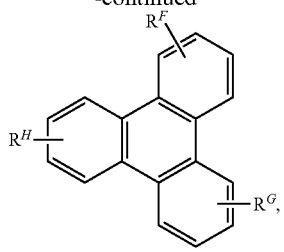

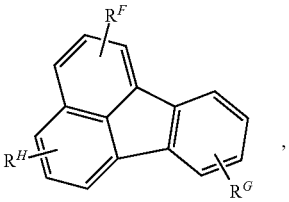

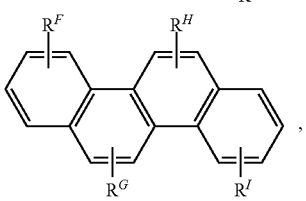

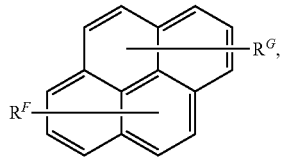

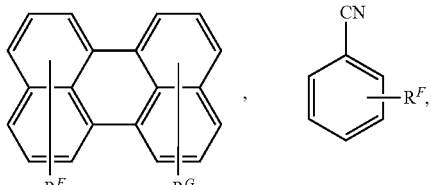

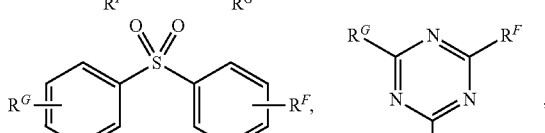

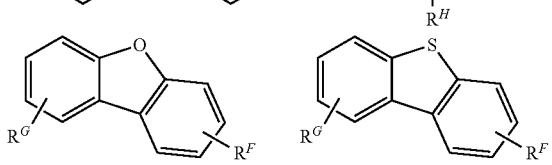

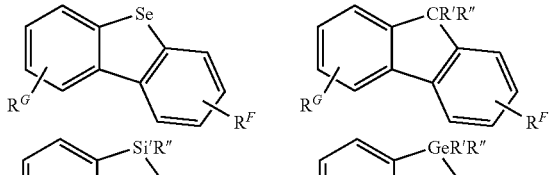

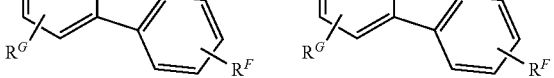

and any aza-analogue of each thereof, each of which is optionally substituted with R$^P$, wherein R$^P$ is selected from the group consisting of deuterium, fluorine, alkyl, cycloalkyl, amino, aryl, heteroaryl, silyl, nitrile, and combinations thereof.

2. The compound of claim 1, wherein each $R^1$ to $R^5$, and each $R_A$, $R^B$, $R^C$, $R^D$, and $R^E$ are independently selected from the group consisting of hydrogen, deuterium, fluorine, chlorine, nitrile, alkyl, cycloalkyl, alkoxy, aryloxy, amino, silyl, aryl, heteroaryl, and combinations thereof.

3. The compound of claim 1, wherein the polycyclic group is selected from the group consisting of

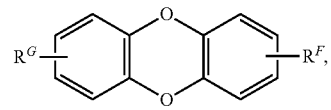

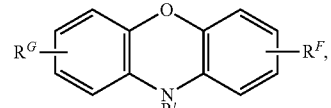

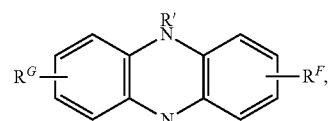

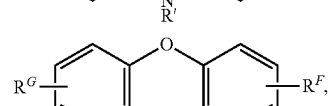

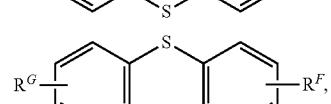

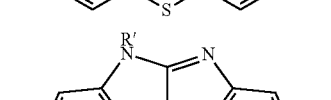

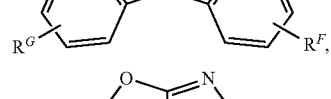

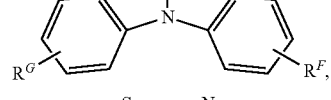

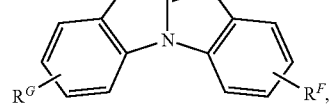

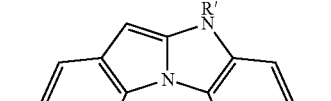

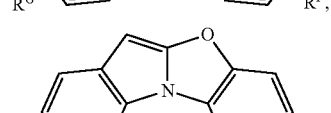

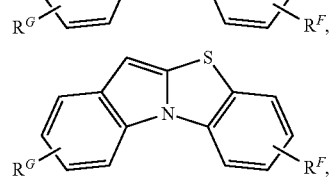

-continued

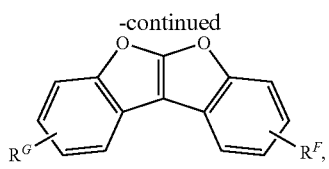

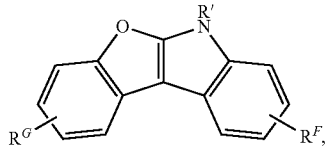

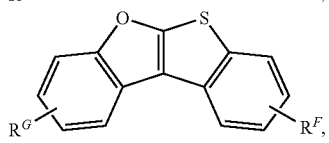

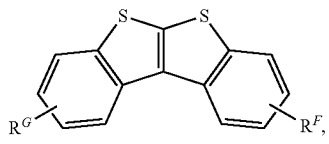

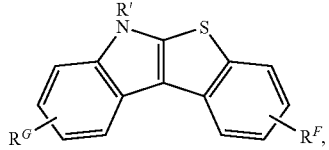

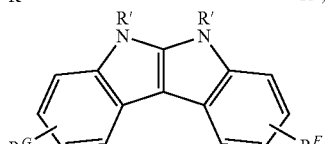

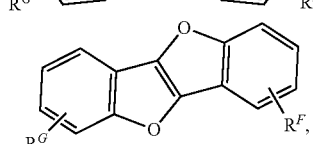

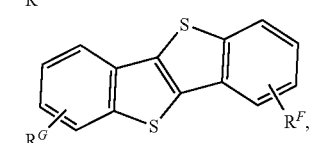

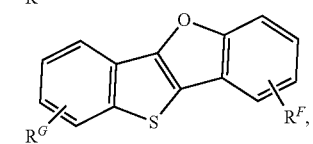

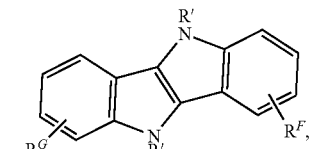

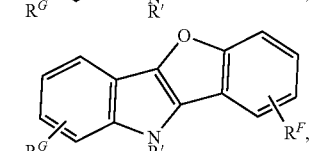

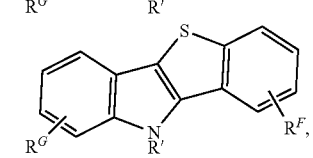

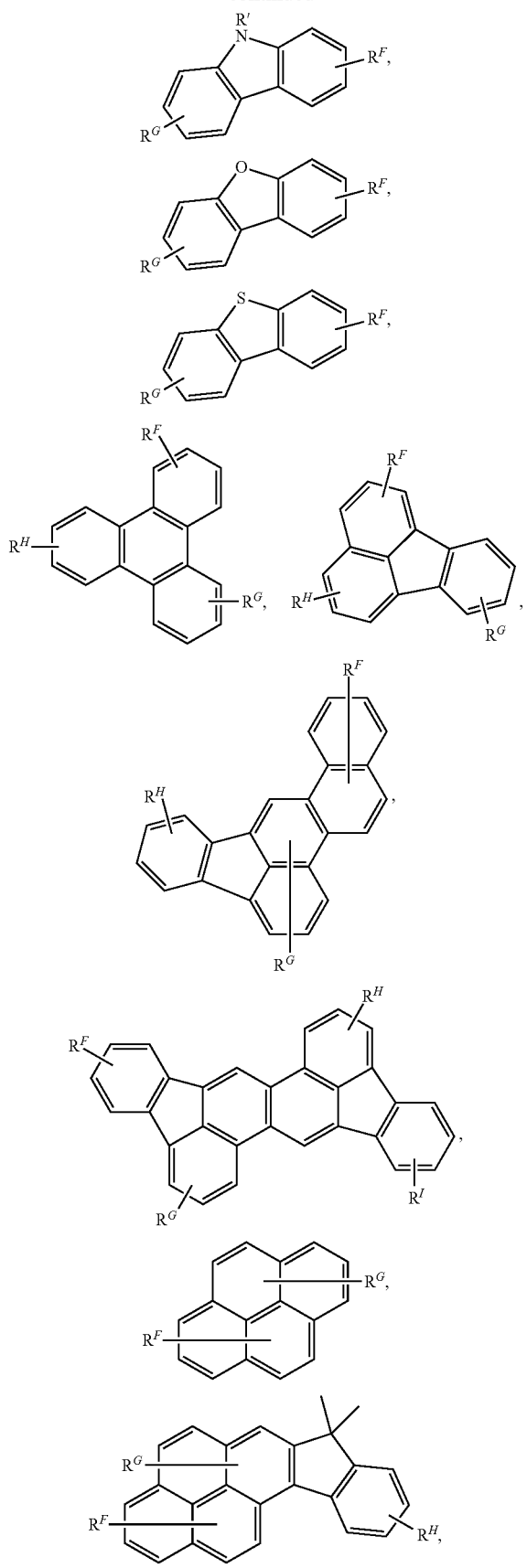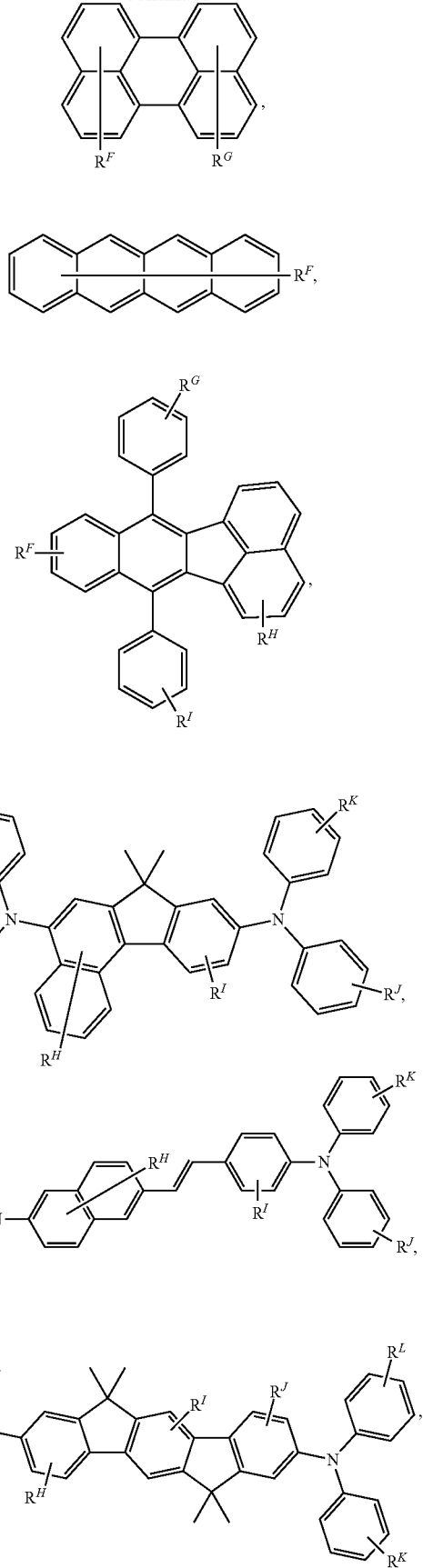

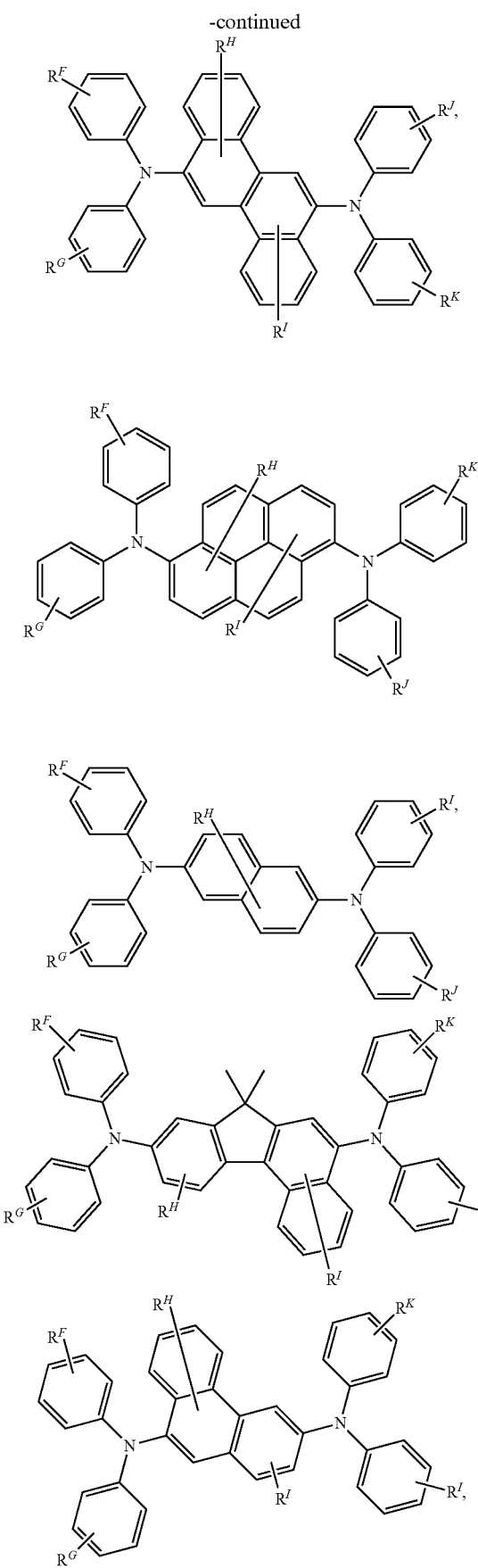
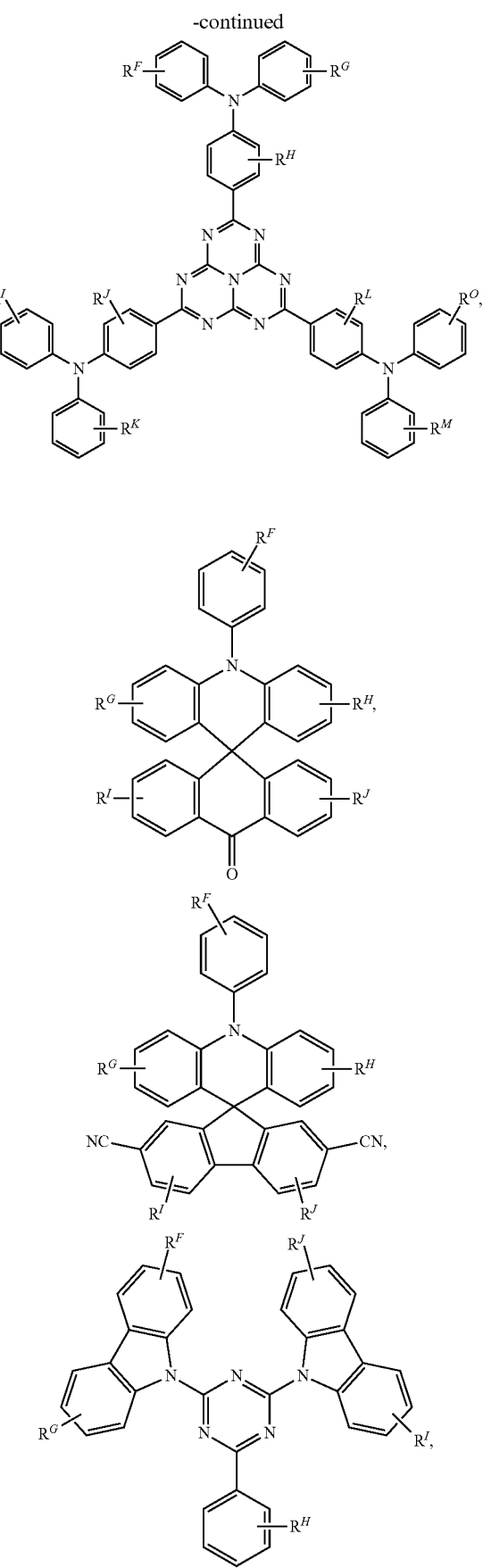

-continued

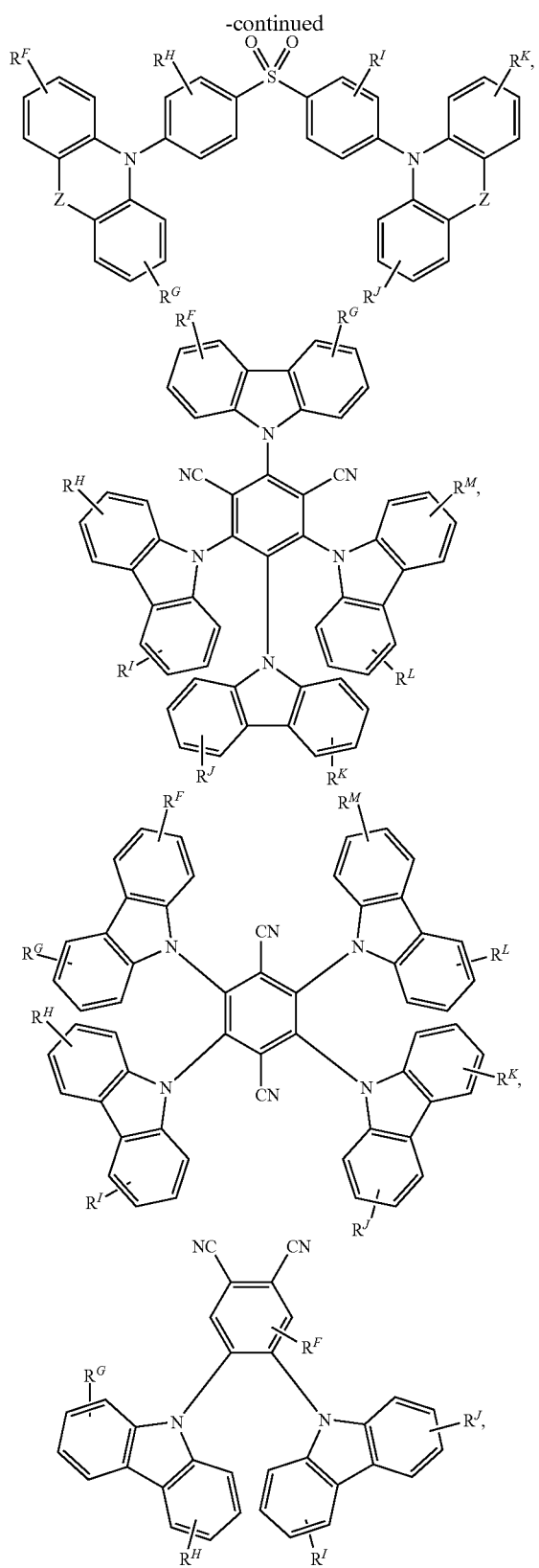

and aza-analogues thereof;
wherein $R^F$ to $R^M$ and $R^O$ are independently selected from the group consisting of deuterium, fluorine, alkyl, cycloalkyl, amino, aryl, heteroaryl, silyl, nitrile, and combinations thereof, and the polycyclic group is attached through one of $R^F$ to $R^M$, $R^O$ or R', wherein R' is independently $R^N$.

4. The compound of claim 1, wherein the compound is selected from the group consisting of:

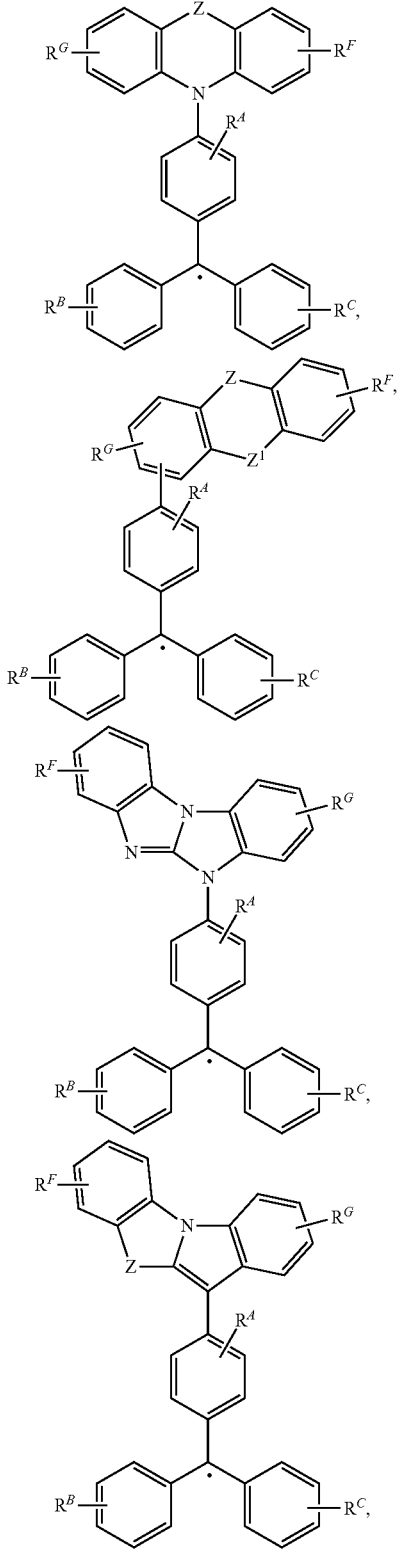

275
-continued
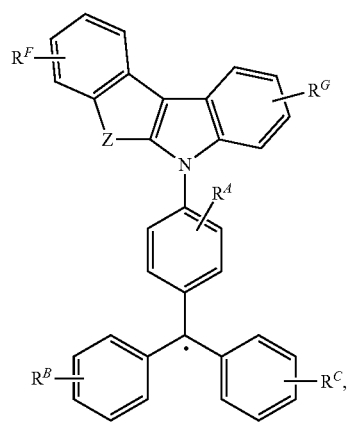
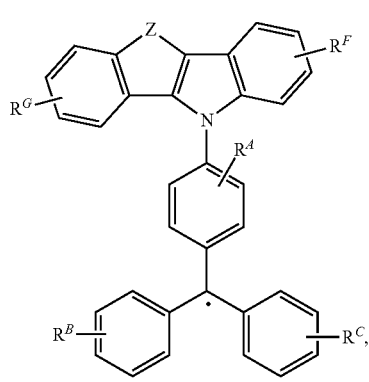
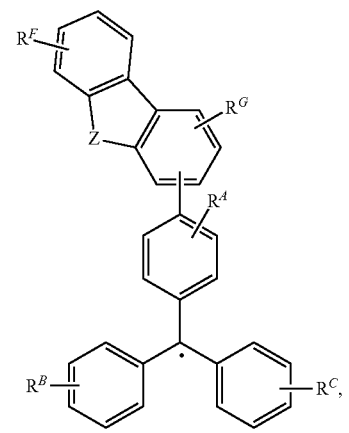
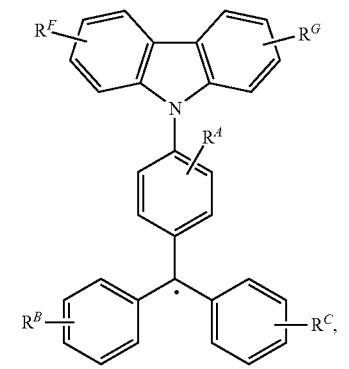
276
-continued
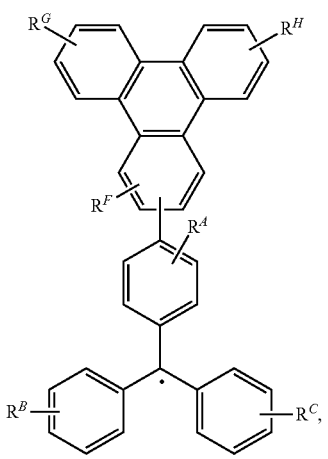
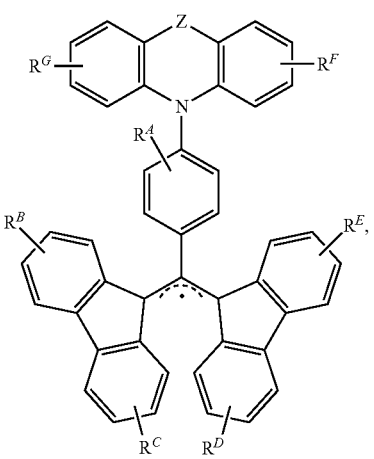
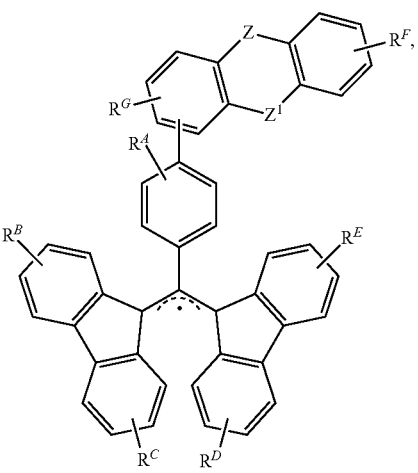

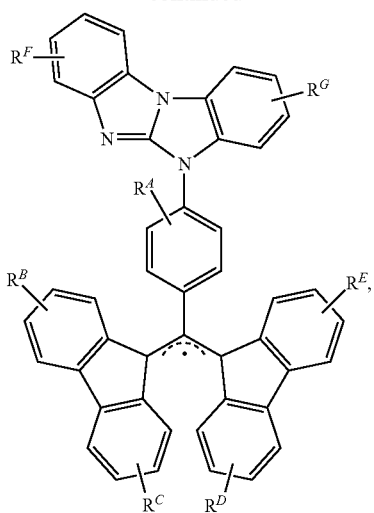
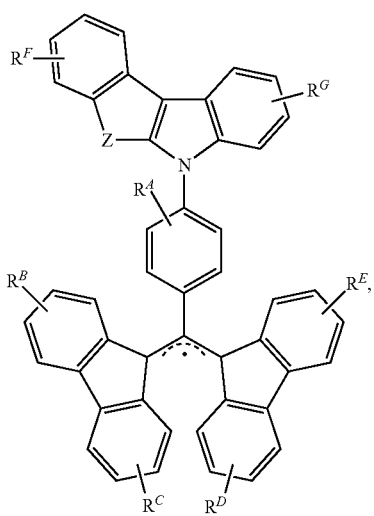
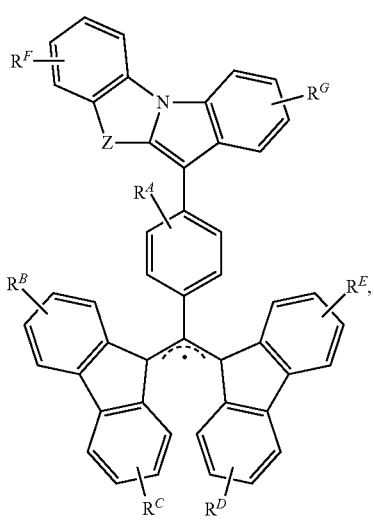
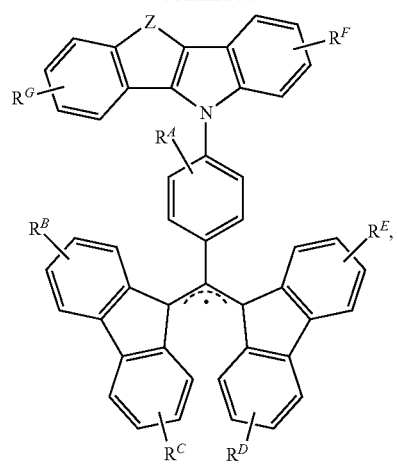
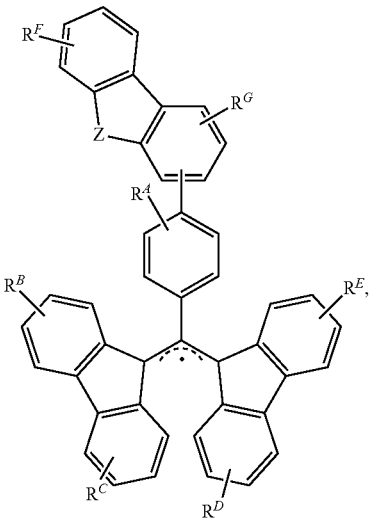
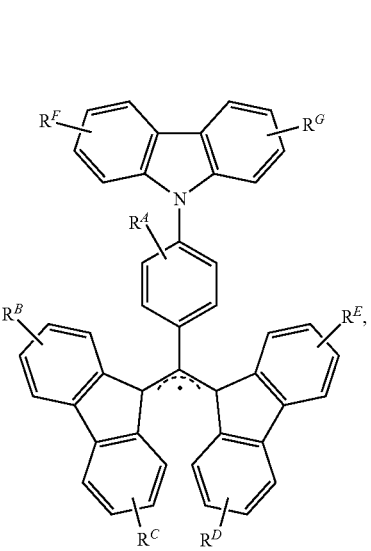

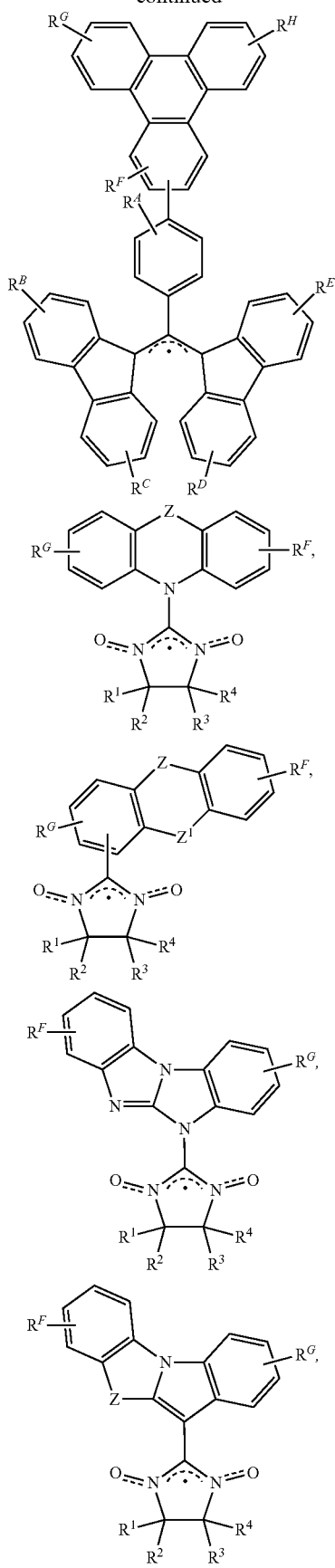
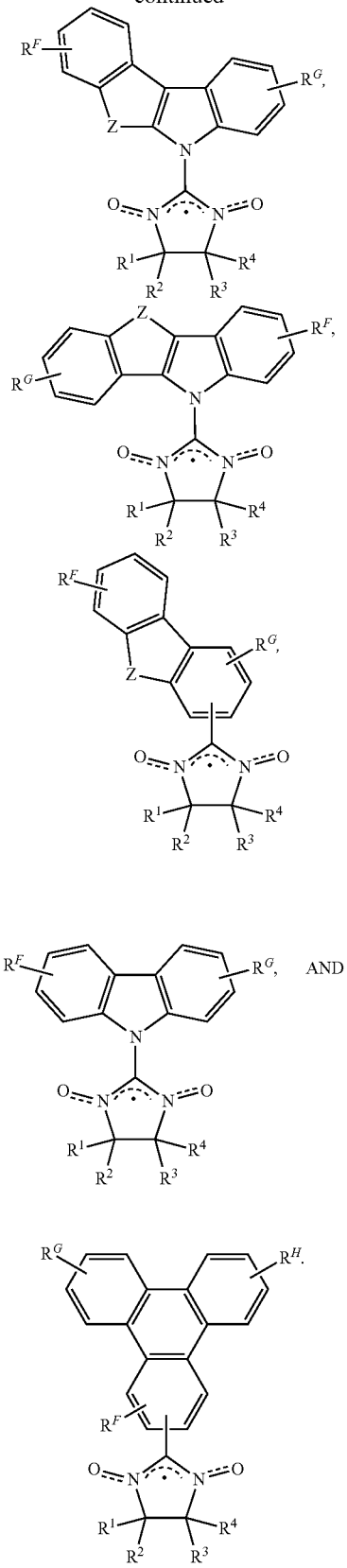
5. The compound of claim 1, wherein the compound is selected from the group consisting of:

281
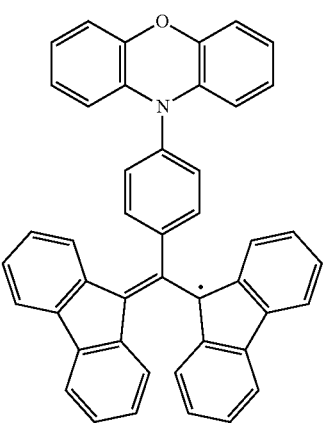
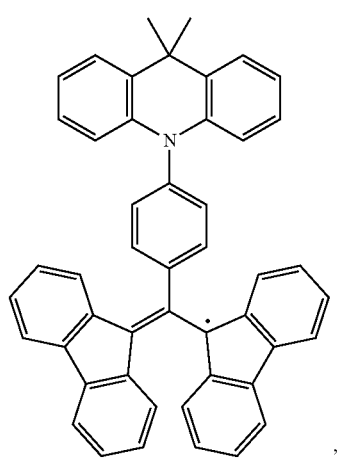
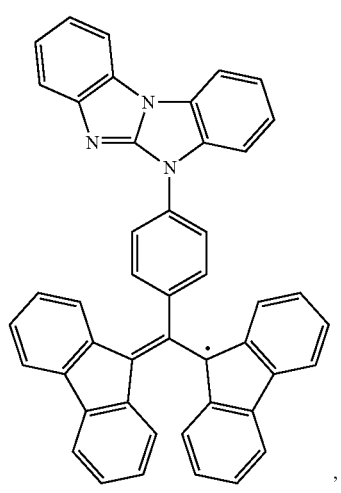
282
-continued
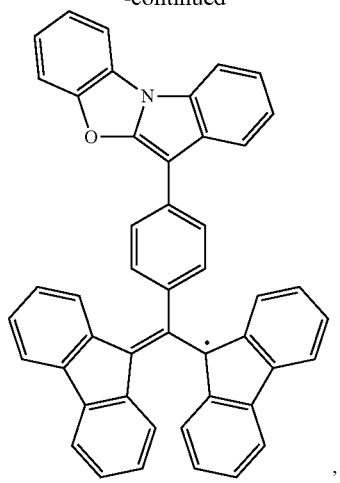
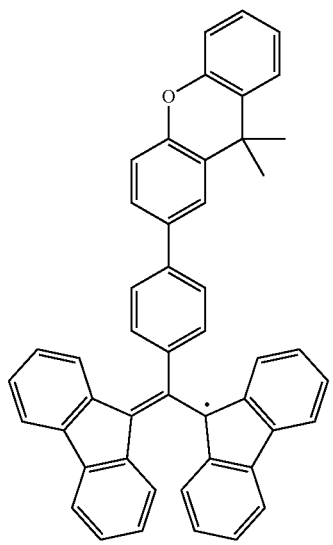
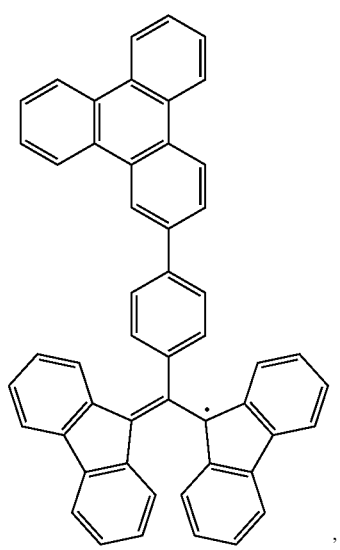

283
-continued
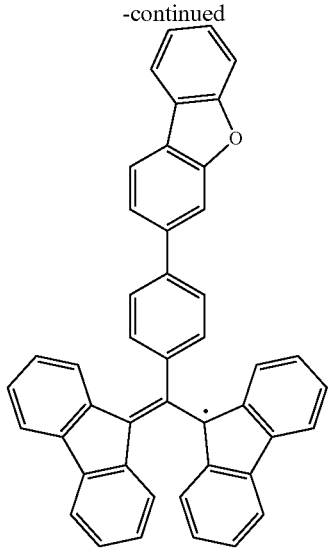
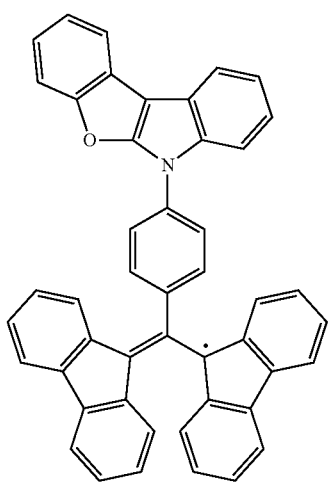
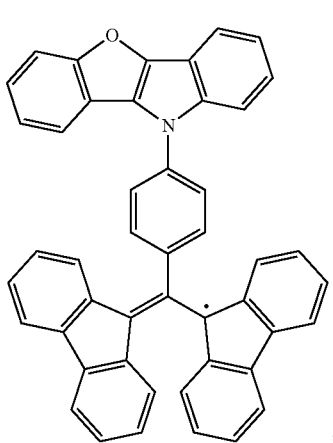
284
-continued
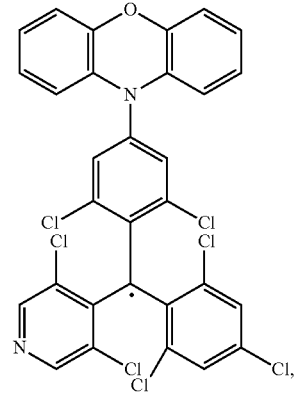
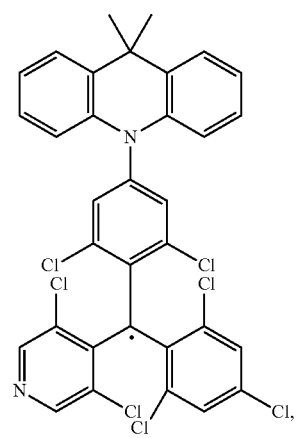
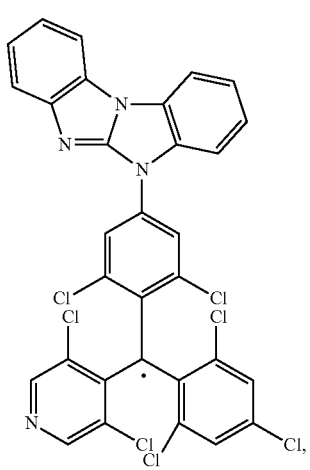

285
-continued
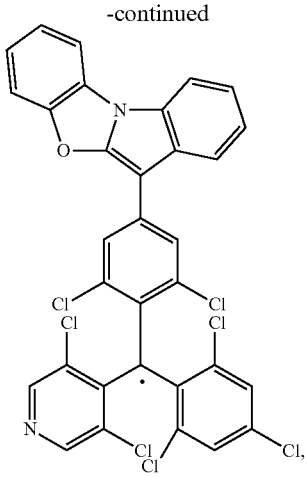
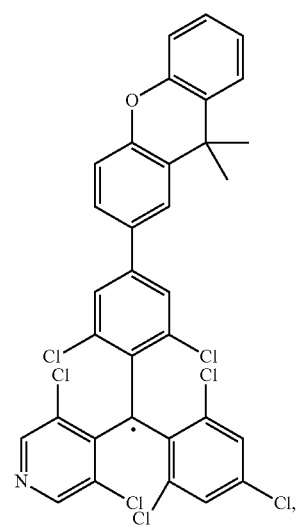
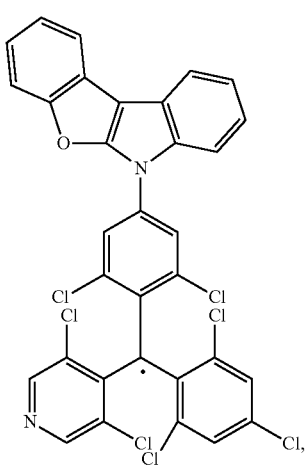
286
-continued
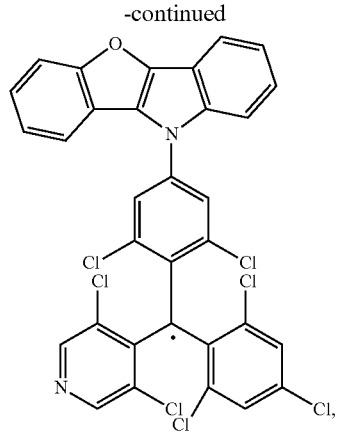
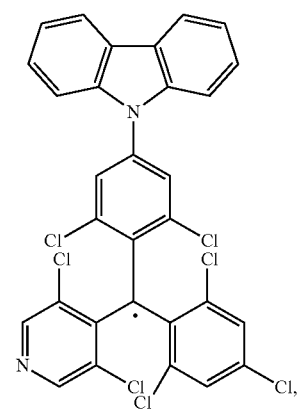
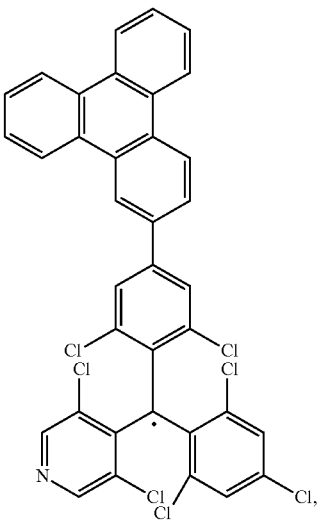

287
-continued
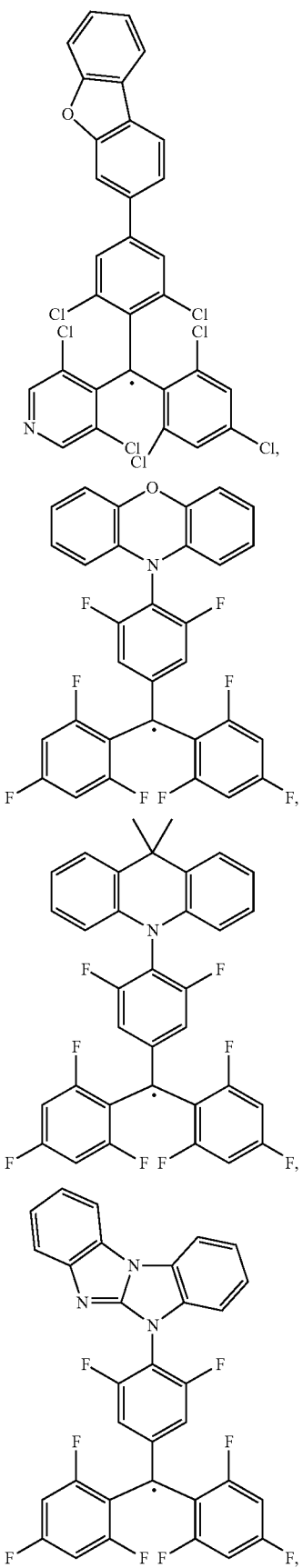
288
-continued
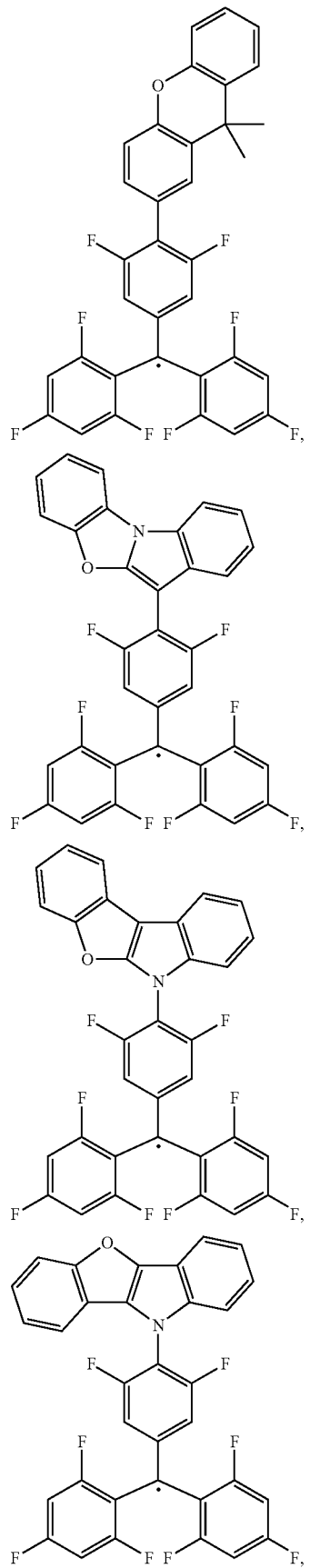

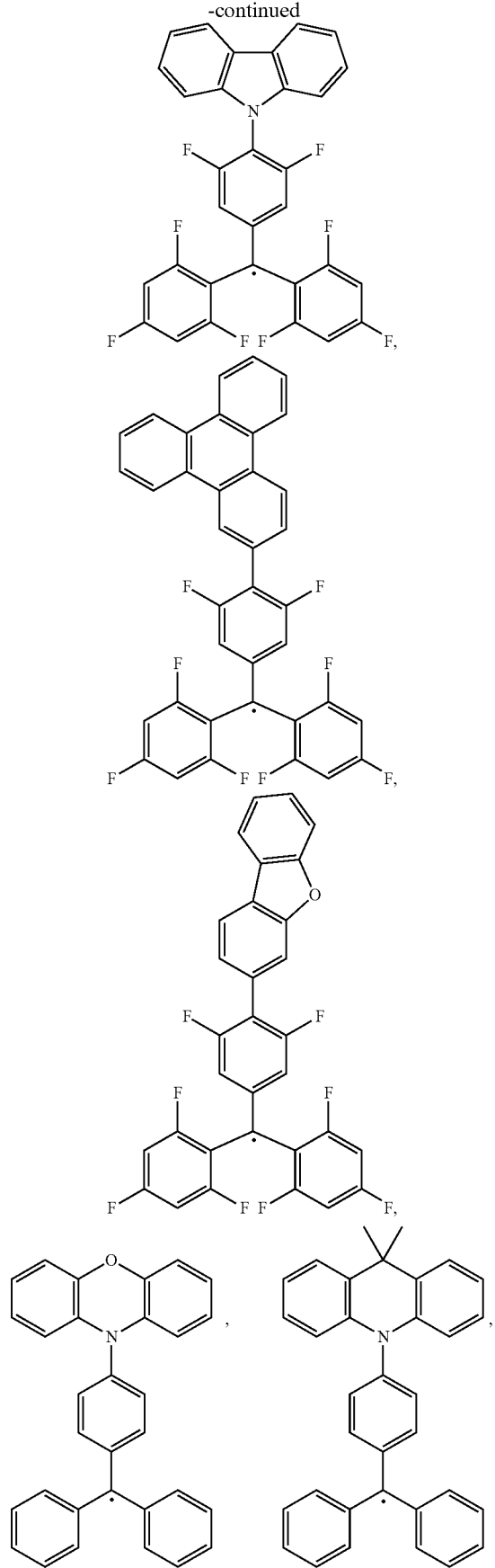
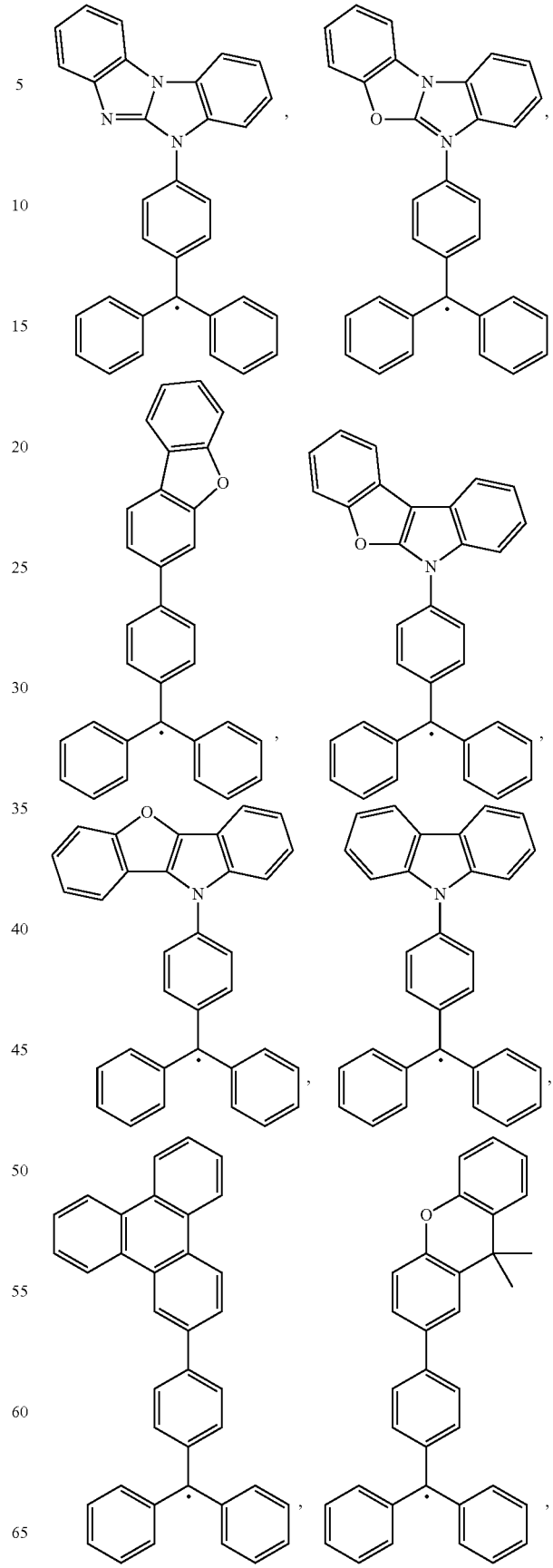

291
-continued
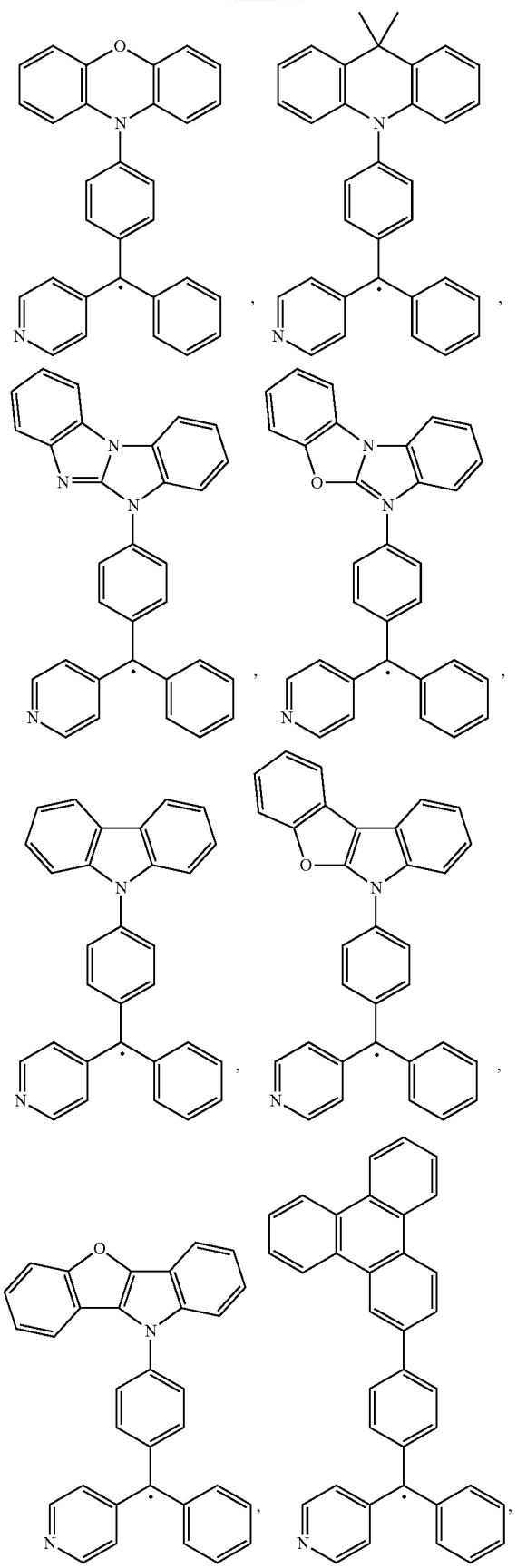
292
-continued
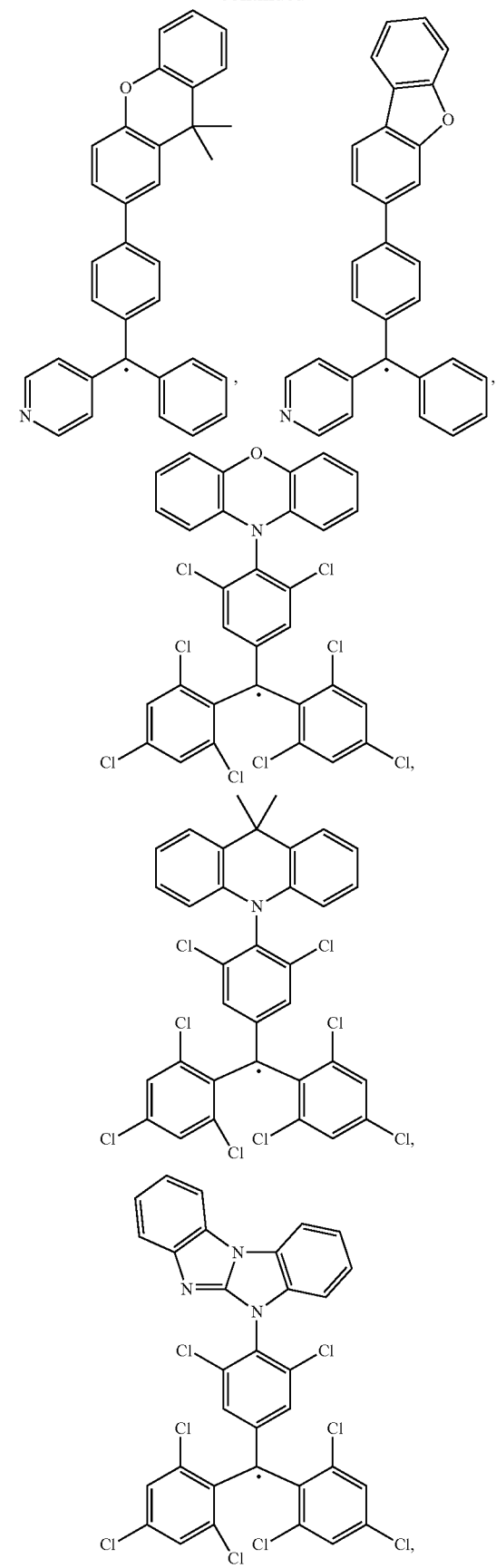

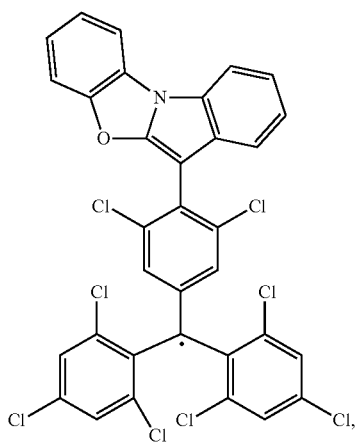
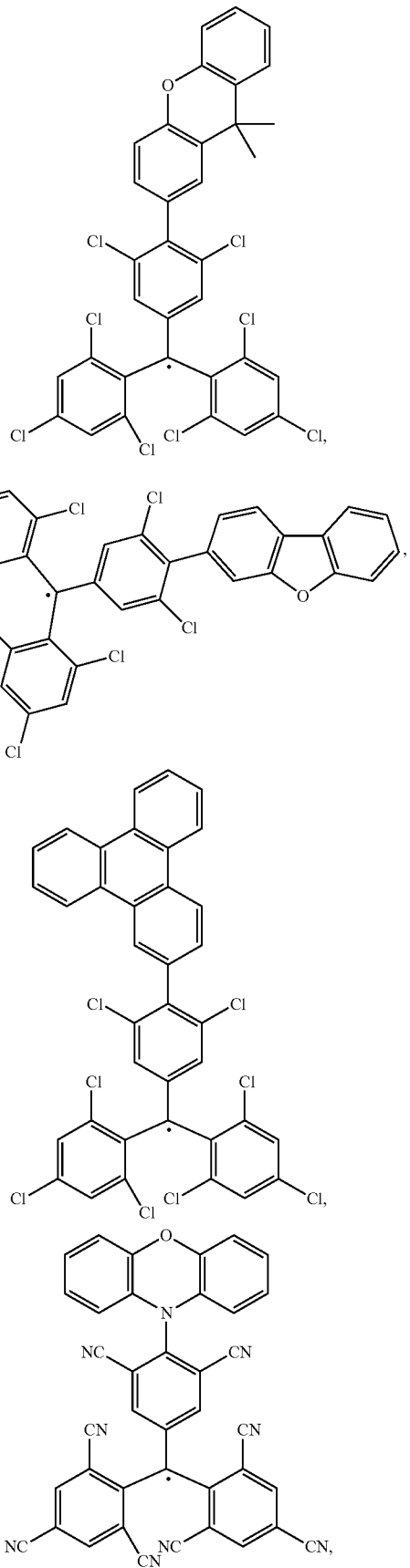

295
-continued
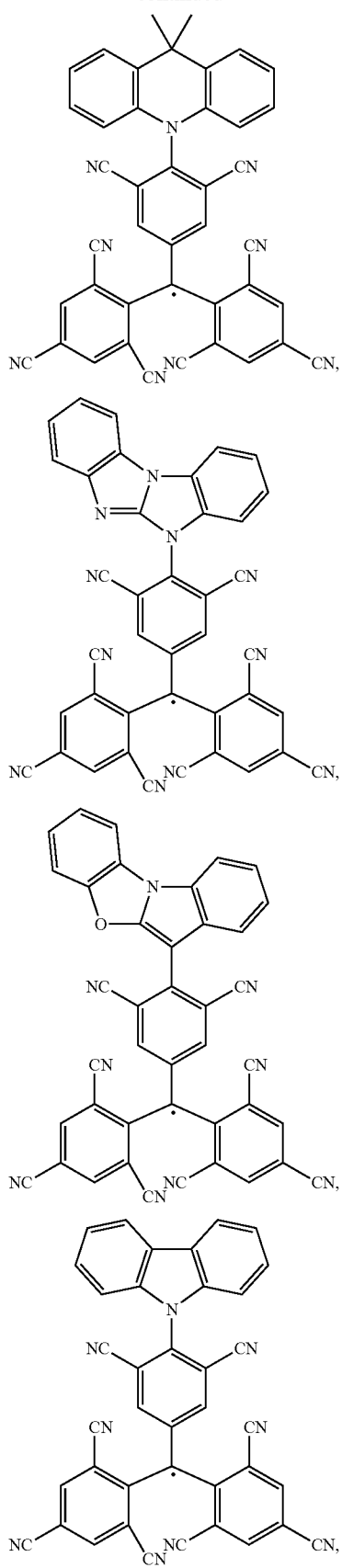
296
-continued
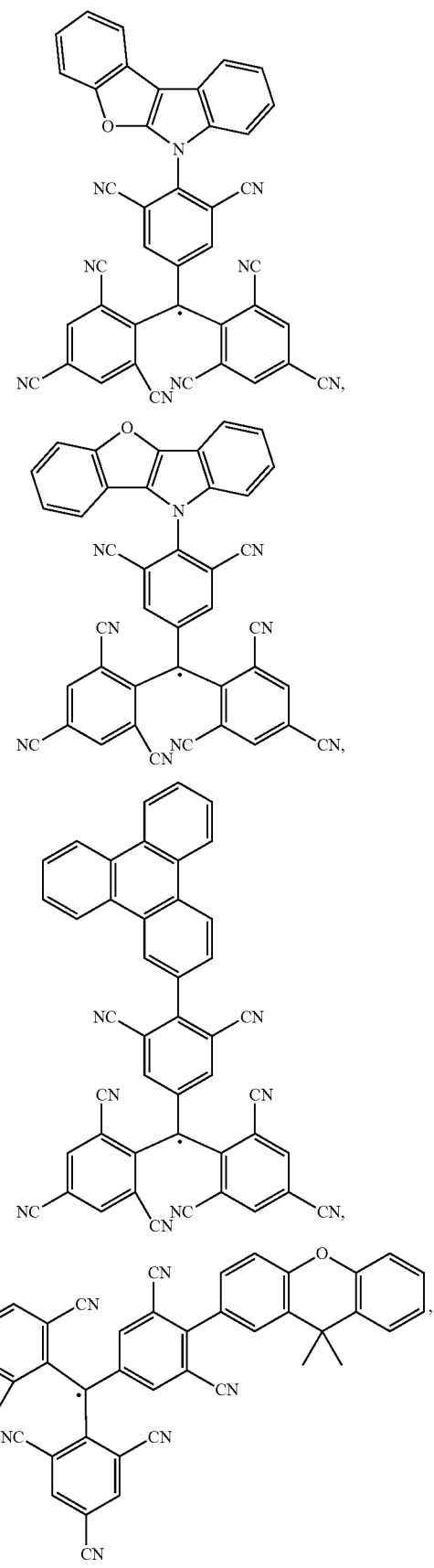

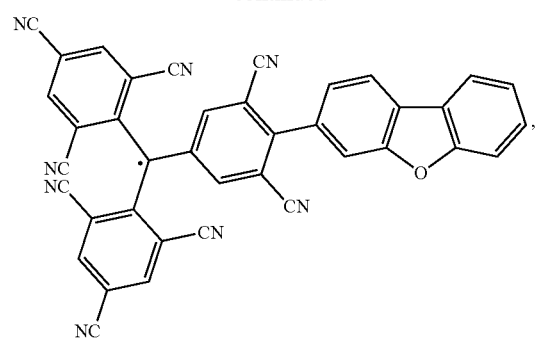
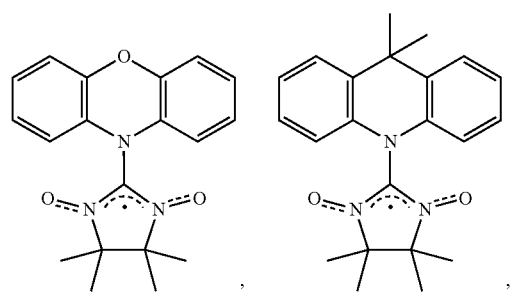
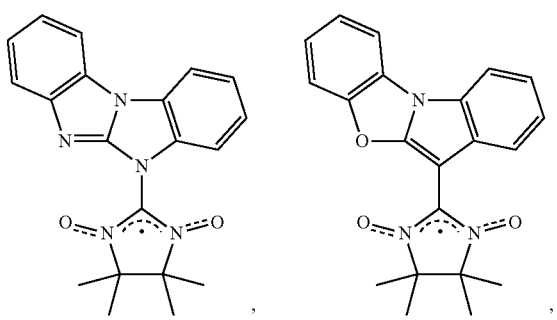
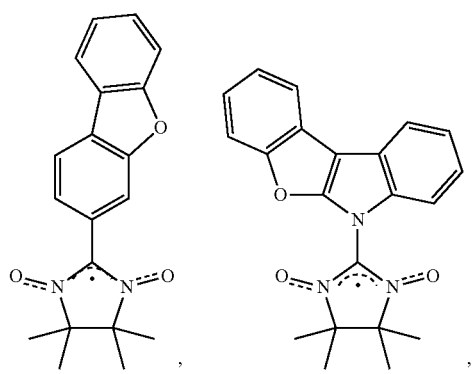
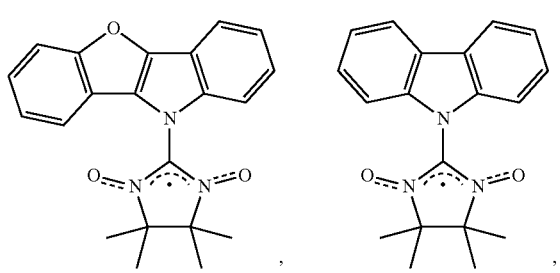
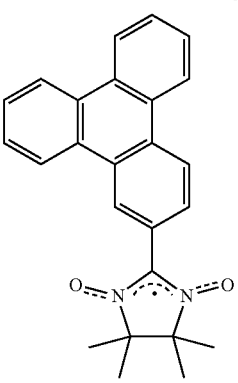
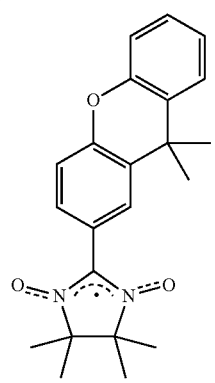
, and .
6. The compound of claim 3, wherein the compound has a peak emission wavelength $\lambda_{max}$ in a range from 700 nm to 1000 nm.
7. An organic light emitting device (OLED) comprising: an anode; a cathode; and an organic layer disposed between the anode and the cathode, the organic layer comprising a compound selected from the group consisting of:
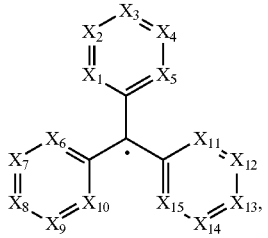
BB
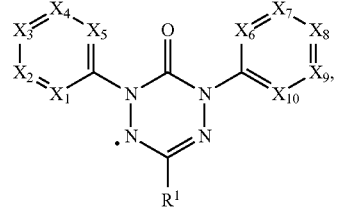
BC
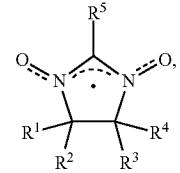
BD
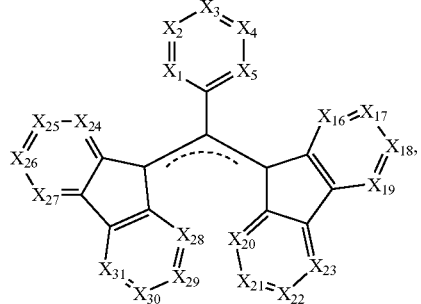
BE

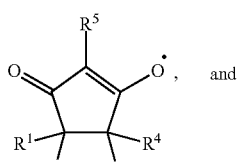

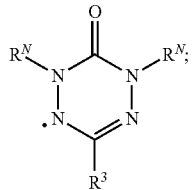

wherein
$X_1$ to $X_5$ are independently selected from $CR^A$ or N;
$X_6$ to $X_{10}$ are independently selected from $CR^B$ or N;
$X_{11}$ to $X_{15}$ are independently selected from $CR^C$ or N;
$X_{16}$ to $X_{23}$ are independently selected from $CR^D$ or N;
$X_{24}$ to $X_{31}$ are independently selected from $CR^E$ or N;
$R^A$, $R^B$, $R^C$, $R^D$, and $R^E$ independently represent mono to the maximum allowable substitution, or no substitution;
each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;
$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;
wherein at least one of $R^1$ to $R^5$, $R^A$, $R^B$, $R^C$, $R^D$, or $R^E$ includes a polycyclic group selected from the group consisting of:

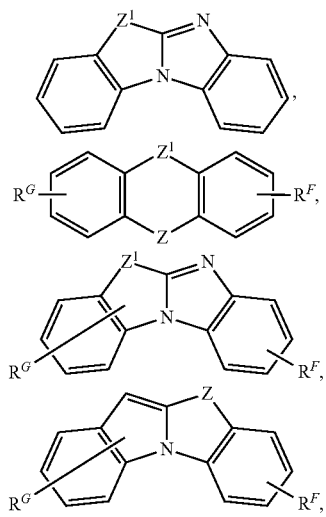

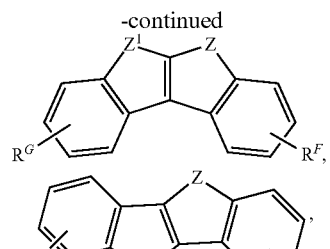

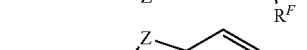

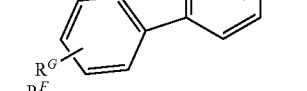

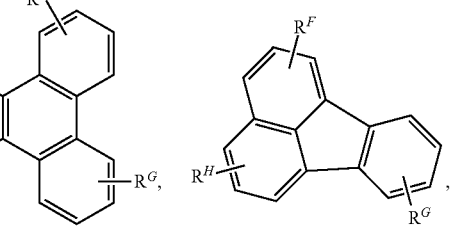

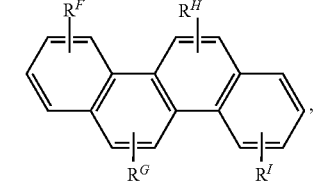

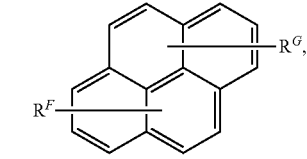

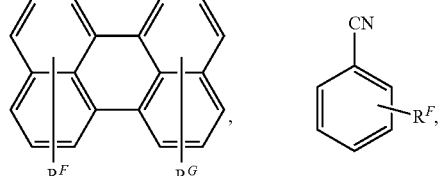

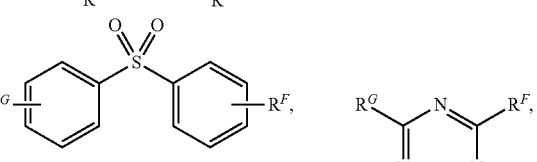

and any aza-analogue of each thereof, each of which is optionally substituted with $R^F$, wherein $R^F$ is selected from the group consisting of deuterium, fluorine, alkyl, cycloalkyl, amino, aryl, heteroaryl, silyl, nitrile, and combinations thereof;
wherein $R^F$ to $R^I$ are independently selected from the group consisting of deuterium, fluorine, alkyl, cycloalkyl, amino, aryl, heteroaryl, silyl, nitrile, and combinations thereof; and
Z and $Z^1$ are independently selected from the group consisting of O, S, Se, $NR^N$, CR'R", SiR'R", and GeR'R", wherein R' and R" are independently $R^N$;

with the proviso that, in Formula BB, $X_1$ and $X_5$ are not $CR^A$, wherein $R^A$ is halide, at the same time; and with the proviso that, in Formula BE at least one of $X_1$ to $X_5$ is $CR^A$, wherein $R^A$ is selected from the group consisting of

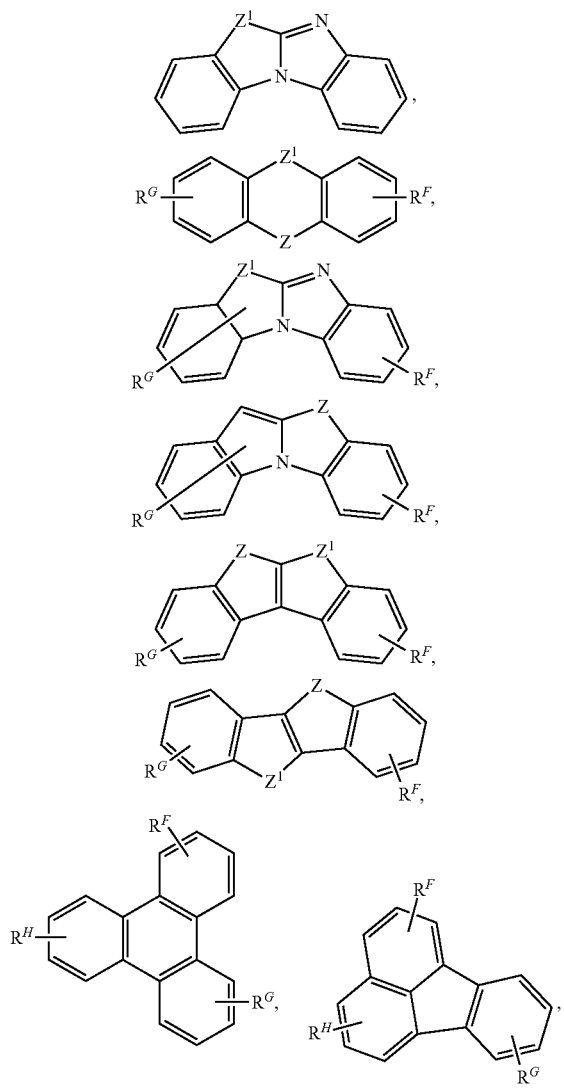

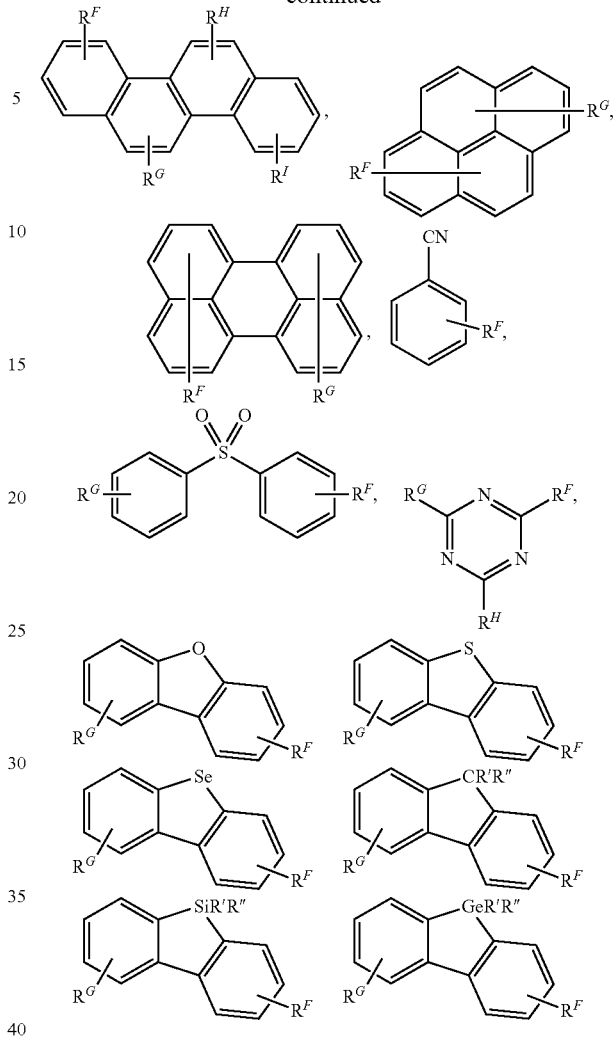

and any aza-analogue of each thereof, each of which is optionally substituted with $R^P$, wherein $R^P$ is selected from the group consisting of deuterium, fluorine, alkyl, cycloalkyl, amino, aryl, heteroaryl, silyl, nitrile, and combinations thereof.

8. The OLED of claim 7, wherein the organic layer further comprises fluorescent emitter.

9. The OLED of claim 8, wherein the fluorescent emitter is selected from the group consisting of:

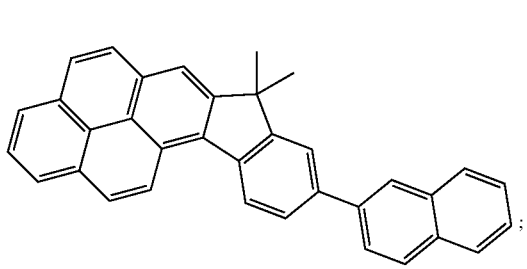

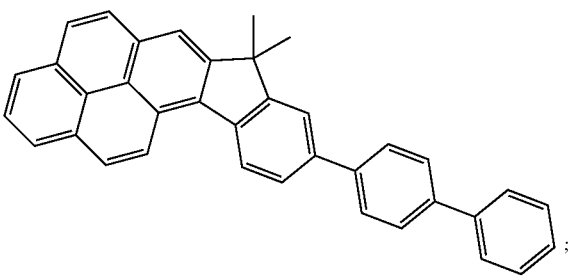

-continued
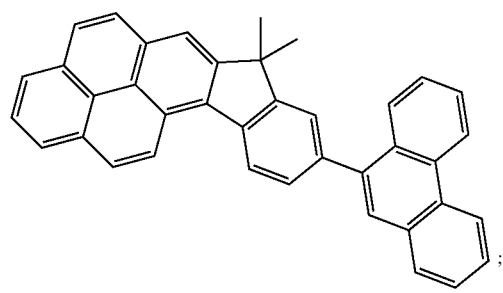
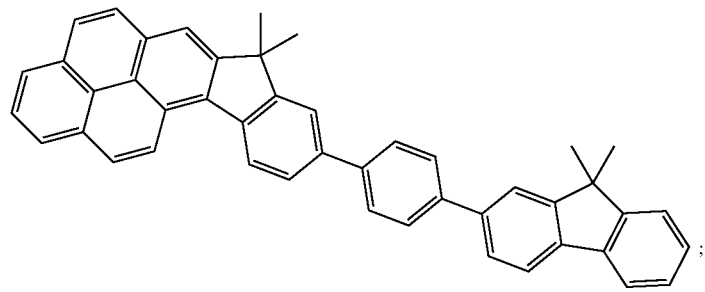
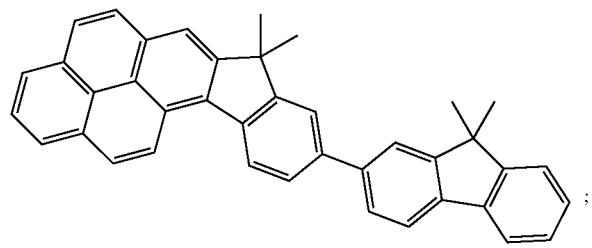
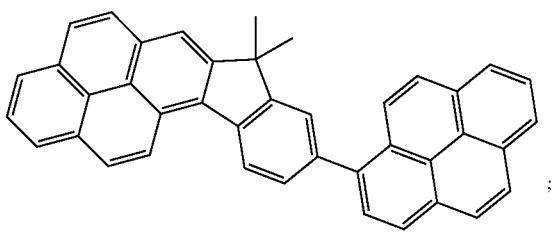
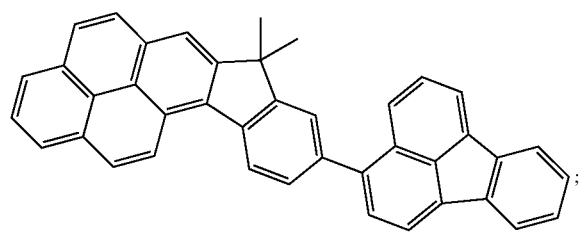
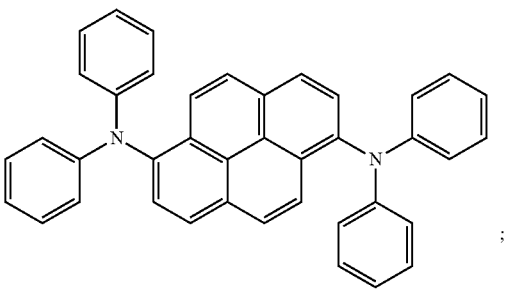
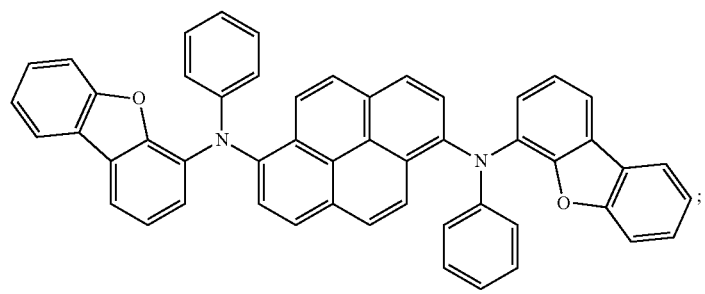
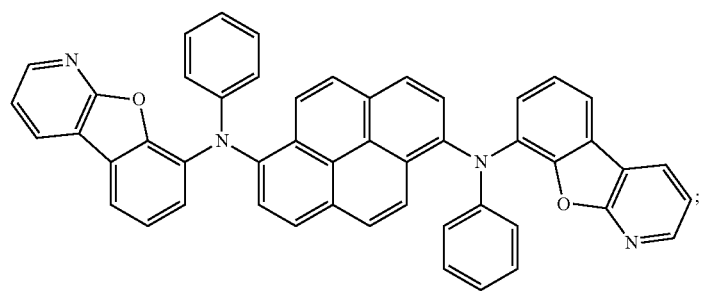

305 306
-continued
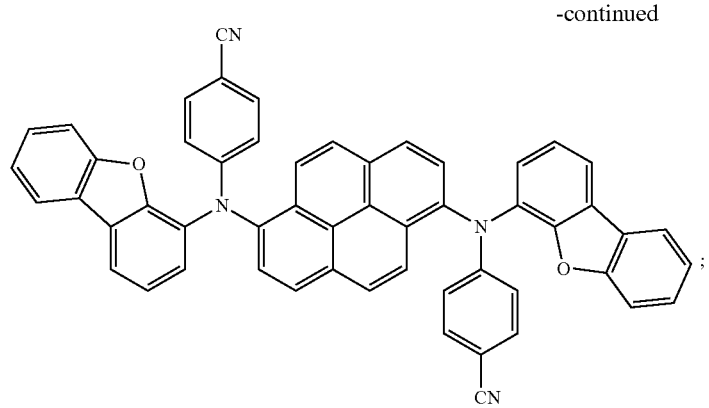
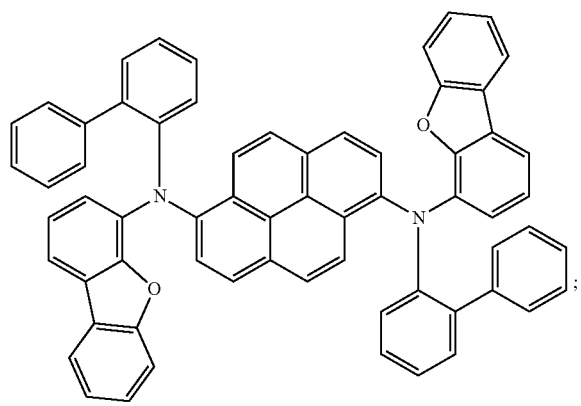
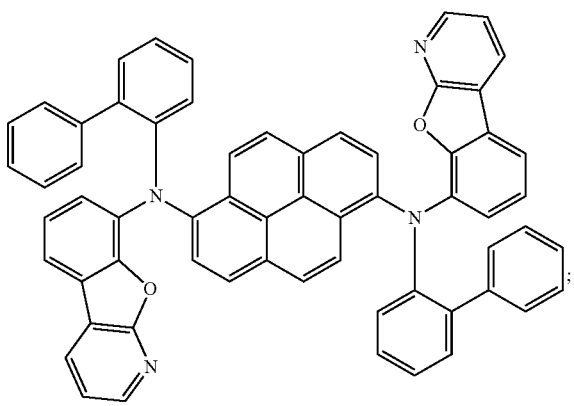
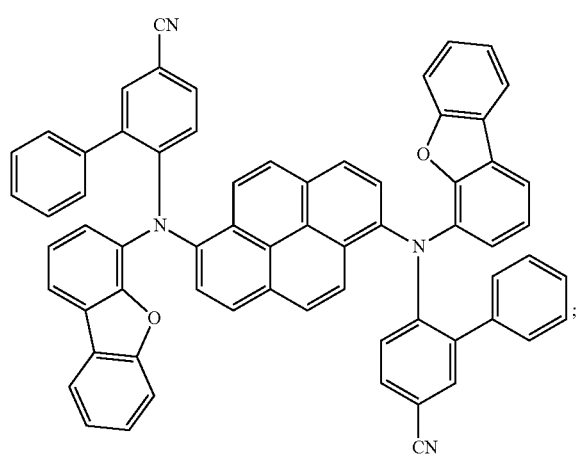
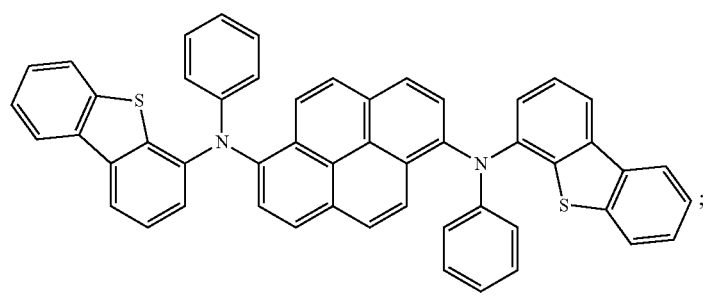

-continued
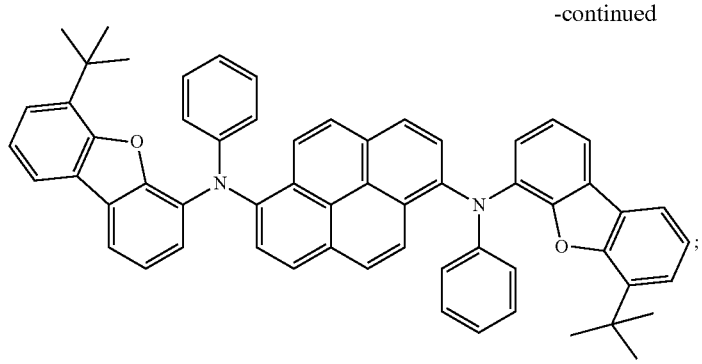
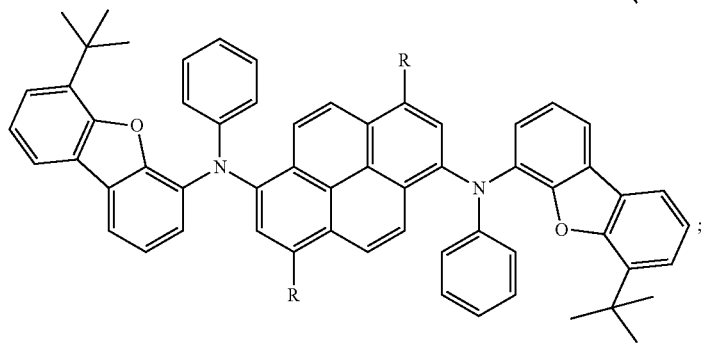
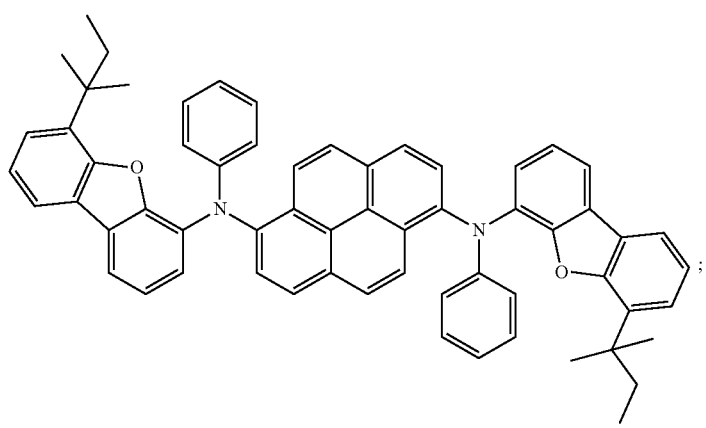
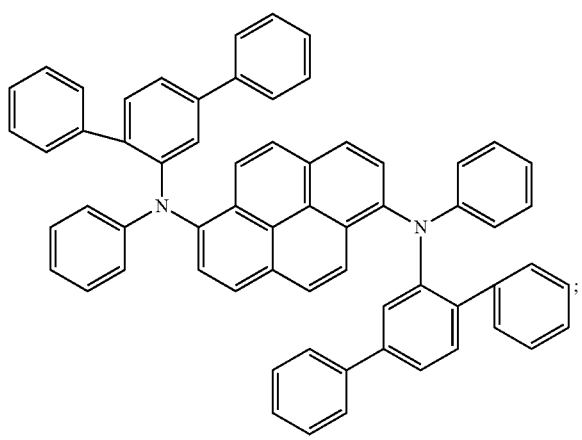

-continued
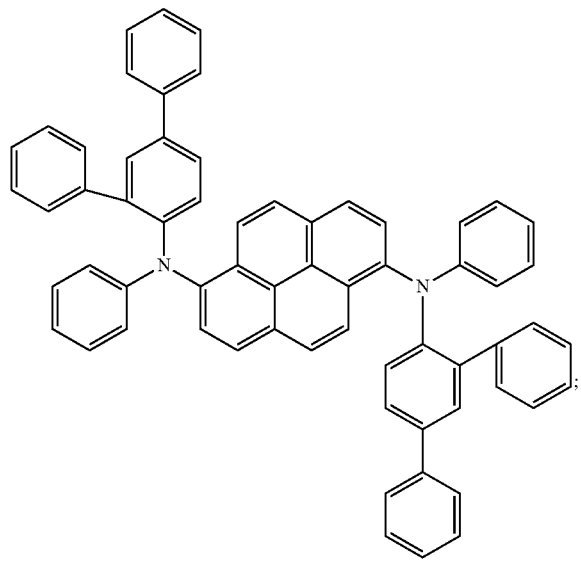
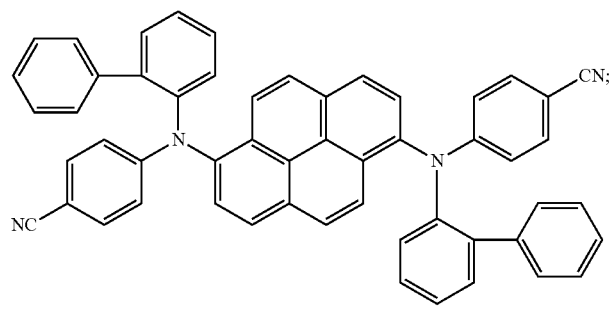
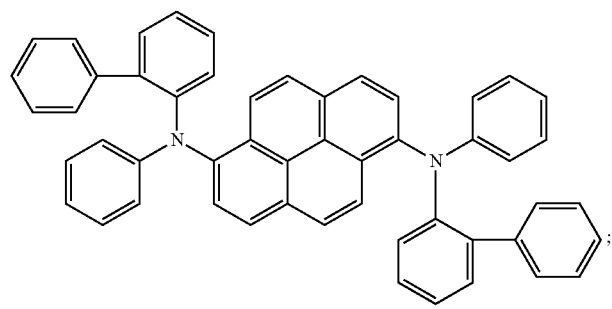
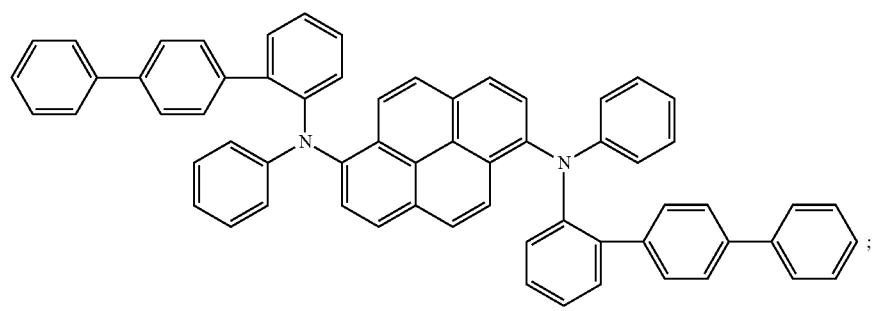

311 312
-continued
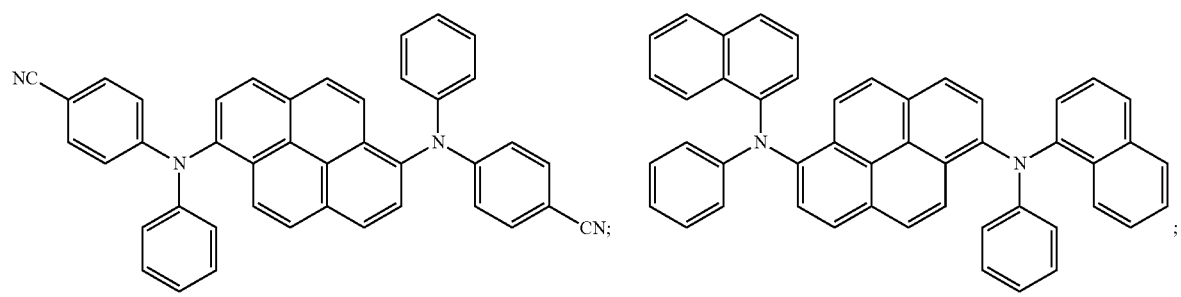
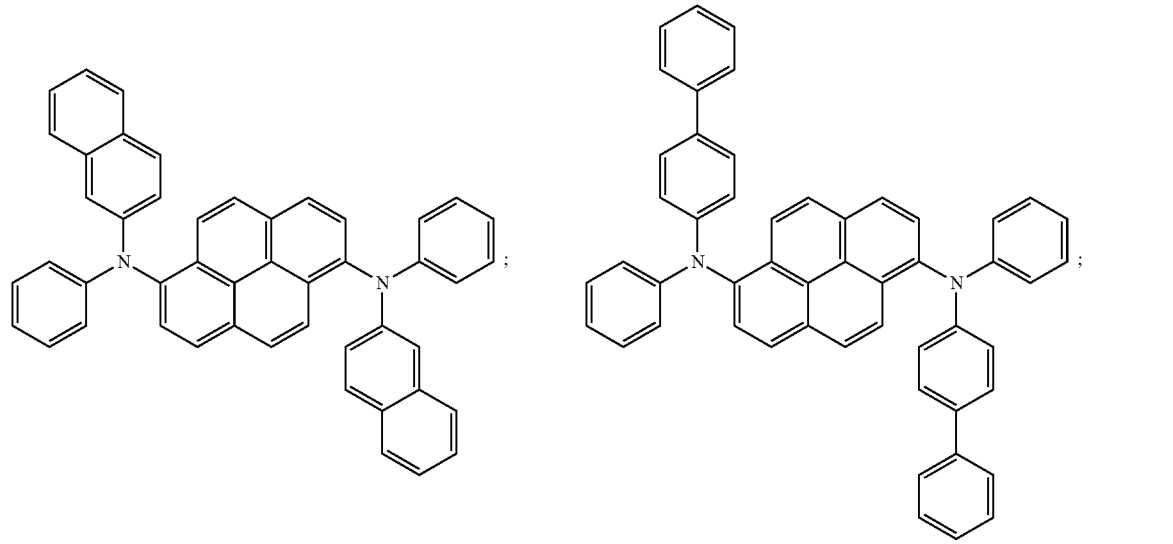
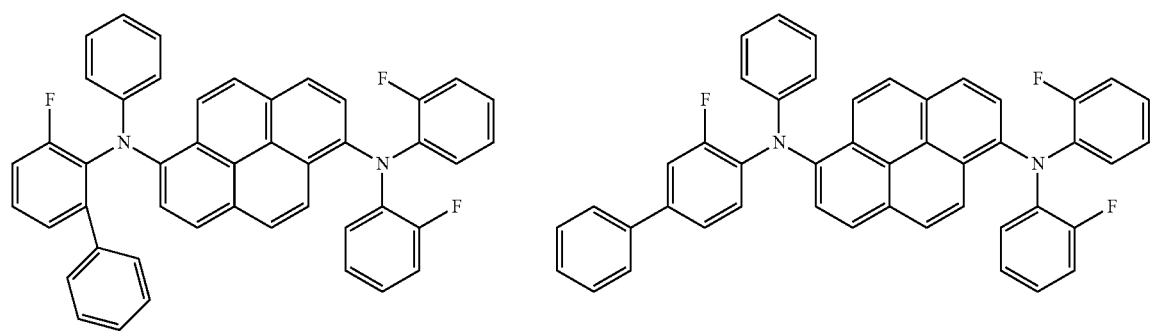
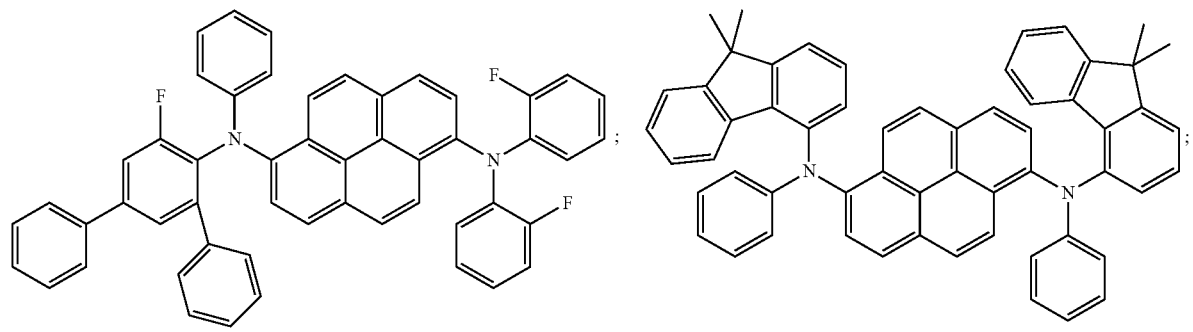

313
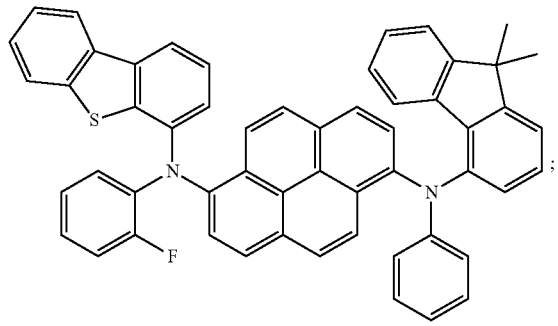
314
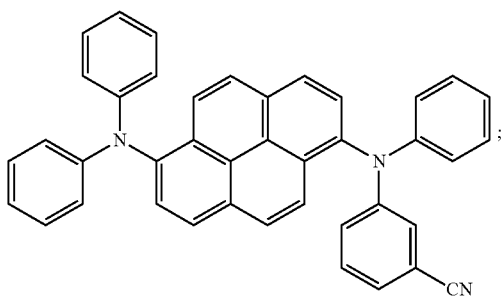
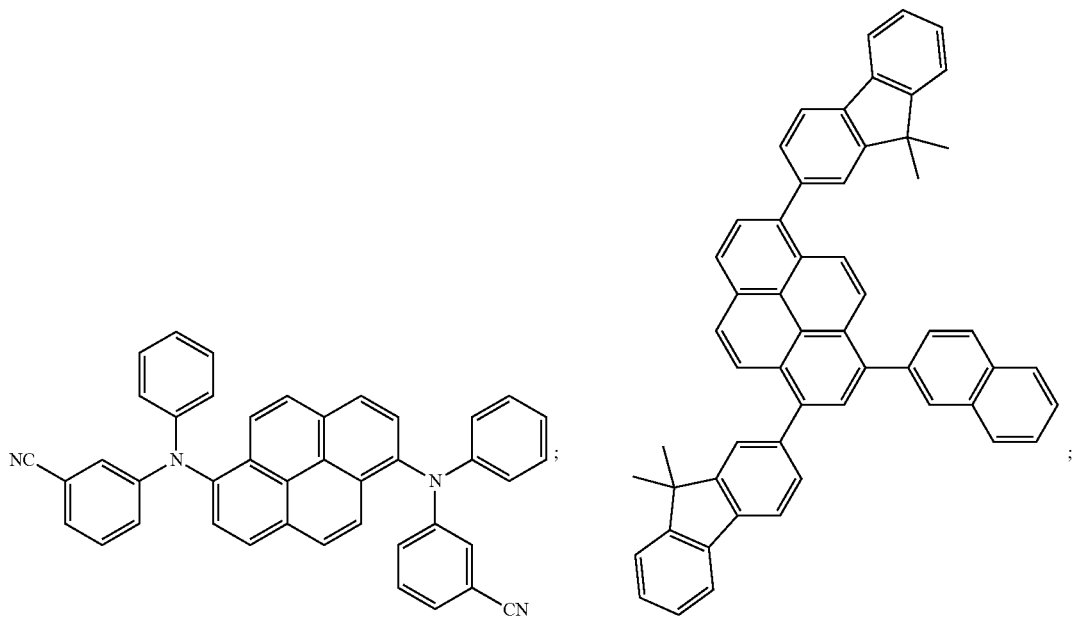
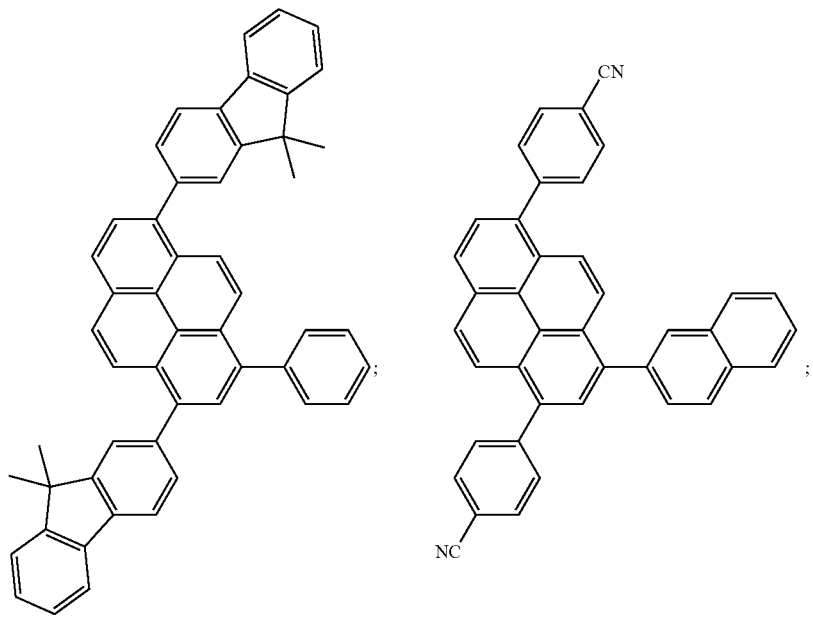

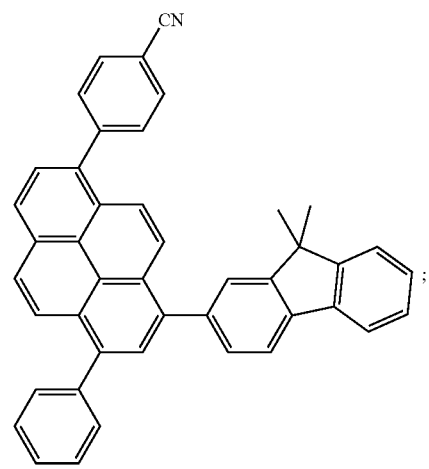
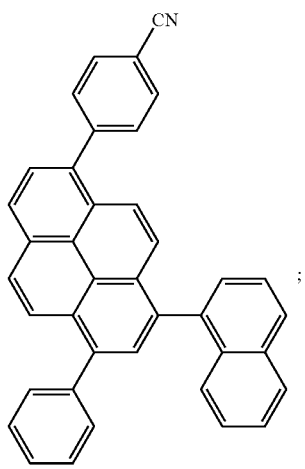
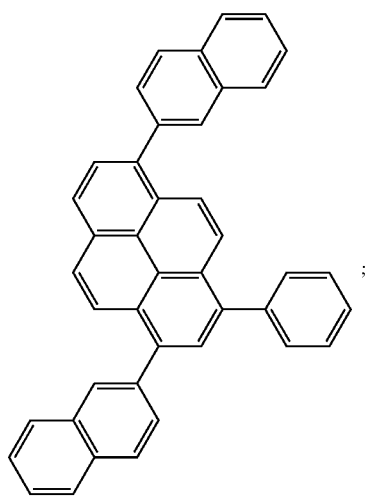
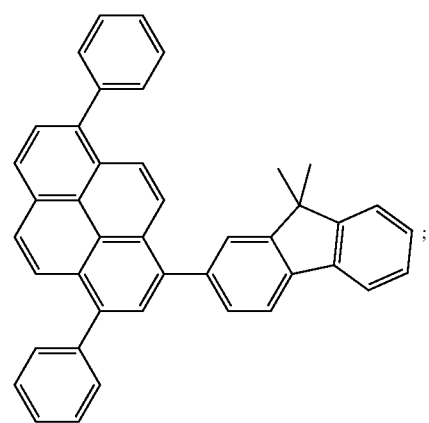
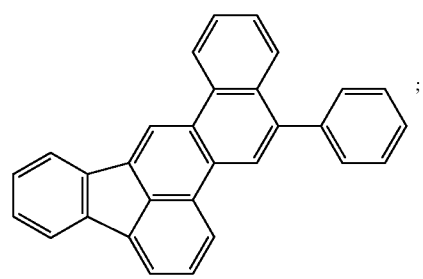
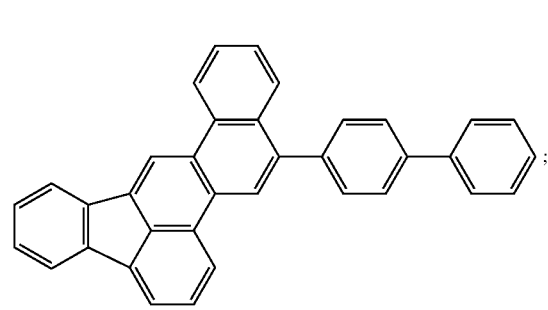
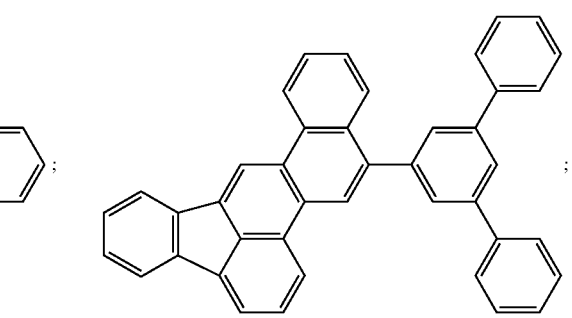
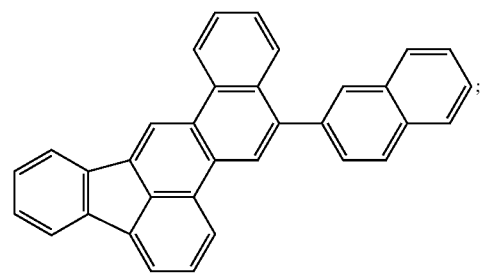
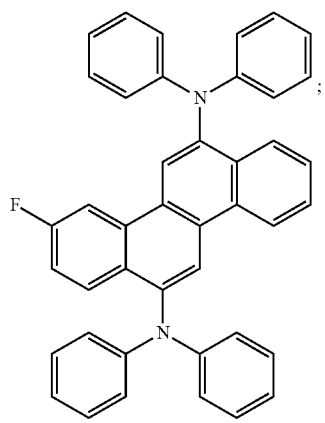

-continued
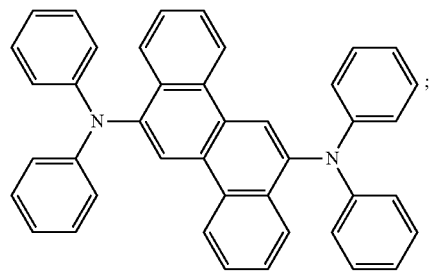
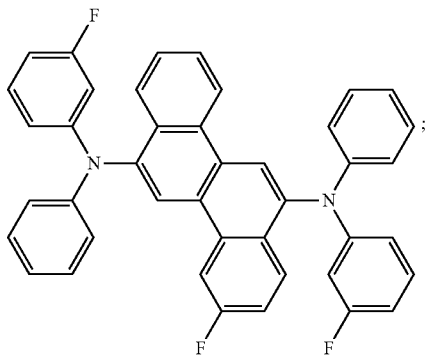
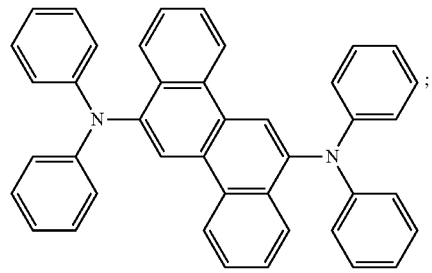
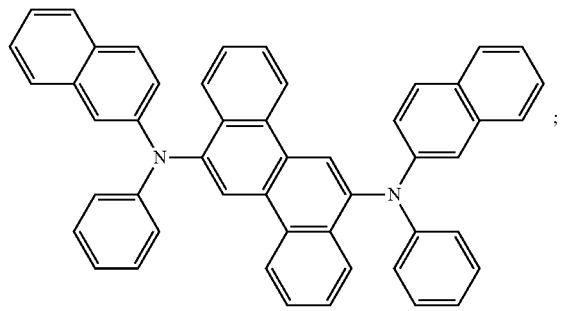
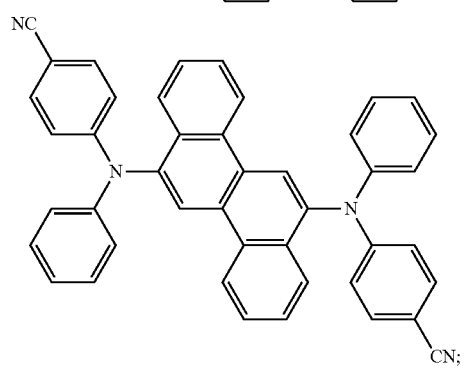
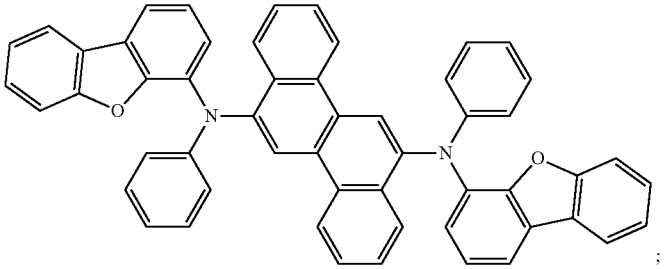
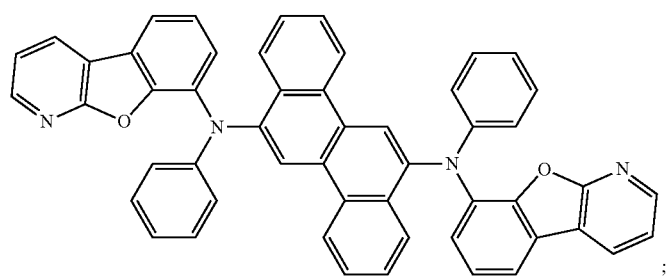
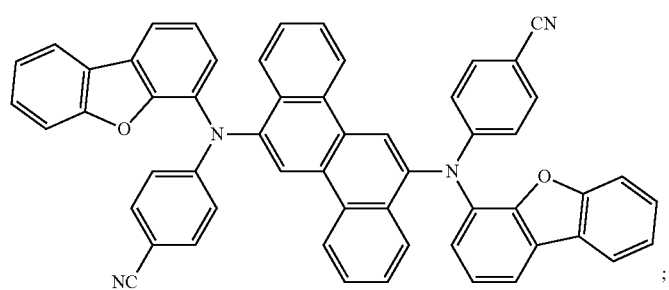

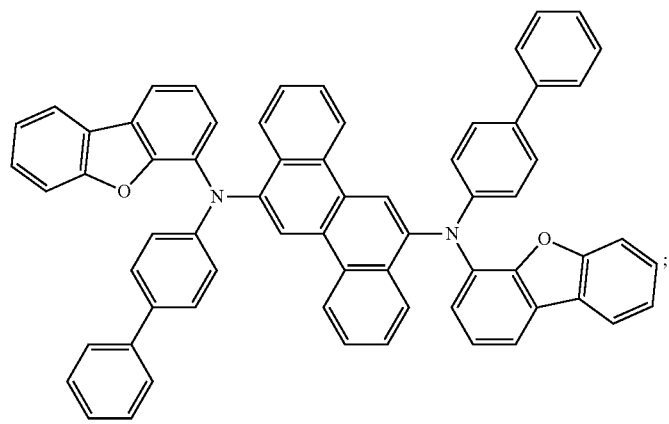
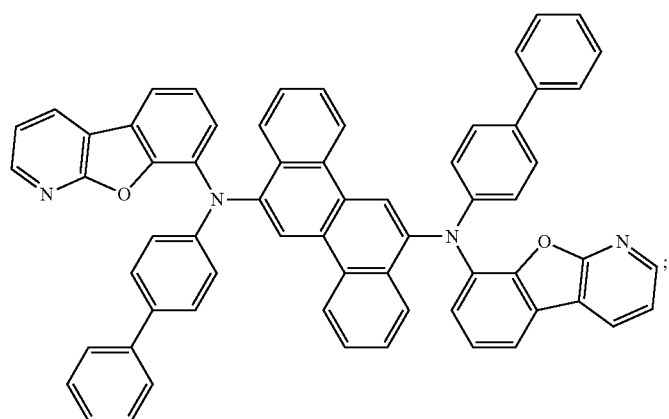
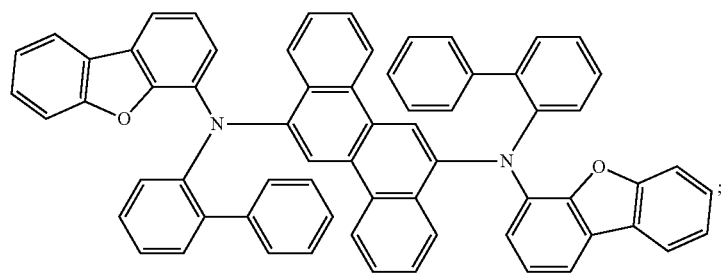
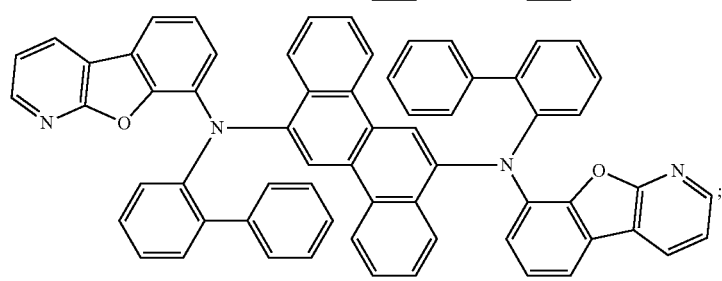
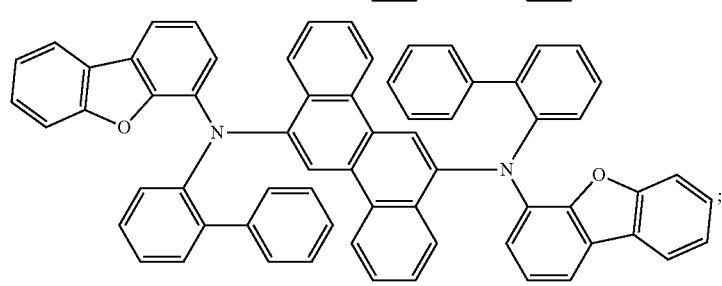

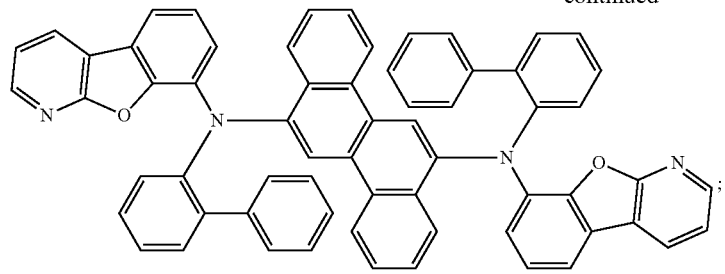
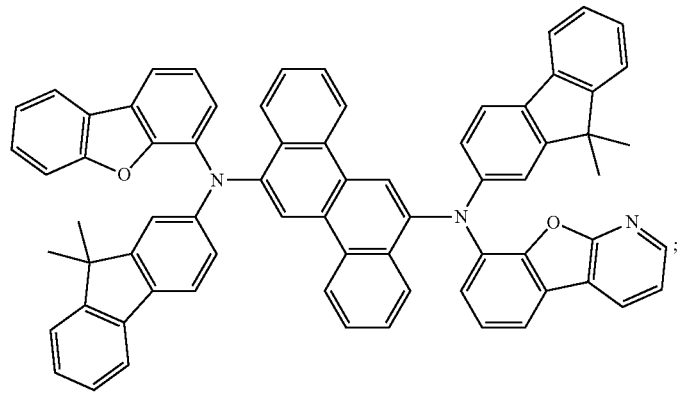
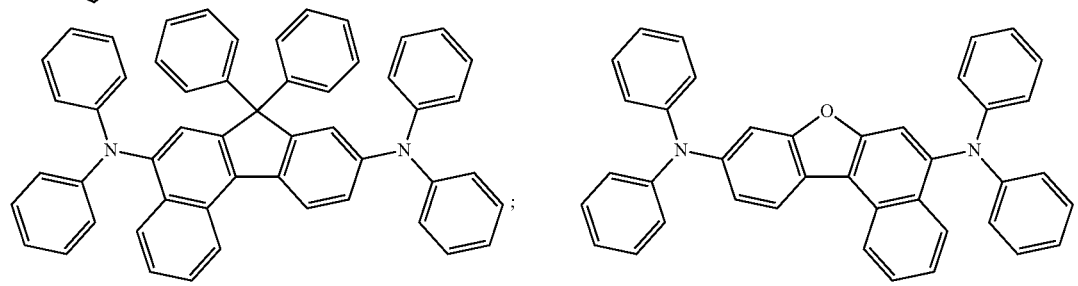
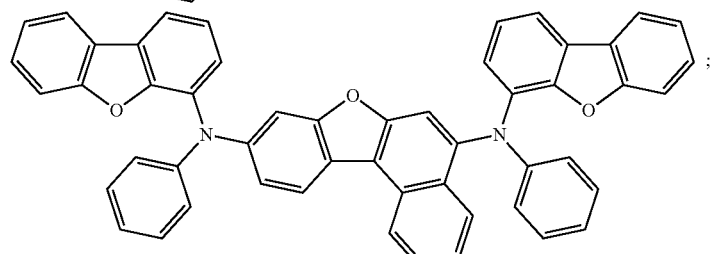
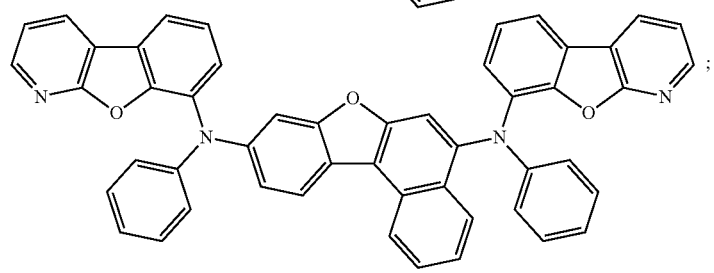
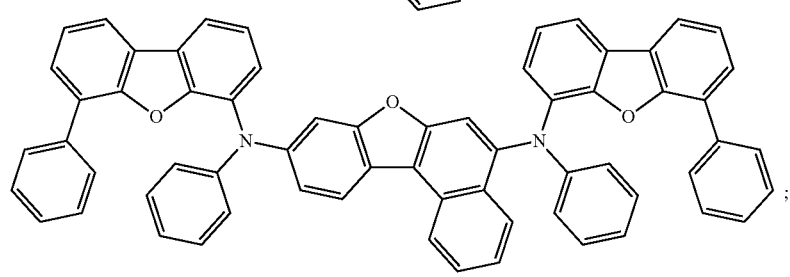

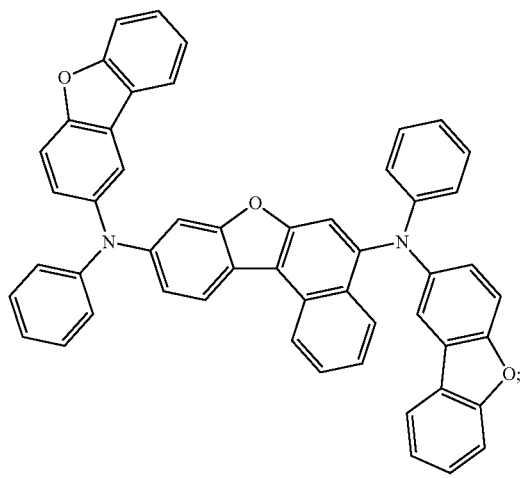
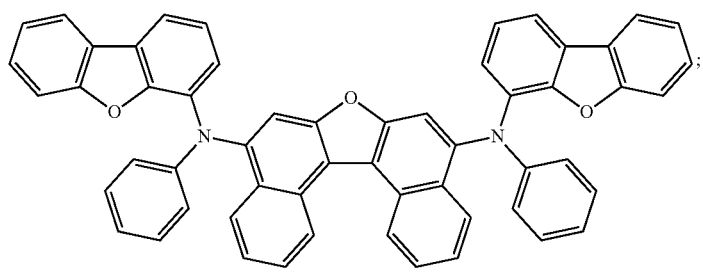
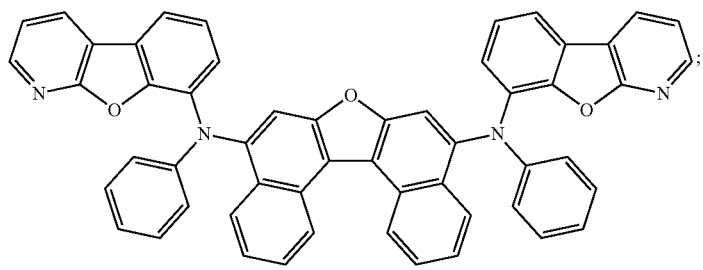
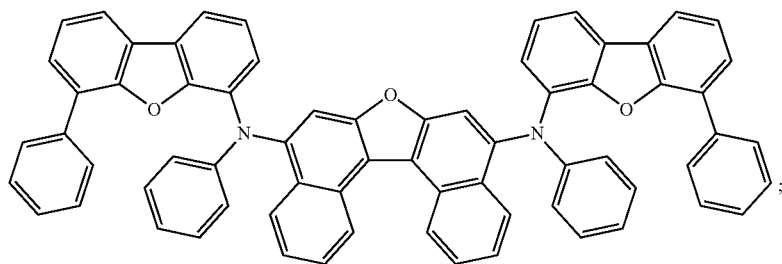
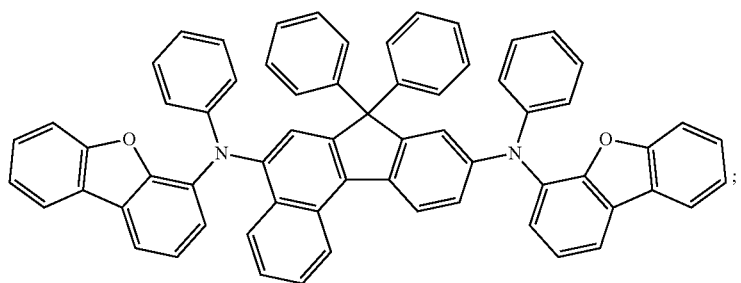

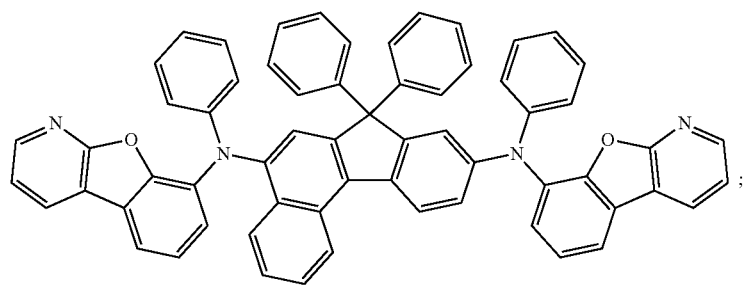
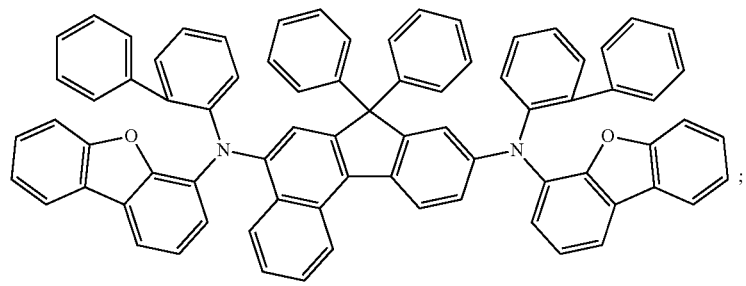
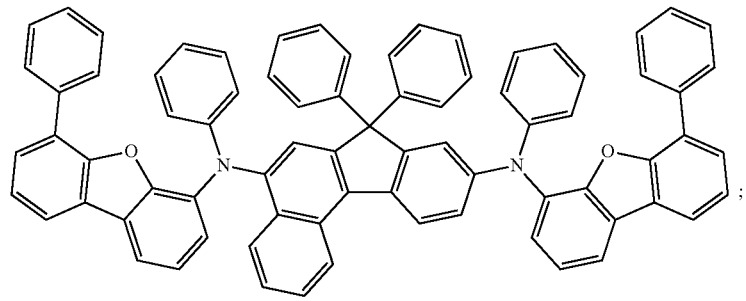
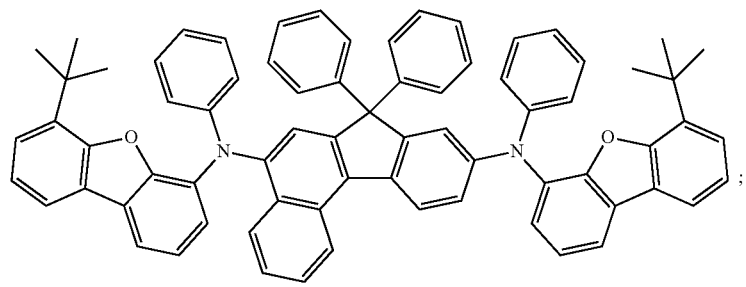
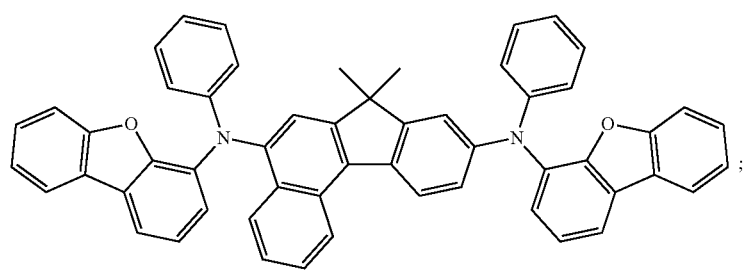
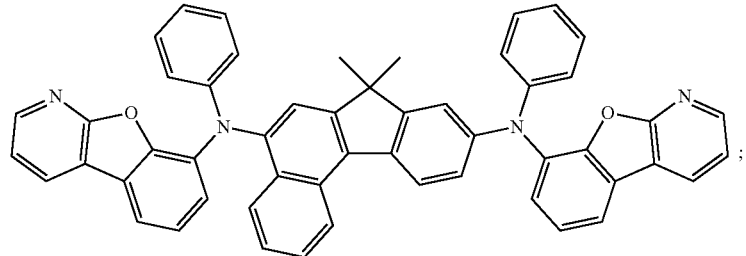

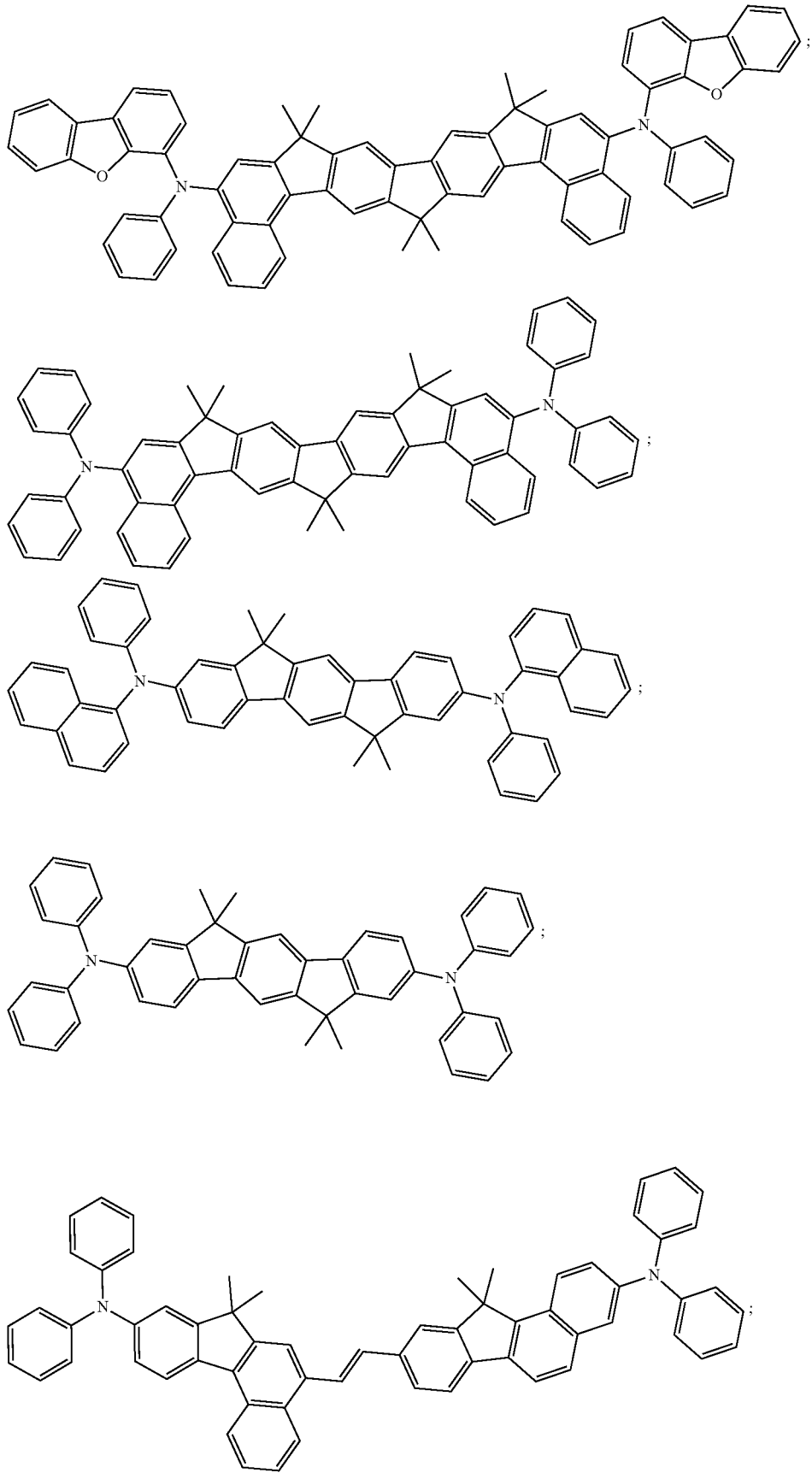

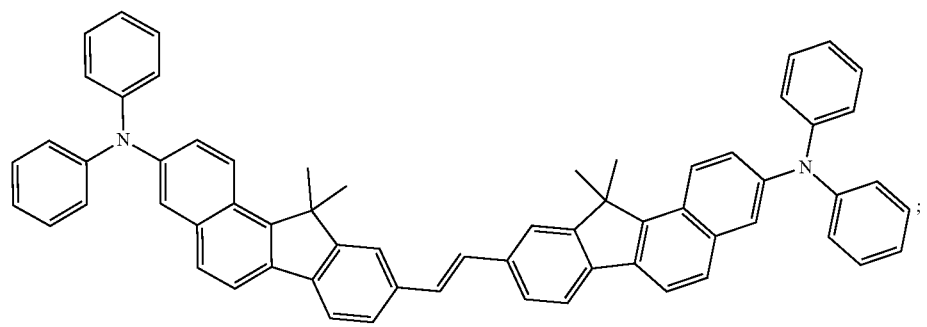
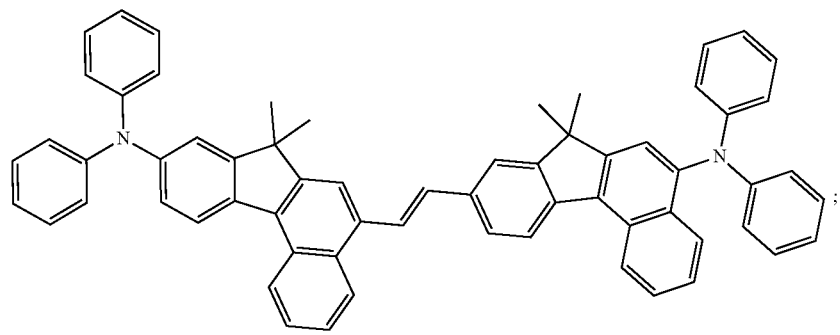
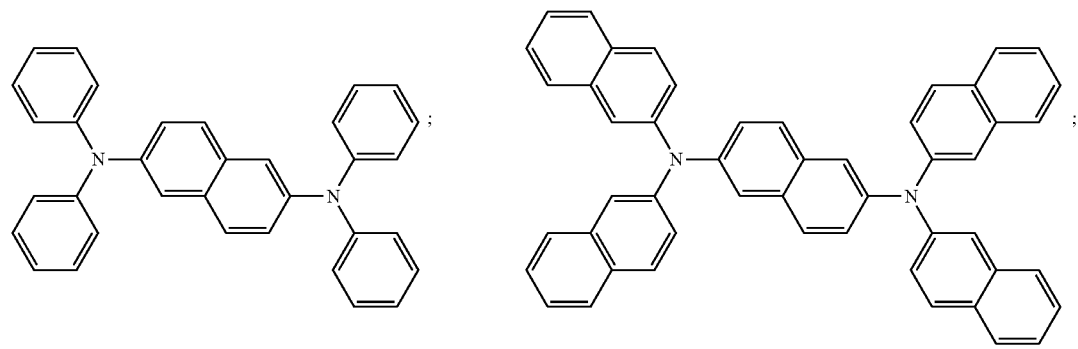
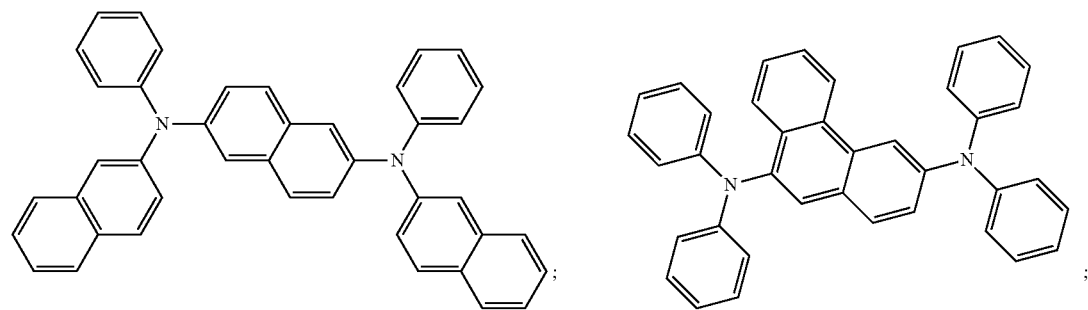
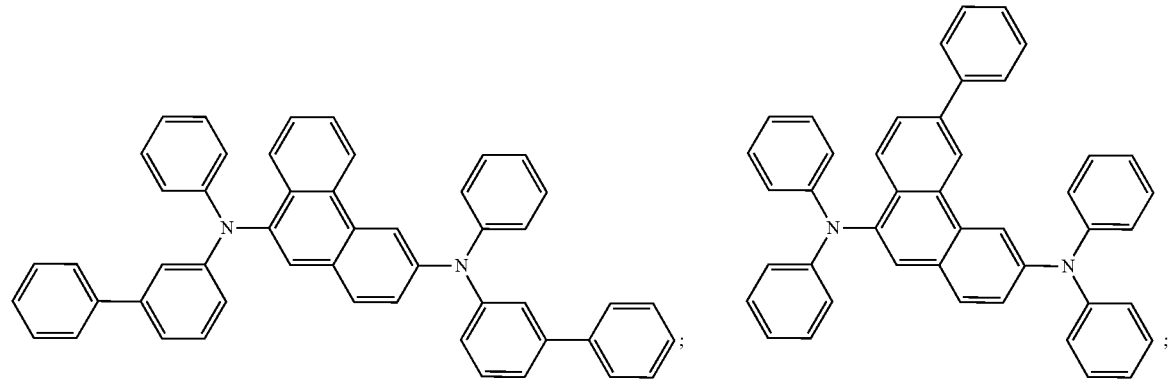

331 332
-continued
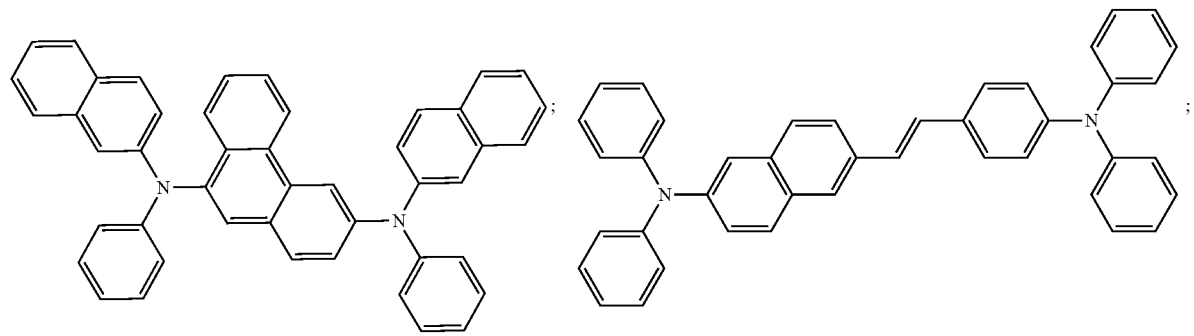
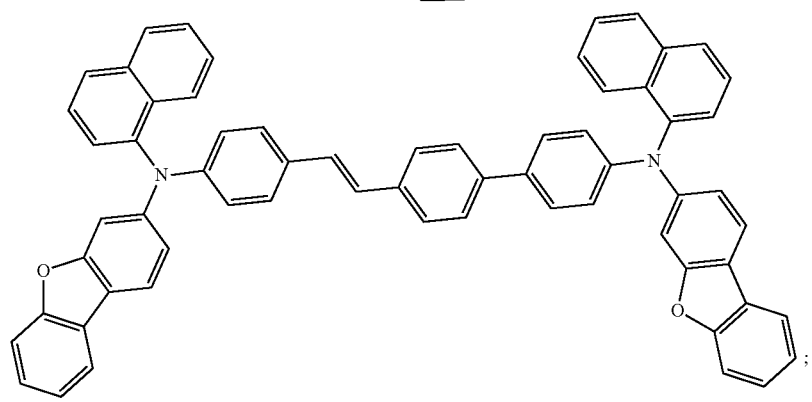
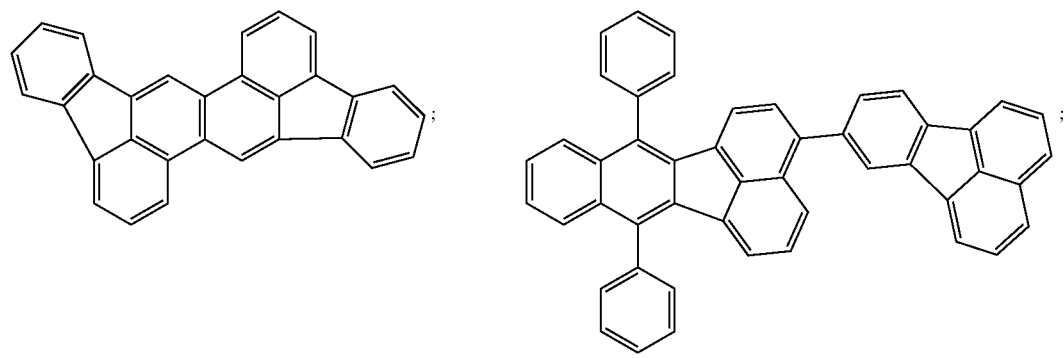
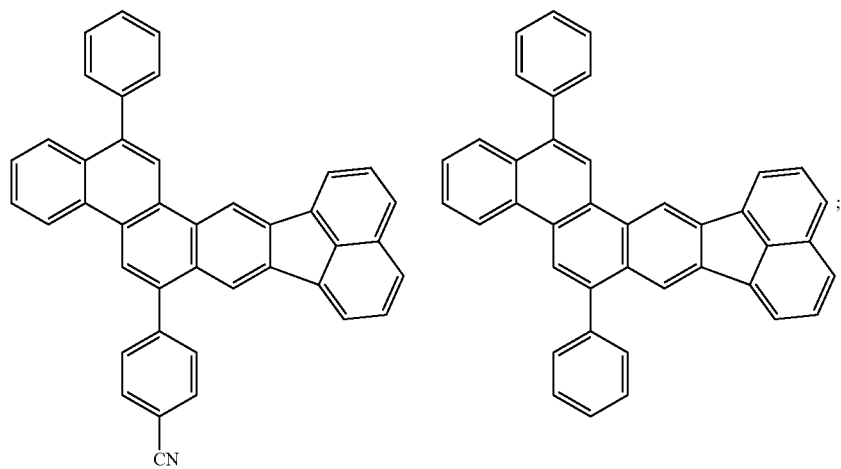

333
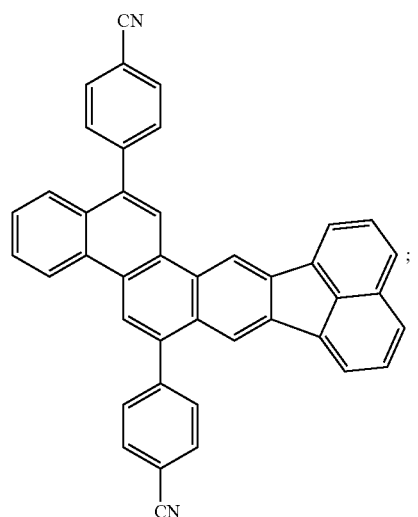
-continued
334
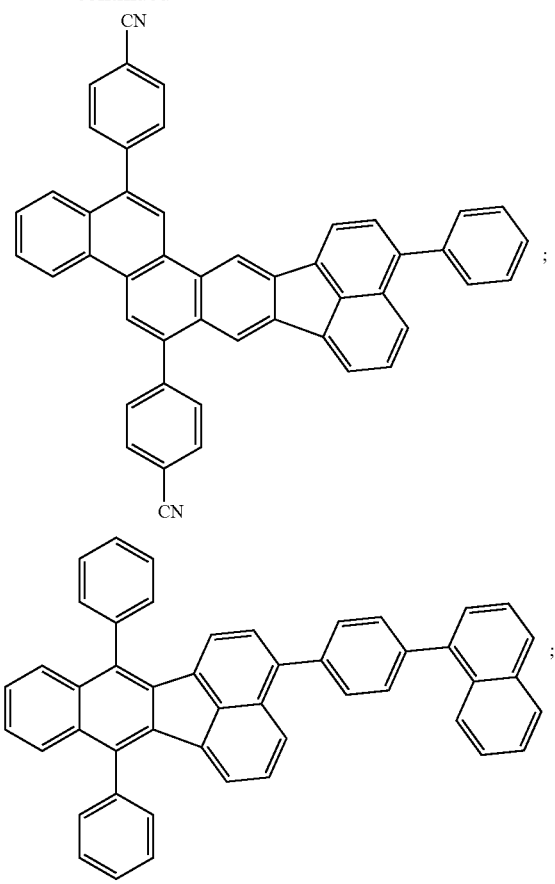
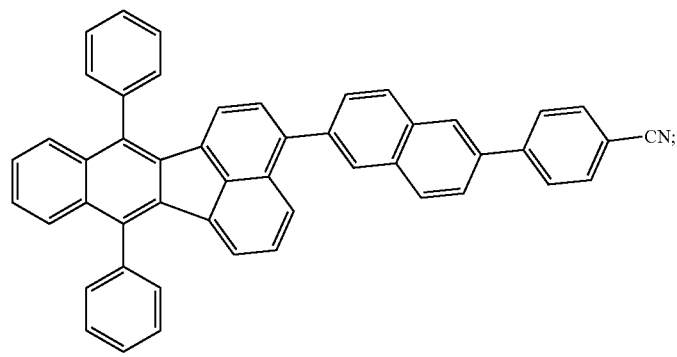
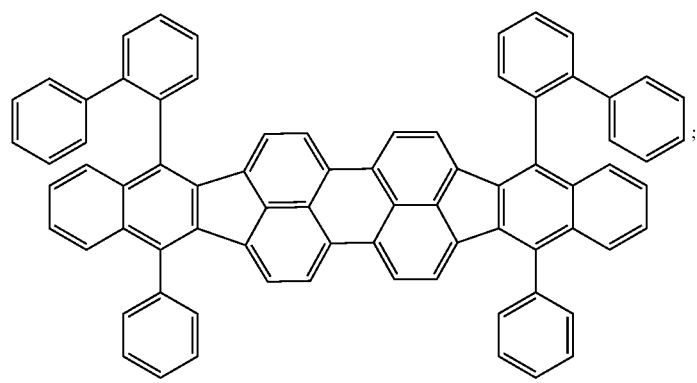

335 336
-continued
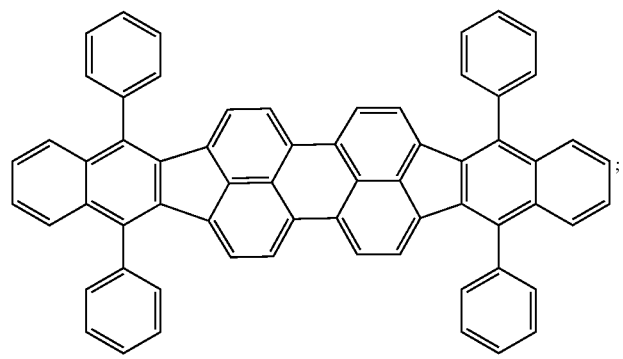 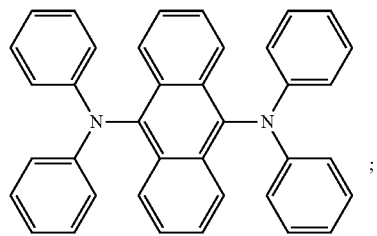
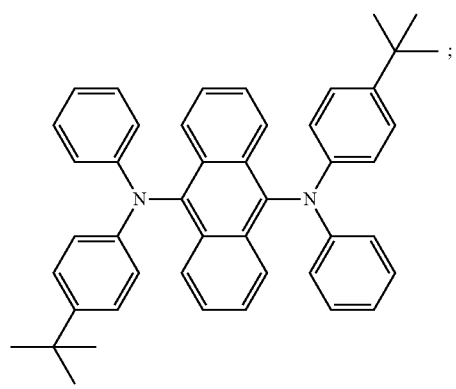 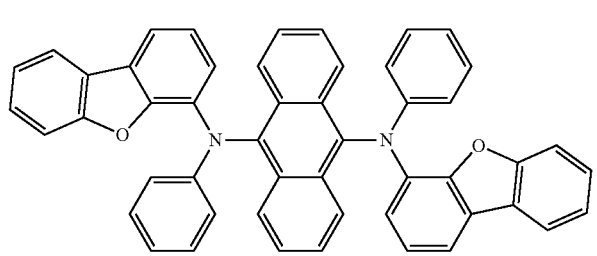
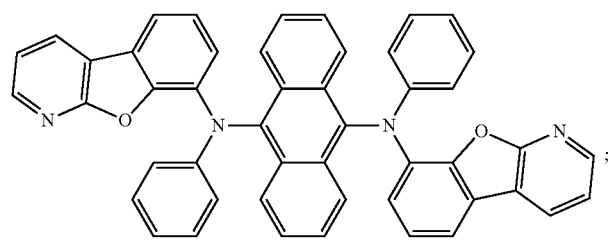
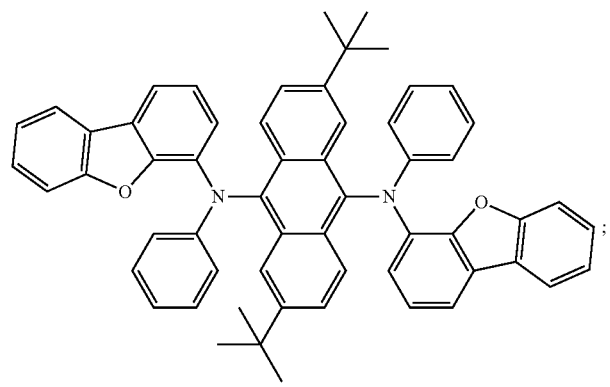

337
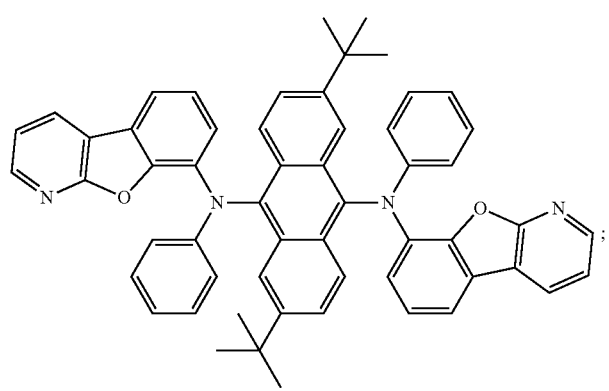
-continued
338
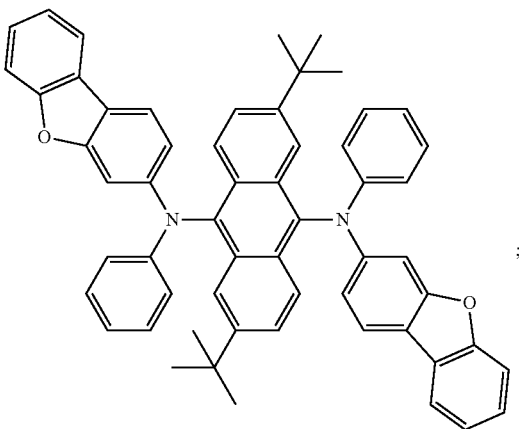
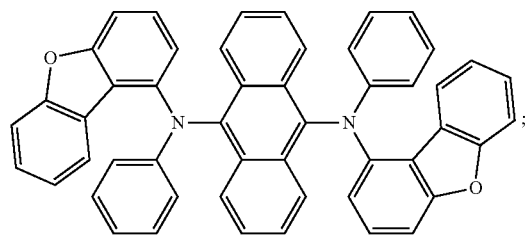
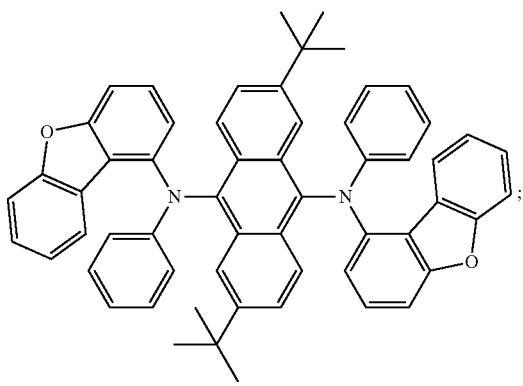
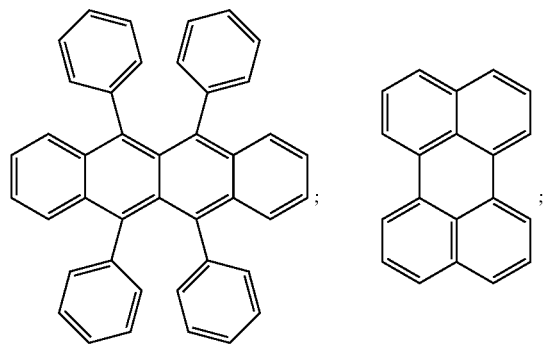 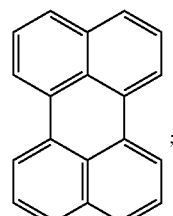

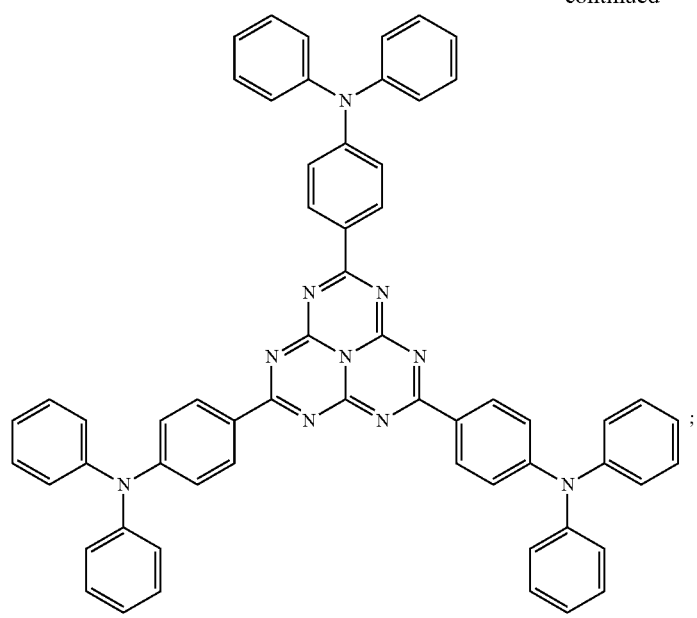
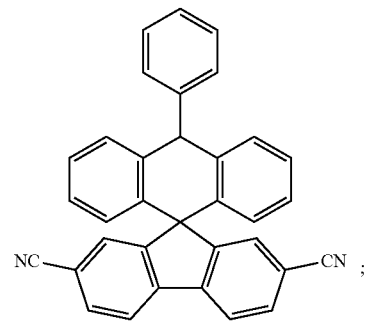
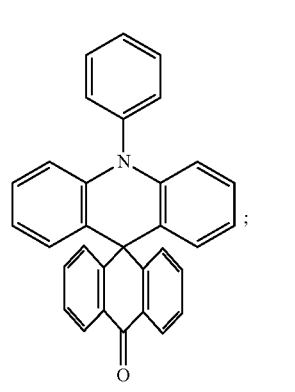
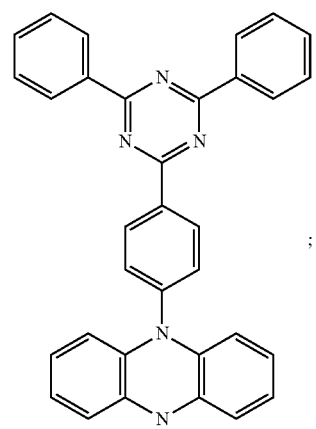
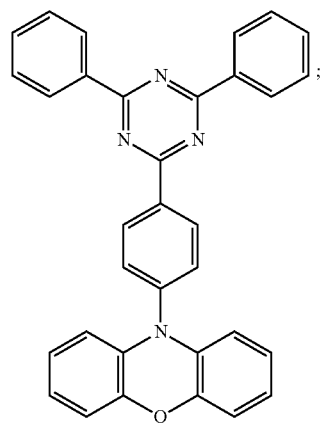
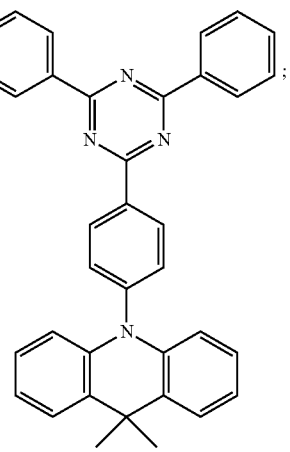
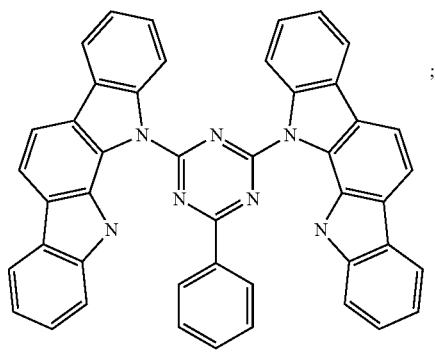

341

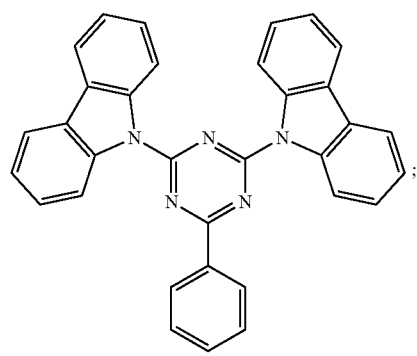

342

-continued

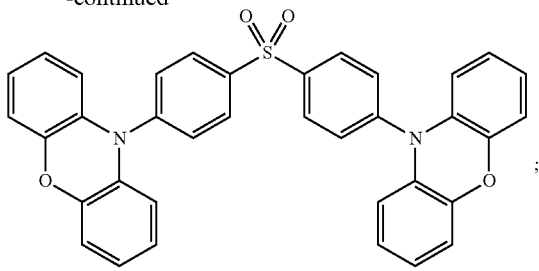

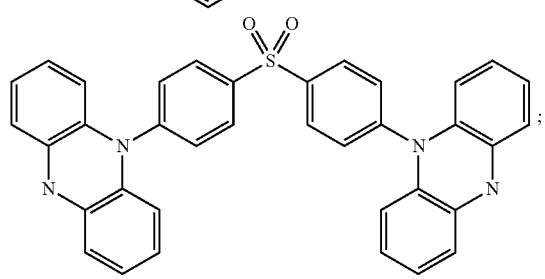

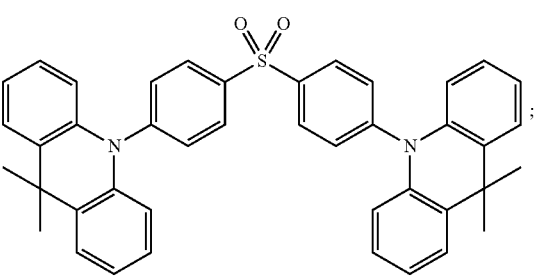

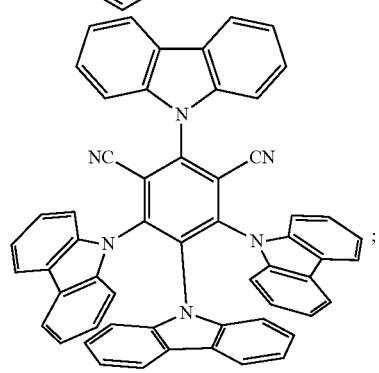

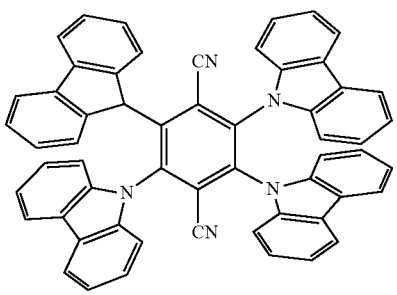; AND

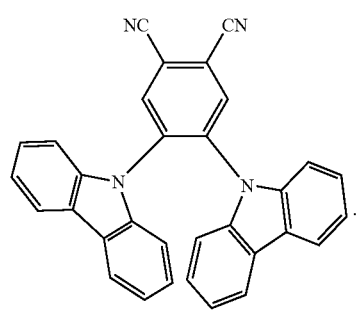

10. The OLED of claim 7, wherein the organic layer further comprises a host, wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

11. The OLED of claim 7, wherein the organic layer further comprises a host and the host is selected from the group consisting of:

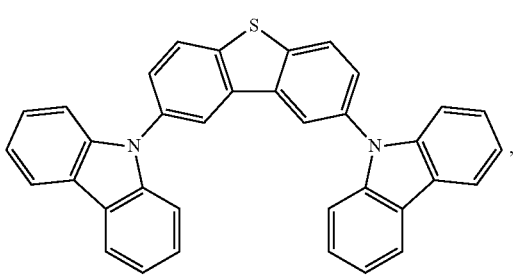

343
-continued
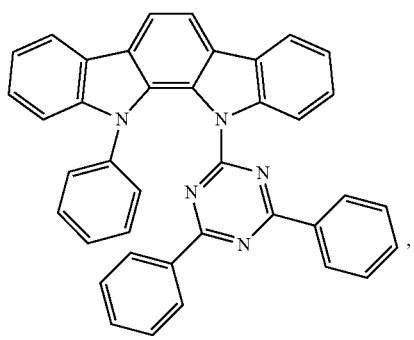
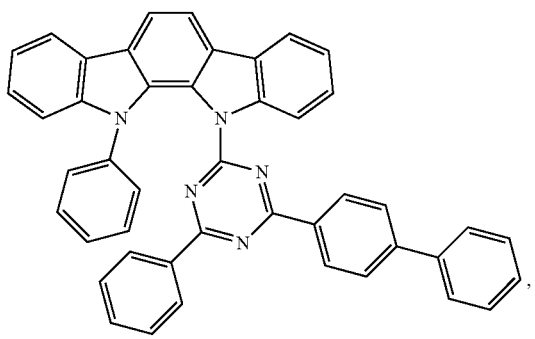
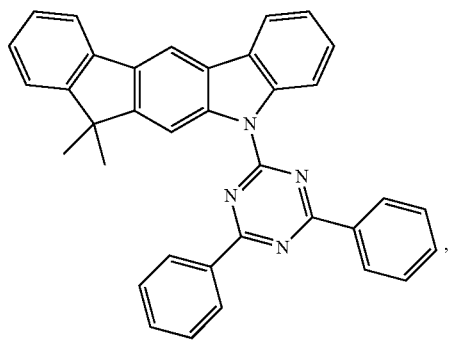
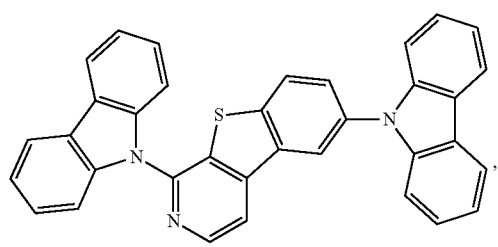
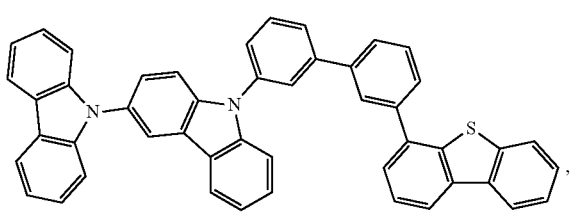
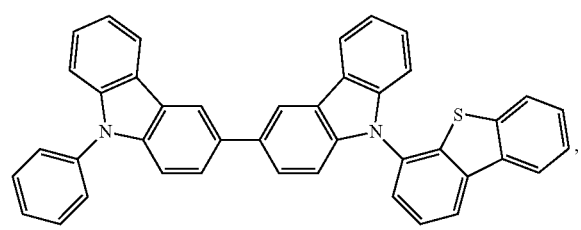
344
-continued
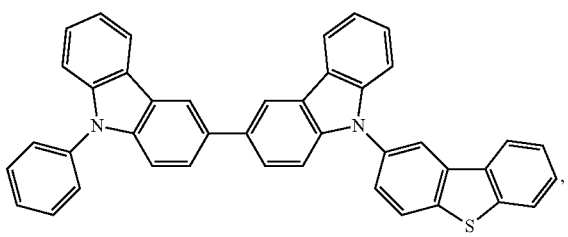
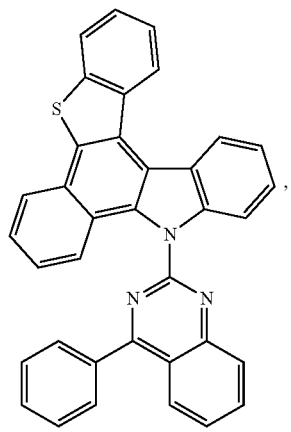
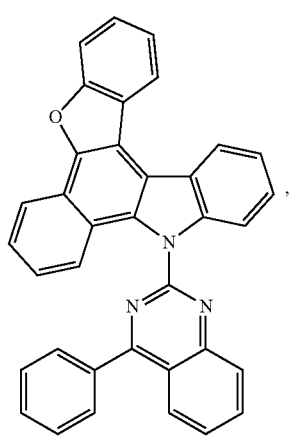
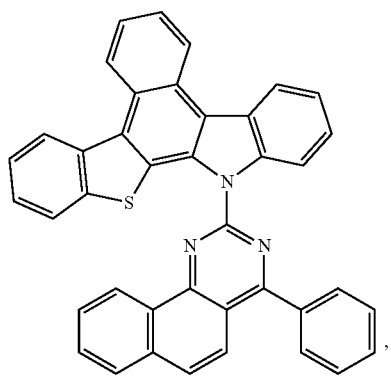

345
-continued
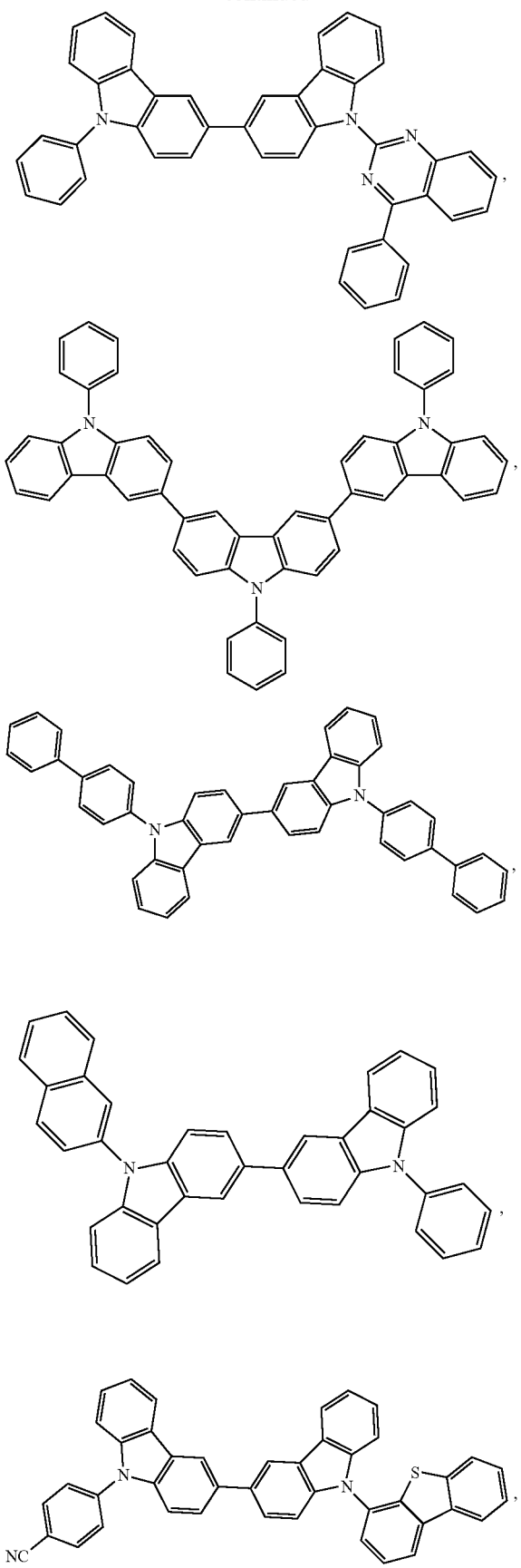
346
-continued
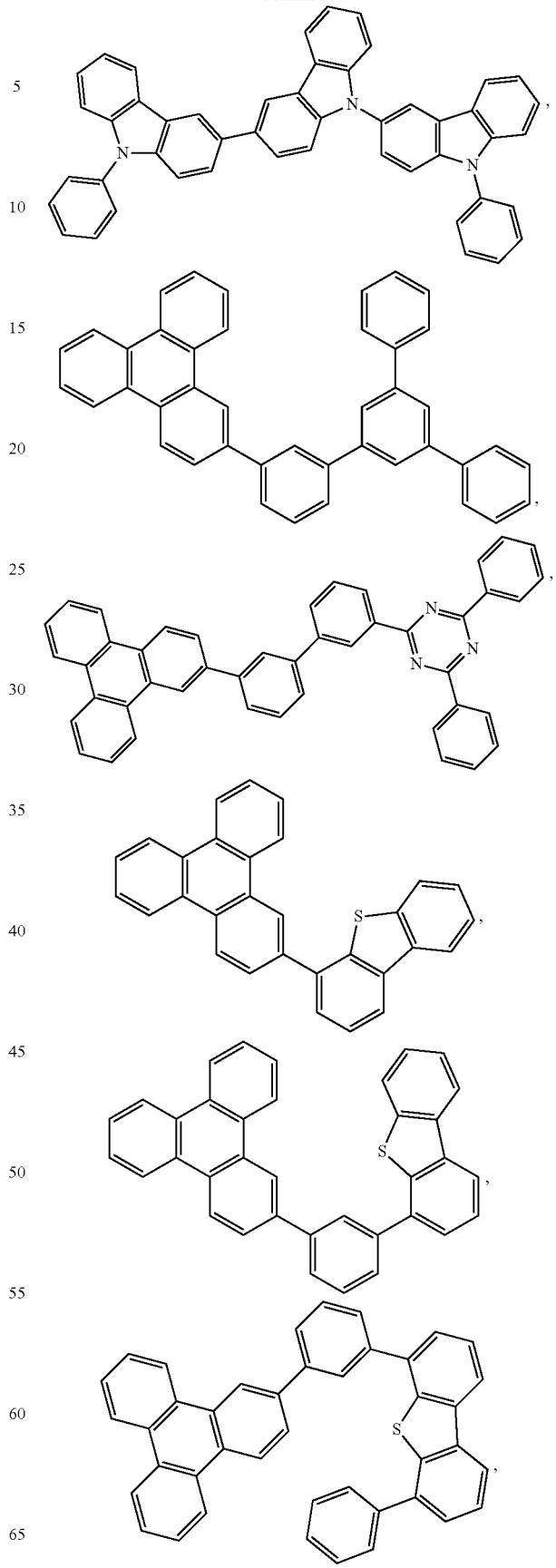

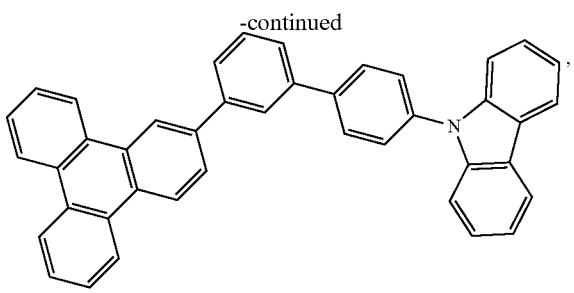

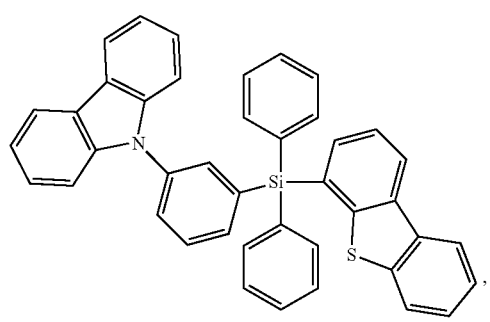

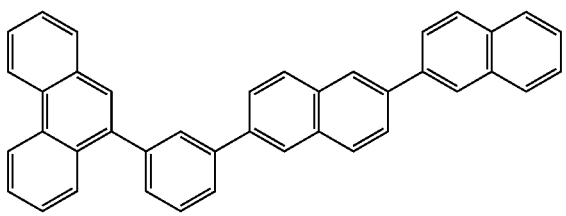

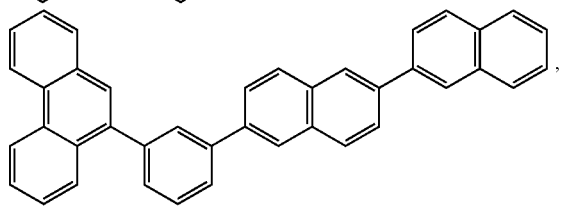

and combinations thereof.

12. A consumer product comprising the device of claim 7, wherein the consumer product is selected from the group consisting of a flat panel display, a curved display, a computer monitor, a medical monitor, a television, a billboard, a light for interior or exterior illumination and/or signaling, a heads-up display, a fully or partially transparent display, a flexible display, a rollable display, a foldable display, a stretchable display, a laser printer, a telephone, a mobile phone, a tablet, a phablet, a personal digital assistant (PDA), a wearable device, a laptop computer, a digital camera, a camcorder, a viewfinder, a micro-display less than 2 inches diagonal, a 3-D display, a virtual reality or augmented reality display, a vehicle, a video wall comprising multiple displays tiled together, a theater or stadium screen, and a sign.

13. A compound of formula A-L-B: wherein Component A is a fluorescent emitter with at least one aromatic ring; Component B is a compound selected from the group consisting of Formulae BB, BC, BD, BE, BF, BG, B1, B2 and B10:

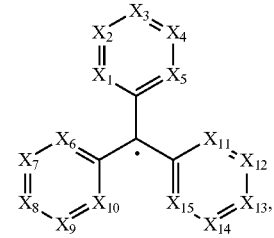

BB

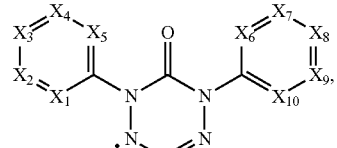

BC

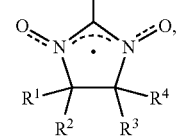

BD

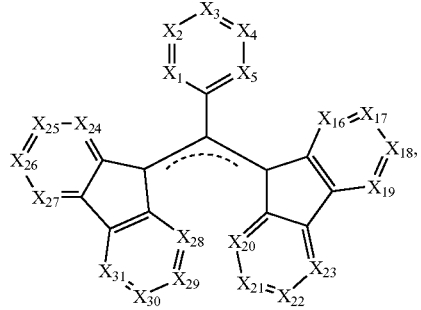

BE

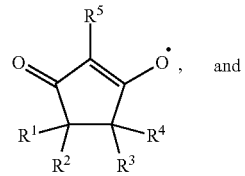

BF

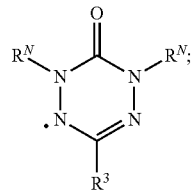

BG wherein
$X_1$ to $X_5$ are independently selected from $CR^A$ or N;
$X_6$ to $X_{10}$ are independently selected from CO or N;
$X_{11}$ to $X_{15}$ are independently selected from $CR^C$ or N;
$X_{16}$ to $X_{23}$ are independently selected from $CR^D$ or N;
$X_{24}$ to $X_{31}$ are independently selected from $CR^E$ or N;
$R^A$, $R^B$, $R^C$, $R^D$, and $R^E$ independently represent mono to the maximum allowable substitution, or no substitution;
each $R^1$ to $R^5$, $R^A$, $R^B$, $R^C$, $R^D$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; or optionally, any two adjacent $R^1$ to $R^4$, or any two adjacent $R^A$, $R^B$, $R^C$, $R^D$, and $R^E$, can join to form a ring;

$R^N$ is independently selected from the group consisting of hydrogen, deuterium, alkyl, cycloalkyl, heteroalkyl, alkenyl, cycloalkenyl, heteroalkenyl, aryl, heteroaryl, and combinations thereof;

wherein at least one of $R^1$ to $R^5$, $R^A$, $R^B$, $R^C$, $R^D$, and $R^E$ includes a polycyclic group selected from the group consisting of:

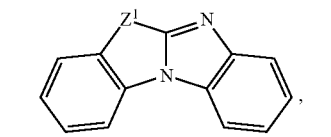

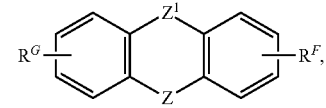

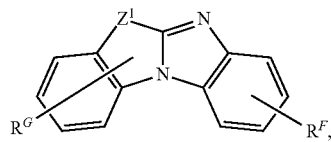

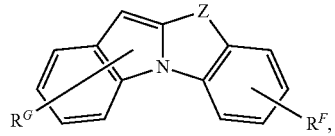

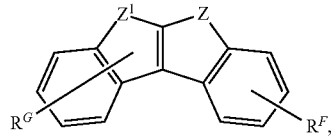

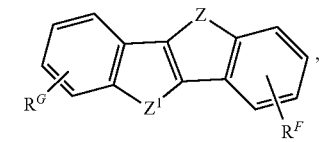

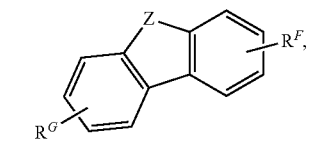

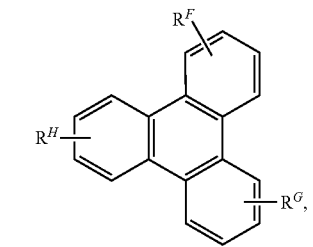

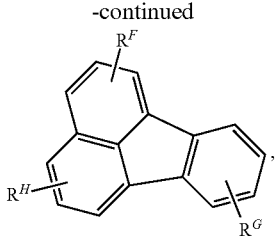

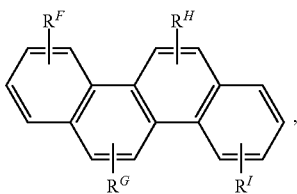

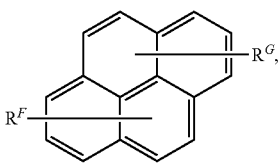 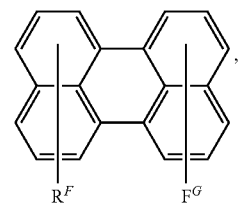

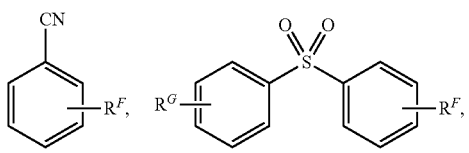

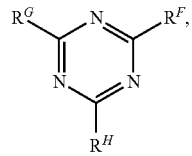

and any aza-analogue of each thereof, each of which is optionally substituted with $R^P$, wherein $R^P$ is selected from the group consisting of deuterium, fluorine, alkyl, cycloalkyl, amino, aryl, heteroaryl, silyl, nitrile, and combinations thereof;

wherein $R^F$ to $R^I$ are independently selected from the group consisting of hydrogen, deuterium, fluorine, alkyl, cycloalkyl, amino, aryl, heteroaryl, silyl, and nitrile; and Z and $Z^1$ are independently selected from the group consisting of O, S, Se, $NR^N$, CR'CR", SiR'R", and GeR'R", wherein R' and R" are independently $R^N$;

with the proviso that the following compound is excluded

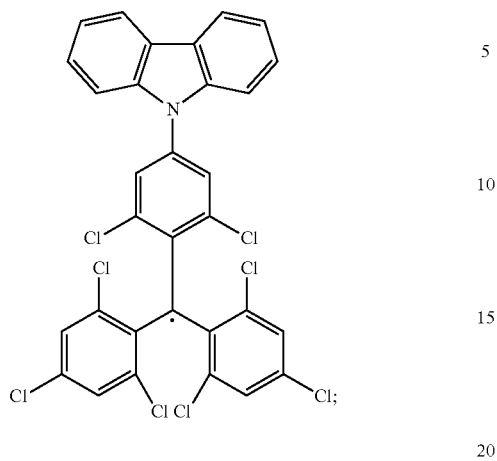

and
L is a direct bond or an organic linker; wherein L, if not a direct bond, is positioned at an aromatic ring carbon of Component A, or if L is a direct bond, then Component B is positioned at an aromatic ring carbon of Component A.

14. A compound of claim 13, wherein Component A comprises a structure selected from the group consisting of:

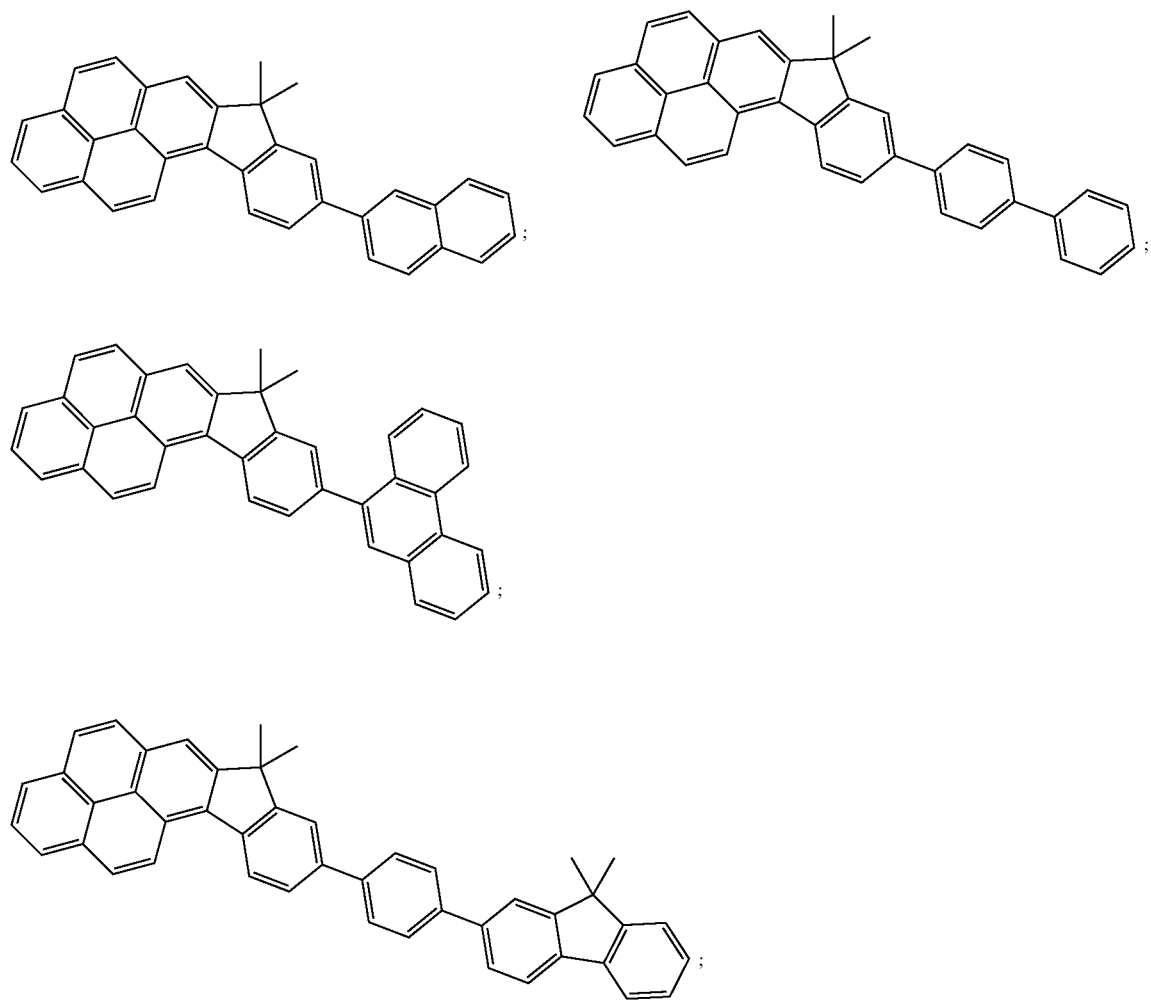

-continued
| 353 | 354 |
|---|---|
| 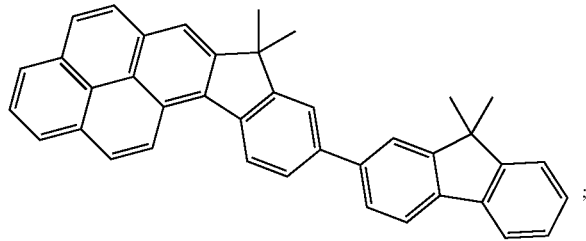 | 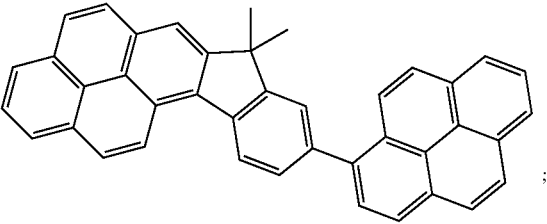 |
| 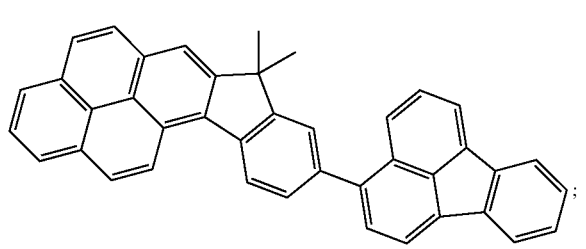 | 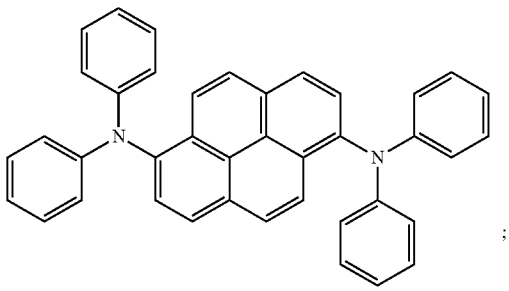 |
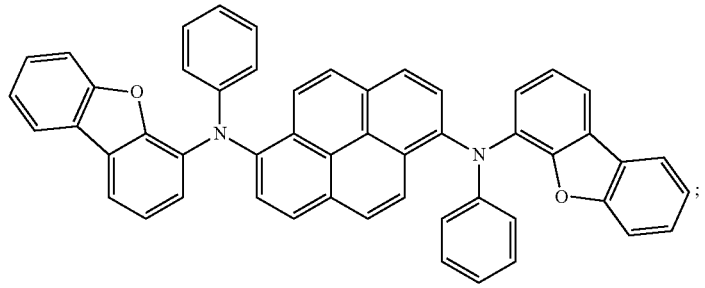
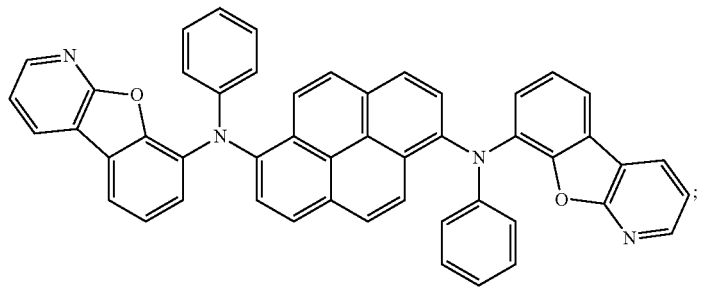
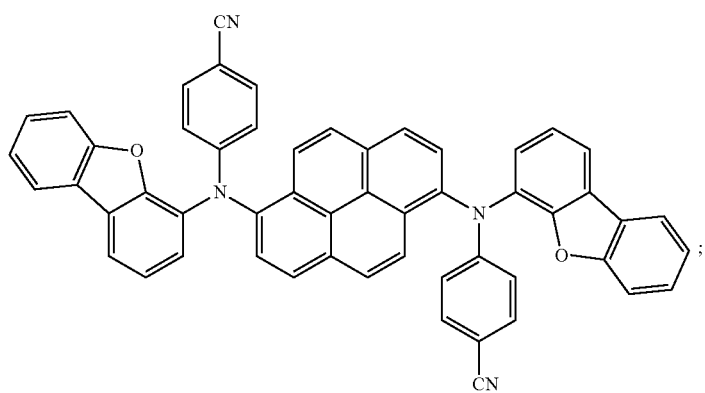

355 356
-continued
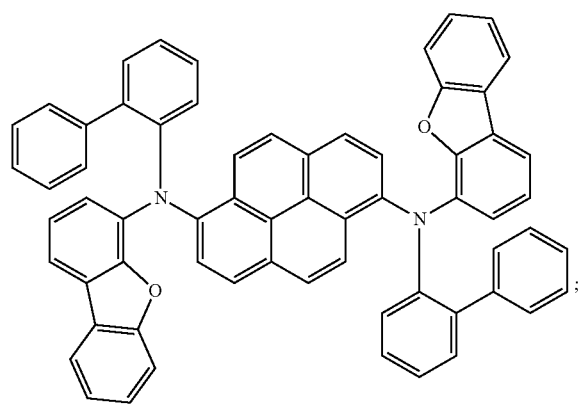
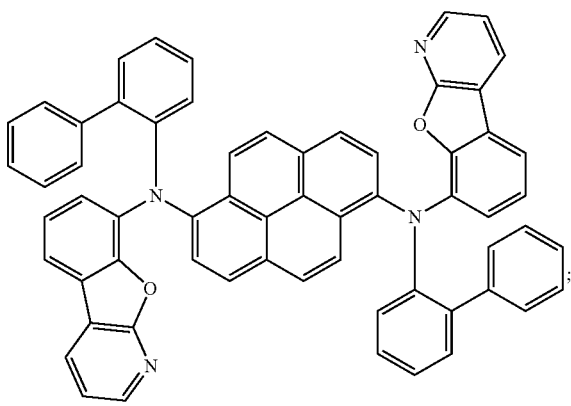
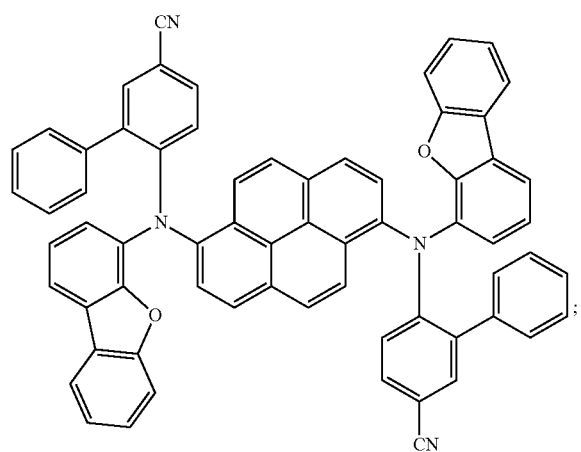
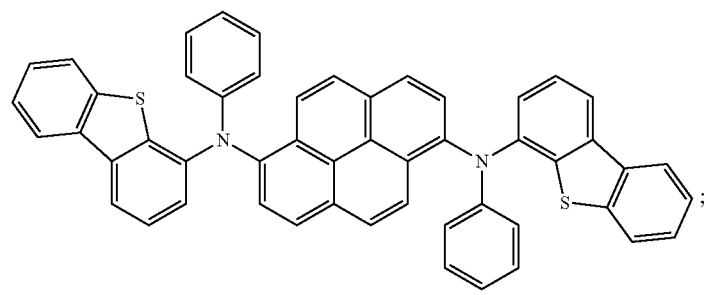
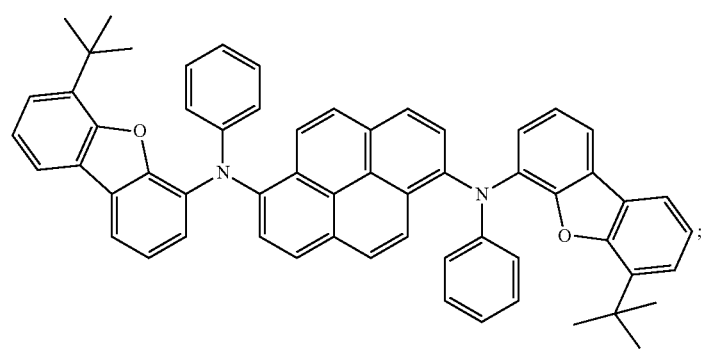

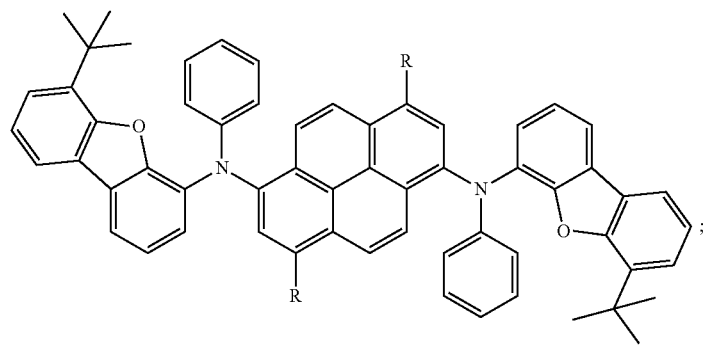
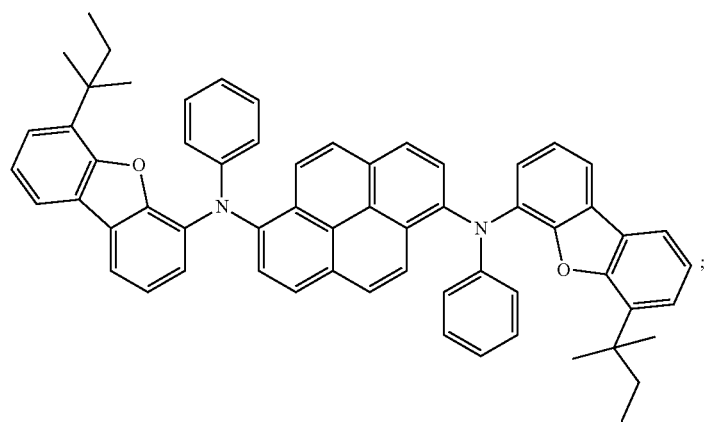
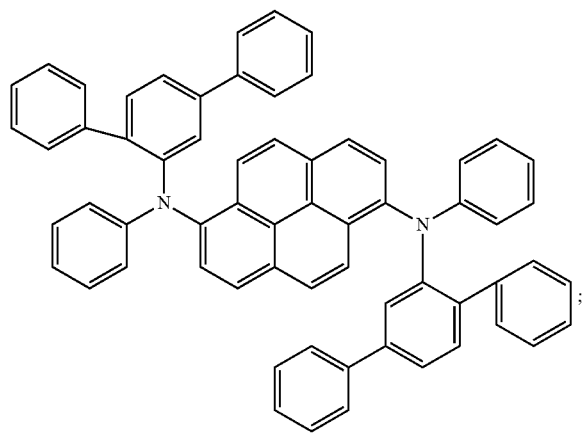

-continued
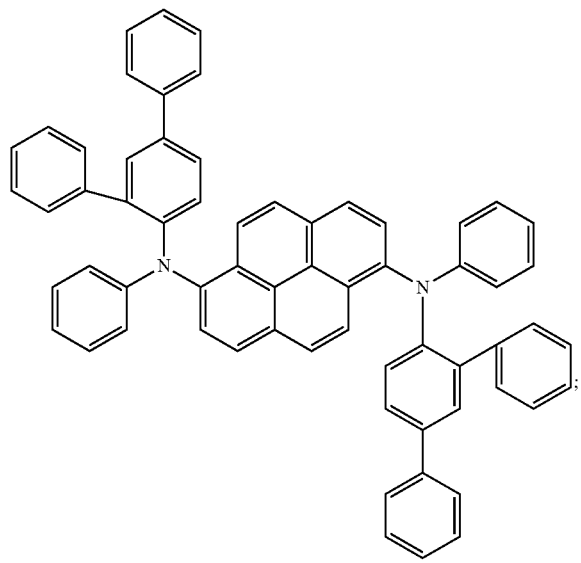
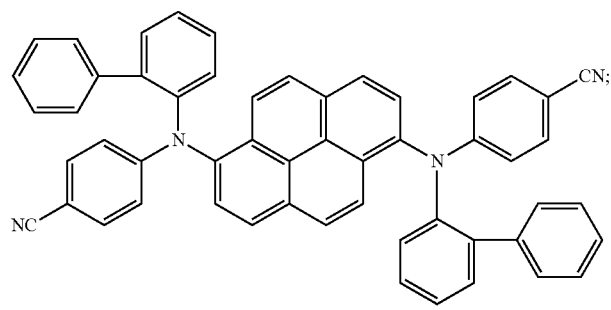
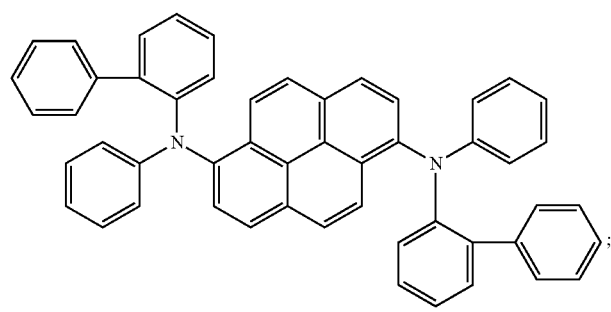
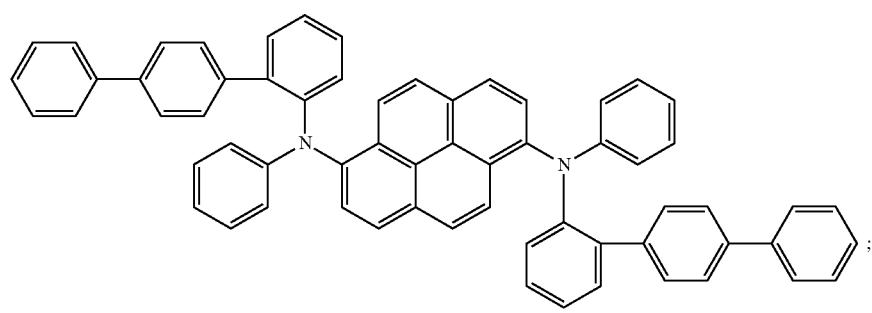

361 362
-continued
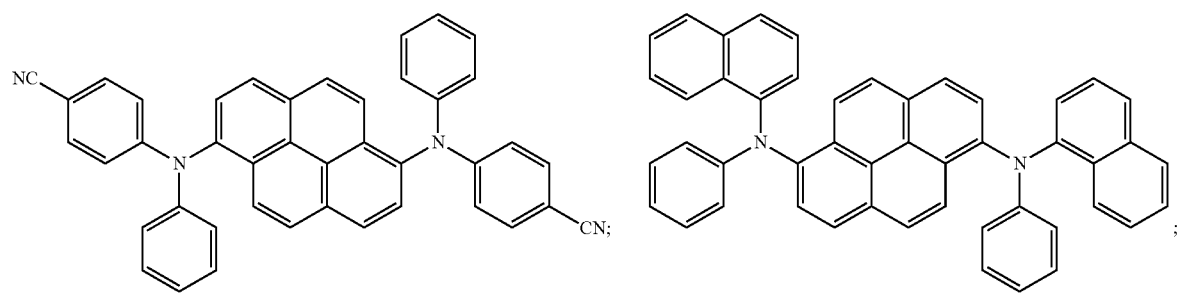
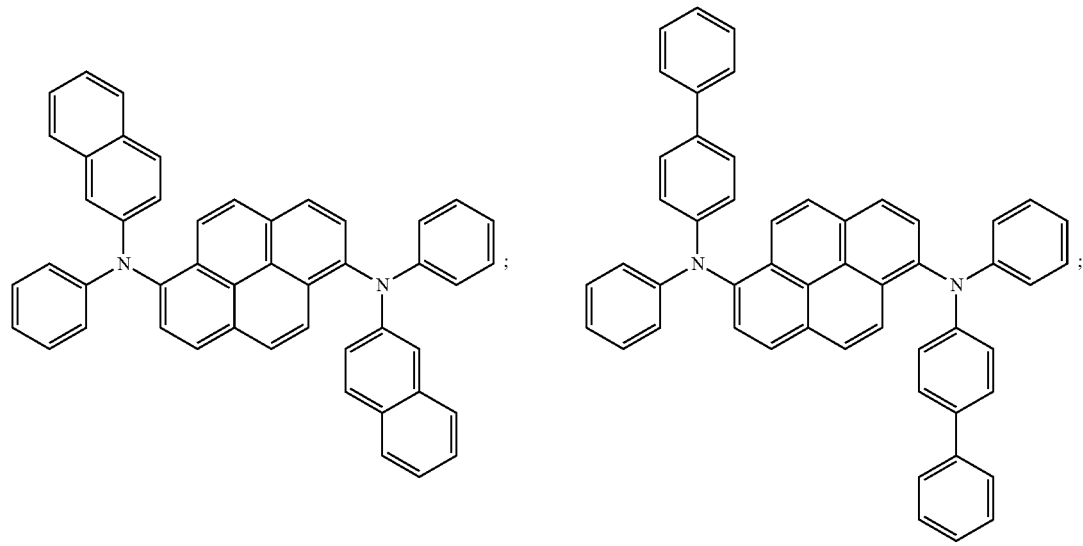
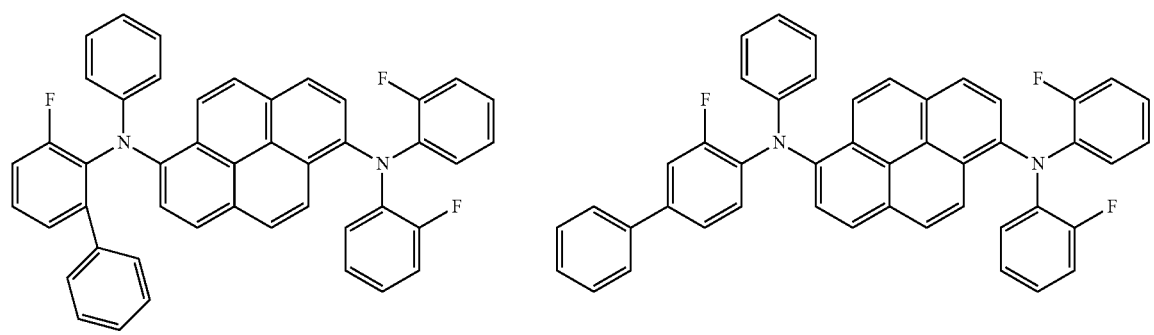
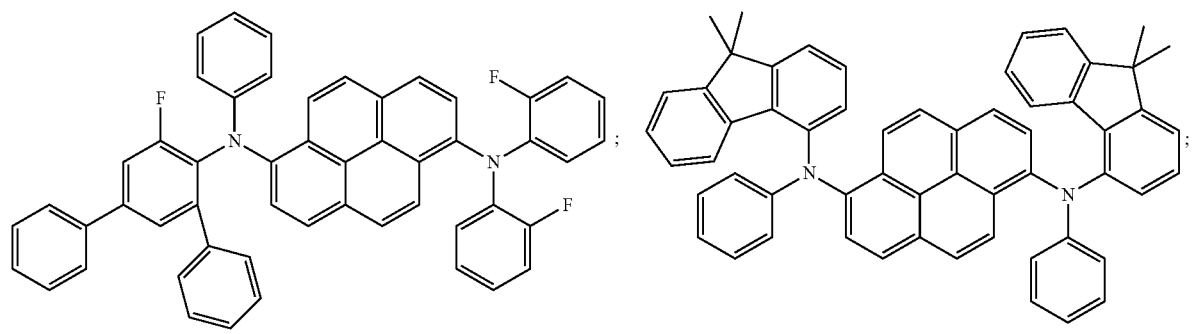

363
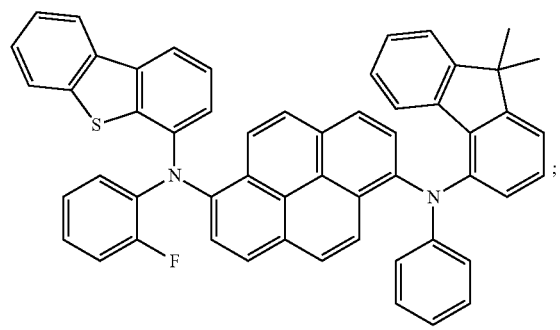
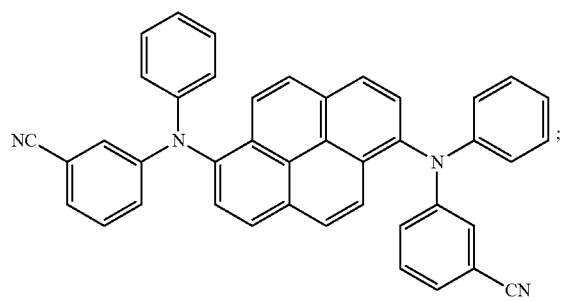
364
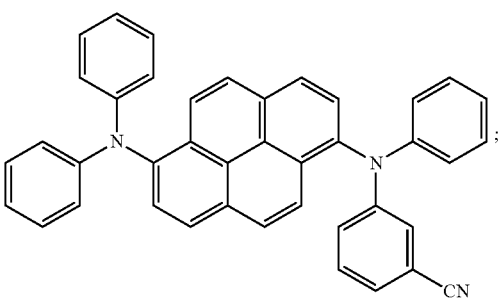
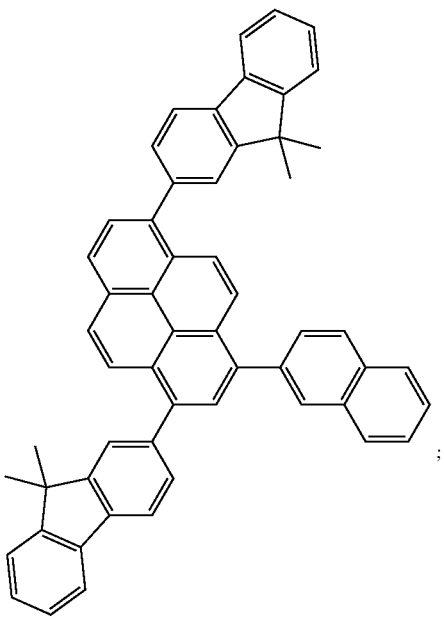
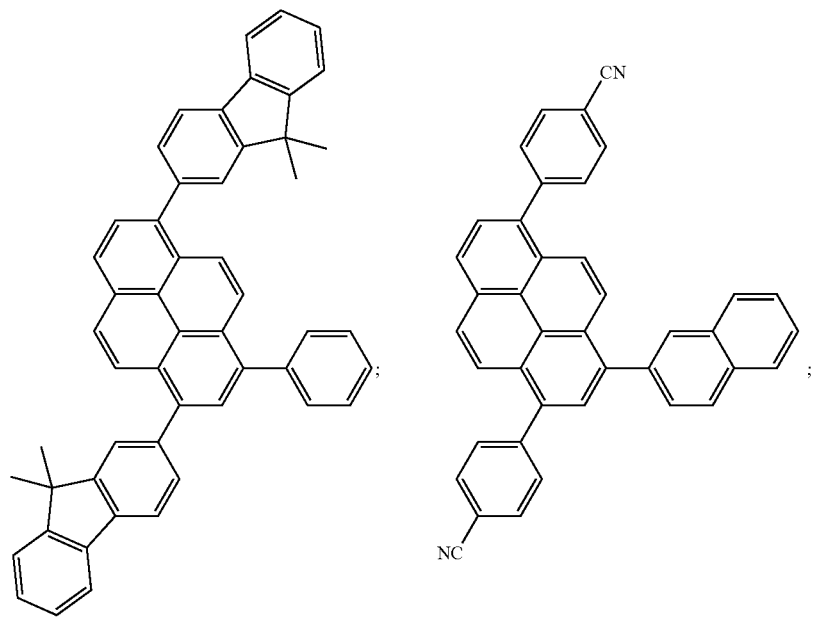

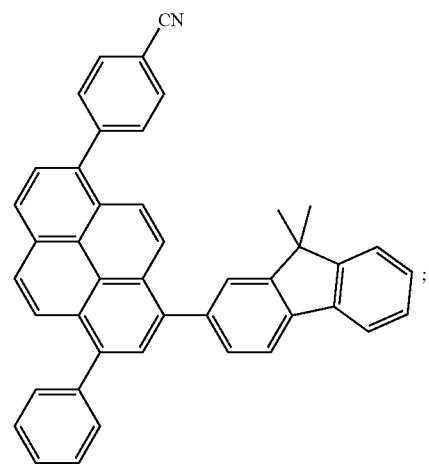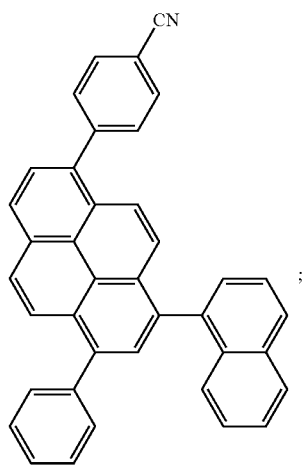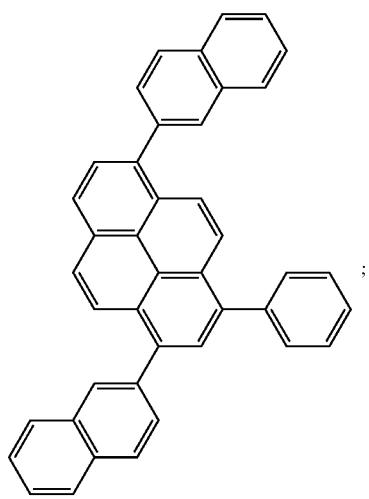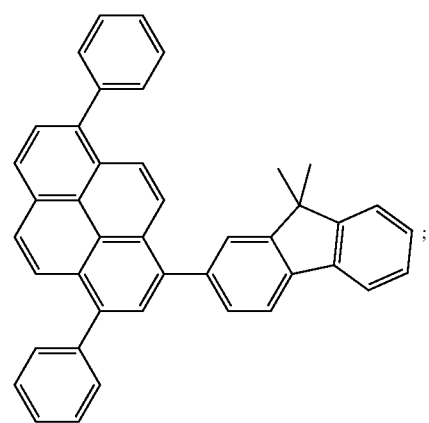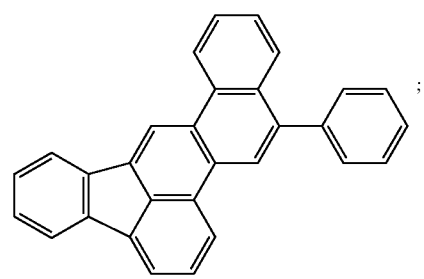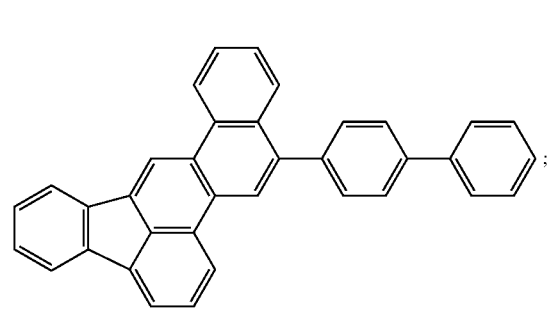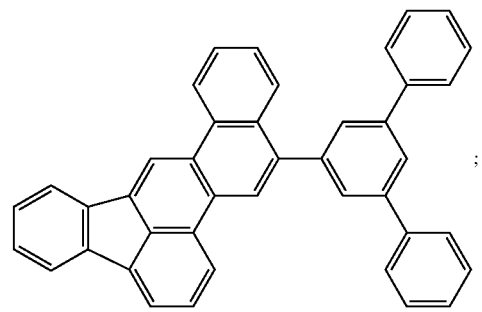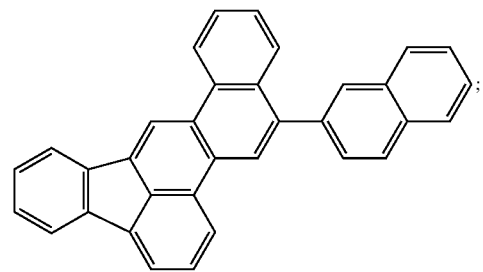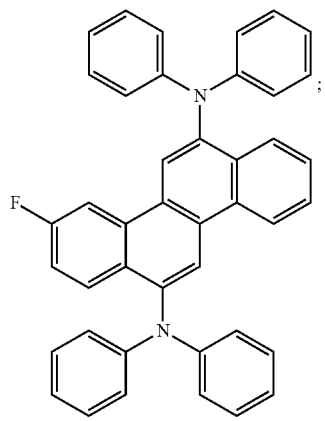

-continued
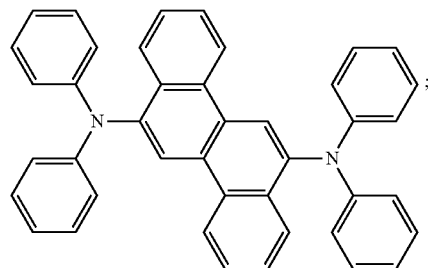
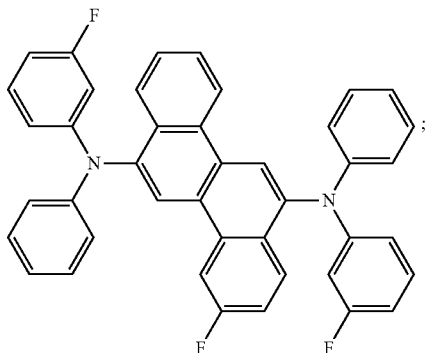
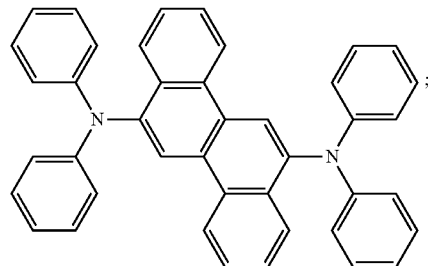
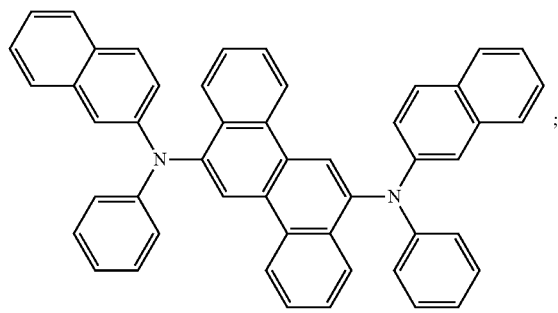
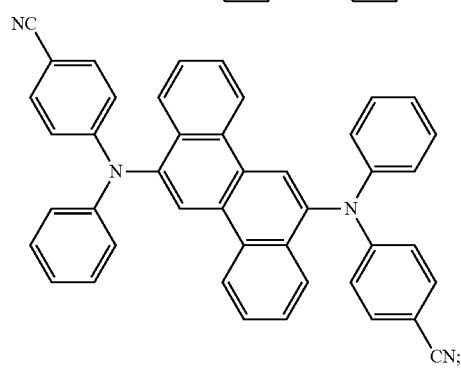
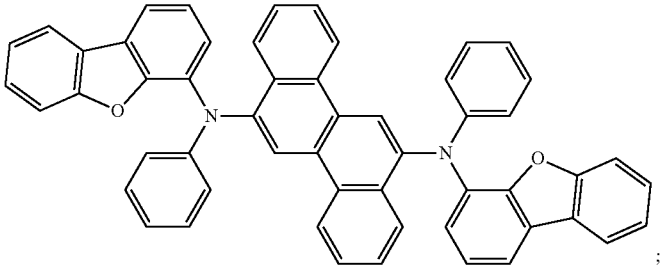
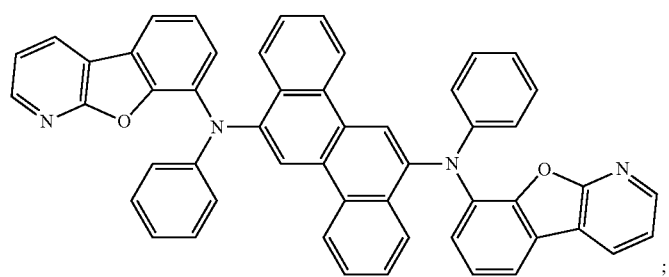
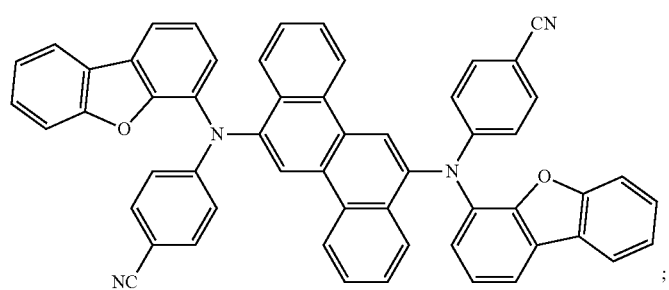

-continued
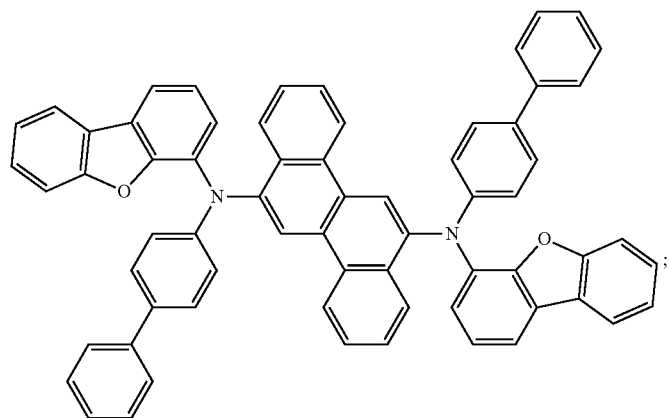
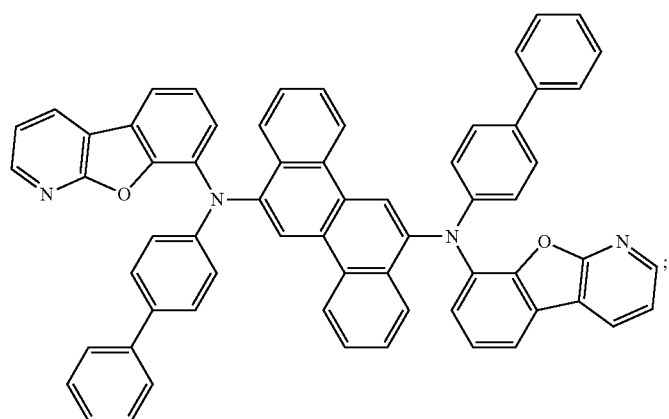
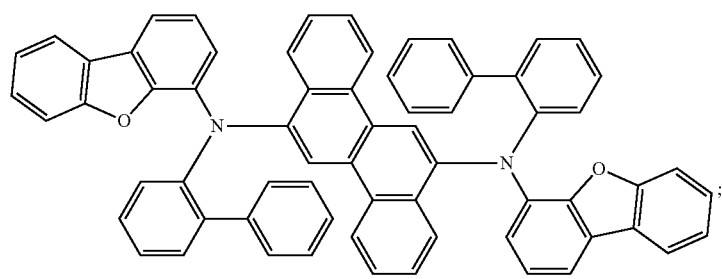
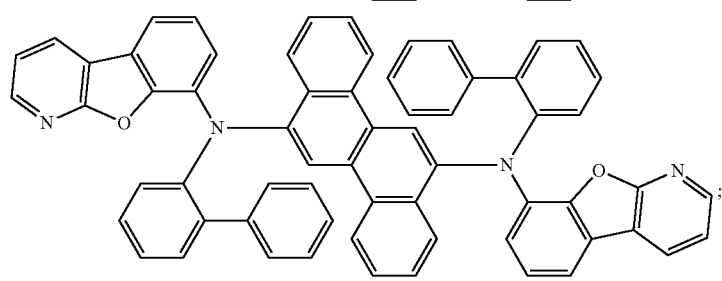
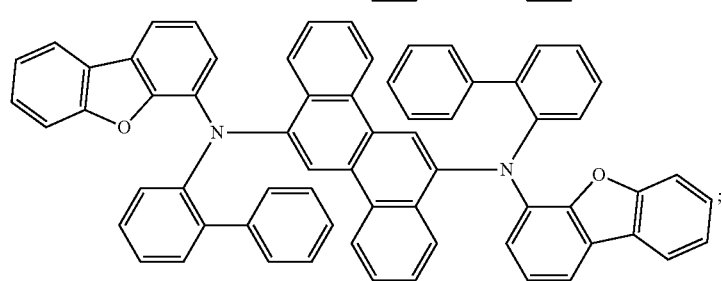

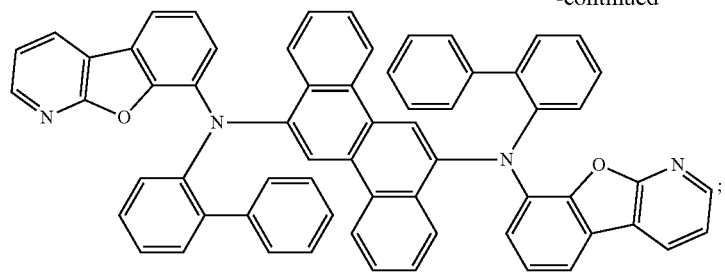
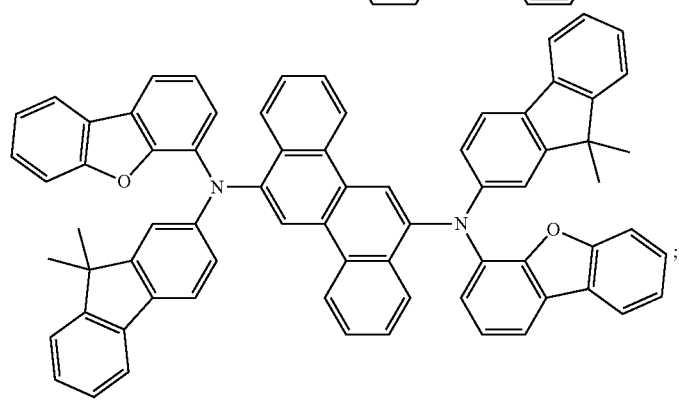
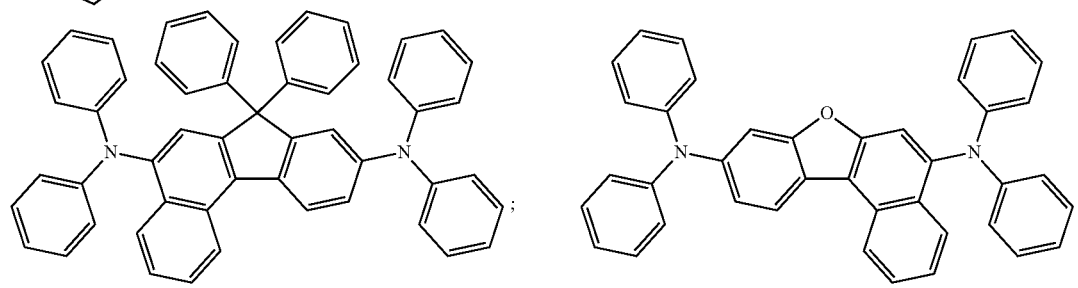
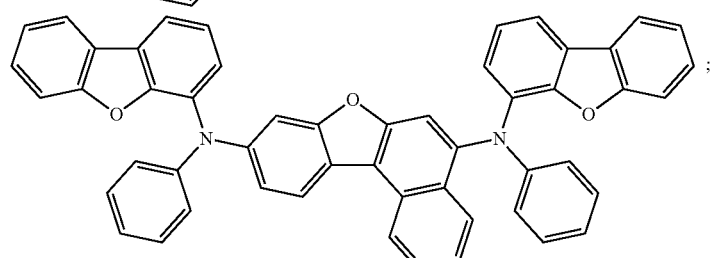
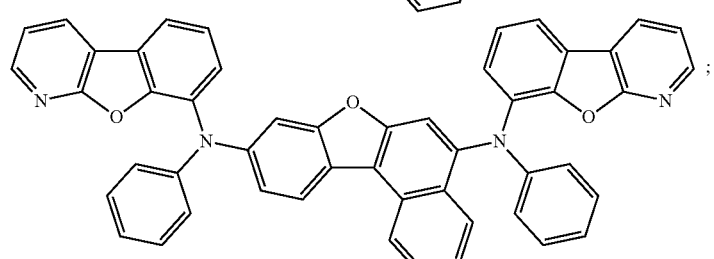
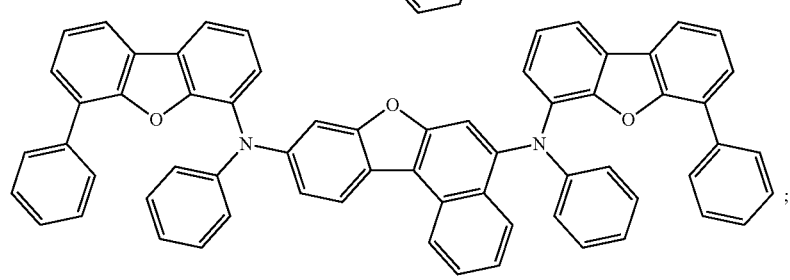

-continued
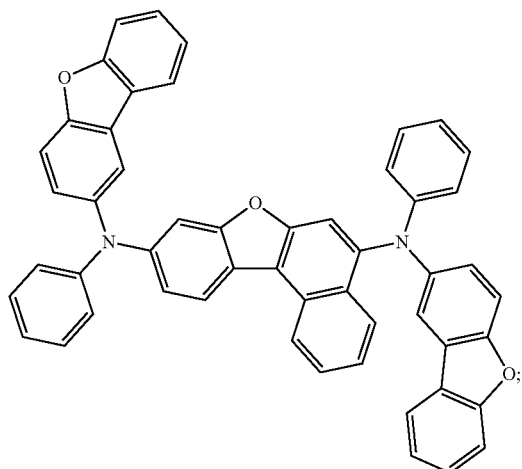
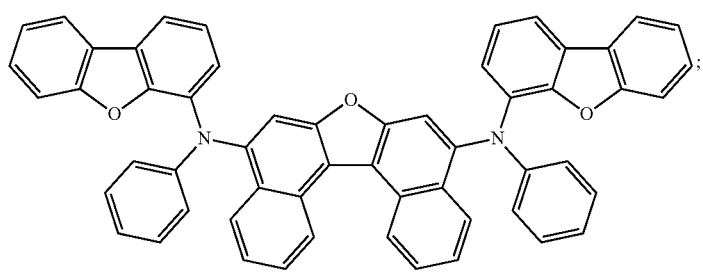
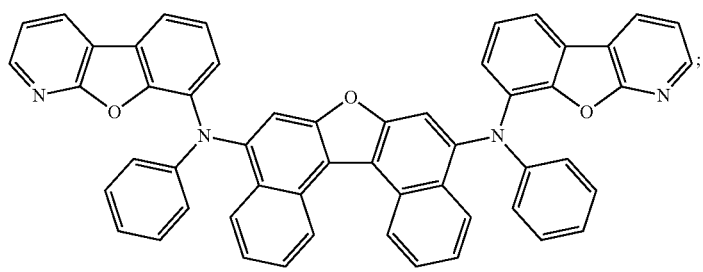
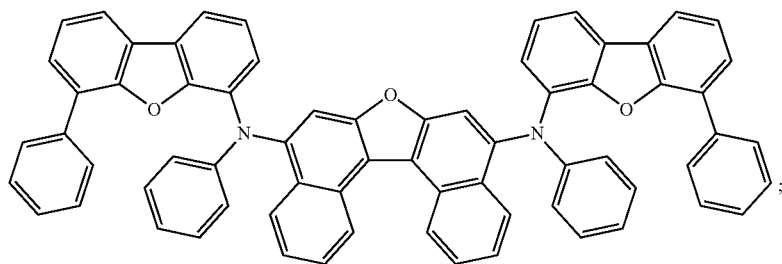
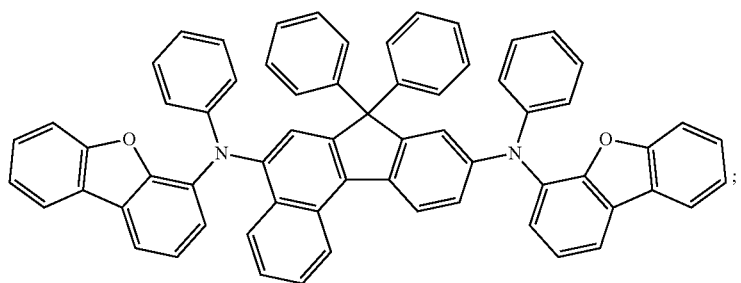

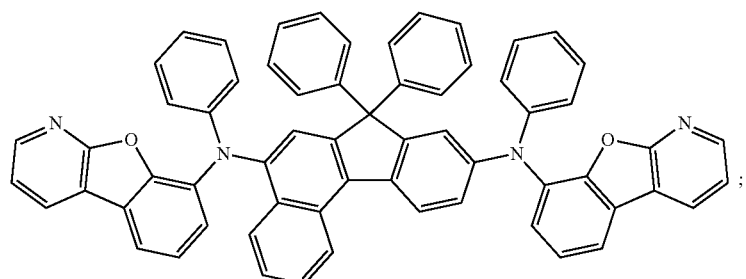
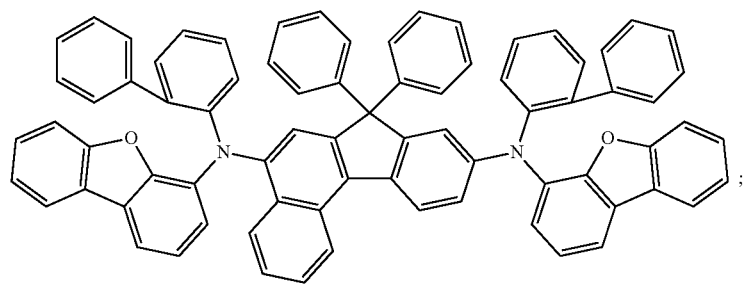
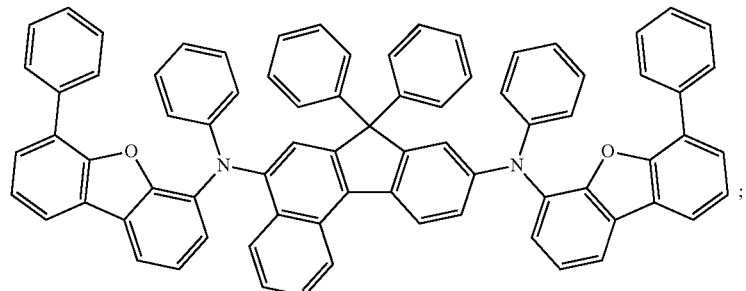
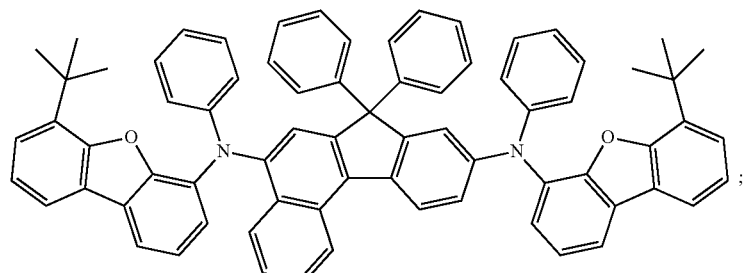
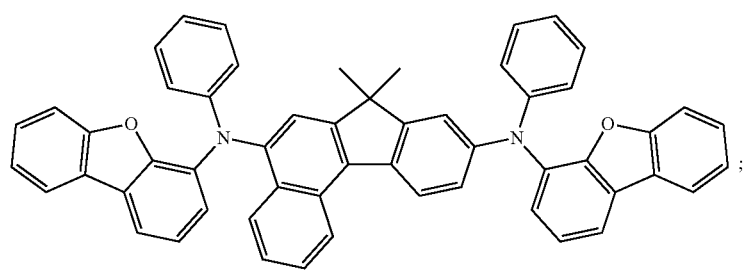
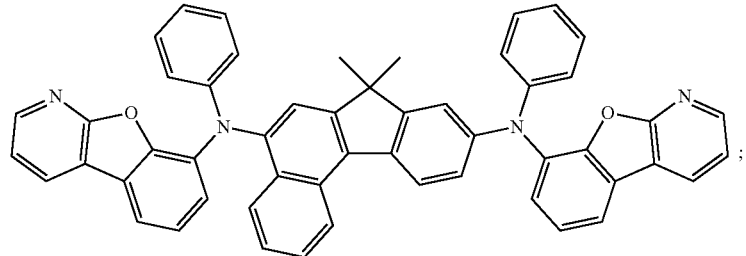

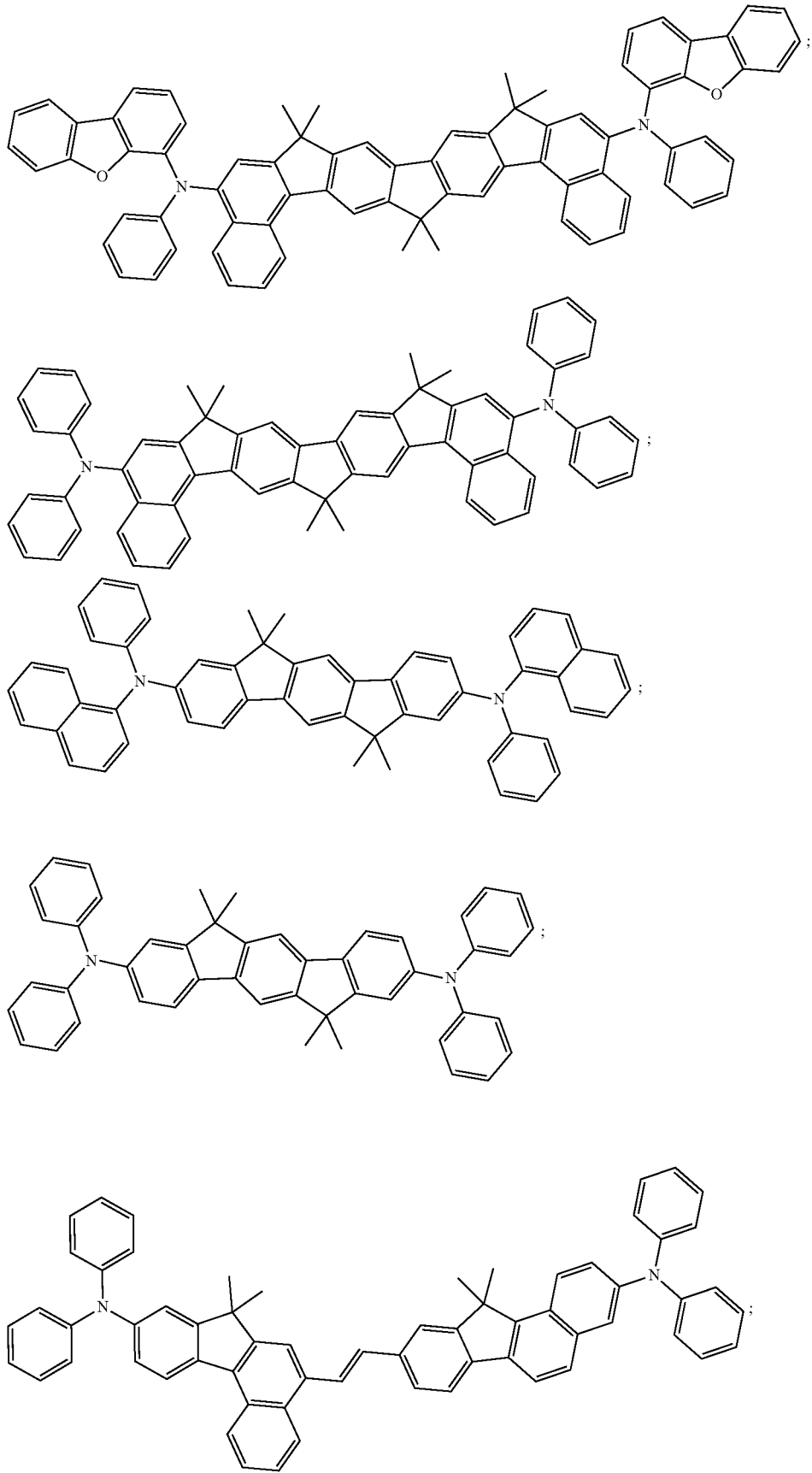

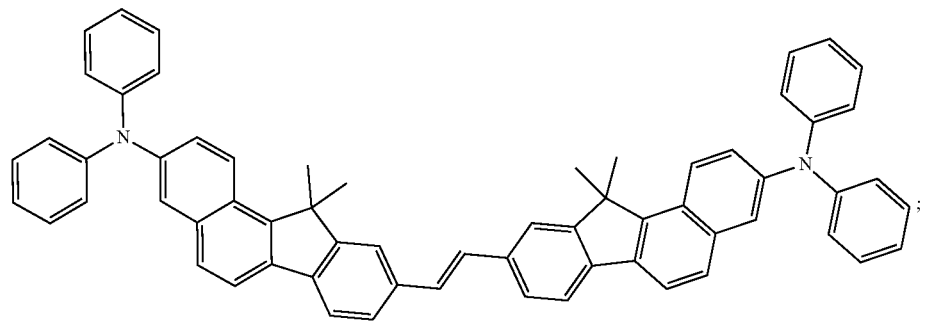
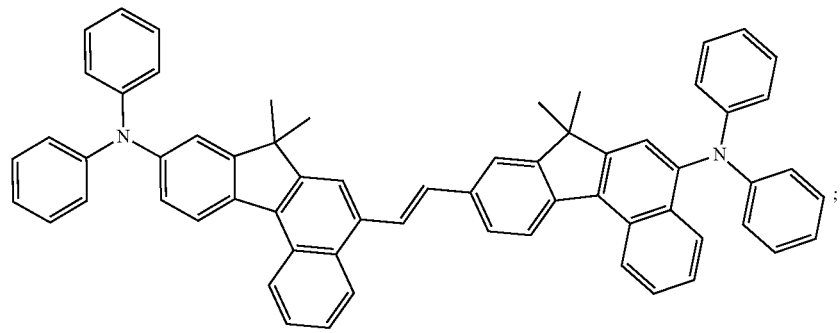
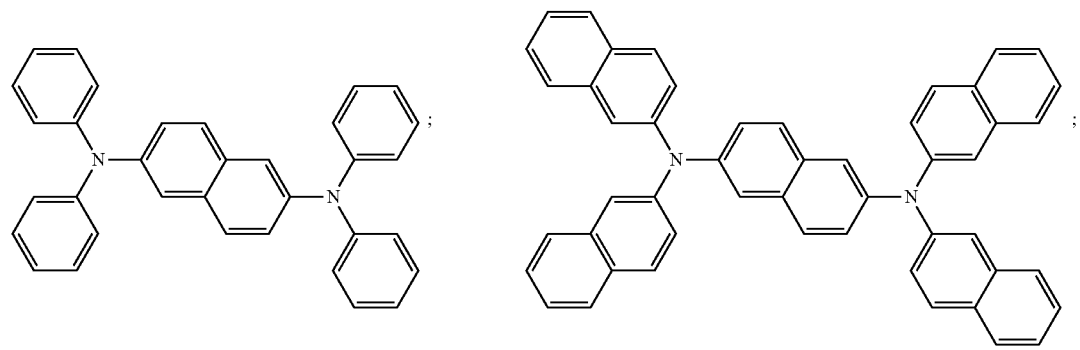
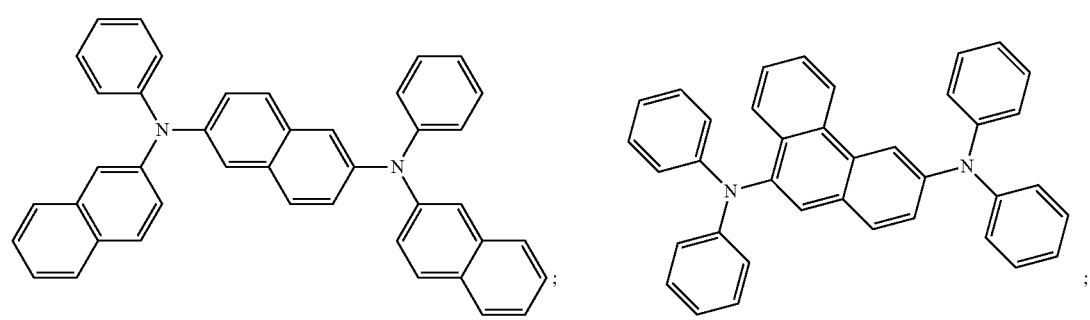
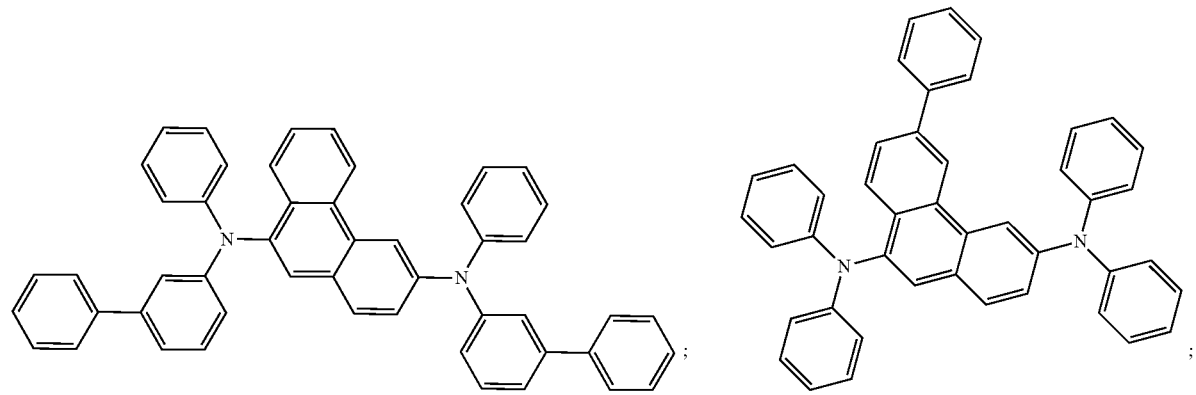

381 382
-continued
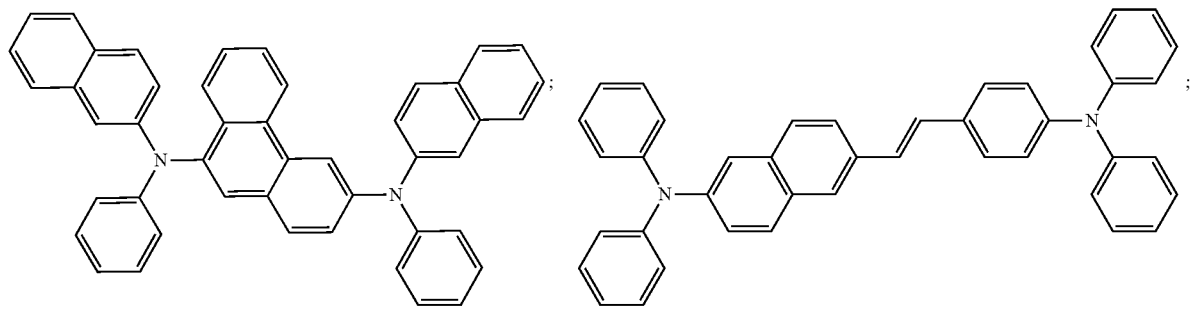
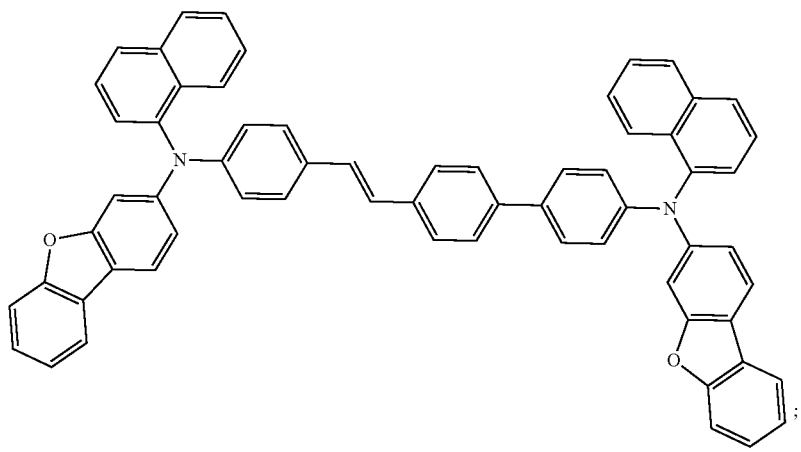
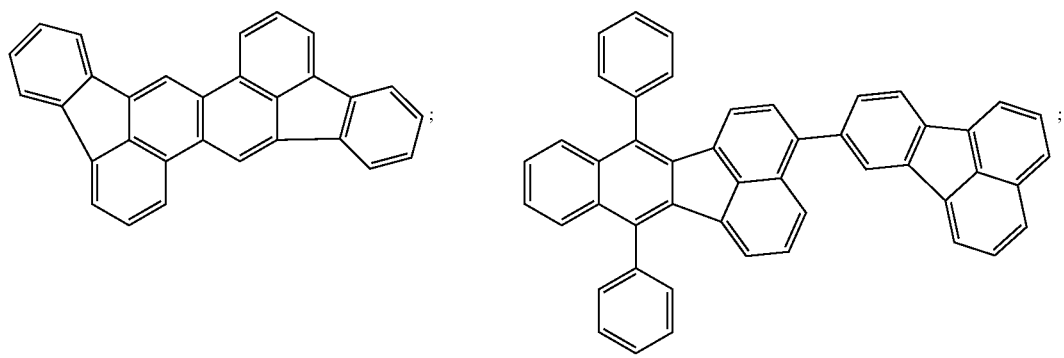
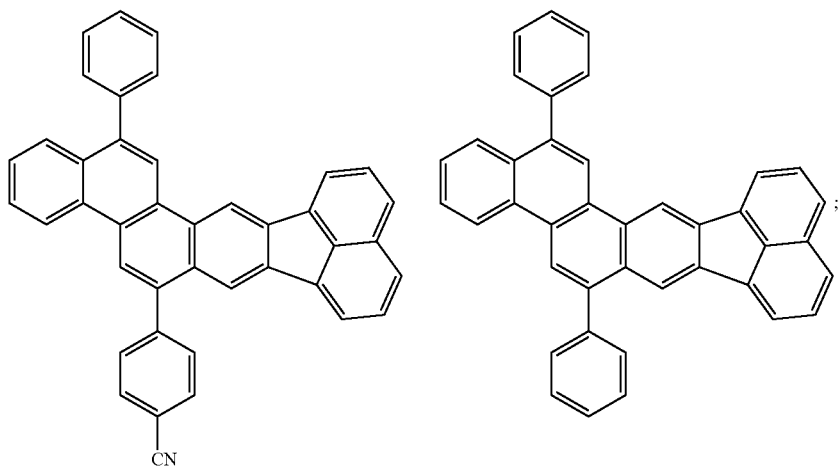

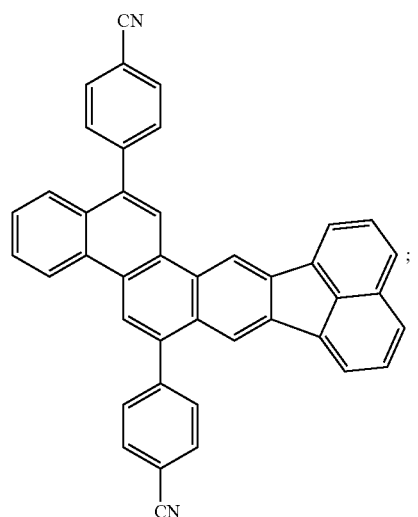
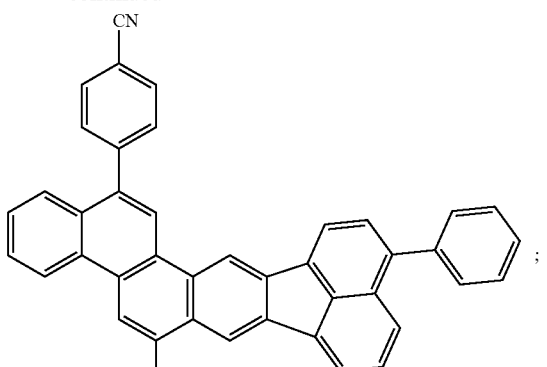
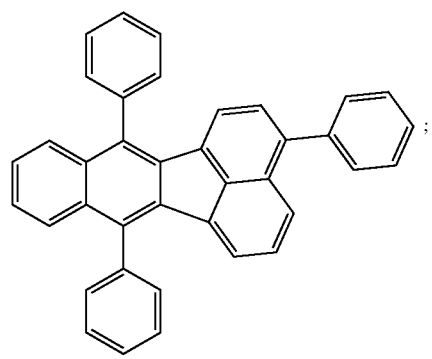
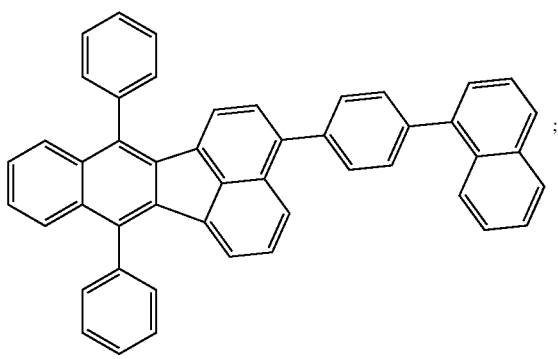
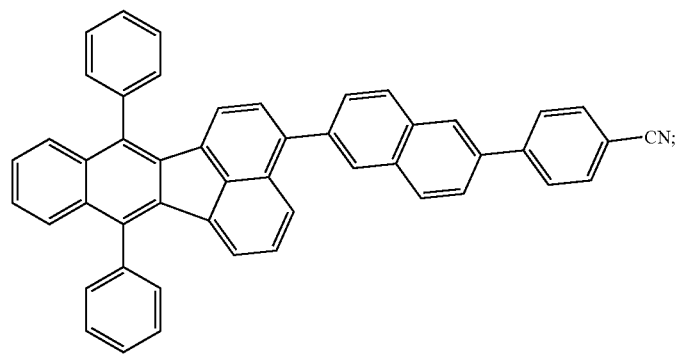
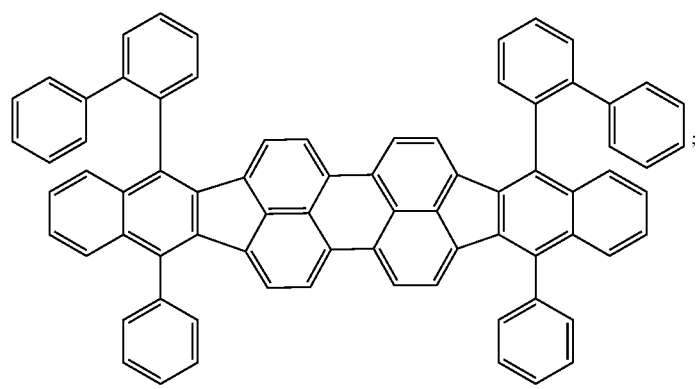

-continued
385
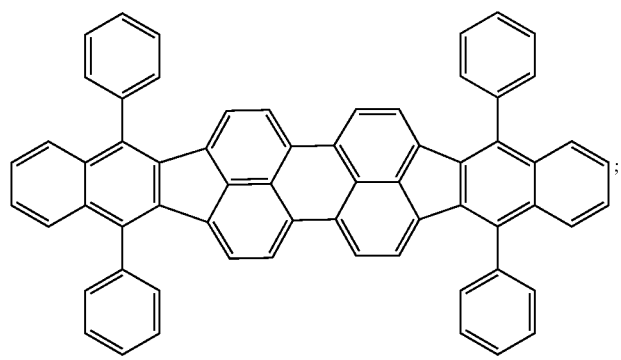
386
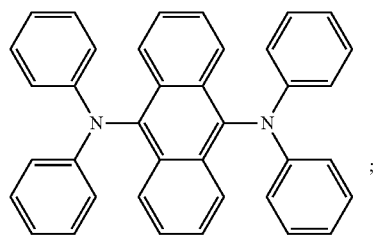
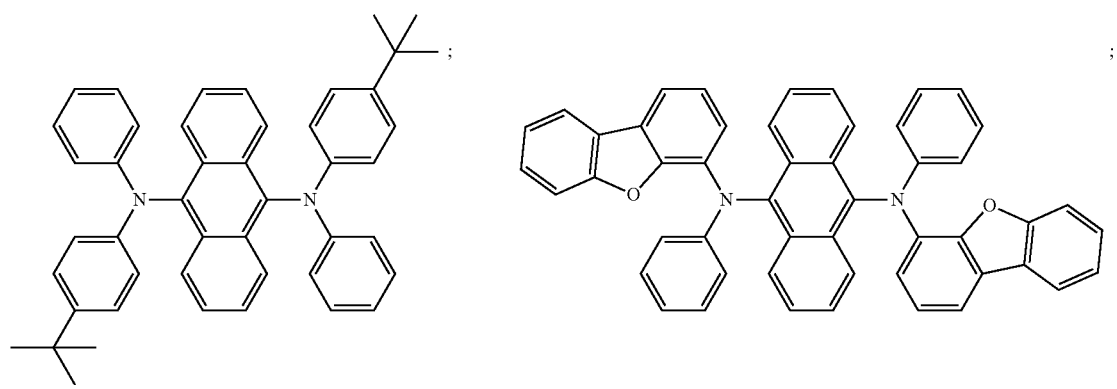
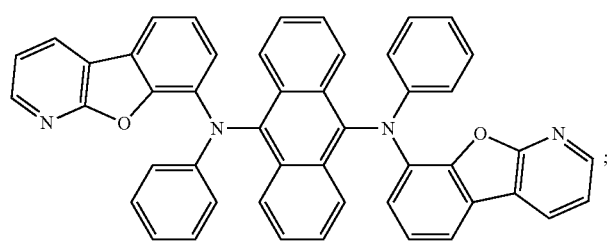
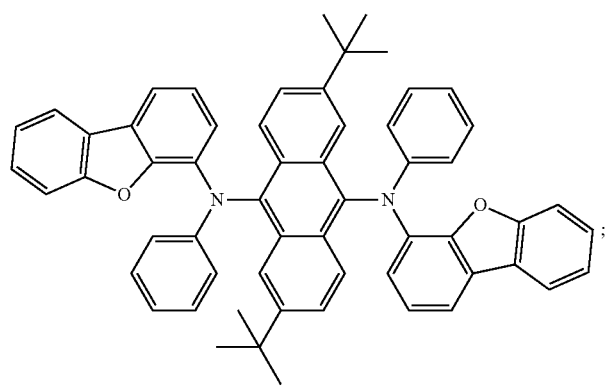

-continued
| 387 | 388 |
|---|---|
| 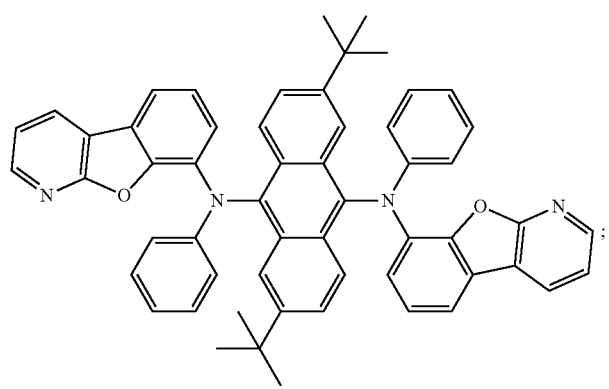 | 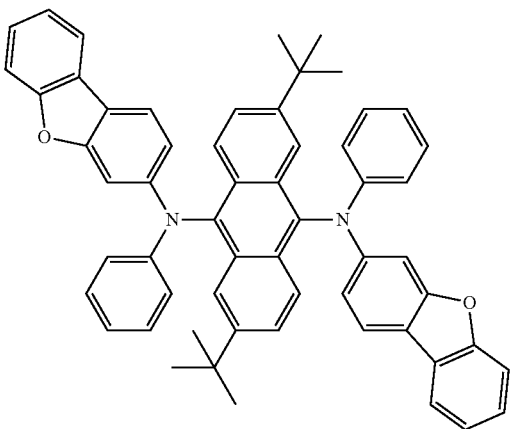 |
| 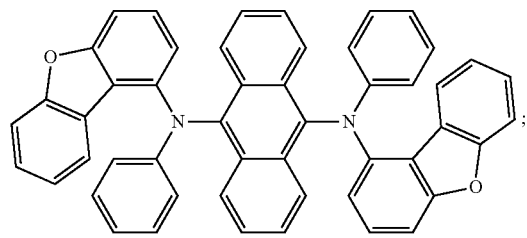 | 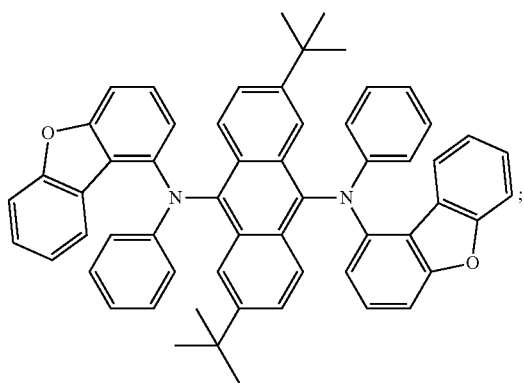 |
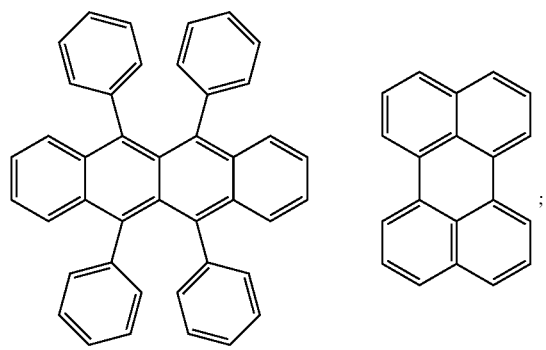

389
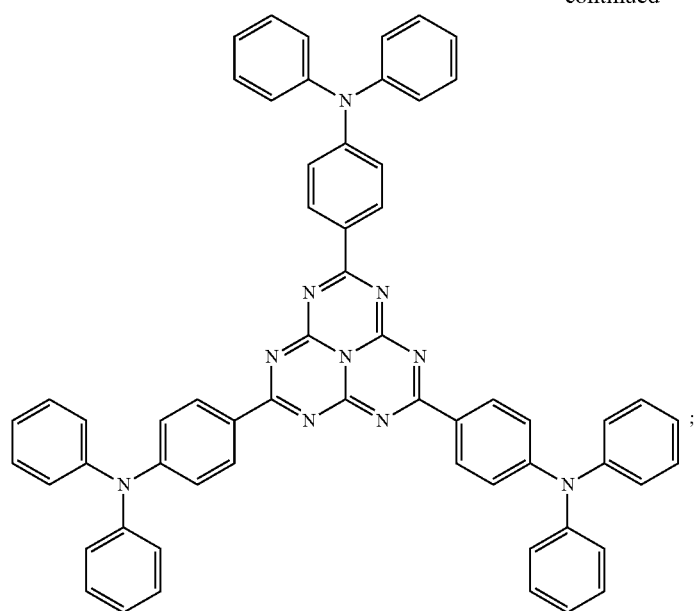
390
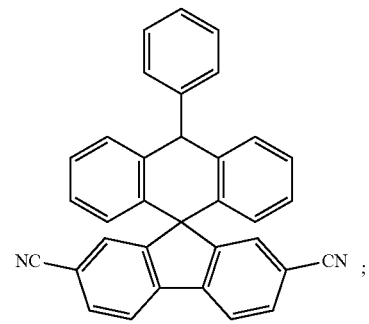
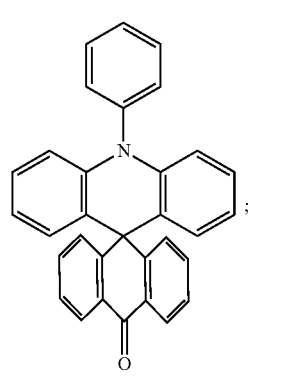
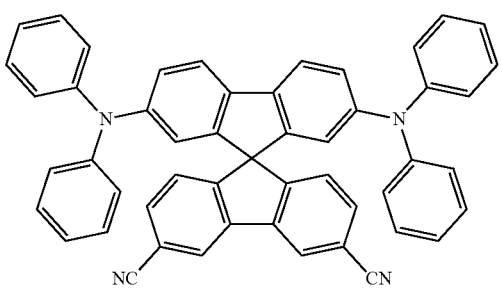
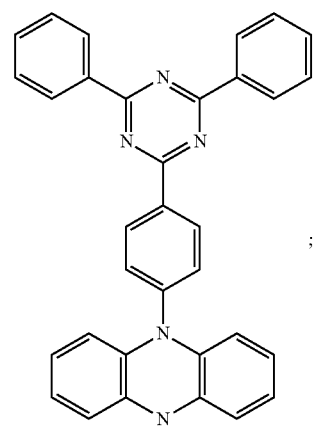
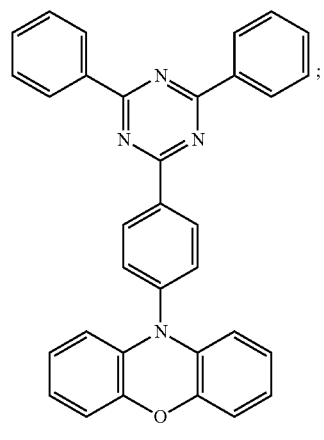
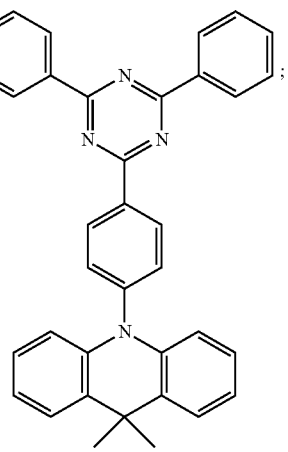
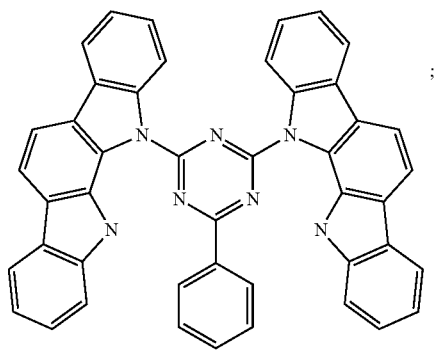

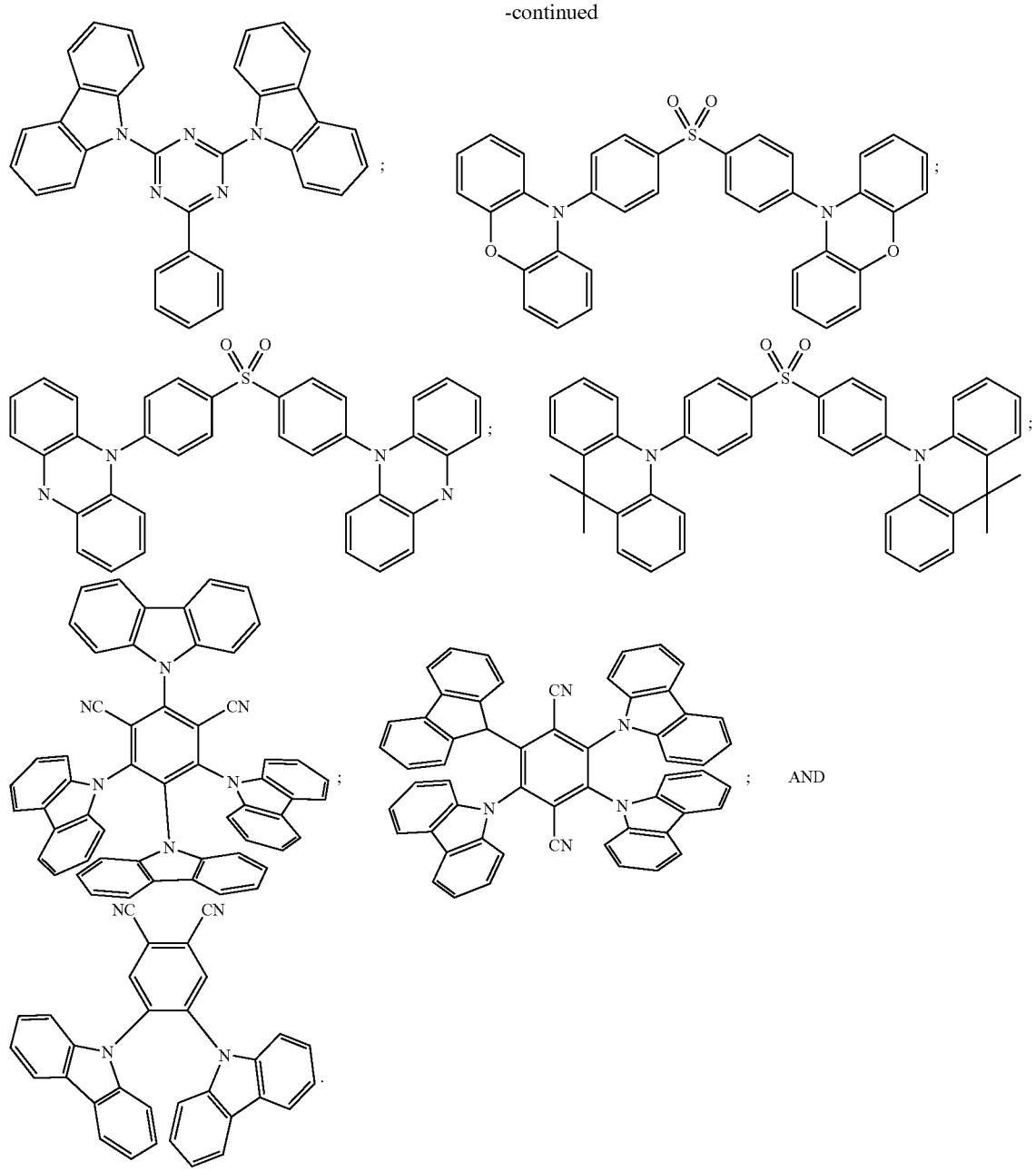
15. The compound of claim 13, wherein the compound is a Compound x having a formula Ai-Lj-Bk; wherein Lj is selected from the group consisting of:
Direct bond  L1
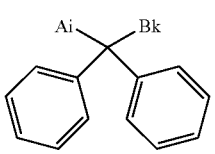 L2
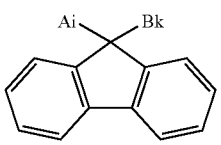 L3

393
-continued
L6 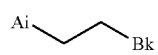
L7 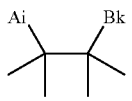
L8 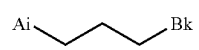
L9 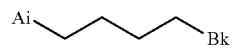
L10 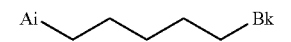
L11 
L12 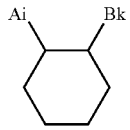
L13 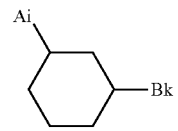
L14 
L15 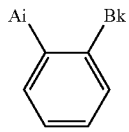
L16 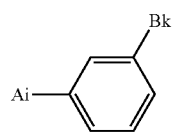
L17 
and Bk is selected from the group consisting of:
B1 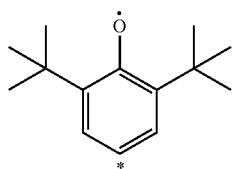
394
-continued
B2 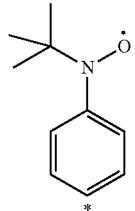
B3 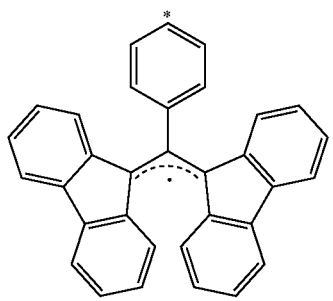
B4 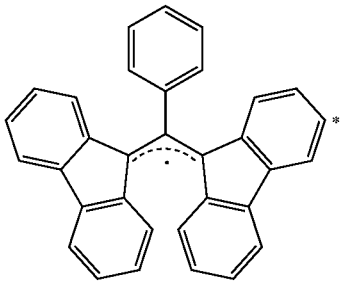
B5 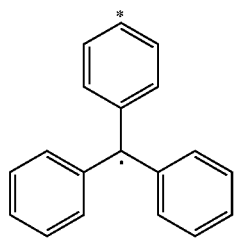
B6 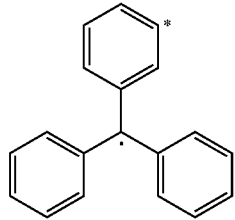
B7 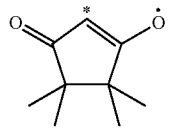
B8 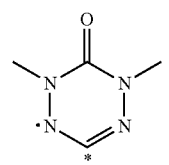

B9

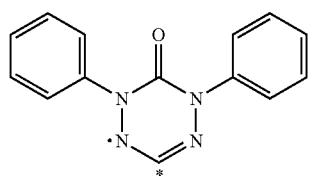

B10

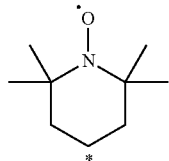

* attaches to Lj
and wherein

| Ai | Ci | Lj | Bk | x equals to | Compound x |
|---|---|---|---|---|---|
| (structure) | i is an integer from 1 to 19 | j is an integer from 1 to 17 | k is an integer from 1 to 10 | 17 (i − 1) + j + 323 (k − 1) | Compound 1-3230 |
| (structure) | i is an integer from 1 to 17 | j is an integer from 1 to 17 | k is an integer from 1 to 10 | 17 (i − 1) + j + 289 (k − 1) + 3230 | Compound 3231-6120 |
| (structure) | i is an integer from 1 to 22 | j is an integer from 1 to 17 | k is an integer from 1 to 10 | 17 (i − 1) + j + 374 (k − 1) + 6120 | Compound 6121-9860 |
| (structure) | i is an integer from 1 to 20 | j is an integer from 1 to 17 | k is an integer from 1 to 10 | 17 (i − 1) + j + 340 (k − 1) + 9860 | Compound 9861-13260 |

| Ai | Ci | Lj | Bk | x equals to | Compound x |
|---|---|---|---|---|---|
| (structure) | $i$ is an integer from 1 to 21 | $j$ is an integer from 1 to 17 | $k$ is an integer from 1 to 10 | $17(i-1) + j + 357(k-1) + 13260$ | Compound 13261-16830 |
| (structure) | $i$ is an integer from 1 to 21 | $j$ is an integer from 1 to 17 | $k$ is an integer from 1 to 10 | $17(i-1) + j + 357(k-1) + 16830$ | Compound 16831-20400 |
| (structure) | $i$ is an integer from 1 to 21 | $j$ is an integer from 1 to 17 | $k$ is an integer from 1 to 10 | $17(i-1) + j + 357(k-1) + 20400$ | Compound 20401-23970 |
| (structure) | $i$ is an integer from 1 to 7 | $j$ is an integer from 1 to 17 | $k$ is an integer from 1 to 10 | $17(i-1) + j + 119(k-1) + 23970$ | Compound 23971-25160 |
| (structure) | $i$ is an integer from 1 to 14 | $j$ is an integer from 1 to 17 | $k$ is an integer from 1 to 10 | $17(i-1) + j + 238(k-1) + 25160$ | Compound 25161-27540 |

-continued

| Ai | Ci | Lj | Bk | x equals to | Compound x |
|---|---|---|---|---|---|
| (structure) | $i$ is an integer from 1 to 11 | $j$ is an integer from 1 to 17 | $k$ is an integer from 1 to 10 | $17(i-1) + j + 187(k-1) + 27540$ | Compound 27541-29410 |
| (structure) | $i = 1$ | $j$ is an integer from 1 to 17 | $k$ is an integer from 1 to 10 | $j + 17(k-1) + 29410$ | Compound 29411-29580 |
| (structure) | $i$ is an integer from 1 to 16 | $j$ is an integer from 1 to 17 | $k$ is an integer from 1 to 10 | $17(i-1) + j + 272(k-1) + 29580$ | Compound 29581-32300 |
| (structure) | $i$ is an integer from 1 to 13 | $j$ is an integer from 1 to 17 | $k$ is an integer from 1 to 10 | $17(i-1) + j + 221(k-1) + 32300$ | Compound 32301-34510 |

-continued

| Ai | Ci | Lj | Bk | x equals to | Compound x |
|---|---|---|---|---|---|
| (structure) | i = 1 | j is an integer from 1 to 17 | k is an integer from 1 to 10 | j + 17 (k − 1) + 34510 | Compound 34511-34680 |
| (structure) | i is an integer from 1 to 13 | j is an integer from 1 to 17 | k is an integer from 1 to 10 | 17 (i − 1) + j + 221 (k − 1) + 34680 | Compound 34681-36890 |
| (structure) | i is an integer from 1 to 10 | j is an integer from 1 to 17 | k is an integer from 1 to 10 | 17 (i − 1) + j + 170 (k − 1) + 36890 | Compound 36891-38590 |
| (structure) | i = 1 | j is an integer from 1 to 17 | k is an integer from 1 to 10 | j + 17 (k − 1) + 38590 | Compound 38591-38760 |
| (structure) | i is an integer from 1 to 13 | j is an integer from 1 to 17 | k is an integer from 1 to 10 | 17 (i − 1) + j + 221 (k − 1) + 38760 | Compound 38761-40970 |

| Ai | Ci | Lj | Bk | x equals to | Compound x |
|---|---|---|---|---|---|
| 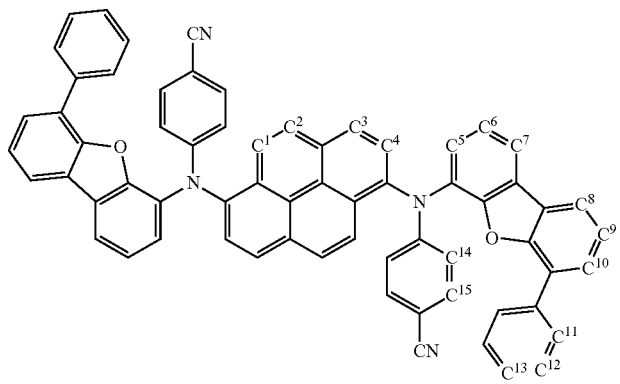 | $i$ is an integer from 1 to 15 | $j$ is an integer from 1 to 17 | $k$ is an integer from 1 to 10 | $17(i-1) + j + 255(k-1) + 40970$ | Compound 40971-43520 |
| 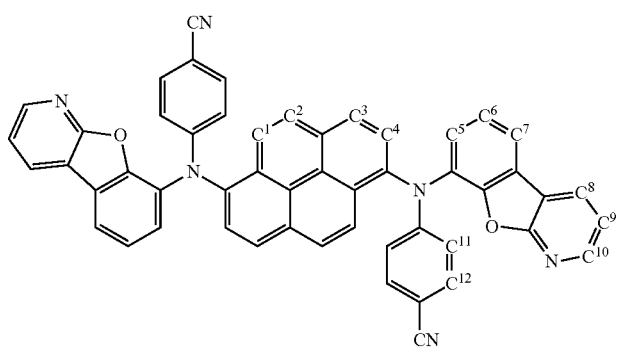 | $i$ is an integer from 1 to 12 | $j$ is an integer from 1 to 17 | $k$ is an integer from 1 to 10 | $17(i-1) + j + 204(k-1) + 43520$ | Compound 43521-45560 |
| 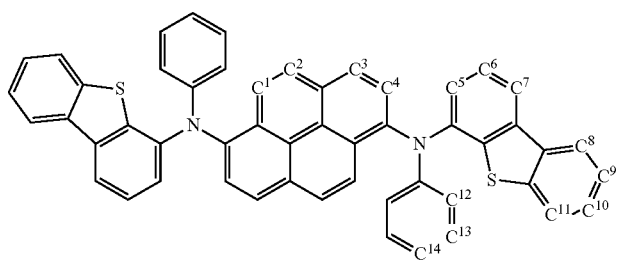 | $i$ is an integer from 1 to 14 | $j$ is an integer from 1 to 17 | $k$ is an integer from 1 to 10 | $17(i-1) + j + 238(k-1) + 45560$ | Compound 45561-47940 |
| 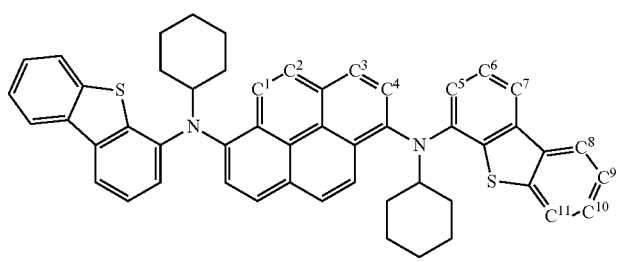 | $i$ is an integer from 1 to 11 | $j$ is an integer from 1 to 17 | $k$ is an integer from 1 to 10 | $17(i-1) + j + 187(k-1) + 47940$ | Compound 47941-49810 |
| 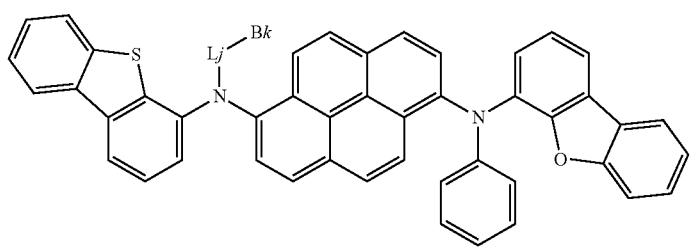 | $i = 1$ | $j$ is an integer from 1 to 17 | $k$ is an integer from 1 to 10 | $j + 17(k-1) + 49810$ | Compound 49811-49980 |

-continued

| Ai | Ci | Lj | Bk | x equals to | Compound x |
|---|---|---|---|---|---|
| 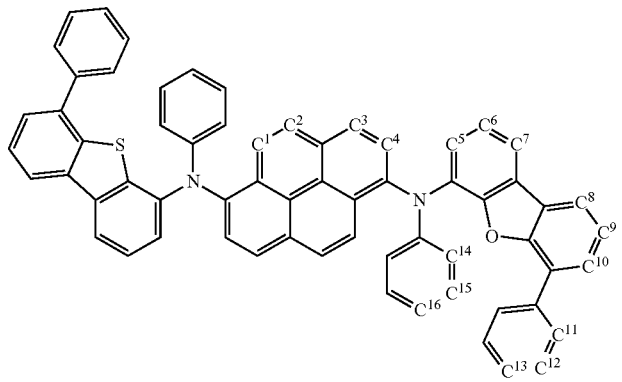 | $i$ is an integer from 1 to 16 | $j$ is an integer from 1 to 17 | $k$ is an integer from 1 to 10 | $17(i-1) + j + 272(k-1) + 49980$ | Compound 49981-52700 |
| 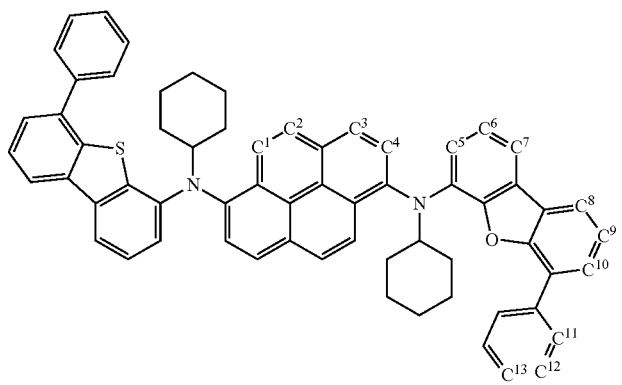 | $i$ is an integer from 1 to 13 | $j$ is an integer from 1 to 17 | $k$ is an integer from 1 to 10 | $17(i-1) + j + 221(k-1) + 52700$ | Compound 52701-54910 |
| 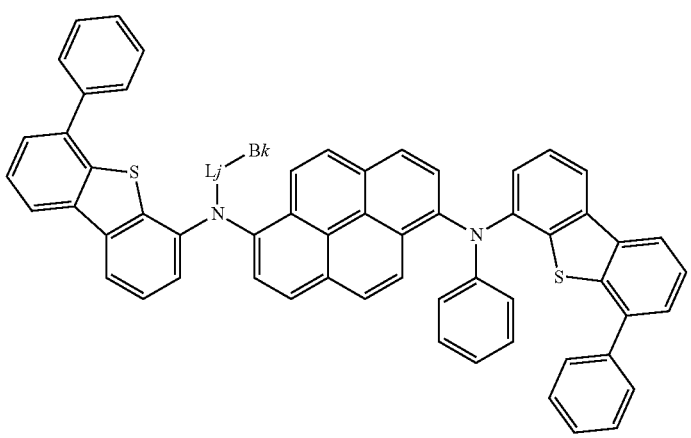 | $i = 1$ | $j$ is an integer from 1 to 17 | $k$ is an integer from 1 to 10 | $j + 17(k-1) + 54910$ | Compound 54911-55080 |
| 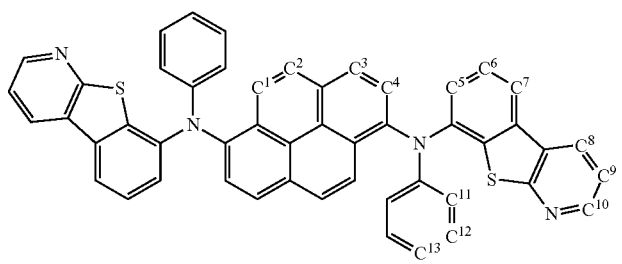 | $i$ is an integer from 1 to 13 | $j$ is an integer from 1 to 17 | $k$ is an integer from 1 to 10 | $17(i-1) + j + 221(k-1) + 55080$ | Compound 55081-57290 |

| Ai | Ci | Lj | Bk | x equals to | Compound x |
|---|---|---|---|---|---|
| (structure) | $i$ is an integer from 1 to 10 | $j$ is an integer from 1 to 17 | $k$ is an integer from 1 to 10 | $17(i-1) + j + 170(k-1) + 57290$ | Compound 57291-58990 |
| (structure) | $i = 1$ | $j$ is an integer from 1 to 17 | $k$ is an integer from 1 to 10 | $j + 17(k-1) + 58990$ | Compound 58991-59160 |
| (structure) | $i$ is an integer from 1 to 13 | $j$ is an integer from 1 to 17 | $k$ is an integer from 1 to 10 | $17(i-1) + j + 221(k-1) + 59160$ | Compound 59161-61370 |
| (structure) | $i$ is an integer from 1 to 15 | $j$ is an integer from 1 to 17 | $k$ is an integer from 1 to 10 | $17(i-1) + j + 255(k-1) + 61370$ | Compound 61371-63920 |
| (structure) | $i$ is an integer from 1 to 12 | $j$ is an integer from 1 to 17 | $k$ is an integer from 1 to 10 | $17(i-1) + j + 204(k-1) + 63920$ | Compound 63921-65960 |

-continued

| Ai | Ci | Lj | Bk | x equals to | Compound x |
|---|---|---|---|---|---|
| 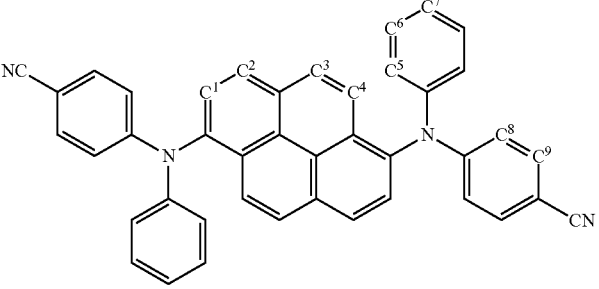 | $i$ is an integer from 1 to 9 | $j$ is an integer from 1 to 17 | $k$ is an integer from 1 to 10 | $17(i-1)+j+153(k-1)+65960$ | Compound 65961-67490 |
| 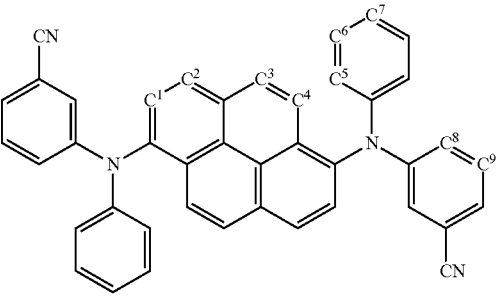 | $i$ is an integer from 1 to 9 | $j$ is an integer from 1 to 17 | $k$ is an integer from 1 to 10 | $17(i-1)+j+153(k-1)+67490$ | Compound 67491-69020 |
| 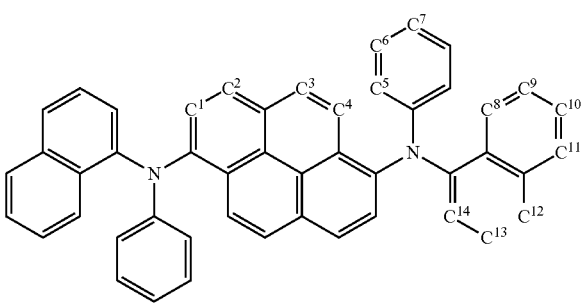 | $i$ is an integer from 1 to 14 | $j$ is an integer from 1 to 17 | $k$ is an integer from 1 to 10 | $17(i-1)+j+238(k-1)+69020$ | Compound 69021-71400 |
| 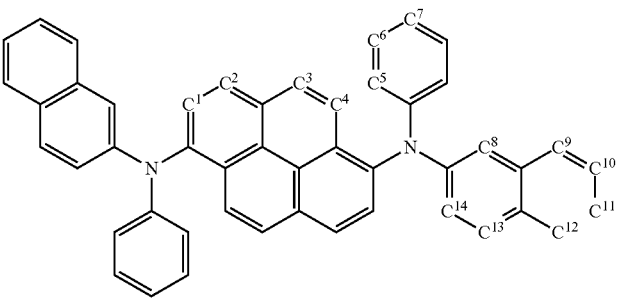 | $i$ is an integer from 1 to 14 | $j$ is an integer from 1 to 17 | $k$ is an integer from 1 to 10 | $17(i-1)+j+238(k-1)+71400$ | Compound 71401-73780 |

| Ai | Ci | Lj | Bk | x equals to | Compound x |
|---|---|---|---|---|---|
| 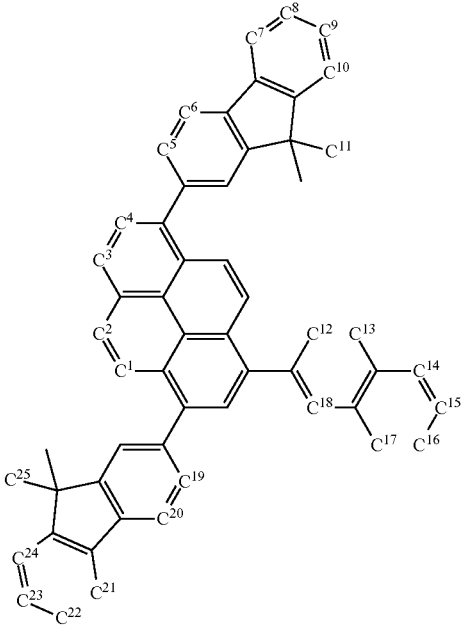 | $i$ is an integer from 1 to 25 | $j$ is an integer from 1 to 17 | $k$ is an integer from 1 to 10 | $17(i-1)+j+425(k-1)+73780$ | Compound 73781-78030 |
| 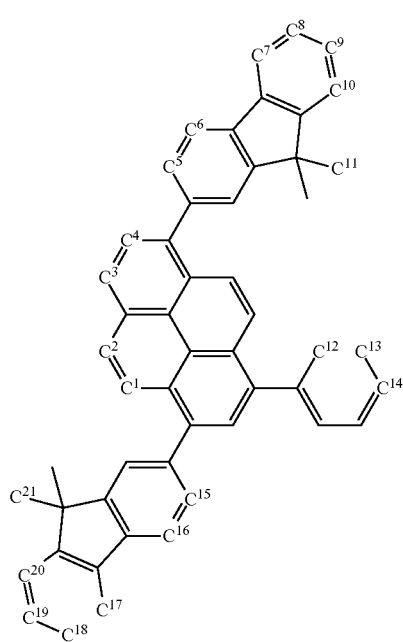 | $i$ is an integer from 1 to 21 | $j$ is an integer from 1 to 17 | $k$ is an integer from 1 to 10 | $17(i-1)+j+357(k-1)+78030$ | Compound 78031-81600 |

-continued
| Ai | Ci | Lj | Bk | x equals to | Compound x |
|---|---|---|---|---|---|
| 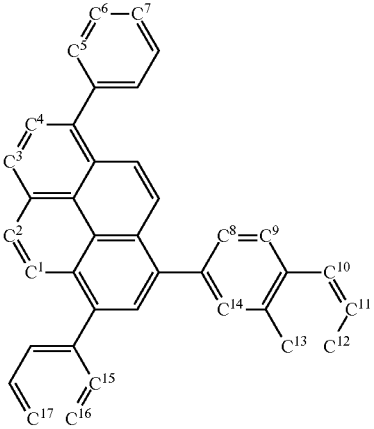 | $i$ is an integer from 1 to 17 | $j$ is an integer from 1 to 17 | $k$ is an integer from 1 to 10 | $17(i-1) + j + 289(k-1) + 81600$ | Compound 81601-84490 |
| 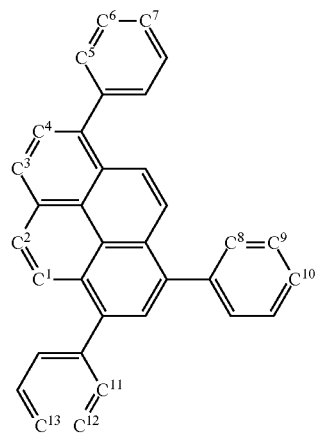 | $i$ is an integer from 1 to 13 | $j$ is an integer from 1 to 17 | $k$ is an integer from 1 to 10 | $17(i-1) + j + 221(k-1) + 84490$ | Compound 84491-86700 |
| 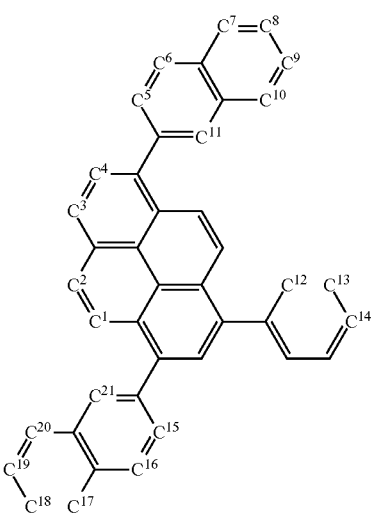 | $i$ is an integer from 1 to 21 | $j$ is an integer from 1 to 17 | $k$ is an integer from 1 to 10 | $17(i-1) + j + 357(k-1) + 86700$ | Compound 86701-90270 |

-continued

| Ai | Ci | Lj | Bk | x equals to | Compound x |
|---|---|---|---|---|---|
| 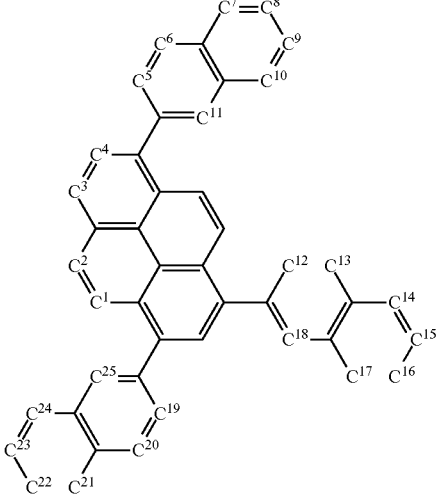 | i is an integer from 1 to 25 | j is an integer from 1 to 17 | k is an integer from 1 to 10 | 17 (i − 1) + j + 425 (k − 1) + 90270 | Compound 90271-94520 |
| 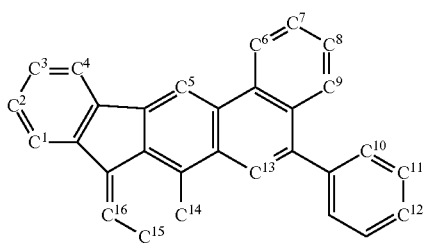 | i is an integer from 1 to 16 | j is an integer from 1 to 17 | k is an integer from 1 to 10 | 17 (i − 1) + j + 272 (k − 1) + 94520 | Compound 94521-97240 |
| 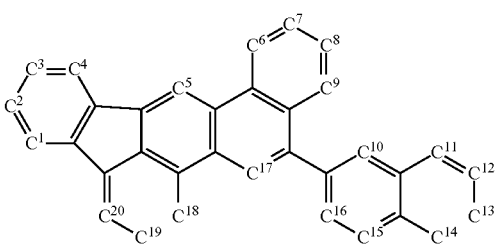 | i is an integer from 1 to 20 | j is an integer from 1 to 17 | k is an integer from 1 to 10 | 17 (i − 1) + j + 340 (k − 1) + 970240 | Compound 97241-100640 |
| 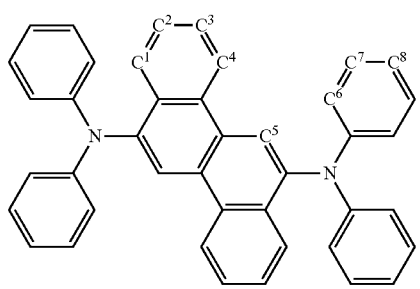 | i is an integer from 1 to 8 | j is an integer from 1 to 17 | k is an integer from 1 to 10 | 17 (i − 1) + j + 136 (k − 1) + 100640 | Compound 100641-102000 |
| 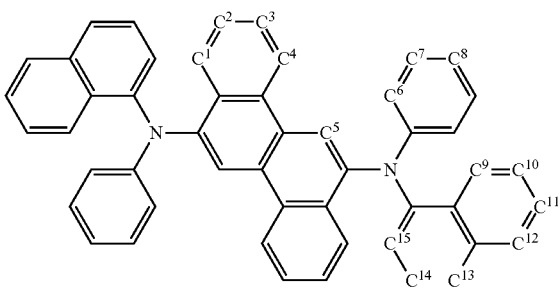 | i is an integer from 1 to 15 | j is an integer from 1 to 17 | k is an integer from 1 to 10 | 17 (i − 1) + j + 255 (k − 1) + 102000 | Compound 102001-104550 |

-continued

| Ai | Ci | Lj | Bk | x equals to | Compound x |
|---|---|---|---|---|---|
| 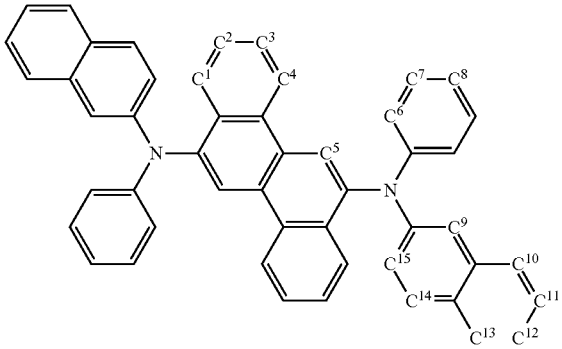 | $i$ is an integer from 1 to 15 | $j$ is an integer from 1 to 17 | $k$ is an integer from 1 to 10 | $17(i-1)+j+255(k-1)+104550$ | Compound 104551-107100 |
| 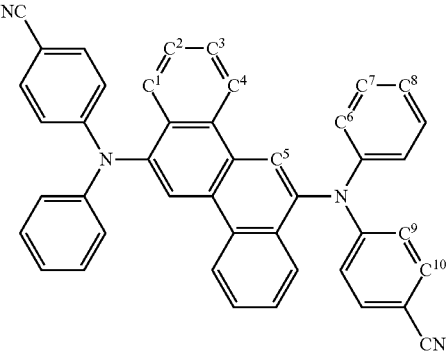 | $i$ is an integer from 1 to 10 | $j$ is an integer from 1 to 17 | $k$ is an integer from 1 to 10 | $17(i-1)+j+170(k-1)+107100$ | Compound 107101-108800 |
| 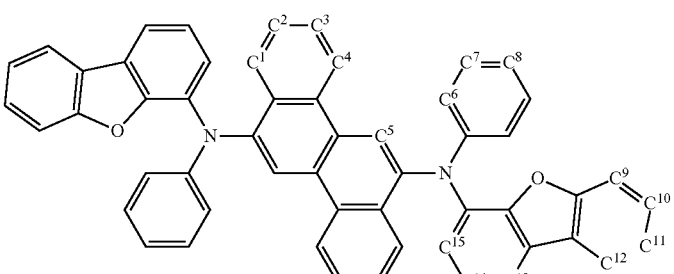 | $i$ is an integer from 1 to 15 | $j$ is an integer from 1 to 17 | $k$ is an integer from 1 to 10 | $17(i-1)+j+255(k-1)+108800$ | Compound 108801-111350 |
| 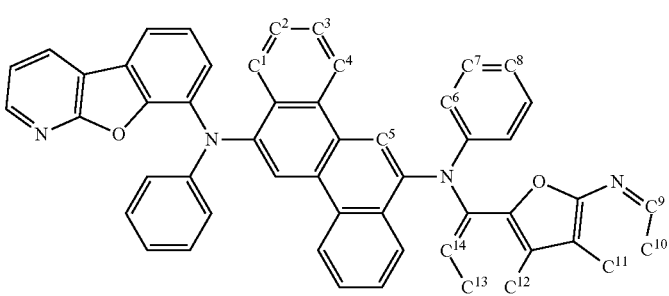 | $i$ is an integer from 1 to 14 | $j$ is an integer from 1 to 17 | $k$ is an integer from 1 to 10 | $17(i-1)+j+238(k-1)+111350$ | Compound 111351-113730 |

| Ai | Ci | Lj | Bk | x equals to | Compound x |
|---|---|---|---|---|---|
| 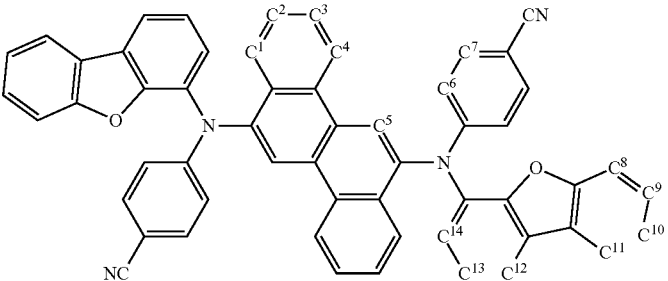 | i is an integer from 1 to 14 | j is an integer from 1 to 17 | k is an integer from 1 to 10 | 17 (i − 1) + j + 238 (k − 1) + 113730 | Compound 113731-116110 |
| 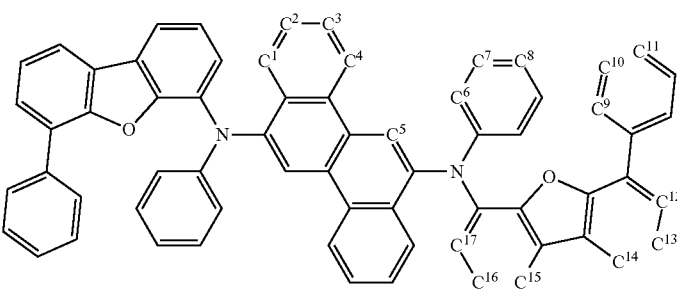 | i is an integer from 1 to 17 | j is an integer from 1 to 17 | k is an integer from 1 to 10 | 17 (i − 1) + j + 289 (k − 1) + 116110 | Compound 116111-119000 |
| 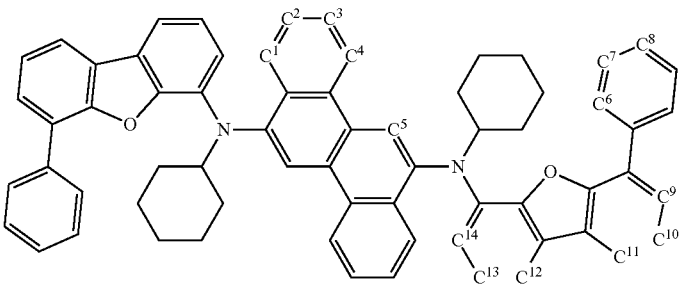 | i is an integer from 1 to 14 | j is an integer from 1 to 17 | k is an integer from 1 to 10 | 17 (i − 1) + j + 238 (k − 1) + 119000 | Compound 119001-121380 |
| 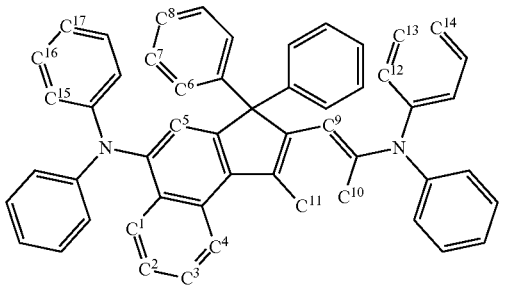 | i is an integer from 1 to 17 | j is an integer from 1 to 17 | k is an integer from 1 to 10 | 17 (i − 1) + j + 289 (k − 1) + 121380 | Compound 121381-124270 |
| 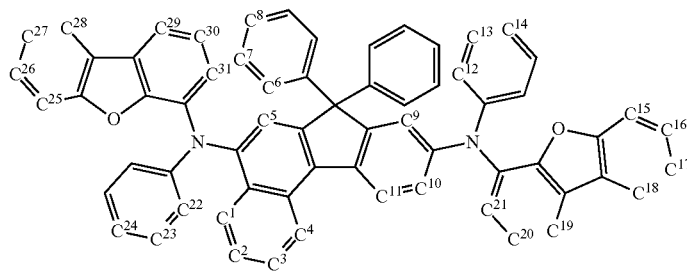 | i is an integer from 1 to 31 | j is an integer from 1 to 17 | k is an integer from 1 to 10 | 17 (i − 1) + j + 527 (k − 1) + 124270 | Compound 124271-129540 |

| Ai | Ci | Lj | Bk | x equals to | Compound x |
|---|---|---|---|---|---|
| (structure) | i is an integer from 1 to 29 | j is an integer from 1 to 17 | k is an integer from 1 to 10 | 17 (i − 1) + j + 493 (k − 1) + 129540 | Compound 129541-134470 |
| (structure) | i is an integer from 1 to 29 | j is an integer from 1 to 17 | k is an integer from 1 to 10 | 17 (i − 1) + j + 493 (k − 1) + 134470 | Compound 134471-139400 |
| (structure) | i is an integer from 1 to 35 | j is an integer from 1 to 17 | k is an integer from 1 to 10 | 17 (i − 1) + j + 595 (k − 1) + 139400 | Compound 139401-145350 |
| (structure) | i is an integer from 1 to 29 | j is an integer from 1 to 17 | k is an integer from 1 to 10 | 17 (i − 1) + j + 493 (k − 1) + 145350 | Compound 145351-150280 |
| (structure) | i is an integer from 1 to 14 | j is an integer from 1 to 17 | k is an integer from 1 to 10 | 17 (i − 1) + j + 238 (k − 1) + 150280 | Compound 150281-152660 |

-continued

| Ai | Ci | Lj | Bk | x equals to | Compound x |
|---|---|---|---|---|---|
| 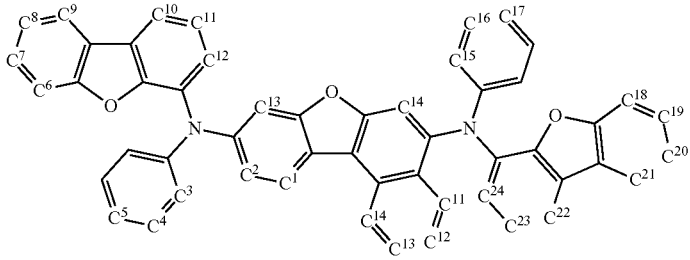 | $i$ is an integer from 1 to 24 | $j$ is an integer from 1 to 17 | $k$ is an integer from 1 to 10 | $17(i-1)+j+408(k-1)+152660$ | Compound 152661-156740 |
| 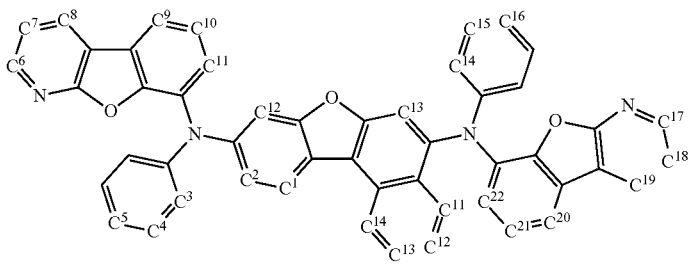 | $i$ is an integer from 1 to 22 | $j$ is an integer from 1 to 17 | $k$ is an integer from 1 to 10 | $17(i-1)+j+374(k-1)+156740$ | Compound 156741-160480 |
| 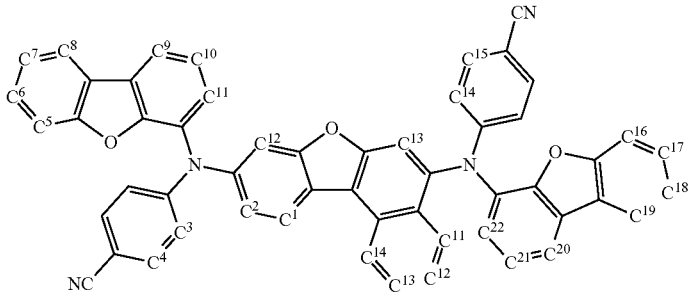 | $i$ is an integer from 1 to 22 | $j$ is an integer from 1 to 17 | $k$ is an integer from 1 to 10 | $17(i-1)+j+374(k-1)+160480$ | Compound 160481-164220 |
| 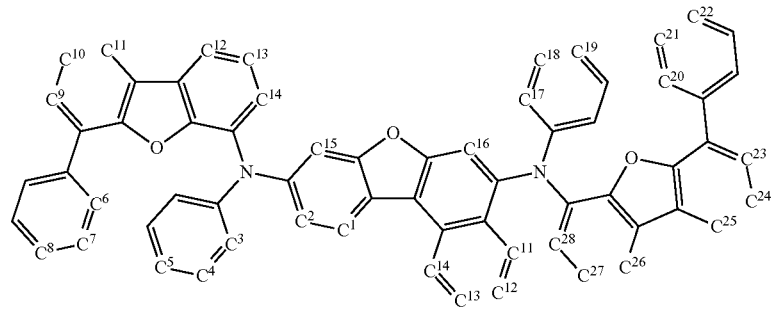 | $i$ is an integer from 1 to 28 | $j$ is an integer from 1 to 17 | $k$ is an integer from 1 to 10 | $17(i-1)+j+476(k-1)+164220$ | Compound 164221-168980 |
| 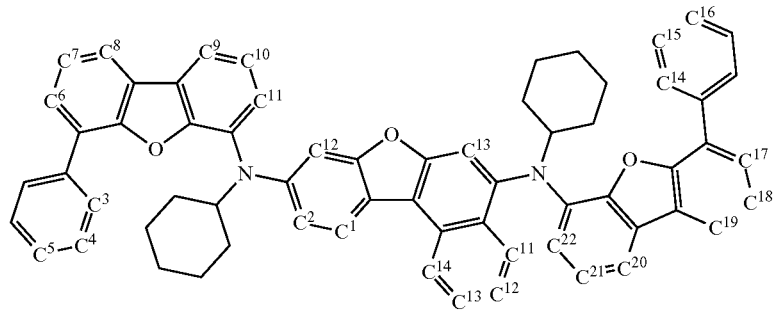 | $i$ is an integer from 1 to 22 | $j$ is an integer from 1 to 17 | $k$ is an integer from 1 to 10 | $17(i-1)+j+374(k-1)+168980$ | Compound 168981-172720 |

-continued

| Ai | Ci | Lj | Bk | x equals to | Compound x |
|---|---|---|---|---|---|
| 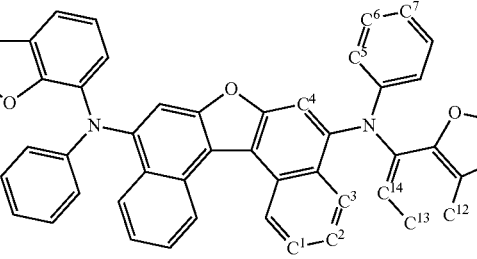 | i is an integer from 1 to 7 | j is an integer from 1 to 17 | k is an integer from 1 to 10 | 17 (i − 1) + j + 119 (k − 1) + 172720 | Compound 172721-173910 |
| 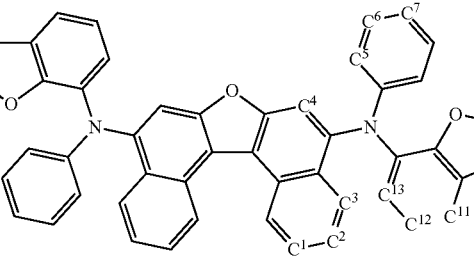 | i is an integer from 1 to 14 | j is an integer from 1 to 17 | k is an integer from 1 to 10 | 17 (i − 1) + j + 238 (k − 1) + 173910 | Compound 173911-176290 |
| 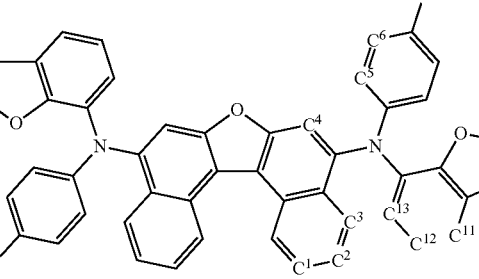 | i is an integer from 1 to 13 | j is an integer from 1 to 17 | k is an integer from 1 to 10 | 17 (i − 1) + j + 221 (k − 1) + 176290 | Compound 176291-178500 |
|  | i is an integer from 1 to 13 | j is an integer from 1 to 17 | k is an integer from 1 to 10 | 17 (i − 1) + j + 221 (k − 1) + 178500 | Compound 178501-180710 |
| 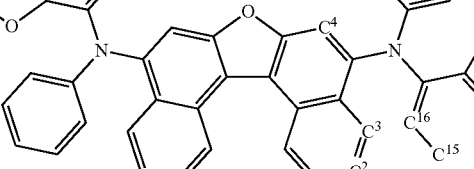 | i is an integer from 1 to 16 | j is an integer from 1 to 17 | k is an integer from 1 to 10 | 17 (i − 1) + j + 272 (k − 1) + 180710 | Compound 180711-183430 |

-continued

| Ai | Ci | Lj | Bk | x equals to | Compound x |
|---|---|---|---|---|---|
| 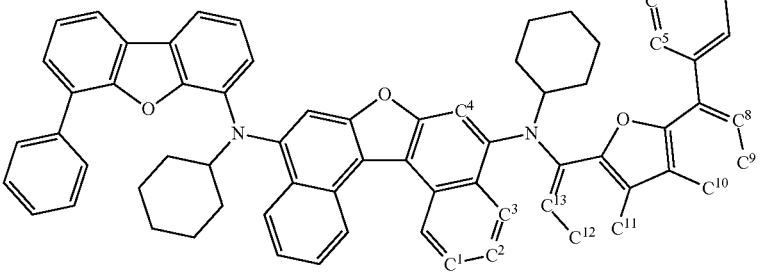 | i is an integer from 1 to 13 | j is an integer from 1 to 17 | k is an integer from 1 to 10 | 17 (i − 1) + j + 221 (k − 1) + 183430 | Compound 183431-185640 |
| 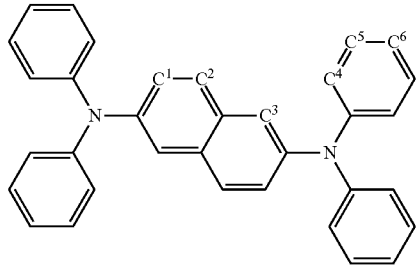 | i is an integer from 1 to 6 | j is an integer from 1 to 17 | k is an integer from 1 to 10 | 17 (i − 1) + j + 102 (k − 1) + 185640 | Compound 185641-186660 |
| 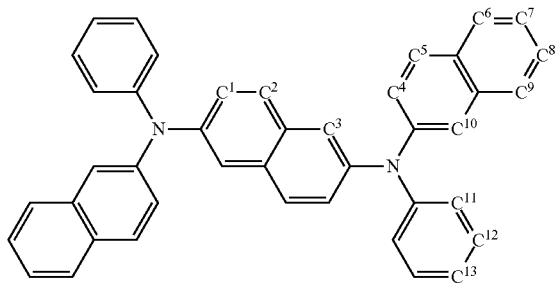 | i is an integer from 1 to 13 | j is an integer from 1 to 17 | k is an integer from 1 to 10 | 17 (i − 1) + j + 221 (k − 1) + 186660 | Compound 186661-188870 |
| 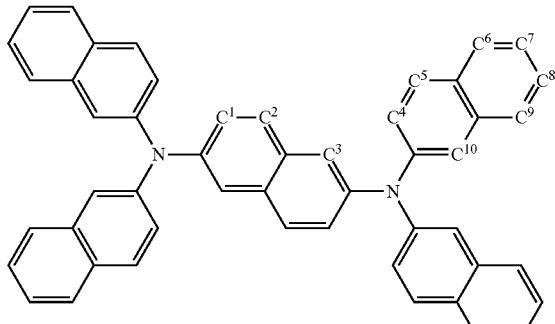 | i is an integer from 1 to 10 | j is an integer from 1 to 17 | k is an integer from 1 to 10 | 17 (i − 1) + j + 170 (k − 1) + 188870 | Compound 188871-190570 |

-continued

| Ai | Ci | Lj | Bk | x equals to | Compound x |
|---|---|---|---|---|---|
| (structure) | i is an integer from 1 to 17 | j is an integer from 1 to 17 | k is an integer from 1 to 10 | 17 (i − 1) + j + 289 (k − 1) + 190570 | Compound 190571-193460 |
| (structure) | i is an integer from 1 to 16 | j is an integer from 1 to 17 | k is an integer from 1 to 10 | 17 (i − 1) + j + 272 (k − 1) + 193460 | Compound 193461-196180 |
| (structure) | i is an integer from 1 to 9 | j is an integer from 1 to 17 | k is an integer from 1 to 10 | 17 (i − 1) + j + 153 (k − 1) + 196180 | Compound 196181-197710 |
| (structure) | i is an integer from 1 to 5 | j is an integer from 1 to 17 | k is an integer from 1 to 10 | 17 (i − 1) + j + 85 (k − 1) + 197710 | Compound 197711-198560 |

| Ai | Ci | Lj | Bk | x equals to | Compound x |
|---|---|---|---|---|---|
| | $i$ is an integer from 1 to 12 | $j$ is an integer from 1 to 17 | $k$ is an integer from 1 to 10 | $17(i-1)+j+204(k-1)+198560$ | Compound 198561-200600 |
| | $i$ is an integer from 1 to 11 | $j$ is an integer from 1 to 17 | $k$ is an integer from 1 to 10 | $17(i-1)+j+187(k-1)+200600$ | Compound 200601-202470 |
| | $i$ is an integer from 1 to 11 | $j$ is an integer from 1 to 17 | $k$ is an integer from 1 to 10 | $17(i-1)+j+187(k-1)+202470$ | Compound 202471-204340 |
| | $i$ is an integer from 1 to 14 | $j$ is an integer from 1 to 17 | $k$ is an integer from 1 to 10 | $17(i-1)+j+238(k-1)+204340$ | Compound 204341-206720 |
| | $i$ is an integer from 1 to 11 | $j$ is an integer from 1 to 17 | $k$ is an integer from 1 to 10 | $17(i-1)+j+187(k-1)+206720$ | Compound 206721-208590 |

| Ai | Ci | Lj | Bk | x equals to | Compound x |
|---|---|---|---|---|---|
| 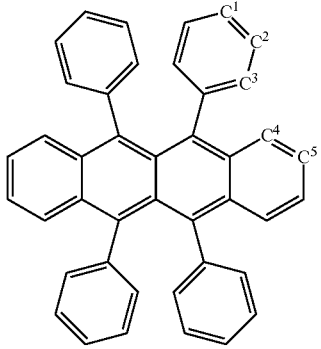 | i is an integer from 1 to 5 | j is an integer from 1 to 17 | k is an integer from 1 to 10 | 17 (i − 1) + j + 85 (k − 1) + 208590 | Compound 208591-290440 |
| 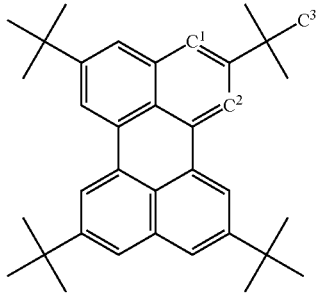 | i is an integer from 1 to 3 | j is an integer from 1 to 17 | k is an integer from 1 to 10 | 17 (i − 1) + j + 51 (k − 1) + 209440 | Compound 209441-209950 |
| 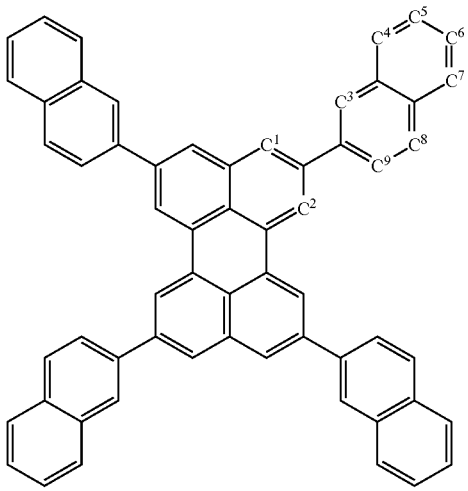 | i is an integer from 1 to 9 | j is an integer from 1 to 17 | k is an integer from 1 to 10 | 17 (i − 1) + j + 153 (k − 1) + 209950 | Compound 209951-211480 |

-continued
| Ai | Ci | Lj | Bk | x equals to | Compound x |
|---|---|---|---|---|---|
| 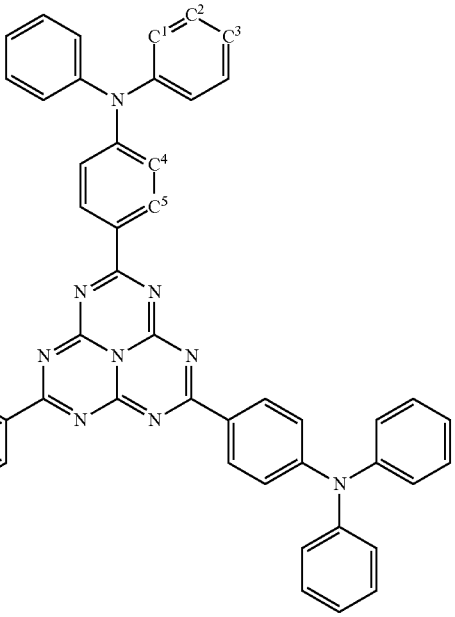 | $i$ is an integer from 1 to 5 | $j$ is an integer from 1 to 17 | $k$ is an integer from 1 to 10 | $17(i-1) + j + 85(k-1) + 211480$ | Compound 211481-212330 |
| 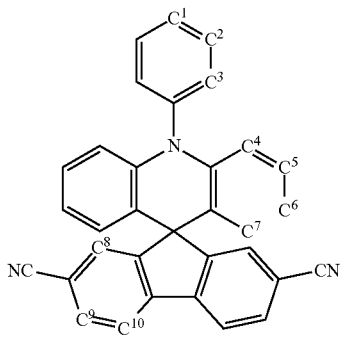 | $i$ is an integer from 1 to 10 | $j$ is an integer from 1 to 17 | $k$ is an integer from 1 to 10 | $17(i-1) + j + 170(k-1) + 212330$ | Compound 212331-214030 |
| 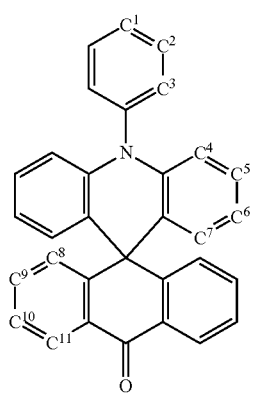 | $i$ is an integer from 1 to 11 | $j$ is an integer from 1 to 17 | $k$ is an integer from 1 to 10 | $17(i-1) + j + 187(k-1) + 214030$ | Compound 214031-215900 |

| Ai | Ci | Lj | Bk | x equals to | Compound x |
|---|---|---|---|---|---|
| 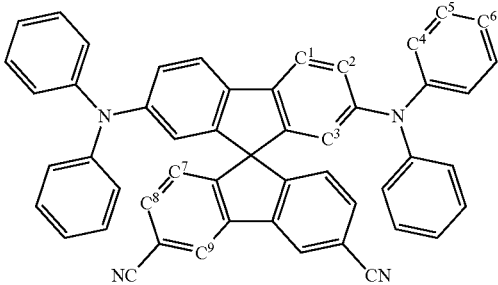 | i is an integer from 1 to 9 | j is an integer from 1 to 17 | k is an integer from 1 to 10 | 17 (i − 1) + j + 153 (k − 1) + 215900 | Compound 215901-217430 |
| 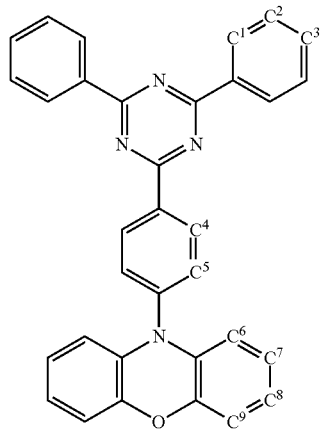 | i is an integer from 1 to 9 | j is an integer from 1 to 17 | k is an integer from 1 to 10 | 17 (i − 1) + j + 153 (k − 1) + 217430 | Compound 217431-218960 |
| 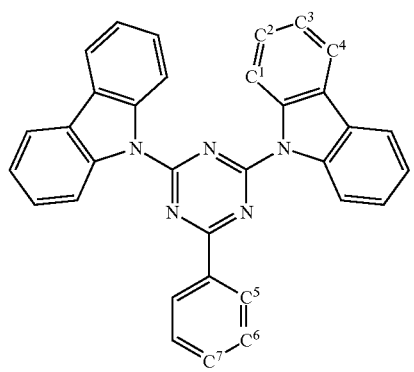 | i is an integer from 1 to 7 | j is an integer from 1 to 17 | k is an integer from 1 to 10 | 17 (i − 1) + j + 119 (k − 1) + 218960 | Compound 218961-220150 |
| 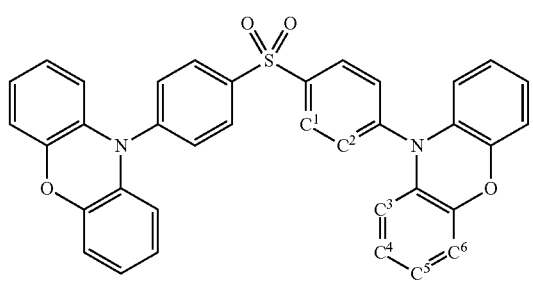 | i is an integer from 1 to 6 | j is an integer from 1 to 17 | k is an integer from 1 to 10 | 17 (i − 1) + j + 102 (k − 1) + 220150 | Compound 220151-221170 |

-continued

| Ai | Ci | Lj | Bk | x equals to | Compound x |
|---|---|---|---|---|---|
| 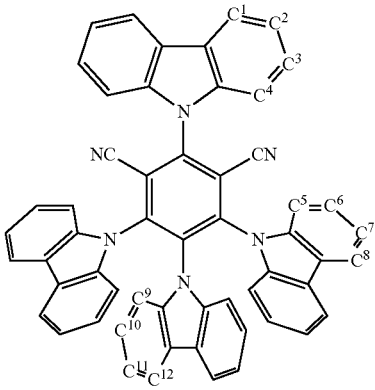 | i is an integer from 1 to 12 | j is an integer from 1 to 17 | k is an integer from 1 to 10 | 17 (i − 1) + j + 204 (k − 1) + 221170 | Compound 221171-223210 |
| 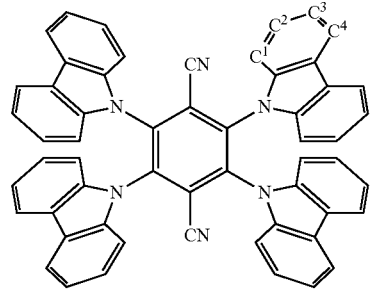 | i is an integer from 1 to 4 | j is an integer from 1 to 17 | k is an integer from 1 to 10 | 17 (i − 1) + j + 68 (k − 1) + 223210 | Compound 223211-223890 |
| 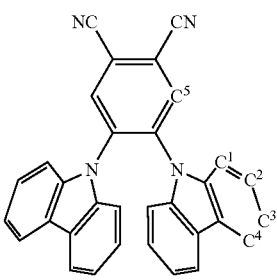 | i is an integer from 1 to 5 | j is an integer from 1 to 17 | k is an integer from 1 to 10 | 17 (i − 1) + j + 85 (k − 1) + 223890 | Compound 223891-224740 |
| 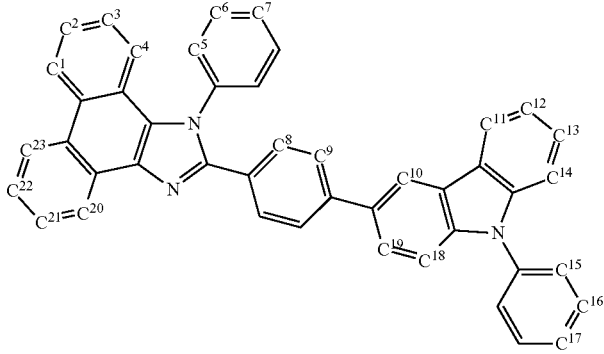 | i is an integer from 1 to 23 | j is an integer from 1 to 17 | k is an integer from 1 to 10 | 17 (i − 1) + j + 391 (k − 1) + 224740 | Compound 224741-228650 |

| Ai | Ci | Lj | Bk | x equals to | Compound x |
|---|---|---|---|---|---|
| 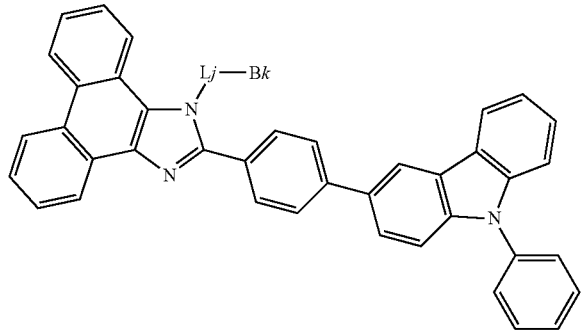 | i = 1 | j is an integer from 1 to 17 | k is an integer from 1 to 10 | j + 17 (k − 1) + 228650 | Compound 228651- 228820 |
| 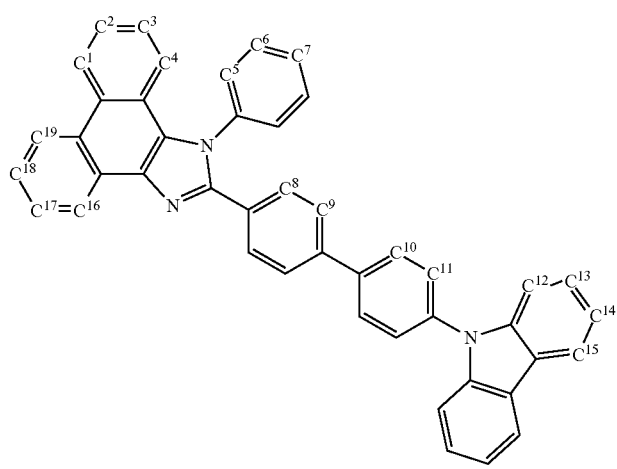 | i is an integer from 1 to 19 | j is an integer from 1 to 17 | k is an integer from 1 to 10 | 17 (i − 1) + j + 323 (k − 1) + 228820 | Compound 228821- 232050 |
| 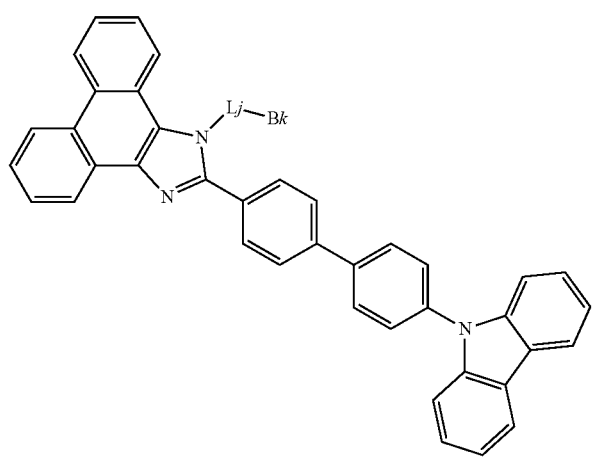 | i = 1 | j is an integer from 1 to 17 | k is an integer from 1 to 10 | j + 17 (k − 1) + 232050 | Compound 232051- 232220 |

-continued
| Ai | Ci | Lj | Bk | x equals to | Compound x |
|---|---|---|---|---|---|
| 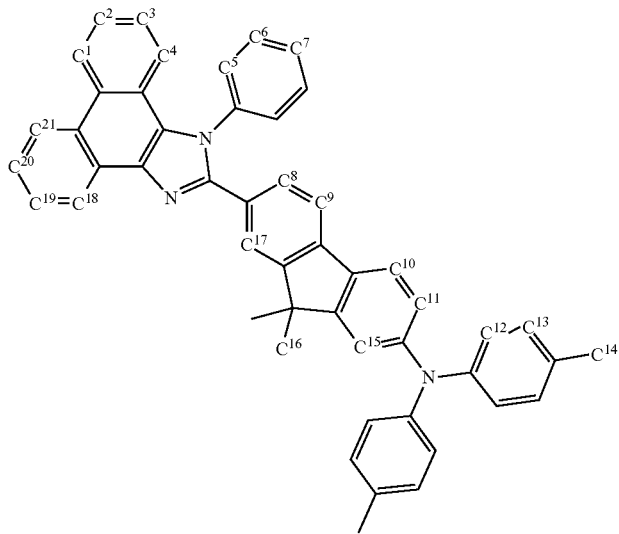 | $i$ is an integer from 1 to 21 | $j$ is an integer from 1 to 17 | $k$ is an integer from 1 to 10 | $17(i-1) + j + 357(k-1) + 232220$ | Compound 232221-235790 |
| 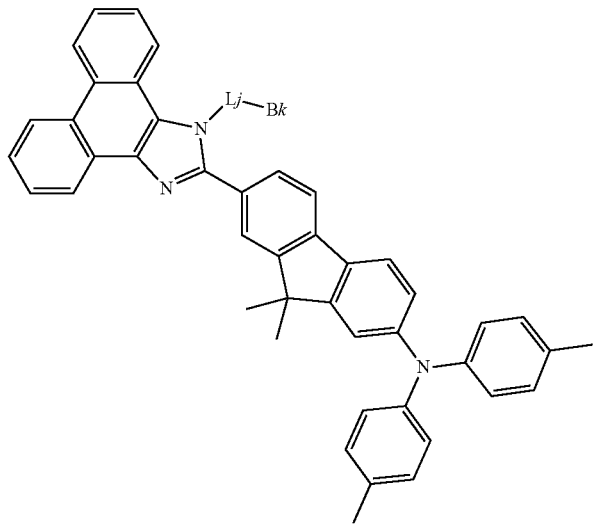 | $i = 1$ | $j$ is an integer from 1 to 17 | $k$ is an integer from 1 to 10 | $j + 17(k-1) + 235790$ | Compound 235791-235960 |
| 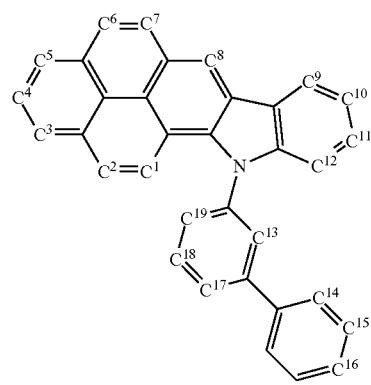 | $i$ is an integer from 1 to 19 | $j$ is an integer from 1 to 17 | $k$ is an integer from 1 to 10 | $17(i-1) + j + 323(k-1) + 235960$ | Compound 235961-239190 |

-continued

| Ai | Ci | Lj | Bk | x equals to | Compound x |
|---|---|---|---|---|---|
| (structure) | $i$ is an integer from 1 to 21 | $j$ is an integer from 1 to 17 | $k$ is an integer from 1 to 10 | $17(i-1) + j + 357(k-1) + 239190$ | Compound 239191-242760 |
| (structure) | $i$ is an integer from 1 to 17 | $j$ is an integer from 1 to 17 | $k$ is an integer from 1 to 10 | $17(i-1) + j + 289(k-1) + 242760$ | Compound 242761-245650 |
| (structure) | $i$ is an integer from 1 to 17 | $j$ is an integer from 1 to 17 | $k$ is an integer from 1 to 10 | $17(i-1) + j + 289(k-1) + 245650$ | Compound 245651-248540 |
| (structure) | $i$ is an integer from 1 to 19 | $j$ is an integer from 1 to 17 | $k$ is an integer from 1 to 10 | $17(i-1) + j + 323(k-1) + 248540$ | Compound 248541-251770. |

1. wherein the integer i is the integer associated with the point of attachment at carbon number in fragment Ai.

16. The compound of claim 14, wherein L is selected from a direct bond, a divalent aryl, or a divalent heteroaryl.

17. An organic light emitting device (OLED) comprising: an anode; a cathode; and an organic layer disposed between the anode and the cathode, the organic layer comprising a compound of claim 15.

18. A formulation comprising a compound of claim 1 and a fluorescent emitter.

19. A formulation comprising a compound of claim 13.

20. The compound of claim 1, wherein the polycyclic group is selected from the group consisting of:

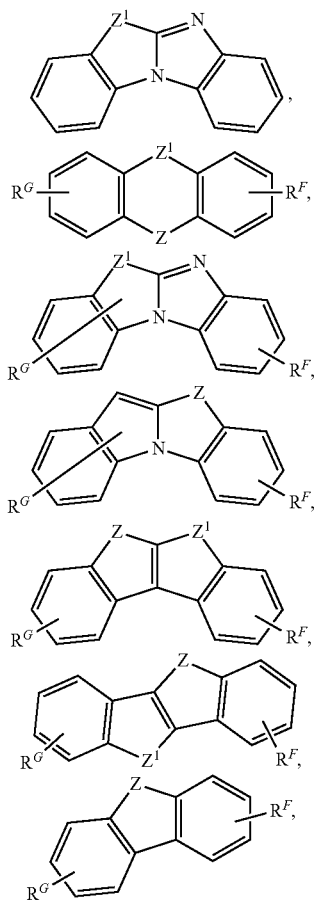

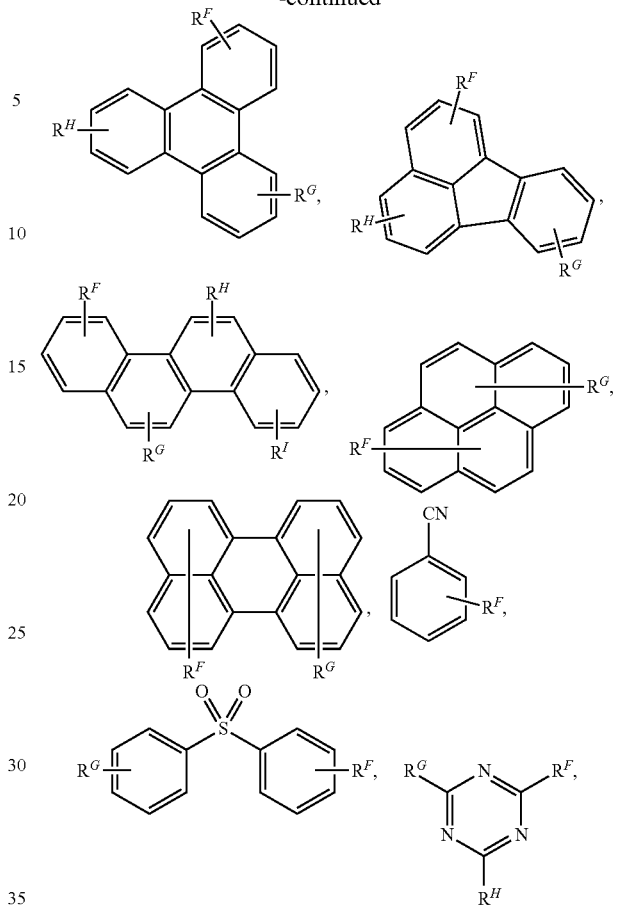

and any aza-analogue of each thereof, each of which is optionally substituted with $R^P$, wherein $R^P$ is selected from the group consisting of deuterium, fluorine, alkyl, cycloalkyl, amino, aryl, heteroaryl, silyl, nitrile, and combinations thereof;

wherein $R^F$ to $R^I$ are independently selected from the group consisting of hydrogen, deuterium, fluorine, alkyl, cycloalkyl, amino, aryl, heteroaryl, silyl, and nitrile; and Z and $Z^1$ are independently selected from the group consisting of O, S, Se, $NR^N$, CR'CR", SiR'R", and GeR'R", wherein R' and R" are independently $R^N$;

with the proviso that unsubstituted carbazole is excluded.

* * * * *